United States Patent
Abeywardane et al.

(10) Patent No.: US 8,946,203 B2
(45) Date of Patent: Feb. 3, 2015

(54) BENZODIOXANE INHIBITORS OF LEUKOTRIENE PRODUCTION

(71) Applicants: Asitha Abeywardane, Danbury, CT (US); Steven Richard Brunette, New Milford, CT (US); Michael J. Burke, Cheshire, CT (US); Suresh R. Kapadia, Danbury, CT (US); Thomas Martin Kirrane, Middlebury, CT (US); Matthew Russell Netherton, Danbury, CT (US); Hossein Razavi, Danbury, CT (US); Sonia Rodriguez, New Milford, CT (US); Anjan Saha, Hamden, CT (US); Robert Sibley, North Haven, CT (US); Lana Louise Smith-Keenan, Poughquag, NY (US); Hidenori Takahashi, LaGrangeville, NY (US); Michael Robert Turner, Danbury, CT (US); Jiang-Ping Wu, Danbury, CT (US); Erick Richard Roush Young, Danbury, CT (US); Qiang Zhang, Woodbury, CT (US); Qing Zhang, Tianjin (CH); Renee M. Zindell, New Milford, CT (US)

(72) Inventors: Asitha Abeywardane, Danbury, CT (US); Steven Richard Brunette, New Milford, CT (US); Michael J. Burke, Cheshire, CT (US); Suresh R. Kapadia, Danbury, CT (US); Thomas Martin Kirrane, Middlebury, CT (US); Matthew Russell Netherton, Danbury, CT (US); Hossein Razavi, Danbury, CT (US); Sonia Rodriguez, New Milford, CT (US); Anjan Saha, Hamden, CT (US); Robert Sibley, North Haven, CT (US); Lana Louise Smith-Keenan, Poughquag, NY (US); Hidenori Takahashi, LaGrangeville, NY (US); Michael Robert Turner, Danbury, CT (US); Jiang-Ping Wu, Danbury, CT (US); Erick Richard Roush Young, Danbury, CT (US); Qiang Zhang, Woodbury, CT (US); Qing Zhang, Tianjin (CH); Renee M. Zindell, New Milford, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/785,034

(22) Filed: Mar. 5, 2013

(65) Prior Publication Data
US 2013/0244996 A1 Sep. 19, 2013

Related U.S. Application Data

(60) Provisional application No. 61/607,136, filed on Mar. 6, 2012.

(51) Int. Cl.
C07D 519/00 (2006.01)
C07D 491/04 (2006.01)
(Continued)

(52) U.S. Cl.
CPC .......... *C07D 491/052* (2013.01); *C07D 405/10* (2013.01); *C07D 295/096* (2013.01);
(Continued)

(58) Field of Classification Search
USPC .......................... 546/16, 114, 115, 122, 197; 514/210.18, 211.15, 217.03, 218, 221, 514/233.8, 249, 253.04, 254.11, 278, 300, 514/301, 302, 321; 544/148, 350, 362, 377; 540/544, 568, 575, 596
See application file for complete search history.

(56) References Cited

U.S. PATENT DOCUMENTS 4,918,092 A 4/1990 Frenette et al.
5,120,758 A 6/1992 Satoh
(Continued)

FOREIGN PATENT DOCUMENTS

WO 2007040682 A1 4/2007
WO 2011114220 A1 9/2011
(Continued)

OTHER PUBLICATIONS

Davies, D. R. et al., "Discovery of Leukotriene A4 Hydrolase Inhibitors Using Metabolomics Biased Fragment Crystallography +", Journal of Medicanal Chemistry, vol. 52, No. 15, Aug. 13, 2009, pp. 4694-4715.
(Continued)

*Primary Examiner* — Niloofar Rahmani
(74) *Attorney, Agent, or Firm* — Michael P. Morris; David L. Kershner

(57) ABSTRACT

The present invention relates to compounds of formula (I):

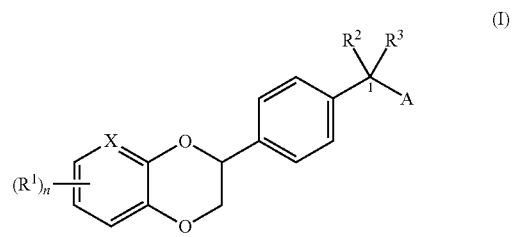

wherein $R^1$ to $R^3$, A, X and n are as defined herein. The compounds of formula (I) are useful as inhibitors of leukotriene $A_4$ hydrolase (LTA4H) and treating LTA4H related disorder. The present invention also relates to pharmaceutical compositions comprising the compounds of formula (I), methods of using these compounds in the treatment of various diseases and disorders, and processes for preparing these compounds.

16 Claims, No Drawings

(51) Int. Cl.
*C07D 487/08* (2006.01)
*A61K 31/357* (2006.01)
*C07D 491/052* (2006.01)
*C07D 405/10* (2006.01)
*C07D 295/096* (2006.01)
*C07D 295/155* (2006.01)
*C07D 513/04* (2006.01)
*C07D 405/14* (2006.01)
*C07D 319/20* (2006.01)
*C07D 405/12* (2006.01)
*C07D 487/10* (2006.01)
*C07D 413/10* (2006.01)
*C07D 417/10* (2006.01)
*C07D 417/14* (2006.01)
*C07D 471/10* (2006.01)
*C07D 487/04* (2006.01)

(52) U.S. Cl.
CPC .......... *C07D 295/155* (2013.01); *C07D 513/04* (2013.01); *C07D 405/14* (2013.01);*A61K 31/357* (2013.01); *C07D 319/20* (2013.01); *C07D 405/12* (2013.01); *C07D 487/10* (2013.01); *C07D 413/10* (2013.01); *C07D 417/10* (2013.01); *C07D 417/14* (2013.01); *C07D 471/10* (2013.01); *C07D 487/04* (2013.01); *C07D 487/08* (2013.01); *C07D 491/04* (2013.01); *C07D 519/00* (2013.01)
USPC ............ 514/210.18; 514/211.15; 514/217.03; 514/218; 514/221; 514/233.8; 514/249; 514/253.04; 514/254.11; 544/148; 544/350; 544/362; 544/377; 540/544; 540/568; 540/575; 540/596

(56) References Cited

U.S. PATENT DOCUMENTS

| | | | |
|---|---|---|---|
| 6,180,637 B1 | 1/2001 | Schindler et al. | |
| 7,098,222 B2 | 8/2006 | Altenbach et al. | |
| 7,429,665 B2 | 9/2008 | Verhoest et al. | |
| 7,674,802 B2 | 3/2010 | Sandanayaka et al. | |
| 8,551,982 B2 * | 10/2013 | Abeywardane et al. | . 514/211.03 |
| 2002/0132822 A1 | 9/2002 | Noe et al. | |
| 2006/0223792 A1 | 10/2006 | Butler et al. | |
| 2007/0066820 A1 | 3/2007 | Sandanayaka et al. | |
| 2013/0236468 A1 | 9/2013 | Bylock | |
| 2013/0244996 A1 | 9/2013 | Abeywardane et al. | |
| 2014/0031339 A1 | 1/2014 | Abeywardane et al. | |

FOREIGN PATENT DOCUMENTS

| | | |
|---|---|---|
| WO | 2012125598 A1 | 9/2012 |
| WO | 2013012844 A1 | 1/2013 |
| WO | 2014014874 A1 | 1/2014 |

OTHER PUBLICATIONS

Grice, C.A. et al., "Current Status of Leukotriene A4 Hydrolase Inhibitors". Expert Opinion on Therapeutic Patents, vol. 18, No. 12, Dec. 1, 2008, p. 1333-1350.
International Search Report and Written Opinion for PCT/US2012/028843 mailed May 7, 2012.
Minami, M. et al., "Molecular Cloning of a cDNA Coding for Human Leukotriene A4 Hydrolase". The Journal of Biological Chemistry, vol. 262, No. 29, 1987, p. 13873-13876.
Sandanayaka, V. et al., "Discovery of 4-[(2 S)-24[4-(4-Chlorophenoxy)phenoxy]methyl}-1-pyrrolidinyl]butanoic Acid (DG-051) as a Novel Leukotriene B4 Biosynthesis". Journal of Medicinal Chemistry, vol. 53, No. 2, Jan. 28, 2010, p. 573-585.
Sandanayaka, V. et al., "Discovery of novel leukotriene A4 hydrolase inhibitors based on piperidine and piperazine scaffolds". Bioorganice and Medicinal Chemistry Letters, Pergamon, Elsevier Science, GB, vol. 20, No. 9, May 1, 2010, pp. 2851-2854.
Thangapandian, Sundarapandian et al., "Molecular Docking and Pharacophore Filtering in the Discovery of Dual-Inhibitors for Human Leukotreine A4 Hydrolase and Leukotriene C4 Synthase", Journal of Chemical Information and Modeling, vol. 51, No. 1, Jan. 24, 2011, pp. 33-44.
U.S. Appl. No. 13/785,034, filed Mar. 5, 2013, Inventor: Asitha Abeywardane.
U.S. Appl. No. 13/785,097, filed Mar. 5, 2013, Inventor: Lars Anders Bylock.
U.S. Appl. No. 13/942,988, filed Jul. 16, 2013, Inventor: Asitha Abeywardane.
International Search Report and Written Opinion for PCT/US2013/029054 mailed May 21, 2013.
U.S. Appl. No. 14/330,297, filed Jul. 14, 2014—Inhibitors of Leukotriene Production. Inventor: Asitha Abeywardane et al.
U.S. Appl. No. 14/330,307, filed Jul. 14, 2014—Inhibitors of Leukotriene Production. Inventor: Asitha Abeywardane et al.

* cited by examiner

BENZODIOXANE INHIBITORS OF LEUKOTRIENE PRODUCTION

FIELD OF THE INVENTION

This invention relates to benzodioxanes that are useful as inhibitors of leukotriene $A_4$ hydrolase ($LTA_4H$) and are thus useful for treating a variety of diseases and disorders that are mediated or sustained through the activity of leukotrienes including asthma, allergy and cardiovascular diseases including atherosclerosis, myocardial infarction and stroke. This invention also relates to pharmaceutical compositions comprising these compounds, methods of using these compounds in the treatment of various diseases and disorders, processes for preparing these compounds and intermediates useful in these processes.

BACKGROUND OF THE INVENTION

Leukotrienes (LT) are oxidized lipids that are produced by several cell types including neutrophils, mast cells, eosinophils, basophils, monocytes and macrophages. The first committed step in the intracellular synthesis of LTs involves oxidation of arachidonic acid by 5-lipoxygenase (5-LO) to leukotriene $A_4$ ($LTA_4$), a process requiring the 5-lipoxygenase-activating protein (FLAP). Leukotriene $A_4$ hydrolase ($LTA_4H$) catalyzes the hydrolysis of $LTA_4$ to produce leukotriene $B_4$ ($LTB_4$). Through the engagement of the $LTB_4$ receptors (BLT1, BLT2), $LTB_4$ stimulates an array of pro-inflammatory responses (leukocyte chemotaxis, cytokine release, etc.). The leukotriene pathway has been implicated in diseases in which inflammation is a critical component of the pathology; these include cancer, asthma, atherosclerosis, colitis, glomerularnephritis, and pain (for a review, see M. Peters-Golden and W. R. Henderson, Jr., M.D., N. Engl. J. Med., 2007, 357, 1841-1854).

BRIEF SUMMARY OF THE INVENTION

The present invention provides novel compounds which inhibit leukotriene $A_4$ hydrolase ($LTA_4H$) and are thus useful for treating a variety of diseases and disorders that are mediated or sustained through the activity of leukotrienes, including allergic, pulmonary, fibrotic, inflammatory and cardiovascular diseases and cancer.

In one embodiment, the invention relates to a compound of formula (I):

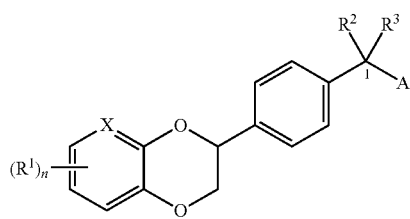

(I)

or a pharmaceutically acceptable salt thereof, wherein:
X is N or CH;
n is an integer from 0 to 3;
$R^1$ is selected from halo, —OH, —CN, —($C_1$-$C_6$)alkyl, —O($C_1$-$C_6$)alkyl, and —($C_3$-$C_6$)cycloalkyl;
$R^2$ and $R^3$ are each independently selected from —H and —($C_1$-$C_6$)alkyl; wherein $R^2$ and $R^3$ may join to form a 3- to 6-membered ring optionally comprising one to three heteroatoms, and further optionally substituted with one to three groups selected from halo, —OH, (=O), —($C_1$-$C_6$)alkyl, —O($C_1$-$C_6$)alkyl, —C(O)O—H, —C(O)($C_1$-$C_6$)alkyl, and —C(O)$NH_2$;
A is a group of formula —$NR^4R^5$, wherein
  $R^4$ and $R^5$ are each independently selected from —H, —($C_1$-$C_6$)alkyl, —($C_3$-$C_6$)cycloalkyl, -(4- to 14-membered)heterocycloalkyl, —($C_6$-$C_{10}$)aryl, and -(5- to 11-membered)heteroaryl; wherein each of the foregoing —($C_1$-$C_6$)alkyl, —($C_3$-$C_6$)cycloalkyl, -(4- to 14-membered)heterocycloalkyl, —($C_6$-$C_{10}$)aryl, and -(5- to 11-membered)heteroaryl of said $R^4$ and $R^5$ groups is optionally independently substituted by one to three $R^6$ groups; wherein two $R^6$ groups when attached to the same carbon atom of said —($C_1$-$C_6$)alkyl may join to form a 3- to 6-membered ring optionally comprising one to three heteroatoms, and further optionally substituted with one to three groups selected from halo, —OH, (=O), —($C_1$-$C_6$)alkyl, —O($C_1$-$C_6$)alkyl, —C(O)O—H, —C(O)($C_1$-$C_6$)alkyl, and —C(O)$NH_2$;
A is a (4- to 14-membered)N-heterocyclic ring of formula B:

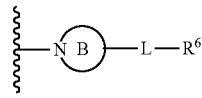

wherein said ring B is:
(a) a non-aromatic 4-8 membered monocyclic radical; or
(b) a bridged bicyclic radical, a spirocyclic radical, or a 6 to 11-membered fused bicyclic radical, wherein each of said bridged bicyclic radical, spirocyclic radical, and 6 to 11-membered fused bicyclic radical comprises at least a nonaromatic N-heterocyclic ring which is attached to the carbon atom 1 of the compound of formula (I); wherein each of said bridged bicyclic radical, spirocyclic radical, and 6 to 11-membered fused bicyclic radical may optionally comprise an aromatic ring;
wherein said ring B may additionally comprise one to three additional ring heteroatoms independently selected from N, O and S;
wherein said ring B may be further optionally substituted by one to three groups selected from halo, —OH, (=O), —C(O)O—H, —C(O)O—($C_1$-$C_6$)alkyl, and —($C_1$-$C_6$) alkyl; and
wherein L is absent or a linker selected from —($C_1$-$C_6$) alkylene-;
each $R^6$ is independently selected from halo, —$OR^7$, —$CF_3$, —CN, —($C_1$-$C_6$)alkyl, —O($C_1$-$C_6$)alkyl, —C(O)$R^7$, —C(O)$_2R^7$, —C(O)N($R^7$)$_2$, —N($R^7$)$_2$, —NHC(O)$R^7$, —NHC(O)N($R^7$)$_2$, —S(O)$_2R^7$, —NH—S(O)$_2$—$R^7$, —($C_3$-$C_6$)cycloalkyl, -(4- to 14-membered)heterocycloalkyl, —($C_6$-$C_{10}$)aryl, and -(5- to 11-membered)heteroaryl; wherein each of said, —($C_1$-$C_6$)alkyl, —O($C_1$-$C_6$)alkyl, —($C_3$-$C_6$)cycloalkyl, -(4- to 14-membered)heterocycloalkyl, —($C_6$-$C_{10}$)aryl, and -(5- to to 11-membered)heteroaryl of said $R^6$ group is optionally substituted where possible with one to three groups selected from halo, —OH, —$CF_3$, —CN, (=O), —($C_1$-$C_6$)alkyl, —C(O)O—H, —C(O)O—($C_1$-$C_6$) alkyl, —$NH_2$, —NH($C_1$-$C_6$)alkyl, —N(($C_1$-$C_6$)alkyl)$_2$, —S(O)$_2$($C_1$-$C_6$)alkyl, —($C_3$-$C_6$)cycloalkyl, -(4- to 14-membered)heterocycloalkyl, —($C_6$-$C_{10}$)aryl, and -(5- to 11-membered)heteroaryl; and
each $R^7$ is independently selected from —H, —($C_1$-$C_6$)alkyl, —($C_1$-$C_6$)alkyl-OH, —($C_1$-$C_6$)alkyl-O—($C_1$-$C_6$)alkyl, —O($C_1$-$C_6$)alkyl, —($C_3$-$C_6$)cycloalkyl, —($C_3$-$C_6$)cycloalkyl-OH, -(4- to 14-membered)heterocycloalkyl, —($C_6$-$C_{10}$)aryl, and -(5- to 11-membered)heteroaryl; wherein each of said $R^7$ group is optionally substituted where possible with a group selected from —OH, —NH($C_1$-$C_6$)alkyl, —NHC(O)($C_1$-$C_6$)alkyl, —C(O)N$H_2$, —S(O)$_2$($C_1$-$C_6$)alkyl, and -(4- to 14-membered)heterocycloalkyl; wherein said -(4- to 14-membered)heterocycloalkyl group is optionally substituted where possible with a (=O) group.

This invention also relates to pharmaceutical compositions comprising the compounds of formula (I), methods of using these compounds in the treatment of various diseases and disorders, processes for preparing these compounds and intermediates useful in these processes.

DETAILED DESCRIPTION OF THE INVENTION

Definitions

DCE=dichloroethane
DCM=dichloromethane
DEA=diethylamine
DIBAL-H=diisobutylaluminum hydride
DIPEA=diisopropylethylamine
DMA=dimethylacetamide
DMAP=4-dimethylaminopyridine
DME=dimethyl ether
DMF=dimethylformamide
DMSO=dimethylsulfoxide
$Et_2$O=ethylether
EtOAc=ethyl acetate
EtOH=ethanol
HATU=O-(7-azabenzotriazol-1-yl)-N,N,N',N'-tetramethyluronium hexafluorophosphate
IPA=isopropyl alcohol
KHMDS=potassium bis(trimethylsilyl)amide
MeCN=acetonitrile
MeOH=methanol
TBTU=2-(1H-benzotriazole-1-yl)-1,1,3,3-tetramethyluronium tetrafluoroborate
TEA=triethylamine
TFA=trifluoroacetic acid
THF=tetrahydrofuran
TMSCF$_3$=(trifluoromethyl)trimethylsilane It will be understood that the terms "compounds of formula (I)" and "compounds of the invention" have the same meaning unless indicated otherwise.

In its broadest embodiment ("the first embodiment of the invention"), the invention relates to compounds of formula (I) as described above, and pharmaceutically acceptable salts thereof, as described above in the summary of the invention.

In another embodiment ("the second embodiment of the invention"), the invention relates to a compound of formula (I) as described in the first embodiment immediately of the invention, or a pharmaceutically acceptable salt thereof, wherein group A is a group of formula —NR$^4$R$^5$.

In another embodiment ("the third embodiment of the invention"), the invention relates to a compound of formula (I) as described in the first embodiment of the invention, or a pharmaceutically acceptable salt thereof, wherein group A is a (4- to 14-membered)N-heterocyclic ring of formula B:

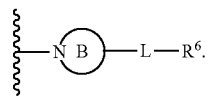

In another embodiment, the invention relates to a compound of formula (I) as described in the second embodiment of the invention, or a pharmaceutically acceptable salt thereof, wherein $R^4$ is —H or —($C_1$-$C_6$)alkyl, and $R^5$ is —($C_1$-$C_6$)alkyl; wherein each —($C_1$-$C_6$)alkyl of said $R^4$ and $R^5$ groups, when present, is optionally independently substituted by one to three $R^6$ groups.

In another embodiment, the invention relates to a compound of formula (I) as described in the embodiment immediately above, or a pharmaceutically acceptable salt thereof, wherein $R^4$ is H or —($C_1$-$C_6$)alkyl, and $R^5$ is —($C_1$-$C_6$)alkyl; wherein said —($C_1$-$C_6$)alkyl of said $R^5$ group is substituted by —($C_3$-$C_6$)cycloalkyl, -(4- to 14-membered)heterocycloalkyl, —($C_6$-$C_{10}$)aryl, or -(5- to 11-membered)heteroaryl; wherein each of said, —($C_3$-$C_6$)cycloalkyl, -(4- to 14-membered)heterocycloalkyl, —($C_6$-$C_{10}$)aryl, and -(5- to 11-membered)heteroaryl is optionally substituted with one to three groups independently selected from —($C_1$-$C_6$)alkyl, —CF$_3$, and —C(O)OR$^8$.

In another embodiment, the invention relates to a compound of formula (I) as described in the second embodiment of the invention, or a pharmaceutically acceptable salt thereof, wherein $R^4$ is —H or —($C_1$-$C_6$)alkyl, and $R^5$ is —($C_1$-$C_6$)alkyl; wherein said —($C_1$-$C_6$)alkyl of said $R^5$ group is independently substituted by one to three groups selected from —($C_1$-$C_6$)alkyl, —O($C_1$-$C_6$)alkyl, —C(O)R$^8$, —C(O)OR$^8$, —S(O)$_2$R$^8$, and —NHC(O)R$^8$.

In another embodiment, the invention relates to a compound of formula (I) as described in the second embodiment of the invention, or a pharmaceutically acceptable salt thereof, wherein $R^4$ and $R^5$ are each independently selected from H or —($C_1$-$C_6$)alkyl.

In another embodiment, the invention relates to a compound of formula (I) as described in the second embodiment of the invention, or a pharmaceutically acceptable salt thereof, wherein $R^4$ is H or —($C_1$-$C_6$)alkyl, and $R^5$ is —($C_3$-$C_6$)cycloalkyl, -(4- to 14-membered)heterocycloalkyl, —($C_6$-$C_{10}$)aryl, and -(5- to 11-membered)heteroaryl; wherein each of the foregoing —($C_3$-$C_6$)cycloalkyl, -(4- to 14-membered)heterocycloalkyl, —($C_6$-$C_{10}$)aryl, and -(5- to 11-membered)heteroaryl groups of said $R^5$ is optionally independently substituted by one to three groups selected from —($C_1$-$C_6$)alkyl, —O($C_1$-$C_6$)alkyl, —C(O)R$^8$, —C(O)OR$^8$, —S(O)$_2$R$^8$, and —NHC(O)R$^8$.

In another embodiment, the invention relates to a compound of formula (I) as described in the third embodiment of the invention, or a pharmaceutically acceptable salt thereof, wherein said ring B is 4- to 8-membered monocyclic radical.

In another embodiment, the invention relates to a compound of formula (I) as described in the embodiment immediately above, or a pharmaceutically acceptable salt thereof, wherein said 4-8 membered monocyclic radical is selected from the group consisting of azetidine, tetrahydropyrrole, piperidine, hexamethyleneimine, 1,2-diazetidine, pyrazolidine, imidazolidine, piperazine, hexahydrodiazepine, isoxazolidine, oxazolidine, tetrahydro-2H-1,3-oxazine, morpholine, and hexahydro-1,4-oxazepine; wherein said monocyclic ring may be further optionally substituted by one to three groups selected from halo, —OH, (=O), —C(O)OH, —C(O)O—($C_1$-$C_6$)alkyl, and —($C_1$-$C_6$)alkyl.

In another embodiment, the invention relates to a compound of formula (I) as described in the third embodiment of the invention, or a pharmaceutically acceptable salt thereof, wherein said ring B is a spirocyclic heterocyclic radical, wherein said spirocyclic heterocyclic radical optionally comprises an aromatic ring;

In another embodiment, the invention relates to a compound of formula (I) as described in the embodiment immediately above, or a pharmaceutically acceptable salt thereof, wherein said spirocyclic heterocyclic radical is selected from:

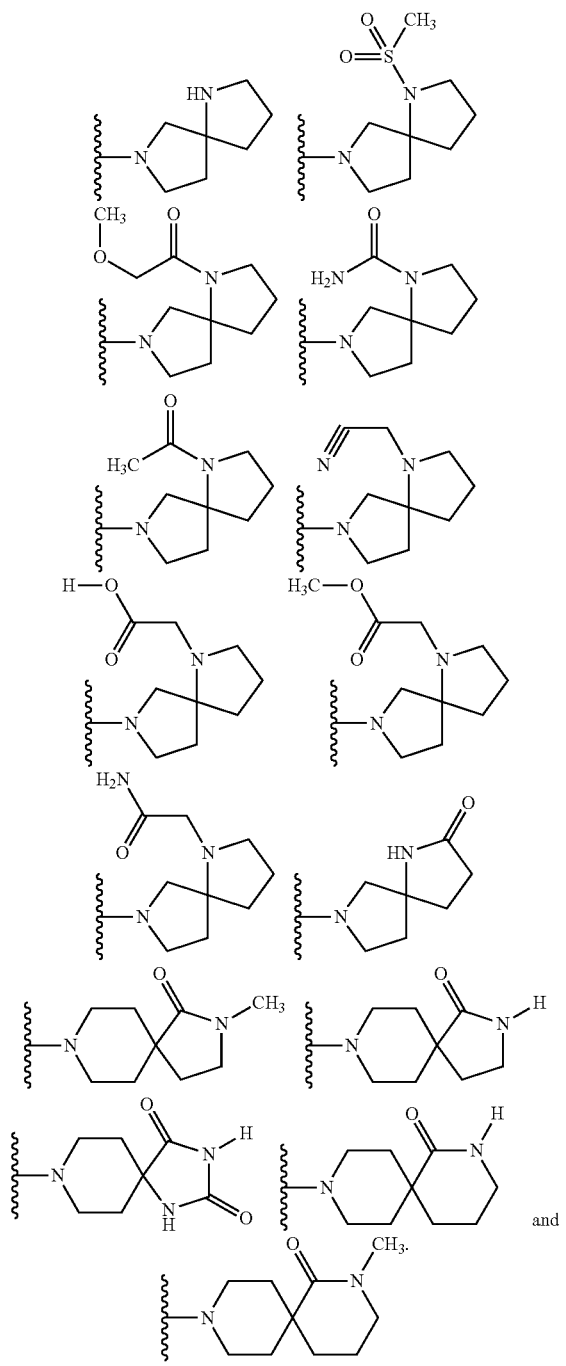

In another embodiment, the invention relates to a compound of formula (I) as described in the third embodiment of the invention, or a pharmaceutically acceptable salt thereof, wherein said ring B is a bridged bicyclic radical or a 6 to 11-membered fused bicyclic radical wherein each of said bridged bicyclic radical and 6 to 11-membered fused bicyclic radical may optionally comprise an aromatic ring;

In another embodiment, the invention relates to a compound of formula (I) as described in the embodiment immediately above, or a pharmaceutically acceptable salt thereof, wherein said 6 to 11-membered fused bicyclic radical or bridged bicyclic radical is selected from:

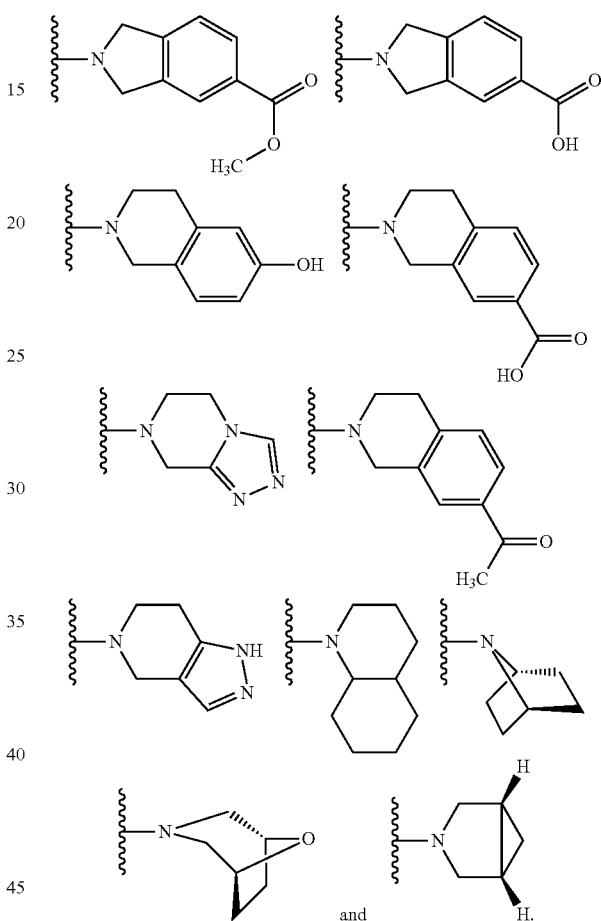

In another embodiment, the invention relates to a compound of formula (I) as described in the third embodiment of the invention, or a pharmaceutically acceptable salt thereof, wherein L is —CH$_2$—.

In another embodiment, the invention relates to a compound of formula (I) as described in the third embodiment of the invention, or a pharmaceutically acceptable salt thereof, wherein L is absent.

In another embodiment, the invention relates to a compound of formula (I) as described in the third embodiment of the invention, or a pharmaceutically acceptable salt thereof, wherein said 4-8-membered heterocyclic ring B is a selected from azetidinyl, pyrrolidinyl, piperidinyl, piperazinyl and azepanyl; wherein each of the foregoing azetidinyl, pyrrolidinyl, piperidinyl, piperazinyl and azepanyl rings is optionally substituted by one to three groups selected from halo, —OH, (=O), —C(O)O—H, C(O)O—(C$_1$-C$_6$)alkyl, and —(C$_1$-C$_6$)alkyl; and wherein
- L is absent or a linker selected from —(C$_1$-C$_6$)alkylene-; and wherein
- R$^6$ is selected from halo, —OR$^7$, —CF$_3$, —CN, —(C$_1$-C$_6$)alkyl, —O(C$_1$-C$_6$)alkyl, —C(O)R$^7$, —C(O)$_2$R$^7$, —C(O)N(R$^7$)$_2$, —N(R$^7$)$_2$, —NHC(O)R$^7$, —NHC(O)N(R$^7$)$_2$, —S(O)$_2$R$^7$, —NH—S(O)$_2$—R$^7$, —(C$_3$-C$_6$)cycloalkyl, -(4- to 14-membered)heterocycloalkyl, —(C$_6$-C$_{10}$)aryl, and -(5- to 11-membered)heteroaryl; wherein each of said, —(C$_1$-C$_6$)alkyl, —O(C$_1$-C$_6$)alkyl, —(C$_3$-C$_6$)cycloalkyl, -(4- to 14-membered)heterocycloalkyl, —(C$_6$-C$_{10}$)aryl, and -(5- to 11-membered)heteroaryl of said R$^6$ group is optionally substituted where possible with one to three groups selected from halo, —OH, —CF$_3$, —CN, (=O), —(C$_1$-C$_6$)alkyl, —C(O)O—H, —C(O)O—(C$_1$-C$_6$)alkyl, —NH$_2$, —NH(C$_1$-C$_6$)alkyl, —N((C$_1$-C$_6$)alkyl)$_2$, —S(O)$_2$(C$_1$-C$_6$)alkyl, —(C$_3$-C$_6$)cycloalkyl, -(4- to 14-membered)heterocycloalkyl, —(C$_6$-C$_{10}$)aryl, and -(5- to 11-membered)heteroaryl.

In another embodiment, the invention relates to a compound of formula (I) as described in the broadest embodiment above, or a pharmaceutically acceptable salt thereof, wherein -L-R$^6$ together represent —C(O)—(C$_1$-C$_6$)alkyl, wherein said C(O)—(C$_1$-C$_6$)alkyl group is substituted by a group selected from —N(H)(C$_1$-C$_6$)alkyl, —N(H)C(O)(C$_1$-C$_6$) alkyl, —C(O)NH$_2$, —S(O)$_2$(C$_1$-C$_6$)alkyl, and -(4- to 14-membered)heterocycloalkyl.

In another embodiment, the invention relates to a compound of formula (I) as described in the broadest embodiment above, or a pharmaceutically acceptable salt thereof, wherein -L-R$^6$ together represent —N(H)—C(O)—(C$_1$-C$_6$)alkyl, wherein said —N(H)—C(O)—(C$_1$-C$_6$)alkyl group is substituted by a group selected from —NH$_2$, —N(H)(C$_1$-C$_6$)alkyl, —N(H)C(O)(C$_1$-C$_6$)alkyl, —C(O)NH$_2$, —S(O)$_2$(C$_1$-C$_6$) alkyl, and -(4- to 14-membered)heterocycloalkyl In another embodiment, the invention relates to a compound of formula (I) as described in the broadest embodiment above, or a pharmaceutically acceptable salt thereof, wherein -L-R$^6$ together represent —O—(C$_1$-C$_6$)alkyl, wherein said —O—(C$_1$-C$_6$)alkyl is substituted by a group selected from —NH$_2$, —N(H)(C$_1$-C$_6$)alkyl, —N(H)C(O)(C$_1$-C$_6$)alkyl, —C(O)NH$_2$, —S(O)$_2$(C$_1$-C$_6$)alkyl, and -(4- to 14-membered)heterocycloalkyl In another embodiment, the invention relates to a compound of formula (I) as described in any of the embodiments above, or a pharmaceutically acceptable salt thereof, wherein X is N.

In another embodiment, the invention relates to a compound of formula (I) as described in any of the embodiments above except the embodiment immediately above, or a pharmaceutically acceptable salt thereof, wherein X is CH.

In another embodiment, the invention relates to a compound of formula (I) as described in any of the embodiments above, or a pharmaceutically acceptable salt thereof, where n is 0.

The following are representative compounds of the invention which can be made by the general synthetic schemes, the examples, and known methods in the art.

TABLE 1

Exemplary compounds of the invention.

| Cpd No. | Structure | Name |
| --- | --- | --- |
| 1 | 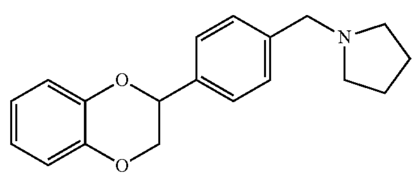 [SMILES: c1ccc2c(c1)OCC(c1ccc(CN3CCCC3)cc1)O2] | 1-[4-(2,3-dihydro-1,4-benzodioxin-2-yl)benzyl]pyrrolidine |
| 2 | 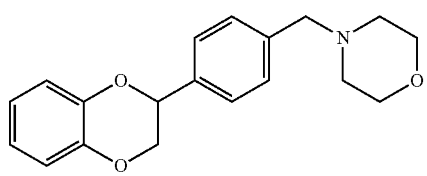 | 4-[4-(2,3-dihydro-1,4-benzodioxin-2-yl)benzyl]morpholine |
| 3 | 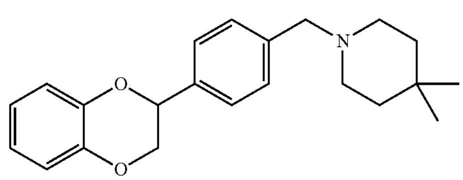 [SMILES: CC1(C)CCN(Cc2ccc(C3COc4ccccc4O3)cc2)CC1] | 1-[4-(2,3-dihydro-1,4-benzodioxin-2-yl)benzyl]-4,4-dimethylpiperidine |
| 4 | 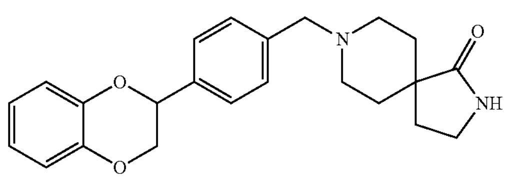 [SMILES: O=C1NCCC12CCN(Cc1ccc(C3COc4ccccc4O3)cc1)CC2] | 8-[4-(2,3-dihydro-1,4-benzodioxin-2-yl)benzyl]-2,8-diazaspiro[4.5]decan-1-one |

TABLE 1-continued

Exemplary compounds of the invention.

| Cpd No. | Structure | Name |
|---|---|---|
| 5 | 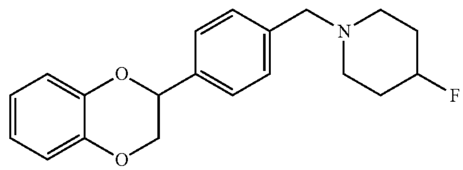 [SMILES: FC1CCN(Cc2ccc(C3COc4ccccc4O3)cc2)CC1] | 1-[4-(2,3-dihydro-1,4-benzodioxin-2-yl)benzyl]-4-fluoropiperidine |
| 6 | 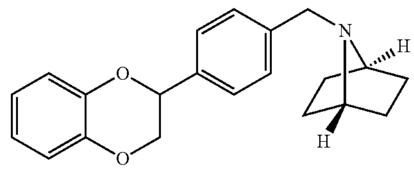 [SMILES: c1ccc2c(c1)OCC(c1ccc(CN3[C@H]4CC[C@@H]3CC4)cc1)O2] | (1s,4s)-7-[4-(2,3-dihydro-1,4-benzodioxin-2-yl)benzyl]-7-azabicyclo[2.2.1]heptane |
| 7 | 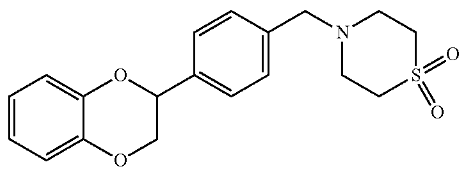 [SMILES: O=S1(=O)CCN(Cc2ccc(C3COc4ccccc4O3)cc2)CC1] | 4-[4-(2,3-dihydro-1,4-benzodioxin-2-yl)benzyl]thiomorpholine 1,1-dioxide |
| 8 | 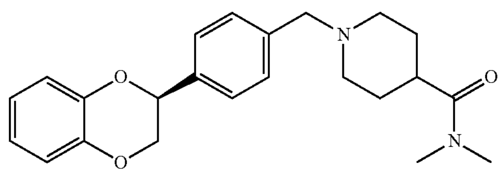 [SMILES: CN(C)C(=O)C1CCN(Cc2ccc([C@H]3COc4ccccc4O3)cc2)CC1] | 1-{4-[(2S)-2,3-dihydro-1,4-benzodioxin-2-yl]benzyl}-N,N-dimethylpiperidine-4-carboxamide |
| 9 | 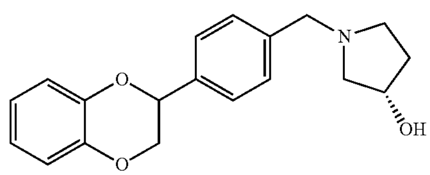 [SMILES: O[C@H]1CCN(Cc2ccc(C3COc4ccccc4O3)cc2)C1] | (3S)-1-[4-(2,3-dihydro-1,4-benzodioxin-2-yl)benzyl]pyrrolidin-3-ol |
| 10 | 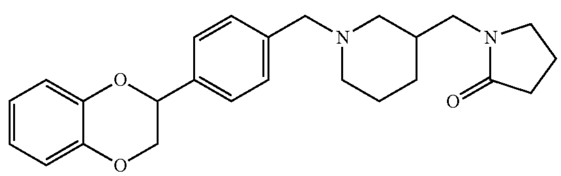 [SMILES: O=C1CCCN1CC1CCCN(Cc2ccc(C3COc4ccccc4O3)cc2)C1] | 1-({1-[4-(2,3-dihydro-1,4-benzodioxin-2-yl)benzyl]piperidin-3-yl}methyl)pyrrolidin-2-one |
| 11 | 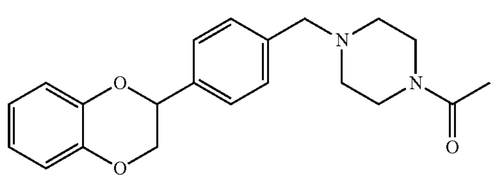 [SMILES: CC(=O)N1CCN(Cc2ccc(C3COc4ccccc4O3)cc2)CC1] | 1-{4-[4-(2,3-dihydro-1,4-benzodioxin-2-yl)benzyl]piperazin-1-yl}ethanone |
| 12 | 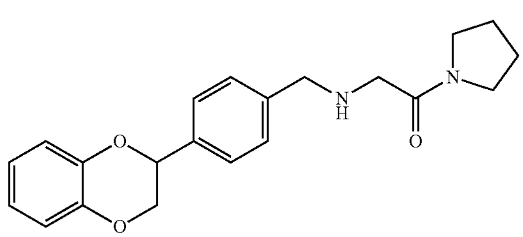 [SMILES: O=C(CNCc1ccc(C2COc3ccccc3O2)cc1)N1CCCC1] | 2-{[4-(2,3-dihydro-1,4-benzodioxin-2-yl)benzyl]amino}-1-(pyrrolidin-1-yl)ethanone |

TABLE 1-continued

Exemplary compounds of the invention.

| Cpd No. | Structure | Name |
|---|---|---|
| 13 | 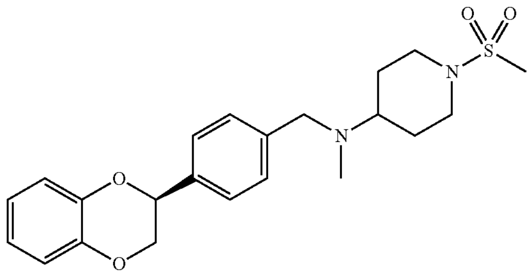 [SMILES: CN(Cc1ccc([C@H]2COc3ccccc3O2)cc1)C1CCN(S(C)(=O)=O)CC1] | N-{4-[(2S)-2,3-dihydro-1,4-benzodioxin-2-yl]benzyl}-N-methyl-1-(methylsulfonyl)piperidin-4-amine |
| 14 | 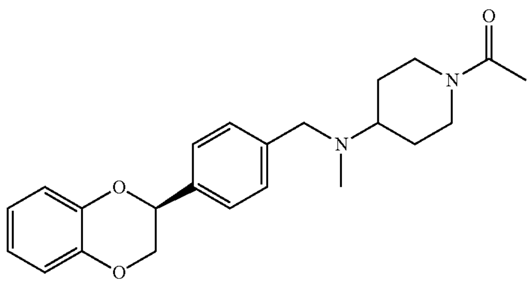 [SMILES: CC(=O)N1CCC(N(C)Cc2ccc([C@H]3COc4ccccc4O3)cc2)CC1] | 1-{4-[{4-[(2S)-2,3-dihydro-1,4-benzodioxin-2-yl]benzyl}(methyl)amino]piperidin-1-yl}ethanone |
| 15 | 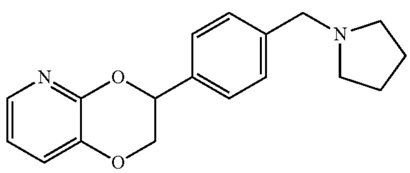 [SMILES: c1cnc2c(c1)OCC(c1ccc(CN3CCCC3)cc1)O2] | 3-[4-(pyrrolidin-1-ylmethyl)phenyl]-2,3-dihydro[1,4]dioxin[2,3-b]pyridine |
| 16 | 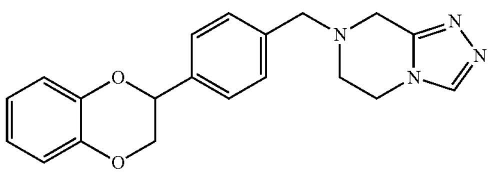 [SMILES: c1ccc2c(c1)OCC(c1ccc(CN3CCn4cnnc4C3)cc1)O2] | 7-[4-(2,3-dihydro-1,4-benzodioxin-2-yl)benzyl]-5,6,7,8-tetrahydro[1,2,4]triazolo[4,3-a]pyrazine |
| 17 | 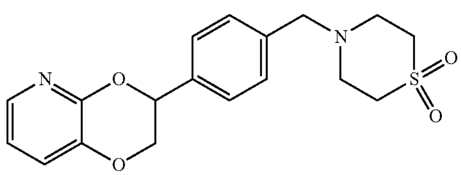 [SMILES: O=S1(=O)CCN(Cc2ccc(C3COc4cccnc4O3)cc2)CC1] | 3-{4-[(1,1-dioxidothiomorpholin-4-yl)methyl]phenyl}-2,3-dihydro[1,4]dioxin[2,3-b]pyridine |
| 18 | 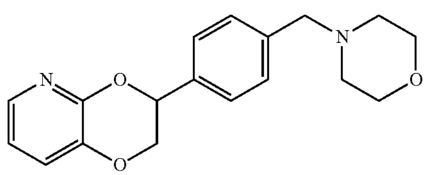 [SMILES: c1cnc2c(c1)OCC(c1ccc(CN3CCOCC3)cc1)O2] | 3-[4-(morpholin-4-ylmethyl)phenyl]-2,3-dihydro[1,4]dioxino[2,3-b]pyridine |
| 19 | 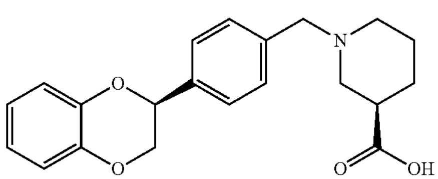 [SMILES: O=C(O)[C@@H]1CCCN(Cc2ccc([C@H]3COc4ccccc4O3)cc2)C1] | (3R)-1-{4-[(2S)-2,3-dihydro-1,4-benzodioxin-2-yl]benzyl}piperidine-3-carboxylic acid |

TABLE 1-continued

Exemplary compounds of the invention.

| Cpd No. | Structure | Name |
| --- | --- | --- |
| 20 | 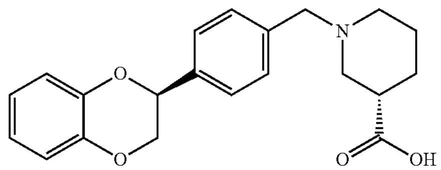 [SMILES: O=C(O)[C@H]1CCCN(Cc2ccc([C@H]3COc4ccccc4O3)cc2)C1] | (3S)-1-{4-[(2S)-2,3-dihydro-1,4-benzodioxin-2-yl]benzyl}piperidin-3-carboxylic acid |
| 21 | 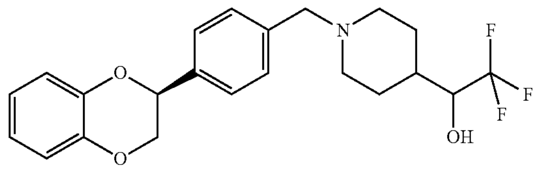 [SMILES: OC(C1CCN(Cc2ccc([C@H]3COc4ccccc4O3)cc2)CC1)C(F)(F)F] | 1-(1-{4-[(2S)-2,3-dihydro-1,4-benzodioxin-2-yl]benzyl}piperidin-4-yl)-2,2,2-trifluoroethanol |
| 22 | 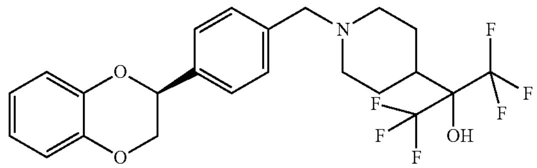 [SMILES: OC(C1CCN(Cc2ccc([C@H]3COc4ccccc4O3)cc2)CC1)(C(F)(F)F)C(F)(F)F] | 2-(1-{4-[(2S)-2,3-dihydro-1,4-benzodioxin-2-yl]benzyl}piperidin-4-yl)-1,1,1,3,3,3-hexafluoropropan-2-ol |
| 23 | 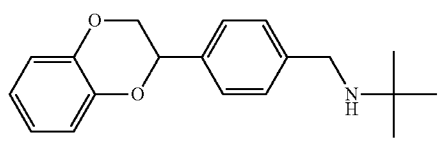 [SMILES: CC(C)(C)NCc1ccc(C2COc3ccccc3O2)cc1] | N-[4-(2,3-dihydro-1,4-benzodioxin-2-yl)benzyl]-2-methylpropan-2-amine |
| 24 | 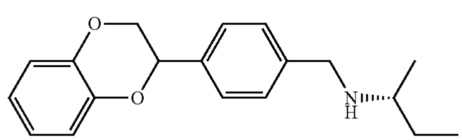 [SMILES: CC[C@@H](C)NCc1ccc(C2COc3ccccc3O2)cc1] | (2R)-N-[4-(2,3-dihydro-1,4-benzodioxin-2-yl)benzyl]butan-2-amine |
| 25 | 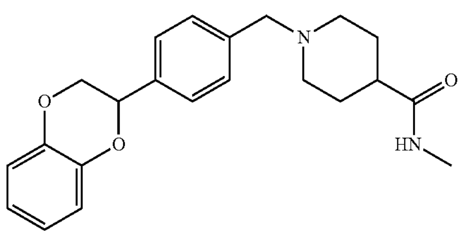 [SMILES: CNC(=O)C1CCN(Cc2ccc(C3COc4ccccc4O3)cc2)CC1] | 1-[4-(2,3-dihydro-1,4-benzodioxin-2-yl)benzyl]-N-methylpiperidine-4-carboxamide |
| 26 | 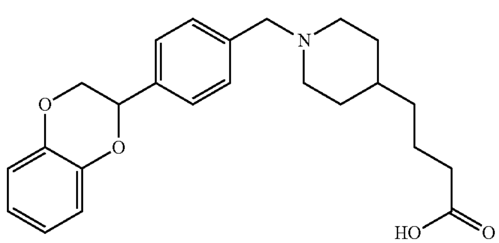 [SMILES: O=C(O)CCCC1CCN(Cc2ccc(C3COc4ccccc4O3)cc2)CC1] | 4-{1-[4-(2,3-dihydro-1,4-benzodioxin-2-yl)benzyl]piperidin-4-yl}butanoic acid |
| 27 | 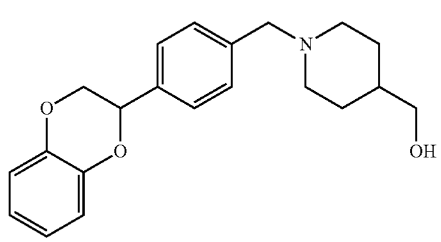 [SMILES: OCC1CCN(Cc2ccc(C3COc4ccccc4O3)cc2)CC1] | {1-[4-(2,3-dihydro-1,4-benzodioxin-2-yl)benzyl]piperidin-4-yl}methanol |

TABLE 1-continued

Exemplary compounds of the invention.

| Cpd No. | Structure | Name |
| --- | --- | --- |
| 28 | 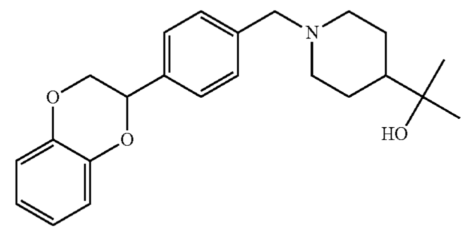 [SMILES: CC(C)(O)C1CCN(Cc2ccc(C3COc4ccccc4O3)cc2)CC1] | 2-{1-[4-(2,3-dihydro-1,4-benzodioxin-2-yl)benzyl]piperidin-4-yl}propan-2-ol |
| 29 | 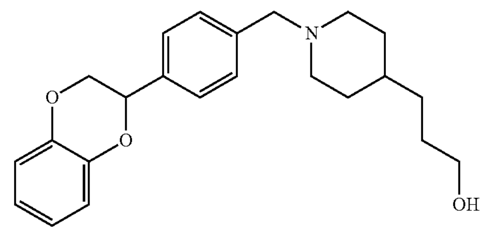 [SMILES: OCCCC1CCN(Cc2ccc(C3COc4ccccc4O3)cc2)CC1] | 3-{1-[4-(2,3-dihydro-1,4-benzodioxin-2-yl)benzyl]piperidin-4-yl}propan-1-ol |
| 30 | 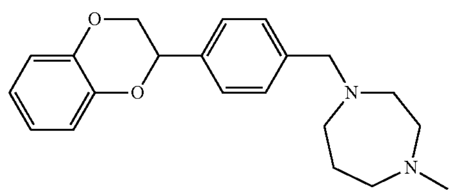 [SMILES: CN1CCCN(Cc2ccc(C3COc4ccccc4O3)cc2)CC1] | 1-[4-(2,3-dihydro-1,4-benzodioxin-2-yl)benzyl]-4-methyl-1,4-diazepane |
| 31 | 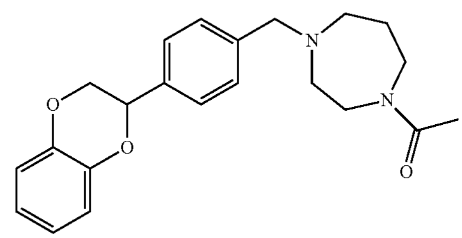 [SMILES: CC(=O)N1CCCN(Cc2ccc(C3COc4ccccc4O3)cc2)CC1] | 1-{4-[4-(2,3-dihydro-1,4-benzodioxin-2-yl)benzyl]-1,4-diazepan-1-yl}ethanone |
| 32 | 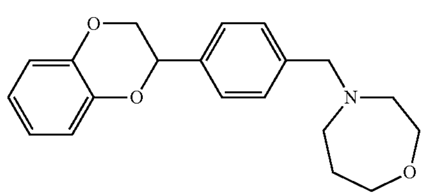 | 4-[4-(2,3-dihydro-1,4-benzodioxin-2-yl)benzyl]-1,4-oxazepan |
| 33 | 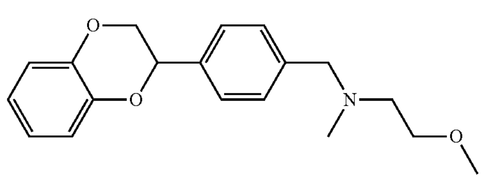 [SMILES: COCCN(C)Cc1ccc(C2COc3ccccc3O2)cc1] | N-[4-(2,3-dihydro-1,4-benzodioxin-2-yl)benzyl]-2-methoxy-N-methylethanamine |
| 34 | 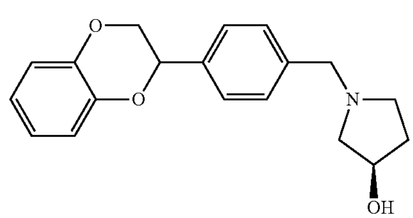 | (3R)-1-[4-(2,3-dihydro-1,4-benzodioxin-2-yl)benzyl]pyrrolidin-3-ol |

TABLE 1-continued

Exemplary compounds of the invention.

| Cpd No. | Structure | Name |
|---|---|---|
| 35 | 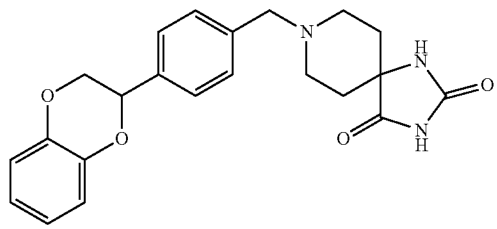 [SMILES: O=C1NC(=O)C2(CCN(Cc3ccc(C4COc5ccccc5O4)cc3)CC2)N1] | 8-[4-(2,3-dihydro-1,4-benzodioxin-2-yl)benzyl]-1,3,8-triazaspiro[4.5]decan-2,4-dione |
| 36 | 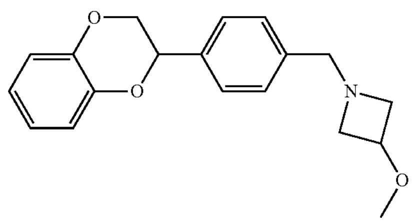 [SMILES: COC1CN(Cc2ccc(C3COc4ccccc4O3)cc2)C1] | 1-[4-(2,3-dihydro-1,4-benzodioxin-2-yl)benzyl]-3-methoxyazetidine |
| 37 | 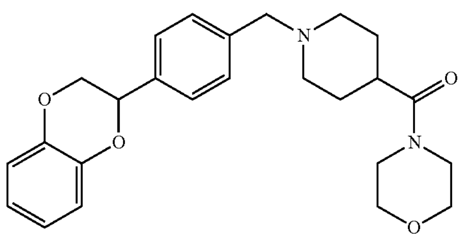 [SMILES: O=C(C1CCN(Cc2ccc(C3COc4ccccc4O3)cc2)CC1)N1CCOCC1] | {1-[4-(2,3-dihydro-1,4-benzodioxin-2-yl)benzyl]piperidin-4-yl}(morpholin-4-yl)methanone |
| 38 | 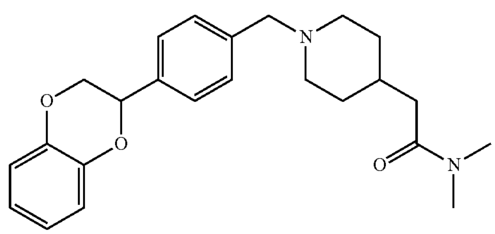 [SMILES: CN(C)C(=O)CC1CCN(Cc2ccc(C3COc4ccccc4O3)cc2)CC1] | 2-{1-[4-(2,3-dihydro-1,4-benzodioxin-2-yl)benzyl]piperidin-4-yl}-N,N-dimethylacetamide |
| 39 | 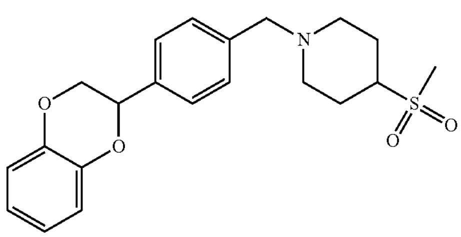 [SMILES: CS(=O)(=O)C1CCN(Cc2ccc(C3COc4ccccc4O3)cc2)CC1] | 1-[4-(2,3-dihydro-1,4-benzodioxin-2-yl)benzyl]-4-(methylsulfonyl)piperidine |
| 40 | 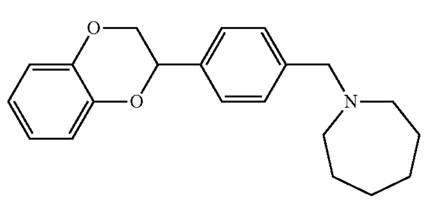 [SMILES: c1ccc2c(c1)OCC(c1ccc(CN3CCCCCC3)cc1)O2] | 1-[4-(2,3-dihydro-1,4-benzodioxin-2-yl)benzyl]azepane |
| 41 | 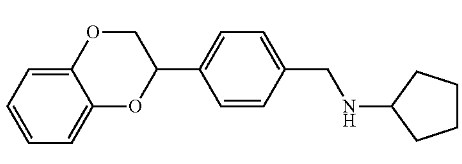 [SMILES: c1ccc2c(c1)OCC(c1ccc(CNC3CCCC3)cc1)O2] | N-[4-(2,3-dihydro-1,4-benzodioxin-2-yl)benzyl]cyclopentanamine |

TABLE 1-continued

Exemplary compounds of the invention.

| Cpd No. | Structure | Name |
| --- | --- | --- |
| 42 | 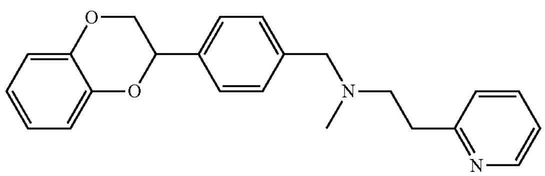 [SMILES: CN(CCc1ccccn1)Cc1ccc(C2COc3ccccc3O2)cc1] | N-[4-(2,3-dihydro-1,4-benzodioxin-2-yl)benzyl]-N-methyl-2-(pyridin-2-yl)ethanamine |
| 43 | 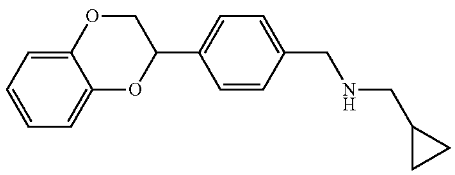 [SMILES: c1ccc2c(c1)OCC(c1ccc(CNCC3CC3)cc1)O2] | 1-cyclopropyl-N-[4-(2,3-dihydro-1,4-benzodioxin-2-yl)benzyl]methanamine |
| 44 | 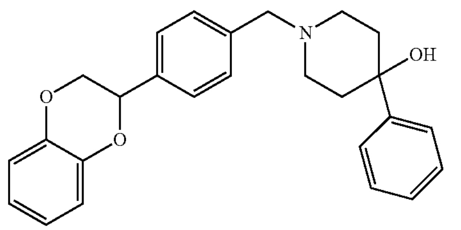 [SMILES: OC1(c2ccccc2)CCN(Cc2ccc(C3COc4ccccc4O3)cc2)CC1] | 1-[4-(2,3-dihydro-1,4-benzodioxin-2-yl)benzyl]-4-phenylpiperidin-4-ol |
| 45 | 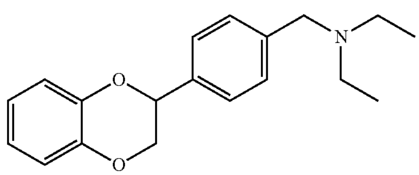 [SMILES: CCN(CC)Cc1ccc(C2COc3ccccc3O2)cc1] | N-[4-(2,3-dihydro-1,4-benzodioxin-2-yl)benzyl]-N-ethylethanamine |
| 46 | 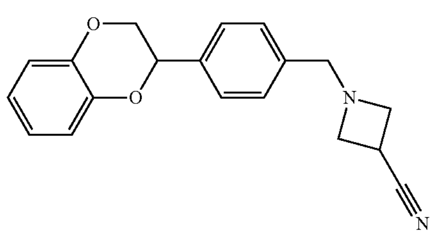 [SMILES: N#CC1CN(Cc2ccc(C3COc4ccccc4O3)cc2)C1] | 1-[4-(2,3-dihydro-1,4-benzodioxin-2-yl)benzyl]azetidine-3-carbonitrile |
| 47 | 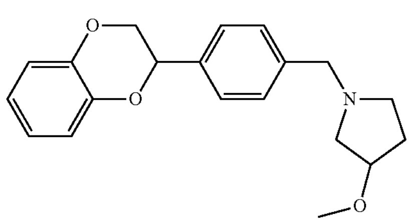 [SMILES: COC1CCN(Cc2ccc(C3COc4ccccc4O3)cc2)C1] | 1-[4-(2,3-dihydro-1,4-benzodioxin-2-yl)benzyl]-3-methoxypyrrolidine |
| 48 | 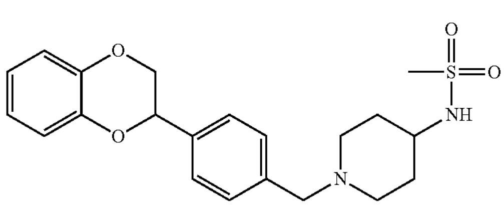 [SMILES: CS(=O)(=O)NC1CCN(Cc2ccc(C3COc4ccccc4O3)cc2)CC1] | N-{1-[4-(2,3-dihydro-1,4-benzodioxin-2-yl)benzyl]piperidin-4-yl}methanesulfonamide |

TABLE 1-continued

Exemplary compounds of the invention.

| Cpd No. | Structure | Name |
|---|---|---|
| 49 | 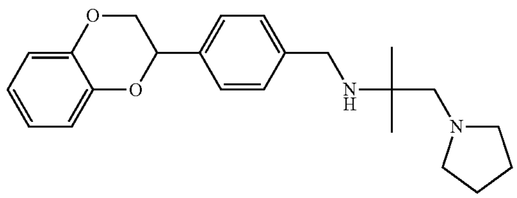 [SMILES: CC(C)(CN1CCCC1)NCc1ccc(C2COc3ccccc3O2)cc1] | N-[4-(2,3-dihydro-1,4-benzodioxin-2-yl)benzyl]-2-methyl-1-(pyrrolidin-1-yl)propan-2-amine |
| 50 | 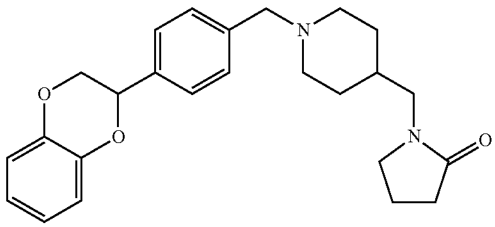 [SMILES: O=C1CCCN1CC1CCN(Cc2ccc(C3COc4ccccc4O3)cc2)CC1] | 1-({1-[4-(2,3-dihydro-1,4-benzodioxin-2-yl)benzyl]piperidin-4-yl}methyl)pyrrolidin-2-one |
| 51 | 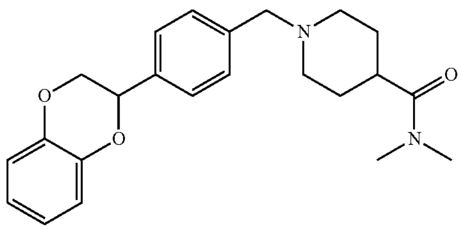 [SMILES: CN(C)C(=O)C1CCN(Cc2ccc(C3COc4ccccc4O3)cc2)CC1] | 1-[4-(2,3-dihydro-1,4-benzodioxin-2-yl)benzyl]-N,N-dimethylpiperidine-4-carboxamide |
| 52 | 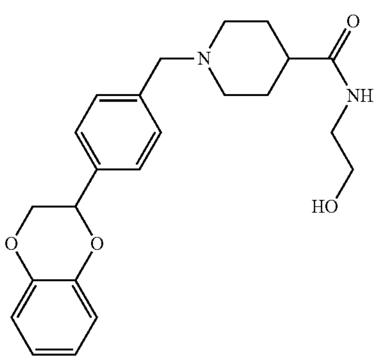 [SMILES: O=C(NCCO)C1CCN(Cc2ccc(C3COc4ccccc4O3)cc2)CC1] | 1-[4-(2,3-dihydro-1,4-benzodioxin-2-yl)benzyl]-N-(2-hydroxyethyl)piperidine-4-carboxamide |
| 53 | 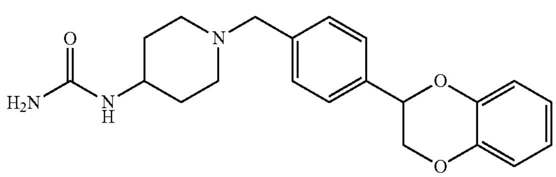 [SMILES: NC(=O)NC1CCN(Cc2ccc(C3COc4ccccc4O3)cc2)CC1] | 1-{1-[4-(2,3-dihydro-1,4-benzodioxin-2-yl)benzyl]piperidin-4-yl}urea |
| 54 | 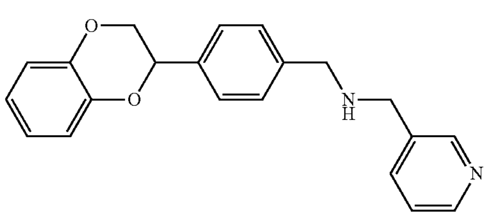 [SMILES: c1cncc(CNCc2ccc(C3COc4ccccc4O3)cc2)c1] | 1-[4-(2,3-dihydro-1,4-benzodioxin-2-yl)phenyl]-N-(pyridin-3-ylmethyl)methanamine |

TABLE 1-continued

Exemplary compounds of the invention.

| Cpd No. | Structure | Name |
|---|---|---|
| 55 | 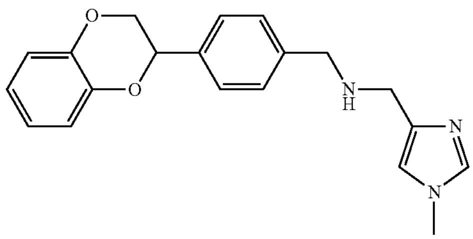 [SMILES: Cn1cnc(CNCc2ccc(C3COc4ccccc4O3)cc2)c1] | 1-[4-(2,3-dihydro-1,4-benzodioxin-2-yl)phenyl]-N-[(1-methyl-1H-imidazol-4-yl)methyl]methanamine |
| 56 | 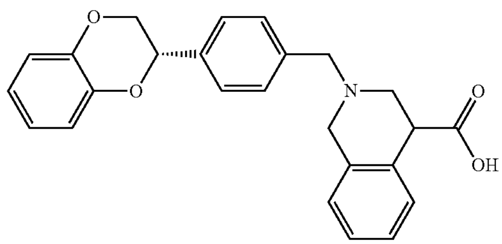 [SMILES: O=C(O)C1CN(Cc2ccc([C@H]3COc4ccccc4O3)cc2)Cc2ccccc21] | 2-{4-[(2S)-2,3-dihydro-1,4-benzodioxin-2-yl]benzyl}-1,2,3,4-tetrahydroisoquinoline-4-carboxylic acid |
| 57 | 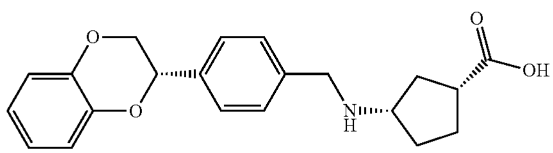 [SMILES: O=C(O)[C@@H]1CC[C@H](NCc2ccc([C@H]3COc4ccccc4O3)cc2)C1] | (1R,3S)-3-({4-[(2S)-2,3-dihydro-1,4-benzodioxin-2-yl]benzyl}amino)cyclopentane-carboxylic acid |
| 58 | 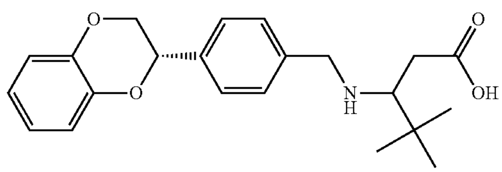 [SMILES: CC(C)(C)C(CC(=O)O)NCc1ccc([C@H]2COc3ccccc3O2)cc1] | 3-({4-[(2S)-2,3-dihydro-1,4-benzodioxin-2-yl]benzyl}amino)-4,4-dimethylpentanoic acid |
| 59 | 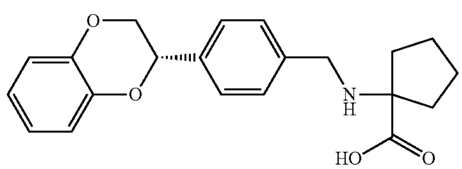 [SMILES: O=C(O)C1(NCc2ccc([C@H]3COc4ccccc4O3)cc2)CCCC1] | 1-({4-[(2S)-2,3-dihydro-1,4-benzodioxin-2-yl]benzyl}amino)cyclopentane-carboxylic acid |
| 60 | 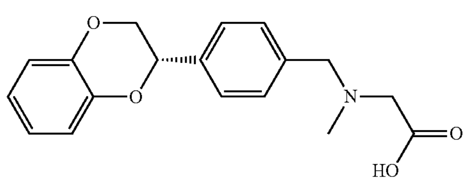 [SMILES: CN(CC(=O)O)Cc1ccc([C@H]2COc3ccccc3O2)cc1] | N-{4-[(2S)-2,3-dihydro-1,4-benzodioxin-2-yl]benzyl}-N-methylglycine |
| 61 | 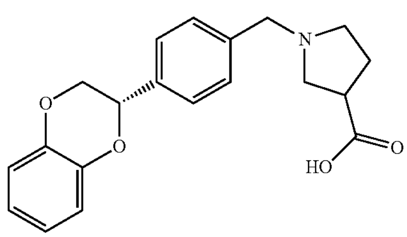 [SMILES: O=C(O)C1CCN(Cc2ccc([C@H]3COc4ccccc4O3)cc2)C1] | 1-{4-[(2S)-2,3-dihydro-1,4-benzodioxin-2-yl]benzyl}pyrrolidine-3-carboxylic acid |
| 62 | 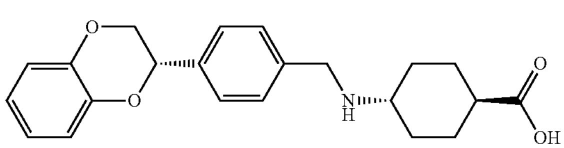 [SMILES: O=C(O)[C@H]1CC[C@H](NCc2ccc([C@H]3COc4ccccc4O3)cc2)CC1] | trans-4-({4-[(2S)-2,3-dihydro-1,4-benzodioxin-2-yl]benzyl}amino)cyclohexane-carboxylic acid |

TABLE 1-continued

Exemplary compounds of the invention.

| Cpd No. | Structure | Name |
|---|---|---|
| 63 | 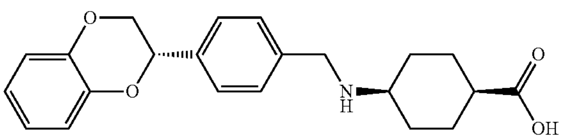 [SMILES: O=C(O)[C@H]1CC[C@@H](NCc2ccc([C@H]3COc4ccccc4O3)cc2)CC1] | cis-4-({4-[(2S)-2,3-dihydro-1,4-benzodioxin-2-yl]benzyl}amino)cyclohexane-carboxylic acid |
| 64 | 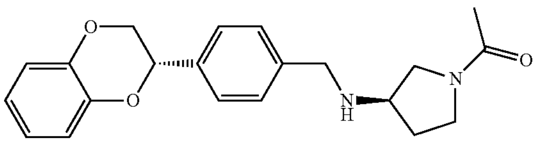 [SMILES: CC(=O)N1CC[C@@H](NCc2ccc([C@H]3COc4ccccc4O3)cc2)C1] | 1-[(3R)-3-({4-[(2S)-2,3-dihydro-1,4-benzodioxin-2-yl]benzyl}amino)pyrrolidin-1-yl]ethanone |
| 65 | 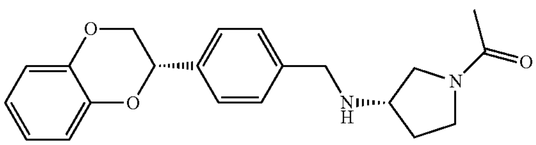 [SMILES: CC(=O)N1CC[C@H](NCc2ccc([C@H]3COc4ccccc4O3)cc2)C1] | 1-[(3S)-3-({4-[(2S)-2,3-dihydro-1,4-benzodioxin-2-yl]benzyl}amino)pyrrolidin-1-yl]ethanone |
| 66 | 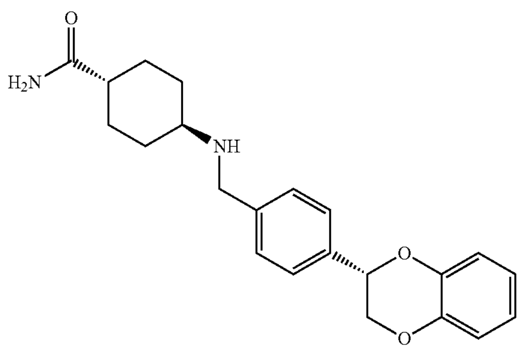 [SMILES: NC(=O)[C@H]1CC[C@H](NCc2ccc([C@H]3COc4ccccc4O3)cc2)CC1] | trans-4-({4-[(2S)-2,3-dihydro-1,4-benzodioxin-2-yl]benzyl}amino)cyclohexane-carboxamide |
| 67 | 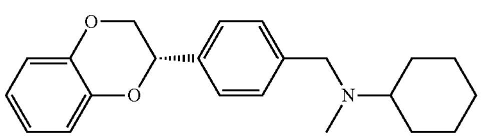 [SMILES: CN(Cc1ccc([C@H]2COc3ccccc3O2)cc1)C1CCCCC1] | N-{4-[(2S)-2,3-dihydro-1,4-benzodioxin-2-yl]benzyl}-N-methylcyclohexanamine |
| 68 | 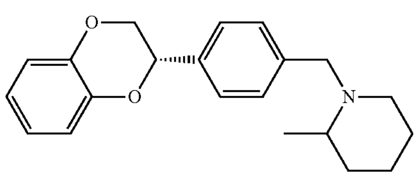 [SMILES: CC1CCCCN1Cc1ccc([C@H]2COc3ccccc3O2)cc1] | 1-{4-[(2S)-2,3-dihydro-1,4-benzodioxin-2-yl]benzyl}-2-methylpiperidine |
| 69 | 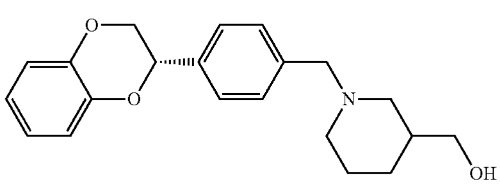 [SMILES: OCC1CCCN(Cc2ccc([C@H]3COc4ccccc4O3)cc2)C1] | (1-{4-[(2S)-2,3-dihydro-1,4-benzodioxin-2-yl]benzyl}piperidin-3-yl)methanol |
| 70 | 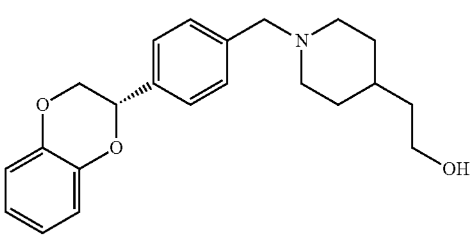 [SMILES: OCCC1CCN(Cc2ccc([C@H]3COc4ccccc4O3)cc2)CC1] | 2-(1-{4-[(2S)-2,3-dihydro-1,4-benzodioxin-2-yl]benzyl}piperidin-4-yl)ethanol |

TABLE 1-continued

Exemplary compounds of the invention.

| Cpd No. | Structure | Name |
| --- | --- | --- |
| 71 | 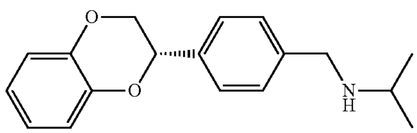 [SMILES: CC(C)NCc1ccc([C@H]2COc3ccccc3O2)cc1] | N-{4-[(2S)-2,3-dihydro-1,4-benzodioxin-2-yl]benzyl}propan-2-amine |
| 72 | 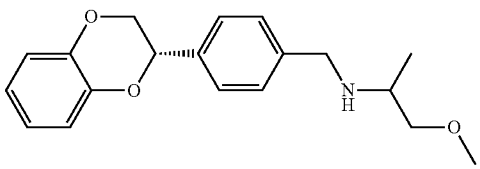 [SMILES: COCC(C)NCc1ccc([C@H]2COc3ccccc3O2)cc1] | N-{4-[(2S)-2,3-dihydro-1,4-benzodioxin-2-yl]benzyl}-1-methoxypropan-2-amine |
| 73 | 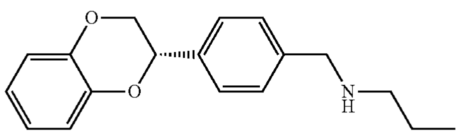 [SMILES: CCCNCc1ccc([C@H]2COc3ccccc3O2)cc1] | N-{4-[(2S)-2,3-dihydro-1,4-benzodioxin-2-yl]benzyl}propan-1-amine |
| 74 | 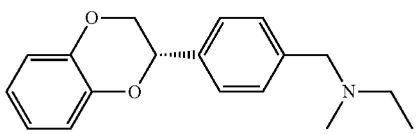 | N-{4-[(2S)-2,3-dihydro-1,4-benzodioxin-2-yl]benzyl}-N-methylethanamine |
| 75 | 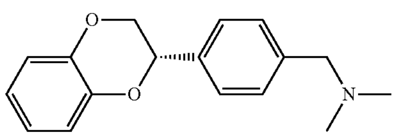 | 1-{4-[(2S)-2,3-dihydro-1,4-benzodioxin-2-yl]phenyl}-N,N-dimethylmethanamine |
| 76 | 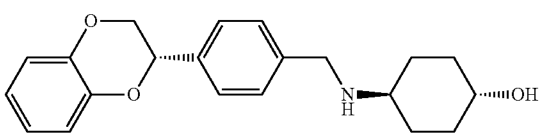 [SMILES: O[C@H]1CC[C@H](NCc2ccc([C@H]3COc4ccccc4O3)cc2)CC1] | trans-4-({4-[(2S)-2,3-dihydro-1,4-benzodioxin-2-yl]benzyl}amino)cyclohexanol |
| 77 | 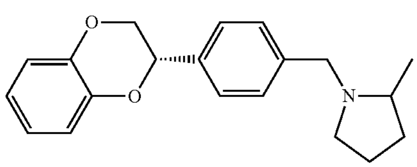 [SMILES: CC1CCCN1Cc1ccc([C@H]2COc3ccccc3O2)cc1] | 1-{4-[(2S)-2,3-dihydro-1,4-benzodioxin-2-yl]benzyl}-2-methylpyrrolidine |
| 78 | 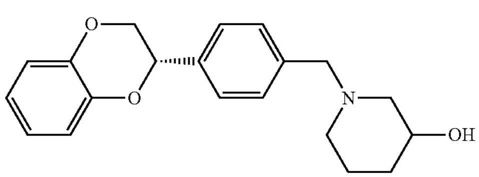 [SMILES: OC1CCCN(Cc2ccc([C@H]3COc4ccccc4O3)cc2)C1] | 1-{4-[(2S)-2,3-dihydro-1,4-benzodioxin-2-yl]benzyl}piperidin-3-ol |
| 79 | 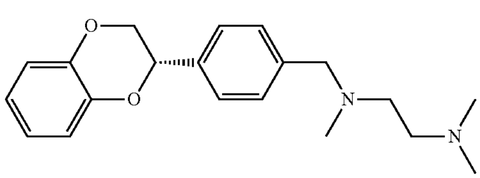 | N-{4-[(2S)-2,3-dihydro-1,4-benzodioxin-2-yl]benzyl}-N,N',N'-trimethylethane-1,2-diamine |

TABLE 1-continued

Exemplary compounds of the invention.

| Cpd No. | Structure | Name |
|---|---|---|
| 80 | 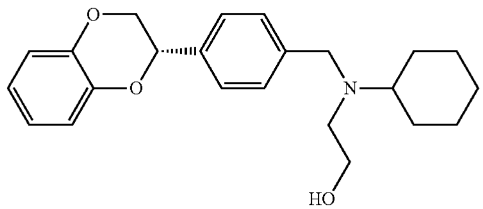 [SMILES: OCCN(Cc1ccc([C@H]2COc3ccccc3O2)cc1)C1CCCCC1] | 2-(cyclohexyl{4-[(2S)-2,3-dihydro-1,4-benzodioxin-2-yl]benzyl}amino)ethanol |
| 81 | 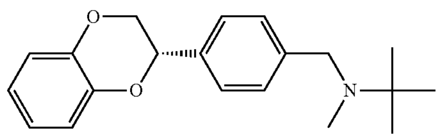 [SMILES: CN(Cc1ccc([C@H]2COc3ccccc3O2)cc1)C(C)(C)C] | N-{4-[(2S)-2,3-dihydro-1,4-benzodioxin-2-yl]benzyl}-N,2-dimethylpropan-2-amine |
| 82 | 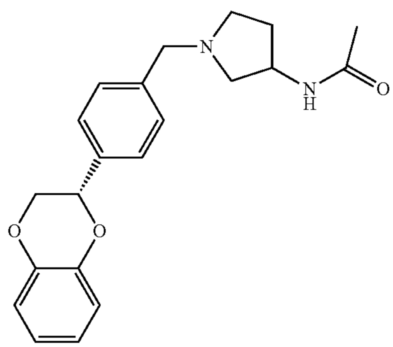 [SMILES: CC(=O)NC1CCN(Cc2ccc([C@H]3COc4ccccc4O3)cc2)C1] | N-(1-{4-[(2S)-2,3-dihydro-1,4-benzodioxin-2-yl]benzyl}pyrrolidin-3-yl)acetamide |
| 83 | 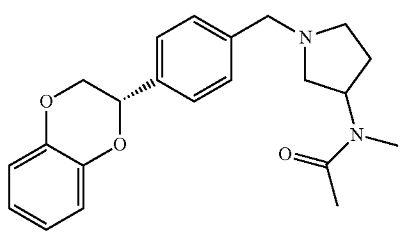 [SMILES: CC(=O)N(C)C1CCN(Cc2ccc([C@H]3COc4ccccc4O3)cc2)C1] | N-(1-{4-[(2S)-2,3-dihydro-1,4-benzodioxin-2-yl]benzyl}pyrrolidin-3-yl)-N-methylacetamide |
| 84 | 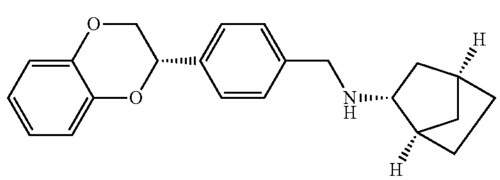 [SMILES: c1ccc2c(c1)OC[C@H](c1ccc(CN[C@@H]3C[C@H]4CC[C@@H]3C4)cc1)O2] | (1R,2R,4S)-N-{4-[(2S)-2,3-dihydro-1,4-benzodioxin-2-yl]benzyl}bicyclo[2.2.1]heptan-2-amine |
| 85 | 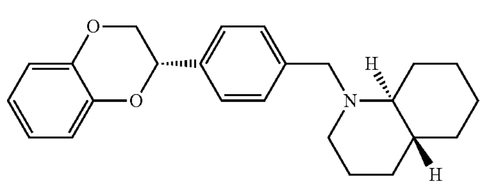 [SMILES: c1ccc2c(c1)OC[C@H](c1ccc(CN3CCC[C@H]4CCCC[C@@H]43)cc1)O2] | (4aR,8aS)-1-{4-[(2S)-2,3-dihydro-1,4-benzodioxin-2-yl]benzyl}decahydroquinoline |
| 86 | 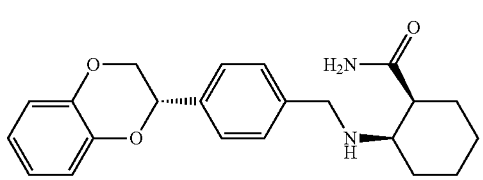 [SMILES: NC(=O)[C@H]1CCCC[C@H]1NCc1ccc([C@H]2COc3ccccc3O2)cc1] | (1S,2R)-2-({4-[(2S)-2,3-dihydro-1,4-benzodioxin-2-yl]benzyl}amino)cyclohexane-carboxamide |

TABLE 1-continued

Exemplary compounds of the invention.

| Cpd No. | Structure | Name |
|---|---|---|
| 87 | 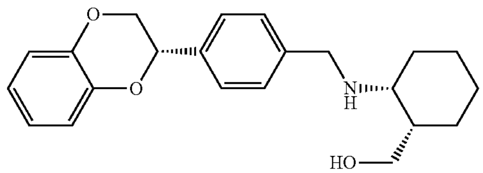 [SMILES: OC[C@H]1CCCC[C@H]1NCc1ccc([C@H]2COc3ccccc3O2)cc1] | [(1S,2R)-2-({4-[(2S)-2,3-dihydro-1,4-benzodioxin-2-yl]benzyl}amino)cyclohexyl]methanol |
| 88 | 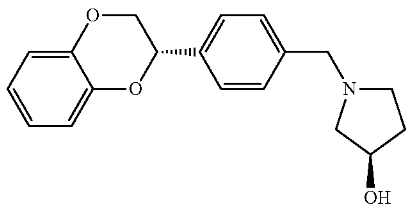 | (3R)-1-{4-[(2S)-2,3-dihydro-1,4-benzodioxin-2-yl]benzyl}pyrrolidin-3-ol |
| 89 | 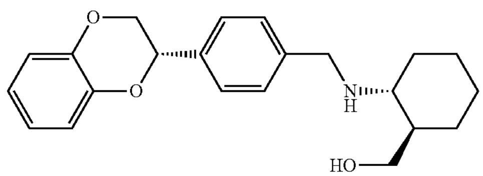 [SMILES: OC[C@@H]1CCCC[C@H]1NCc1ccc([C@H]2COc3ccccc3O2)cc1] | [(1R,2R)-2-({4-[(2S)-2,3-dihydro-1,4-benzodioxin-2-yl]benzyl}amino)cyclohexyl]methanol |
| 90 | 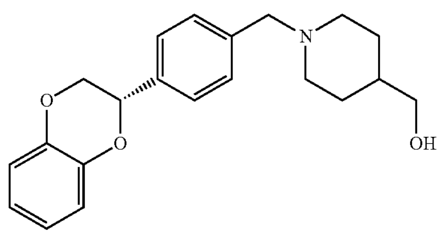 [SMILES: OCC1CCN(Cc2ccc([C@H]3COc4ccccc4O3)cc2)CC1] | (1-{4-[(2S)-2,3-dihydro-1,4-benzodioxin-2-yl]benzyl}piperidin-4-yl)methanol |
| 91 | 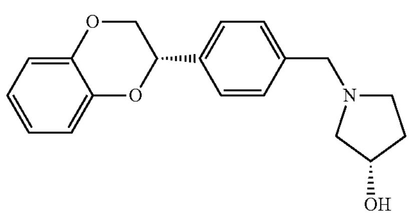 [SMILES: O[C@H]1CCN(Cc2ccc([C@H]3COc4ccccc4O3)cc2)C1] | (3S)-1-{4-[(2S)-2,3-dihydro-1,4-benzodioxin-2-yl]benzyl}pyrrolidin-3-ol |
| 92 | 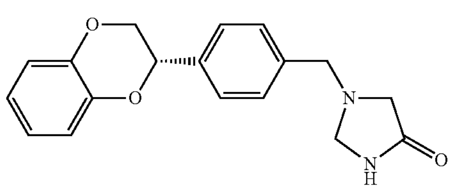 [SMILES: O=C1CN(Cc2ccc([C@H]3COc4ccccc4O3)cc2)CN1] | 1-{4-[(2S)-2,3-dihydro-1,4-benzodioxin-2-yl]benzyl}imidazolidin-4-one |
| 93 | 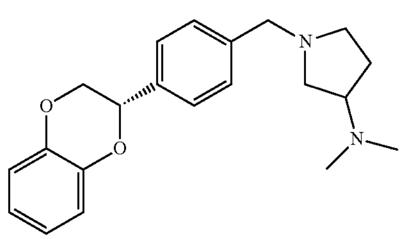 [SMILES: CN(C)C1CCN(Cc2ccc([C@H]3COc4ccccc4O3)cc2)C1] | 1-{4-[(2S)-2,3-dihydro-1,4-benzodioxin-2-yl]benzyl}-N,N-dimethylpyrrolidin-3-amine |

TABLE 1-continued

Exemplary compounds of the invention.

| Cpd No. | Structure | Name |
|---|---|---|
| 94 | 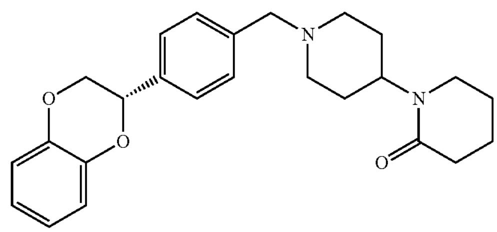 [SMILES: O=C1CCCCN1C1CCN(Cc2ccc([C@H]3COc4ccccc4O3)cc2)CC1] | 1'-{4-[(2S)-2,3-dihydro-1,4-benzodioxin-2-yl]benzyl}-1,4'-bipiperidin-2-one |
| 95 | 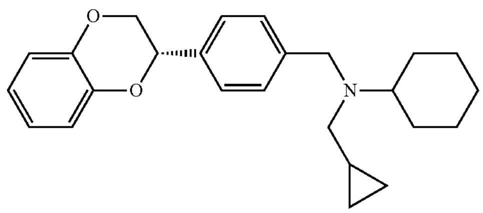 [SMILES: c1ccc2c(c1)OC[C@H](c1ccc(CN(CC3CC3)C3CCCCC3)cc1)O2] | N-(cyclopropylmethyl)-N-{4-[(2S)-2,3-dihydro-1,4-benzodioxin-2-yl]benzyl}cyclohexanamine |
| 96 | 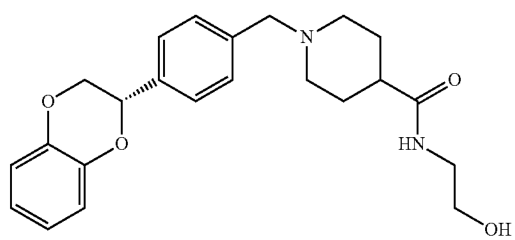 [SMILES: O=C(NCCO)C1CCN(Cc2ccc([C@H]3COc4ccccc4O3)cc2)CC1] | 1-{4-[(2S)-2,3-dihydro-1,4-benzodioxin-2-yl]benzyl}-N-(2-hydroxyethyl)piperidine-4-carboxamide |
| 97 | 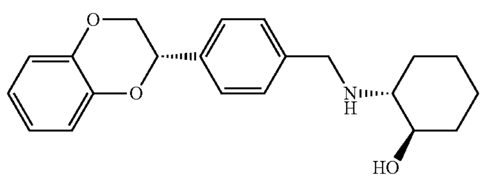 [SMILES: O[C@@H]1CCCC[C@H]1NCc1ccc([C@H]2COc3ccccc3O2)cc1] | (1R,2R)-2-({4-[(2S)-2,3-dihydro-1,4-benzodioxin-2-yl]benzyl}amino)cyclohexanol |
| 98 | 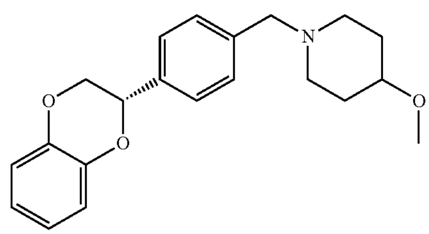 [SMILES: COC1CCN(Cc2ccc([C@H]3COc4ccccc4O3)cc2)CC1] | 1-{4-[(2S)-2,3-dihydro-1,4-benzodioxin-2-yl]benzyl}-4-methoxypiperidine |
| 99 | 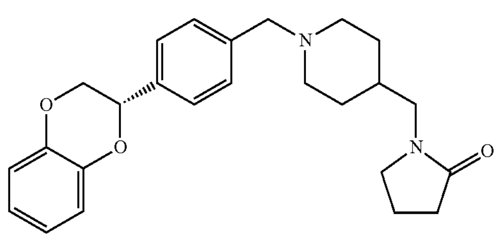 [SMILES: O=C1CCCN1CC1CCN(Cc2ccc([C@H]3COc4ccccc4O3)cc2)CC1] | 1-[(1-{4-[(2S)-2,3-dihydro-1,4-benzodioxin-2-yl]benzyl}piperidin-4-yl)methyl]pyrrolidin-2-one |
| 100 | 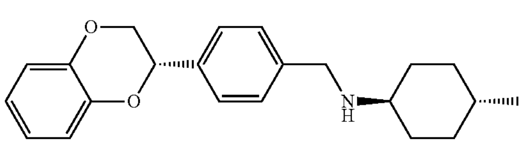 | trans-N-{4-[(2S)-2,3-dihydro-1,4-benzodioxin-2-yl]benzyl}-4-methylcyclohexanamine |

TABLE 1-continued

Exemplary compounds of the invention.

| Cpd No. | Structure | Name |
|---|---|---|
| 101 | 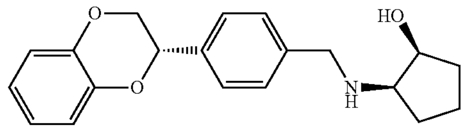 | (1S,2R)-2-({4-[(2S)-2,3-dihydro-1,4-benzodioxin-2-yl]benzyl}amino)cyclopentanol |
| 102 | 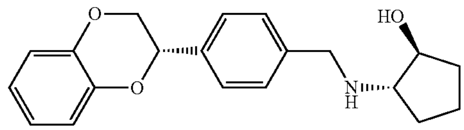 [SMILES: O[C@H]1CCC[C@@H]1NCc1ccc([C@H]2COc3ccccc3O2)cc1] | (1S,2S)-2-({4-[(2S)-2,3-dihydro-1,4-benzodioxin-2-yl]benzyl}amino)cyclopentanol |
| 103 | 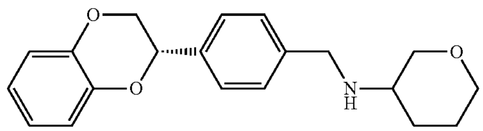 | N-{4-[(2S)-2,3-dihydro-1,4-benzodioxin-2-yl]benzyl}tetrahydro-2H-pyran-3-amine |
| 104 | 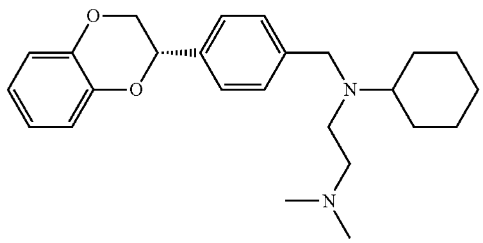 [SMILES: CN(C)CCN(Cc1ccc([C@H]2COc3ccccc3O2)cc1)C1CCCCC1] | N-cyclohexyl-N-{4-[(2S)-2,3-dihydro-1,4-benzodioxin-2-yl]benzyl}-N',N'-dimethylethane-1,2-diamine |
| 105 | 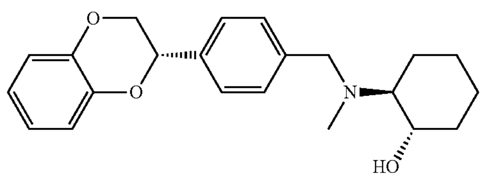 [SMILES: CN(Cc1ccc([C@H]2COc3ccccc3O2)cc1)[C@H]1CCCC[C@@H]1O] | (1S,2S)-2-[{4-[(2S)-2,3-dihydro-1,4-benzodioxin-2-yl]benzyl}(methyl)amino]cyclohexanol |
| 106 | 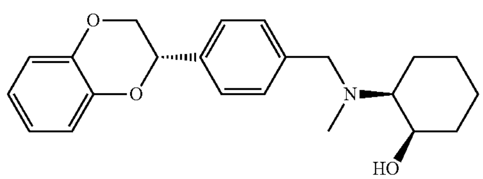 [SMILES: CN(Cc1ccc([C@H]2COc3ccccc3O2)cc1)[C@H]1CCCC[C@H]1O] | (1R,2S)-2-[{4-[(2S)-2,3-dihydro-1,4-benzodioxin-2-yl]benzyl}(methyl)amino]cyclohexanol |
| 107 | 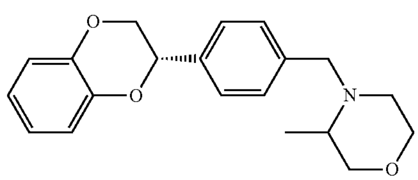 [SMILES: CC1COCCN1Cc1ccc([C@H]2COc3ccccc3O2)cc1] | 4-{4-[(2S)-2,3-dihydro-1,4-benzodioxin-2-yl]benzyl}-3-methylmorpholine |
| 108 | 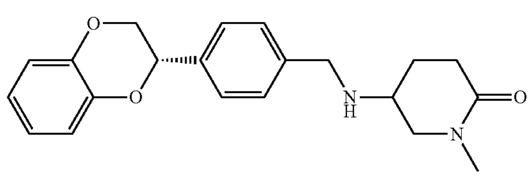 [SMILES: CN1CC(NCc2ccc([C@H]3COc4ccccc4O3)cc2)CCC1=O] | 5-({4-[(2S)-2,3-dihydro-1,4-benzodioxin-2-yl]benzyl}amino)-1-methylpiperidin-2-one |
| 109 | 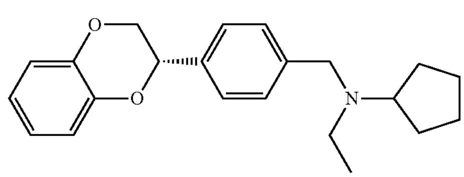 [SMILES: CCN(Cc1ccc([C@H]2COc3ccccc3O2)cc1)C1CCCC1] | N-{4-[(2S)-2,3-dihydro-1,4-benzodioxin-2-yl]benzyl}-N-ethylcyclopentanamine |

TABLE 1-continued

Exemplary compounds of the invention.

| Cpd No. | Structure | Name |
|---|---|---|
| 110 | 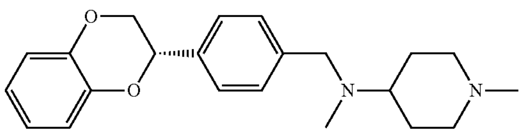 [SMILES: CN1CCC(N(C)Cc2ccc([C@H]3COc4ccccc4O3)cc2)CC1] | N-{4-[(2S)-2,3-dihydro-1,4-benzodioxin-2-yl]benzyl}-N,1-dimethylpiperidin-4-amine |
| 111 | 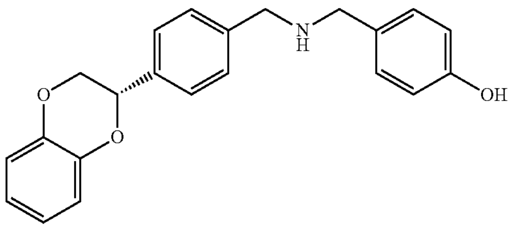 [SMILES: Oc1ccc(CNCc2ccc([C@H]3COc4ccccc4O3)cc2)cc1] | 4-[({4-[(2S)-2,3-dihydro-1,4-benzodioxin-2-yl]benzyl}amino)methyl]phenol |
| 112 | 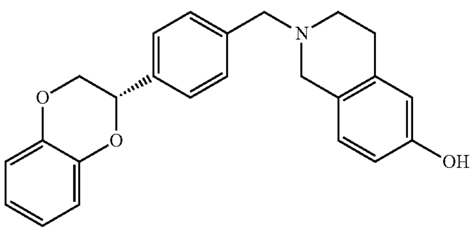 [SMILES: Oc1ccc2c(c1)CCN(Cc1ccc([C@H]3COc4ccccc4O3)cc1)C2] | 2-{4-[(2S)-2,3-dihydro-1,4-benzodioxin-2-yl]benzyl}-1,2,3,4-tetrahydroisoquinolin-6-ol |
| 113 | 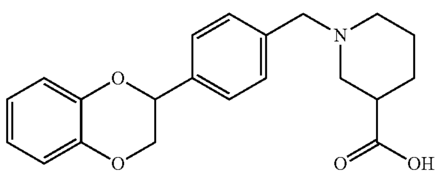 [SMILES: O=C(O)C1CCCN(Cc2ccc(C3COc4ccccc4O3)cc2)C1] | 1-[4-(2,3-dihydro-1,4-benzodioxin-2-yl)benzyl]piperidine-3-carboxylic acid |
| 114 | 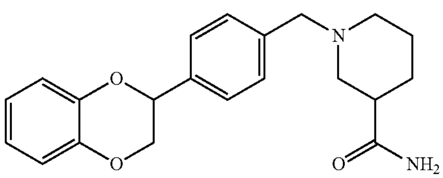 [SMILES: NC(=O)C1CCCN(Cc2ccc(C3COc4ccccc4O3)cc2)C1] | 1-[4-(2,3-dihydro-1,4-benzodioxin-2-yl)benzyl]piperidine-3-carboxamide |
| 115 | 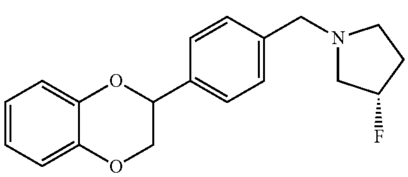 [SMILES: F[C@H]1CCN(Cc2ccc(C3COc4ccccc4O3)cc2)C1] | (3S)-1-[4-(2,3-dihydro-1,4-benzodioxin-2-yl)benzyl]-3-fluoropyrrolidine |
| 116 | 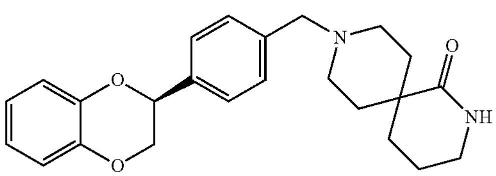 [SMILES: O=C1NCCCC12CCN(Cc1ccc([C@H]3COc4ccccc4O3)cc1)CC2] | 9-{4-[(2S)-2,3-dihydro-1,4-benzodioxin-2-yl]benzyl}-2,9-diazaspiro[5.5]undecan-1-one |
| 117 | 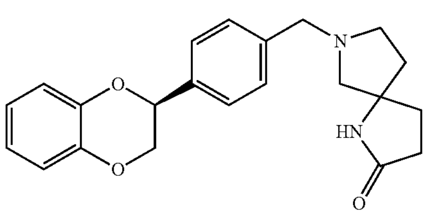 [SMILES: O=C1CCC2(CCN(Cc3ccc([C@H]4COc5ccccc5O4)cc3)C2)N1] | 7-{4-[(2S)-2,3-dihydro-1,4-benzodioxin-2-yl]benzyl}-1,7-diazaspiro[4.4]nonan-2-one |

TABLE 1-continued

Exemplary compounds of the invention.

| Cpd No. | Structure | Name |
| --- | --- | --- |
| 118 | 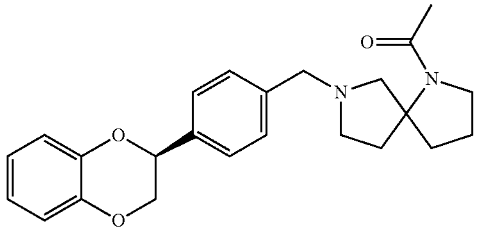 [SMILES: CC(=O)N1CCCC12CCN(Cc1ccc([C@H]3COc4ccccc4O3)cc1)C2] | 1-(7-{4-[(2S)-2,3-dihydro-1,4-benzodioxin-2-yl]benzyl}-1,7-diazaspiro[4.4]non-1-yl)ethanone |
| 119 | 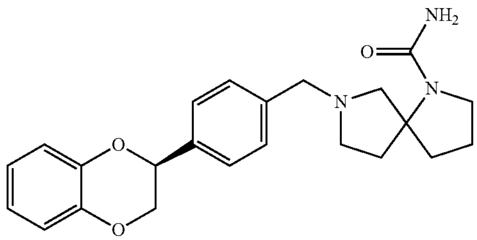 [SMILES: NC(=O)N1CCCC12CCN(Cc1ccc([C@H]3COc4ccccc4O3)cc1)C2] | 7-{4-[(2S)-2,3-dihydro-1,4-benzodioxin-2-yl]benzyl}-1,7-diazaspiro[4.4]nonane-1-carboxamide |
| 120 | 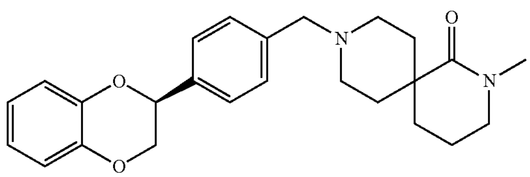 [SMILES: CN1CCCC2(CCN(Cc3ccc([C@H]4COc5ccccc5O4)cc3)CC2)C1=O] | 9-{4-[(2S)-2,3-dihydro-1,4-benzodioxin-2-yl]benzyl}-2-methyl-2,9-diazaspiro[5.5]undecan-1-one |
| 121 | 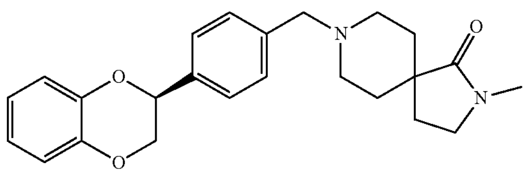 [SMILES: CN1CCC2(CCN(Cc3ccc([C@H]4COc5ccccc5O4)cc3)CC2)C1=O] | 8-{4-[(2S)-2,3-dihydro-1,4-benzodioxin-2-yl]benzyl}-2-methyl-2,8-diazaspiro[4.5]decan-1-one |
| 122 | 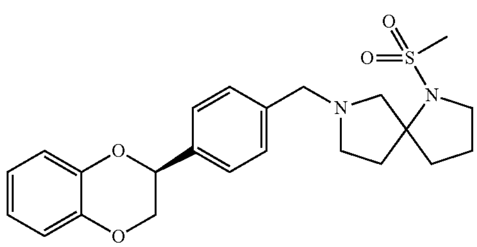 [SMILES: CS(=O)(=O)N1CCCC12CCN(Cc1ccc([C@H]3COc4ccccc4O3)cc1)C2] | 7-{4-[(2S)-2,3-dihydro-1,4-benzodioxin-2-yl]benzyl}-1-(methylsulfonyl)-1,7-diazaspiro[4.4]nonane |
| 123 | 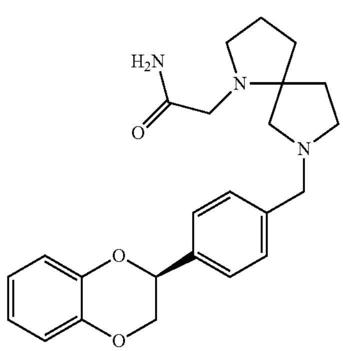 [SMILES: NC(=O)CN1CCCC12CCN(Cc1ccc([C@H]3COc4ccccc4O3)cc1)C2] | 2-(7-{4-[(2S)-2,3-dihydro-1,4-benzodioxin-2-yl]benzyl}-1,7-diazaspiro[4.4]non-1-yl)acetamide |

TABLE 1-continued

Exemplary compounds of the invention.

| Cpd No. | Structure | Name |
| --- | --- | --- |
| 124 | 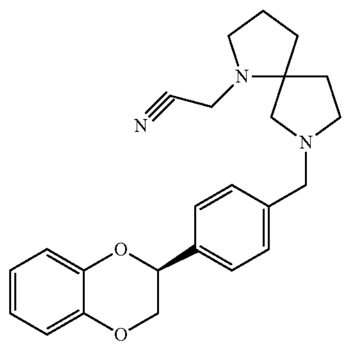 [SMILES: N#CCN1CCCC12CCN(Cc1ccc([C@H]3COc4ccccc4O3)cc1)C2] | (7-{4-[(2S)-2,3-dihydro-1,4-benzodioxin-2-yl]benzyl}-1,7-diazaspiro[4.4]non-1-yl)acetonitrile |
| 125 | 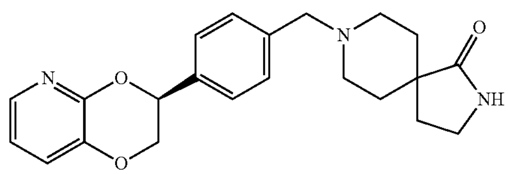 [SMILES: O=C1NCCC12CCN(Cc1ccc([C@H]3COc4cccnc4O3)cc1)CC2] | 8-{4-[(3S)-2,3-dihydro[1,4]dioxino[2,3-b]pyridin-3-yl]benzyl}-2,8-diazaspiro[4.5]decan-1-one |
| 126 | 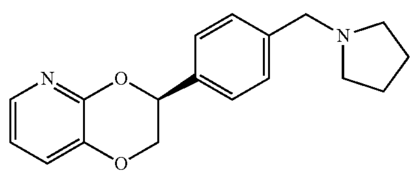 [SMILES: c1cnc2c(c1)OC[C@H](c1ccc(CN3CCCC3)cc1)O2] | (3S)-3-[4-(pyrrolidin-1-ylmethyl)phenyl]-2,3-dihydro[1,4]dioxino[2,3-b]pyridine |
| 127 | 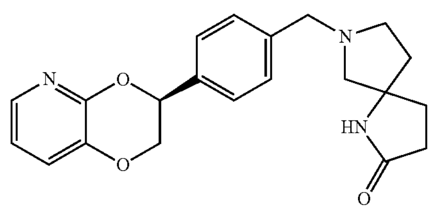 [SMILES: O=C1CCC2(CCN(Cc3ccc([C@H]4COc5cccnc5O4)cc3)C2)N1] | 7-{4-[(3S)-2,3-dihydro[1,4]dioxino[2,3-b]pyridin-3-yl]benzyl}-1,7-diazaspiro[4.4]nonan-2-one |
| 128 | 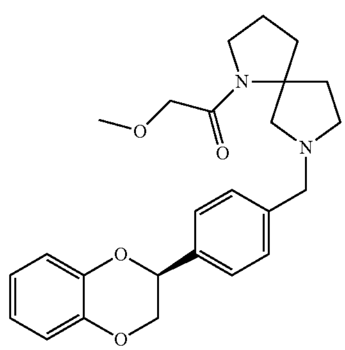 [SMILES: COCC(=O)N1CCCC12CCN(Cc1ccc([C@H]3COc4ccccc4O3)cc1)C2] | 1-(7-{4-[(2S)-2,3-dihydro-1,4-benzodioxin-2-yl]benzyl}-1,7-diazaspiro[4.4]non-1-yl)-2-methoxyethanone |
| 129 | 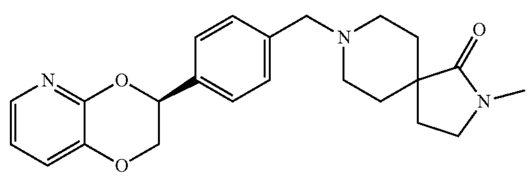 [SMILES: CN1CCC2(CCN(Cc3ccc([C@H]4COc5cccnc5O4)cc3)CC2)C1=O] | 8-{4-[(3S)-2,3-dihydro[1,4]dioxino[2,3-b]pyridin-3-yl]benzyl}-2-methyl-2,8-diazaspiro[4.5]decan-1-one |

TABLE 1-continued

Exemplary compounds of the invention.

| Cpd No. | Structure | Name |
|---|---|---|
| 130 | 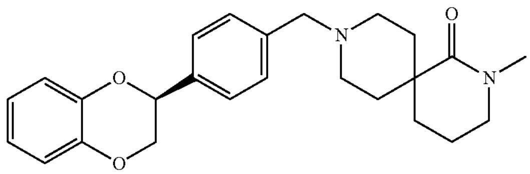 [SMILES: CN1CCCC2(CCN(Cc3ccc([C@H]4COc5ccccc5O4)cc3)CC2)C1=O] | 9-[(S)-4-(2,3-Dihydro-benzo[1,4]dioxin-2-yl)-benzyl]-2-methyl-2,9-diaza-spiro[5.5]undecan-1-one |
| 131 | 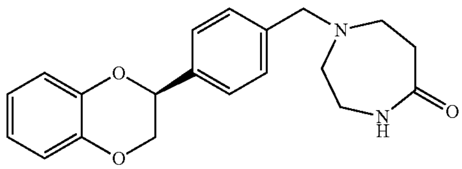 [SMILES: O=C1CCN(Cc2ccc([C@H]3COc4ccccc4O3)cc2)CCN1] | 1-{4-[(2S)-2,3-dihydro-1,4-benzodioxin-2-yl]benzyl}-1,4-diazepan-5-one |
| 132 | 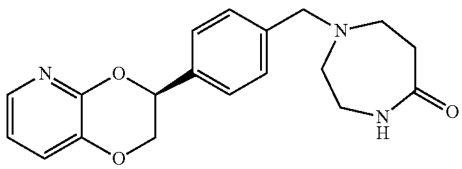 [SMILES: O=C1CCN(Cc2ccc([C@H]3COc4cccnc4O3)cc2)CCN1] | 1-{4-[(3S)-2,3-dihydro[1,4]dioxino[2,3-b]pyridin-3-yl]benzyl}-1,4-diazepan-5-one |
| 133 | 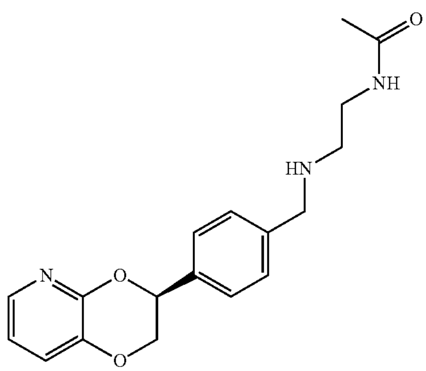 [SMILES: CC(=O)NCCNCc1ccc([C@H]2COc3cccnc3O2)cc1] | N-[2-({4-[(3S)-2,3-dihydro[1,4]dioxino[2,3-b]pyridin-3-yl]benzyl}amino)ethyl]acetamide |
| 134 | 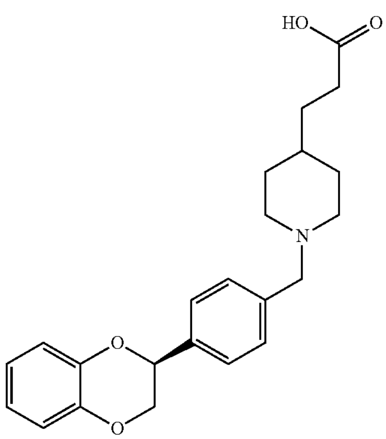 [SMILES: O=C(O)CCC1CCN(Cc2ccc([C@H]3COc4ccccc4O3)cc2)CC1] | 3-(1-{4-[(2S)-2,3-dihydro-1,4-benzodioxin-2-yl]benzyl}piperidin-4-yl)propionic acid |
| 135 | 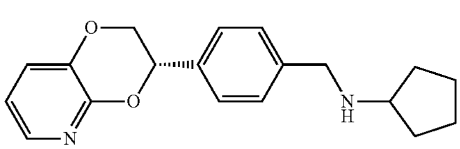 [SMILES: c1cnc2c(c1)OC[C@H](c1ccc(CNC3CCCC3)cc1)O2] | N-{4-[(3S)-2,3-dihydro[1,4]dioxino[2,3-b]pyridin-3-yl]benzyl}cyclopentanamine |

TABLE 1-continued

Exemplary compounds of the invention.

| Cpd No. | Structure | Name |
|---|---|---|
| 136 | 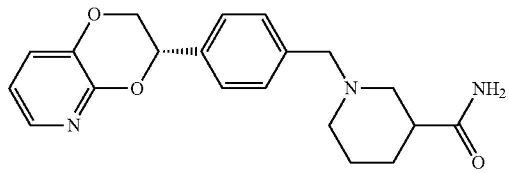 [SMILES: NC(=O)C1CCCN(Cc2ccc([C@H]3COc4cccnc4O3)cc2)C1] | 1-{4-[(3S)-2,3-dihydro[1,4]dioxin[2,3-b]pyridin-3-yl]benzyl}piperidine-3-carboxamide |
| 137 | 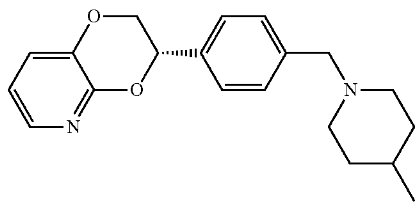 [SMILES: CC1CCN(Cc2ccc([C@H]3COc4cccnc4O3)cc2)CC1] | (3S)-3-{4-[(4-methylpiperidin-1-yl)methyl]phenyl}-2,3-dihydro[1,4]dioxino[2,3-b]pyridine |
| 138 | 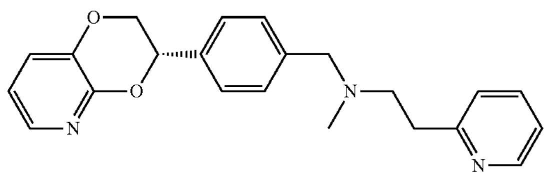 [SMILES: CN(CCc1ccccn1)Cc1ccc([C@H]2COc3cccnc3O2)cc1] | N-{4-[(3S)-2,3-dihydro[1,4]dioxino[2,3-b]pyridin-3-yl]benzyl}-N-methyl-2-(pyridin-2-yl)ethanamine |
| 139 | 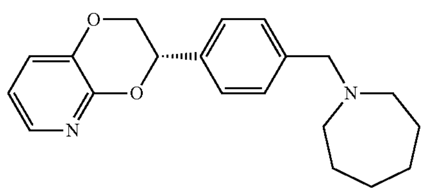 [SMILES: c1cnc2c(c1)OC[C@H](c1ccc(CN3CCCCCC3)cc1)O2] | (3S)-3-[4-(azepan-1-ylmethyl)phenyl]-2,3-dihydro[1,4]dioxino[2,3-b]pyridine |
| 140 | 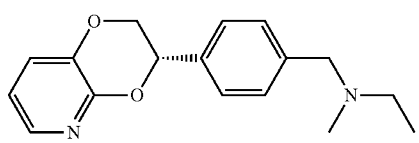 [SMILES: CCN(C)Cc1ccc([C@H]2COc3cccnc3O2)cc1] | N-{4-[(3S)-2,3-dihydro[1,4]dioxino[2,3-b]pyridin-3-yl]benzyl}-N-methylethanamine |
| 141 | 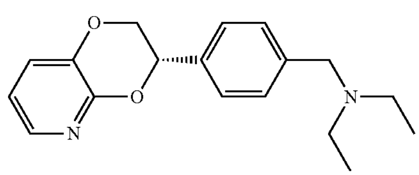 [SMILES: CCN(CC)Cc1ccc([C@H]2COc3cccnc3O2)cc1] | N-{4-[(3S)-2,3-dihydro[1,4]dioxino[2,3-b]pyridin-3-yl]benzyl}-N-ethylethanamine |
| 142 | 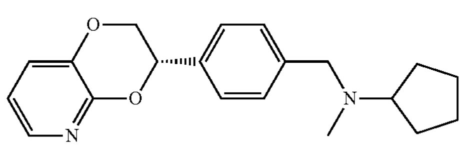 [SMILES: CN(Cc1ccc([C@H]2COc3cccnc3O2)cc1)C1CCCC1] | N-{4-[(3S)-2,3-dihydro[1,4]dioxino[2,3-b]pyridin-3-yl]benzyl}-N-methylcyclopentanamine |
| 143 | 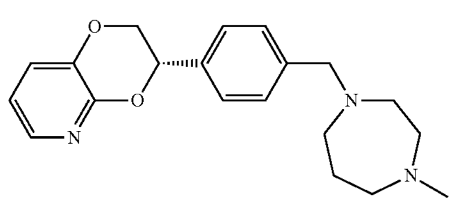 [SMILES: CN1CCCN(Cc2ccc([C@H]3COc4cccnc4O3)cc2)CC1] | (3S)-3-{4-[(4-methyl-1,4-diazepan-1-yl)methyl]phenyl}-2,3-dihydro[1,4]dioxino[2,3-b]pyridine |

TABLE 1-continued

Exemplary compounds of the invention.

| Cpd No. | Structure | Name |
|---|---|---|
| 144 | 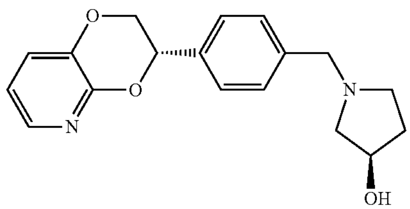 [SMILES: O[C@@H]1CCN(Cc2ccc([C@H]3COc4cccnc4O3)cc2)C1] | (3R)-1-{4-[(3S)-2,3-dihydro[1,4]dioxino[2,3-b]pyridin-3-yl]benzyl}pyrrolidin-3-ol |
| 145 | 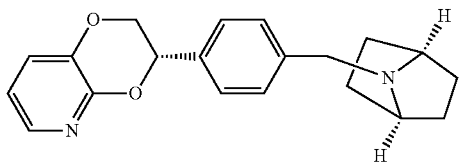 [SMILES: c1cnc2c(c1)OC[C@H](c1ccc(CN3[C@H]4CC[C@@H]3CC4)cc1)O2] | (3S)-3-{4-[(1s,4s)-7-azabicyclo[2.2.1]hept-7-ylmethyl]phenyl}-2,3-dihydro[1,4]dioxino[2,3-b]pyridine |
| 146 | 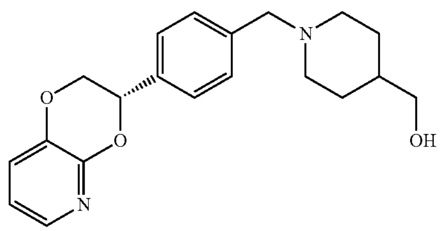 [SMILES: OCC1CCN(Cc2ccc([C@H]3COc4cccnc4O3)cc2)CC1] | (1-{4-[(3S)-2,3-dihydro[1,4]dioxino[2,3-b]pyridin-3-yl]benzyl}piperidin-4-yl)methanol |
| 147 | 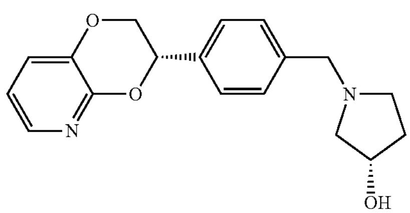 [SMILES: O[C@H]1CCN(Cc2ccc([C@H]3COc4cccnc4O3)cc2)C1] | (3S)-1-{4-[(3S)-2,3-dihydro[1,4]dioxino[2,3-b]pyridin-3-yl]benzyl}pyrrolidin-3-ol |
| 148 | 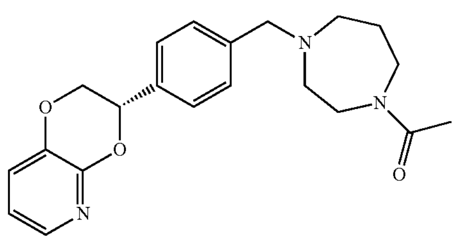 [SMILES: CC(=O)N1CCCN(Cc2ccc([C@H]3COc4cccnc4O3)cc2)CC1] | 1-(4-{4-[(3S)-2,3-dihydro[1,4]dioxino[2,3-b]pyridin-3-yl]benzyl}-1,4-diazepan-1-yl)ethanone |
| 149 | 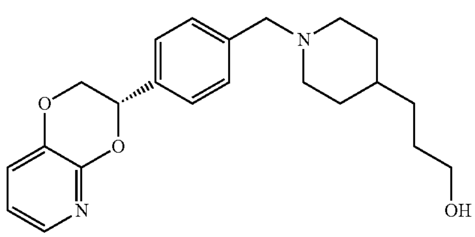 [SMILES: OCCCC1CCN(Cc2ccc([C@H]3COc4cccnc4O3)cc2)CC1] | 3-(1-{4-[(3S)-2,3-dihydro[1,4]dioxino[2,3-b]pyridin-3-yl]benzyl}piperidin-4-yl)propan-1-ol |
| 150 | 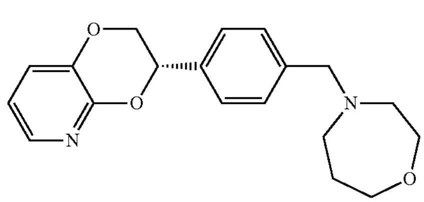 [SMILES: c1cnc2c(c1)OC[C@H](c1ccc(CN3CCCOCC3)cc1)O2] | (3S)-3-[4-(1,4-oxazepan-4-ylmethyl)phenyl]-2,3-dihydro[1,4]dioxino[2,3-b]pyridine |

TABLE 1-continued

Exemplary compounds of the invention.

| Cpd No. | Structure | Name |
|---|---|---|
| 151 | 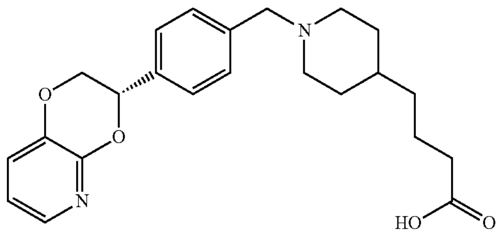 [SMILES: O=C(O)CCCC1CCN(Cc2ccc([C@H]3COc4cccnc4O3)cc2)CC1] | 4-(1-{4-[(3S)-2,3-dihydro[1,4]dioxino[2,3-b]pyridin-3-yl]benzyl}piperidin-4-yl)butanoic acid |
| 152 | 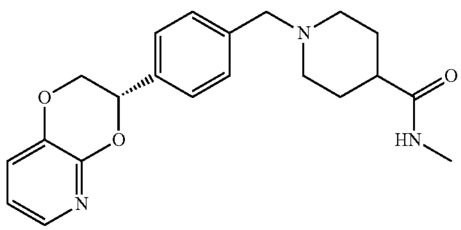 [SMILES: CNC(=O)C1CCN(Cc2ccc([C@H]3COc4cccnc4O3)cc2)CC1] | 1-{4-[(3S)-2,3-dihydro[1,4]dioxino[2,3-b]pyridin-3-yl]benzyl}-N-methylpiperidine-4-carboxamide |
| 153 | 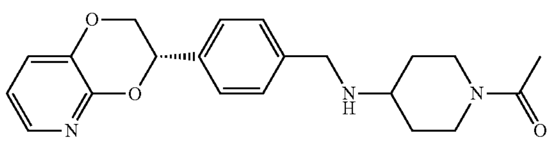 [SMILES: CC(=O)N1CCC(NCc2ccc([C@H]3COc4cccnc4O3)cc2)CC1] | 1-[4-({4-[(3S)-2,3-dihydro[1,4]dioxino[2,3-b]pyridin-3-yl]benzyl}amino)piperidin-1-yl]ethanone |
| 154 | 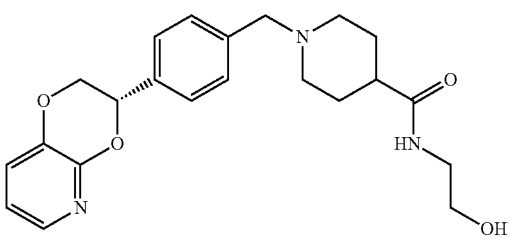 [SMILES: O=C(NCCO)C1CCN(Cc2ccc([C@H]3COc4cccnc4O3)cc2)CC1] | 1-{4-[(3S)-2,3-dihydro[1,4]dioxino[2,3-b]pyridin-3-yl]benzyl}-N-(2-hydroxyethyl)piperidine-4-carboxamide |
| 155 | 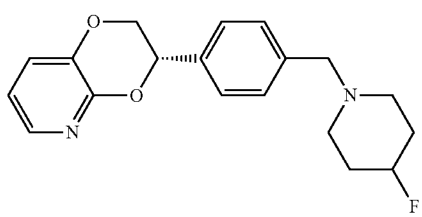 [SMILES: FC1CCN(Cc2ccc([C@H]3COc4cccnc4O3)cc2)CC1] | (3S)-3-{4-[(4-fluoropiperidin-1-yl)methyl]phenyl}-2,3-dihydro[1,4]dioxino[2,3-b]pyridine |
| 156 | 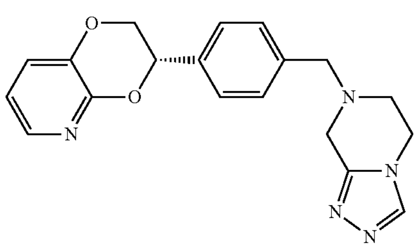 [SMILES: c1cnc2c(c1)OC[C@H](c1ccc(CN3CCn4cnnc4C3)cc1)O2] | (3S)-3-[4-(5,6-dihydro[1,2,4]triazolo[4,3-a]pyrazin-7(8H)-ylmethyl)phenyl]-2,3-dihydro[1,4]dioxino[2,3-b]pyridine |
| 157 | 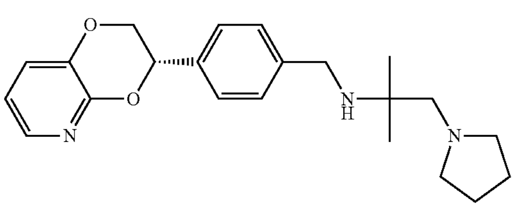 [SMILES: CC(C)(CN1CCCC1)NCc1ccc([C@H]2COc3cccnc3O2)cc1] | N-{4-[(3S)-2,3-dihydro[1,4]dioxino[2,3-b]pyridin-3-yl]benzyl}-2-methyl-1-(pyrrolidin-1-yl)propan-2-amine |

TABLE 1-continued

Exemplary compounds of the invention.

| Cpd No. | Structure | Name |
|---|---|---|
| 158 | 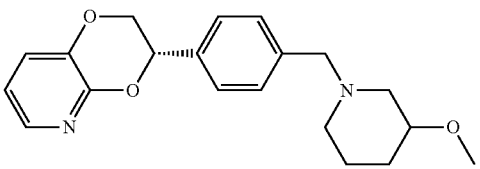 [SMILES: COC1CCCN(Cc2ccc([C@H]3COc4cccnc4O3)cc2)C1] | (3S)-3-{4-[(3-methoxypiperidin-1-yl)methyl]phenyl}-2,3-dihydro[1,4]dioxino[2,3-b]pyridine |
| 159 | 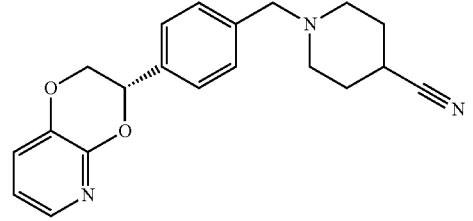 [SMILES: N#CC1CCN(Cc2ccc([C@H]3COc4cccnc4O3)cc2)CC1] | 1-{4-[(3S)-2,3-dihydro[1,4]dioxino[2,3-b]pyridin-3-yl]benzyl}piperidine-4-carbonitrile |
| 160 | 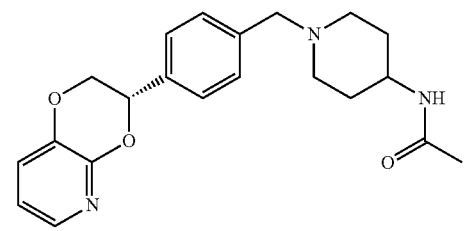 [SMILES: CC(=O)NC1CCN(Cc2ccc([C@H]3COc4cccnc4O3)cc2)CC1] | N-(1-{4-[(3S)-2,3-dihydro[1,4]dioxino[2,3-b]pyridin-3-yl]benzyl}piperidin-4-yl)acetamide |
| 161 | 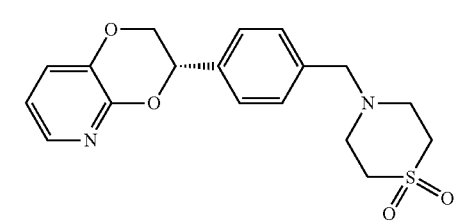 [SMILES: O=S1(=O)CCN(Cc2ccc([C@H]3COc4cccnc4O3)cc2)CC1] | (3S)-3-{4-[(1,1-dioxidothiomorpholin-4-yl)methyl]phenyl}-2,3-dihydro[1,4]dioxino[2,3-b]pyridine |
| 162 | 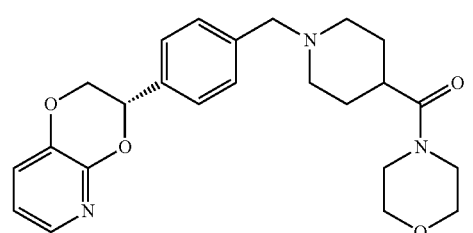 | (1-{4-[(3S)-2,3-dihydro[1,4]dioxino[2,3-b]pyridin-3-yl]benzyl}piperidin-4-yl)(morpholin-4-yl)methanone |
| 163 | 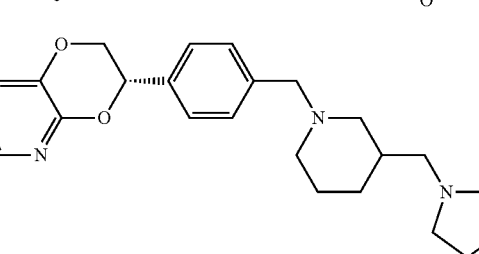 | 1-[(1-{4-[(3S)-2,3-dihydro[1,4]dioxino[2,3-b]pyridin-3-yl]benzyl}piperidin-3-yl)methyl]pyrrolidin-2-one |
| 164 | 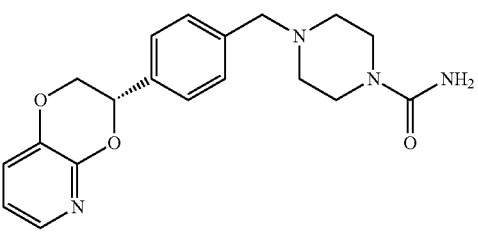 [SMILES: NC(=O)N1CCN(Cc2ccc([C@H]3COc4cccnc4O3)cc2)CC1] | 4-{4-[(3S)-2,3-dihydro[1,4]dioxino-2,3-b]pyridin-3-yl]benzyl}piperazine-1-carboxamide |

TABLE 1-continued

Exemplary compounds of the invention.

| Cpd No. | Structure | Name |
|---|---|---|
| 165 | 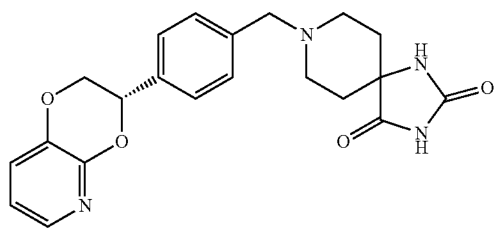 [SMILES: O=C1NC(=O)C2(CCN(Cc3ccc([C@H]4COc5cccnc5O4)cc3)CC2)N1] | 8-{4-[(3S)-2,3-dihydro[1,4]dioxin[2,3-b]pyridin-3-yl]benzyl}-1,3,8-triazaspiro[4.5]decane-2,4-dione |
| 166 | 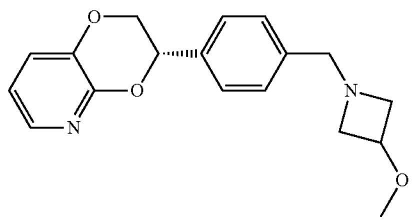 | (3S)-3-{4-[(3-methoxyazetidin-1-yl)methyl]phenyl}-2,3-dihydro[1,4]dioxino[2,3-b]pyridine |
| 167 | 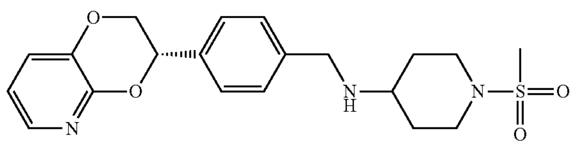 [SMILES: CS(=O)(=O)N1CCC(NCc2ccc([C@H]3COc4cccnc4O3)cc2)CC1] | N-{4-[(3S)-2,3-dihydro[1,4]dioxino[2,3-b]pyridin-3-yl]benzyl}-1-(methylsulfonyl)piperidin-4-amine |
| 168 | 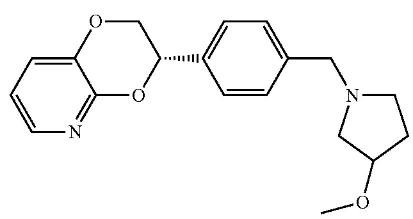 [SMILES: COC1CCN(Cc2ccc([C@H]3COc4cccnc4O3)cc2)C1] | (3S)-3-{4-[(3-methoxypyrrolidin-1-yl)methyl]phenyl}-2,3-dihydro[1,4]dioxino[2,3-b]pyridine |
| 169 | 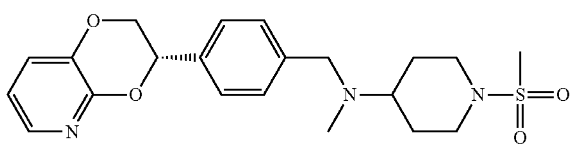 [SMILES: CN(Cc1ccc([C@H]2COc3cccnc3O2)cc1)C1CCN(S(C)(=O)=O)CC1] | N-{4-[(3S)-2,3-dihydro[1,4]dioxino[2,3-b]pyridin-3-yl]benzyl}-N-methyl-1-(methylsulfonyl)piperidin-4-amine |
| 170 | 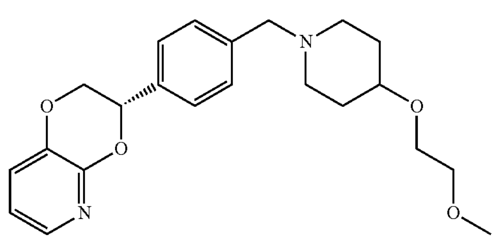 [SMILES: COCCOC1CCN(Cc2ccc([C@H]3COc4cccnc4O3)cc2)CC1] | (3S)-3-(4-{[4-(2-methoxyethoxy)piperidin-1-yl]methyl}phenyl)-2,3-dihydro[1,4]dioxino[2,3-b]pyridine |
| 171 | 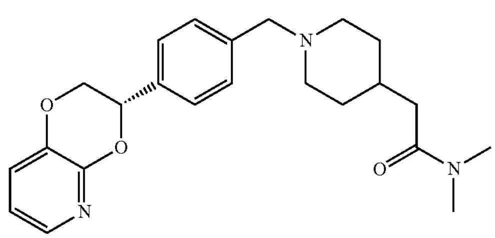 [SMILES: CN(C)C(=O)CC1CCN(Cc2ccc([C@H]3COc4cccnc4O3)cc2)CC1] | 2-(1-{4-[(3S)-2,3-dihydro[1,4]dioxino[2,3-b]pyridin-3-yl]benzyl}piperidin-4-yl)-N,N-dimethylacetamide |

TABLE 1-continued

Exemplary compounds of the invention.

| Cpd No. | Structure | Name |
|---|---|---|
| 172 | 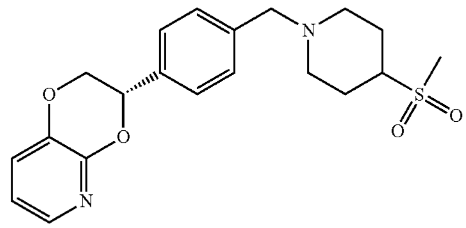 [SMILES: CS(=O)(=O)C1CCN(Cc2ccc([C@H]3COc4cccnc4O3)cc2)CC1] | (3S)-3-(4-{[4-(methylsulfonyl)piperidin-1-yl]methyl}phenyl)-2,3-dihydro[1,4]dioxin[2,3-b]pyridine |
| 173 | 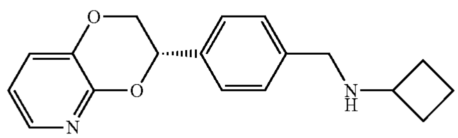 [SMILES: c1cnc2c(c1)OC[C@H](c1ccc(CNC3CCC3)cc1)O2] | N-{4-[(3S)-2,3-dihydro[1,4]dioxino[2,3-b]pyridin-3-yl]benzyl}cyclobutanamine |
| 174 | 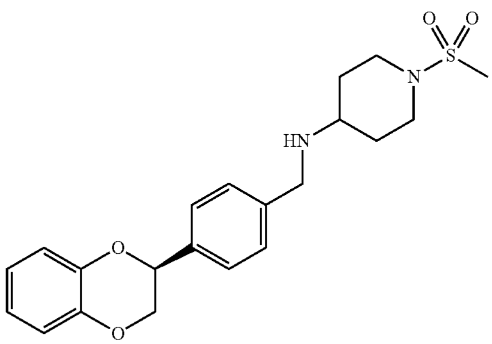 [SMILES: CS(=O)(=O)N1CCC(NCc2ccc([C@H]3COc4ccccc4O3)cc2)CC1] | N-{4-[(2S)-2,3-dihydro-1,4-benzodioxin-2-yl]benzyl}-1-(methylsulfonyl)piperidin-4-amine |
| 175 | 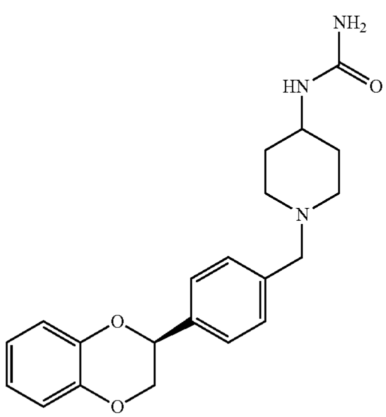 [SMILES: NC(=O)NC1CCN(Cc2ccc([C@H]3COc4ccccc4O3)cc2)CC1] | 1-(1-{4-[(2S)-2,3-dihydro-1,4-benzodioxin-2-yl]benzyl}piperidin-4-yl)urea |
| 176 | 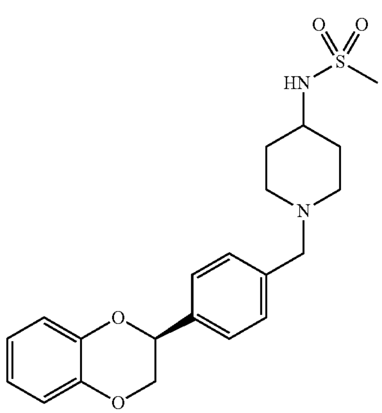 [SMILES: CS(=O)(=O)NC1CCN(Cc2ccc([C@H]3COc4ccccc4O3)cc2)CC1] | N-(1-{4-[(2S)-2,3-dihydro-1,4-benzodioxin-2-yl]benzyl}piperidin-4-yl)methanesulfonamide |

TABLE 1-continued
Exemplary compounds of the invention.
| Cpd No. | Structure | Name |
|---|---|---|
| 177 | 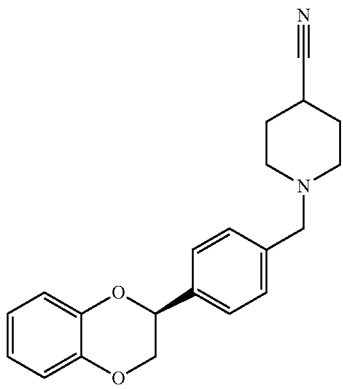 [SMILES: N#CC1CCN(Cc2ccc([C@H]3COc4ccccc4O3)cc2)CC1] | 1-{4-[(2S)-2,3-dihydro-1,4-benzodioxin-2-yl]benzyl}piperidine-4-carbonitrile |
| 178 | 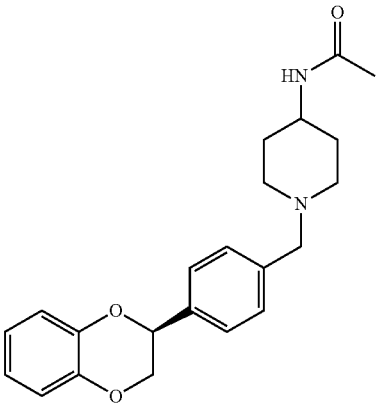 [SMILES: CC(=O)NC1CCN(Cc2ccc([C@H]3COc4ccccc4O3)cc2)CC1] | N-(1-{4-[(2S)-2,3-dihydro-1,4-benzodioxin-2-yl]benzyl}piperidin-4-yl)acetamide |
| 179 | 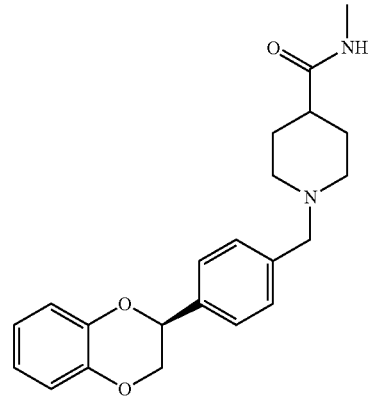 [SMILES: CNC(=O)C1CCN(Cc2ccc([C@H]3COc4ccccc4O3)cc2)CC1] | 1-{4-[(2S)-2,3-dihydro-1,4-benzodioxin-2-yl]benzyl}-N-methylpiperidine-4-carboxamide |

TABLE 1-continued
Exemplary compounds of the invention.
| Cpd No. | Structure | Name |
|---|---|---|
| 180 | 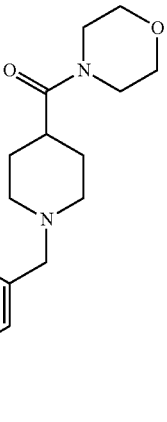 | (1-{4-[(2S)-2,3-dihydro-1,4-benzodioxin-2-yl]benzyl}piperidin-4-yl)(morpholin-4-yl)methanone |
| 181 | 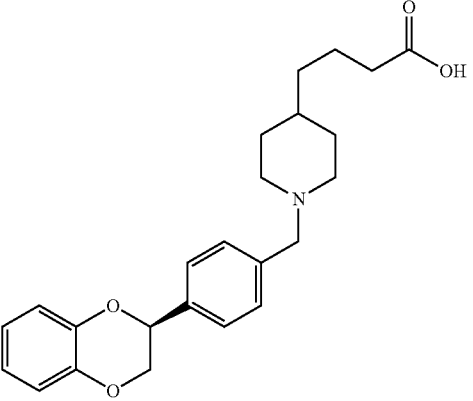 [SMILES: O=C(O)CCCC1CCN(Cc2ccc([C@H]3COc4ccccc4O3)cc2)CC1] | 4-(1-{4-[(2S)-2,3-dihydro-1,4-benzodioxin-2-yl]benzyl}piperidin-4-yl)butanoic acid |
| 182 | 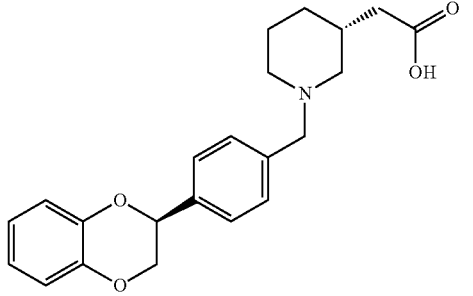 [SMILES: O=C(O)C[C@H]1CCCN(Cc2ccc([C@H]3COc4ccccc4O3)cc2)C1] | [(3R)-1-{4-[(2S)-2,3-dihydro-1,4-benzodioxin-2-yl]benzyl}piperidin-3-yl]acetic acid |
| 183 | 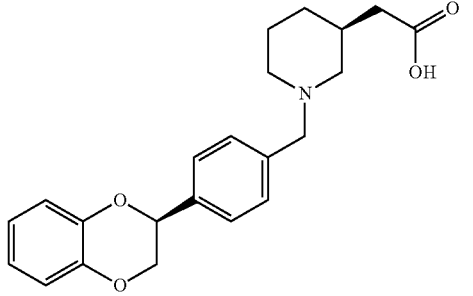 [SMILES: O=C(O)C[C@@H]1CCCN(Cc2ccc([C@H]3COc4ccccc4O3)cc2)C1] | [(3S)-1-{4-[(2S)-2,3-dihydro-1,4-benzodioxin-2-yl]benzyl}piperidin-3-yl]acetic acid |

TABLE 1-continued

Exemplary compounds of the invention.

| Cpd No. | Structure | Name |
|---|---|---|
| 184 | 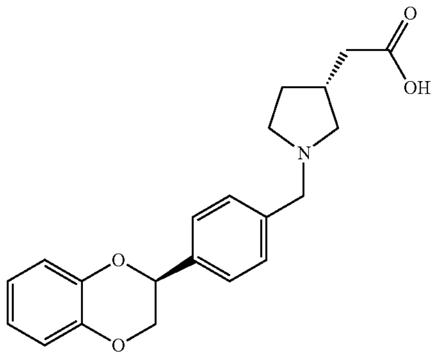 [SMILES: O=C(O)C[C@H]1CCN(Cc2ccc([C@H]3COc4ccccc4O3)cc2)C1] | [(3R)-1-{4-[(2S)-2,3-dihydro-1,4-benzodioxin-2-yl]benzyl}pyrrolidin-3-yl]acetic acid |
| 185 | 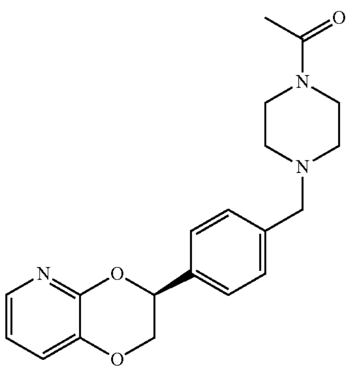 [SMILES: CC(=O)N1CCN(Cc2ccc([C@H]3COc4cccnc4O3)cc2)CC1] | 1-(4-{4-[(3S)-2,3-dihydro[1,4]dioxin[2,3-b]pyridin-3-yl]benzyl}piperazin-1-yl)ethanone |
| 186 | 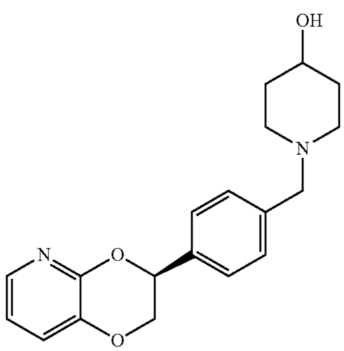 [SMILES: OC1CCN(Cc2ccc([C@H]3COc4cccnc4O3)cc2)CC1] | 1-{4-[(3S)-2,3-dihydro[1,4]dioxino[2,3-b]pyridin-3-yl]benzyl}piperidin-4-ol |
| 187 | 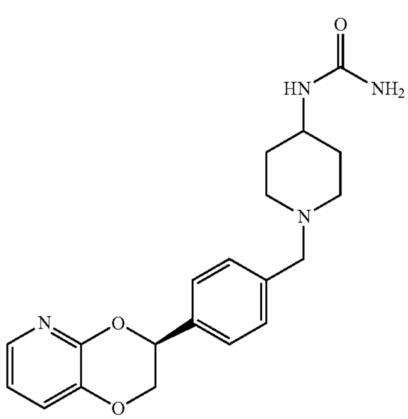 [SMILES: NC(=O)NC1CCN(Cc2ccc([C@H]3COc4cccnc4O3)cc2)CC1] | 1-(1-{4-[(3S)-2,3-dihydro[1,4]dioxino[2,3-b]pyridin-3-yl]benzyl}piperidin-4-yl)urea |

TABLE 1-continued

Exemplary compounds of the invention.

| Cpd No. | Structure | Name |
|---|---|---|
| 188 | 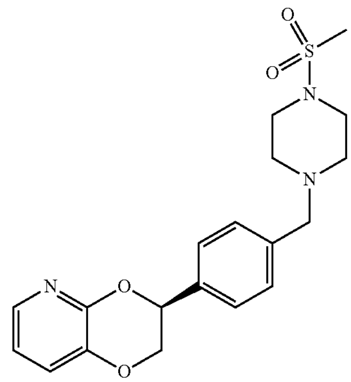 [SMILES: CS(=O)(=O)N1CCN(Cc2ccc([C@H]3COc4cccnc4O3)cc2)CC1] | (3S)-3-(4-{[4-(methylsulfonyl)piperazin-1-yl]methyl}phenyl)-2,3-dihydro[1,4]dioxino[2,3-b]pyridine |
| 189 | 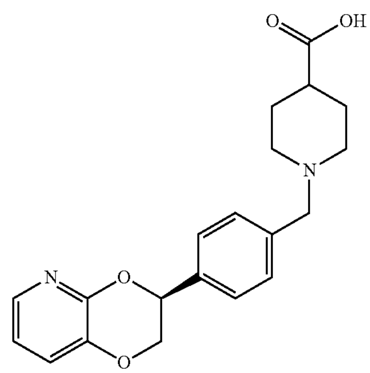 [SMILES: O=C(O)C1CCN(Cc2ccc([C@H]3COc4cccnc4O3)cc2)CC1] | 1-{4-[(3S)-2,3-dihydro[1,4]dioxino[2,3-b]pyridin-3-yl]benzyl}piperidine-4-carboxylic acid |
| 190 | 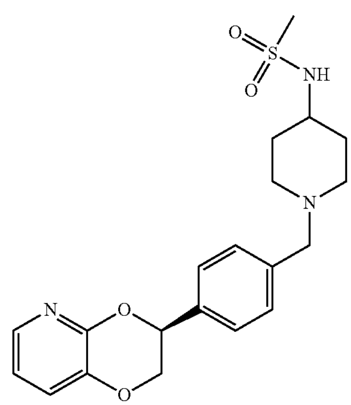 [SMILES: CS(=O)(=O)NC1CCN(Cc2ccc([C@H]3COc4cccnc4O3)cc2)CC1] | N-(1-{4-[(3S)-2,3-dihydro[1,4]dioxino[2,3-b]pyridin-3-yl]benzyl}piperidin-4-yl)methanesulfonamide |
| 191 | 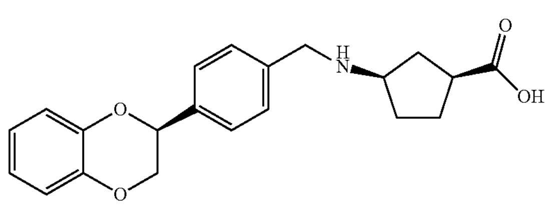 [SMILES: O=C(O)[C@H]1CC[C@@H](NCc2ccc([C@H]3COc4ccccc4O3)cc2)C1] | (1S,3R)-3-({4-[(2S)-2,3-dihydro-1,4-benzodioxin-2-yl]benzyl}amino)cyclopentanecarboxylic acid |
| 192 | 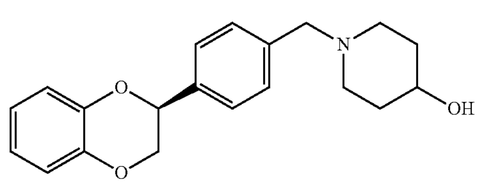 [SMILES: OC1CCN(Cc2ccc([C@H]3COc4ccccc4O3)cc2)CC1] | 1-{4-[(2S)-2,3-dihydro-1,4-benzodioxin-2-yl]benzyl}piperidin-4-ol |

TABLE 1-continued

Exemplary compounds of the invention.

| Cpd No. | Structure | Name |
|---|---|---|
| 193 | 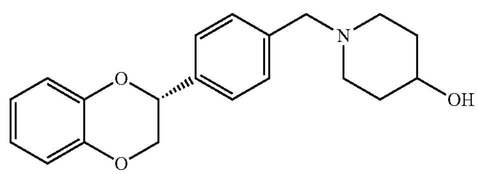 [SMILES: OC1CCN(Cc2ccc([C@@H]3COc4ccccc4O3)cc2)CC1] | 1-{4-[(2R)-2,3-dihydro-1,4-benzodioxin-2-yl]benzyl}piperidin-4-ol |
| 194 | 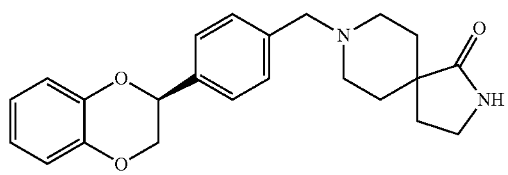 [SMILES: O=C1NCCC12CCN(Cc1ccc([C@H]3COc4ccccc4O3)cc1)CC2] | 8-{4-[(2S)-2,3-dihydro-1,4-benzodioxin-2-yl]benzyl}-2,8-diazaspiro[4.5]decan-1-one |
| 195 | 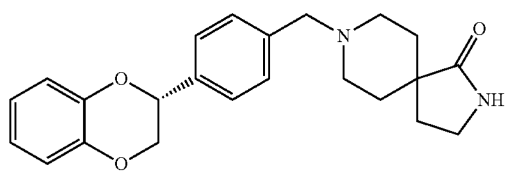 [SMILES: O=C1NCCC12CCN(Cc1ccc([C@@H]3COc4ccccc4O3)cc1)CC2] | 8-{4-[(2R)-2,3-dihydro-1,4-benzodioxin-2-yl]benzyl}-2,8-diazaspiro[4.5]decan-1-one |
| 196 | 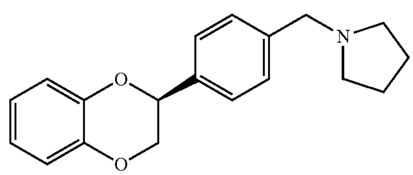 [SMILES: c1ccc2c(c1)OC[C@H](c1ccc(CN3CCCC3)cc1)O2] | 1-{4-[(2S)-2,3-dihydro-1,4-benzodioxin-2-yl]benzyl}pyrrolidine |
| 197 | 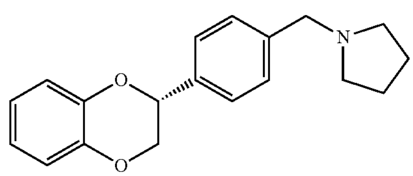 | 1-{4-[(2R)-2,3-dihydro-1,4-benzodioxin-2-yl]benzyl}pyrrolidine |
| 198 | 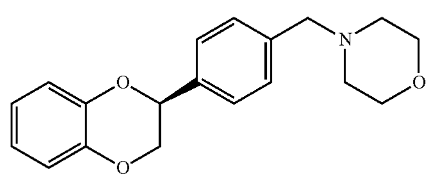 [SMILES: c1ccc2c(c1)OC[C@H](c1ccc(CN3CCOCC3)cc1)O2] | 4-{4-[(2S)-2,3-dihydro-1,4-benzodioxin-2-yl]benzyl}morpholine |
| 199 | 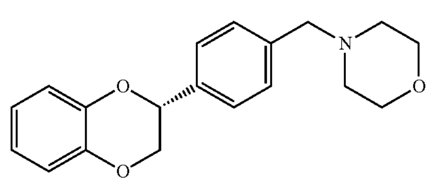 [SMILES: c1ccc2c(c1)OC[C@@H](c1ccc(CN3CCOCC3)cc1)O2] | 4-{4-[(2R)-2,3-dihydro-1,4-benzodioxin-2-yl]benzyl}morpholine |
| 200 | 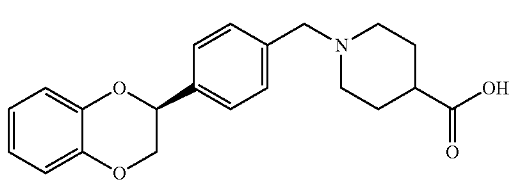 [SMILES: O=C(O)C1CCN(Cc2ccc([C@H]3COc4ccccc4O3)cc2)CC1] | 1-{4-[(2S)-2,3-dihydro-1,4-benzodioxin-2-yl]benzyl}piperidine-4-carboxylic acid |

TABLE 1-continued

Exemplary compounds of the invention.

| Cpd No. | Structure | Name |
| --- | --- | --- |
| 201 | Chiral | 1-{4-[(2R)-2,3-dihydro-1,4-benzodioxin-2-yl]benzyl}piperidine-4-carboxylic acid |
| 202 | 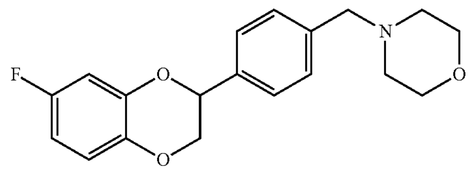 [SMILES: Fc1ccc2c(c1)OC(c1ccc(CN3CCOCC3)cc1)CO2] | 4-[4-(7-fluoro-2,3-dihydro-1,4-benzodioxin-2-yl)benzyl]mopholine |
| 203 | 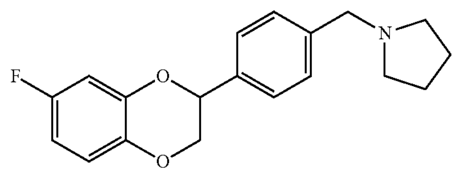 [SMILES: Fc1ccc2c(c1)OC(c1ccc(CN3CCCC3)cc1)CO2] | 1-[4-(7-fluoro-2,3-dihydro-1,4-benzodioxin-2-yl)benzyl]pyrrolidine |
| 204 | 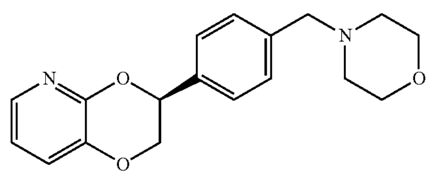 [SMILES: c1cnc2c(c1)OC[C@H](c1ccc(CN3CCOCC3)cc1)O2] | (3S)-3-[4-(morpholin-4-ylmethyl)phenyl]-2,3-dihydro[1,4]dioxino[2,3-b]pyridine |
| 205 | 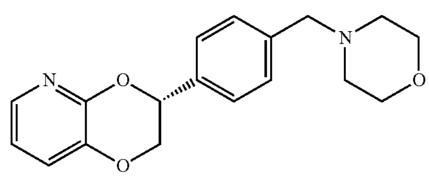 [SMILES: c1cnc2c(c1)OC[C@@H](c1ccc(CN3CCOCC3)cc1)O2] | (3R)-3-[4-(morpholin-4-ylmethyl)phenyl]-2,3-dihydro[1,4]dioxino[2,3-b]pyridine |
| 206 | 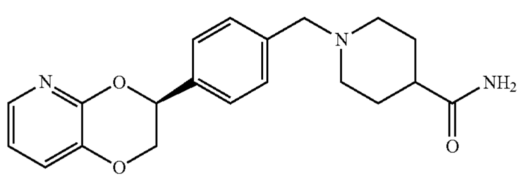 [SMILES: NC(=O)C1CCN(Cc2ccc([C@H]3COc4cccnc4O3)cc2)CC1] | 1-{4-[(3S)-2,3-dihydro[1,4]dioxino[2,3-b]pyridin-3-yl]benzyl}piperidine-4-carboxamide |
| 207 | 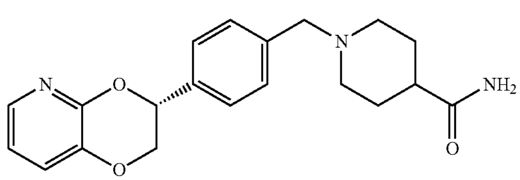 [SMILES: NC(=O)C1CCN(Cc2ccc([C@@H]3COc4cccnc4O3)cc2)CC1] | 1-{4-[(3R)-2,3-dihydro[1,4]dioxino[2,3-b]pyridin-3-yl]benzyl}piperidine-4-carboxamide |
| 208 | 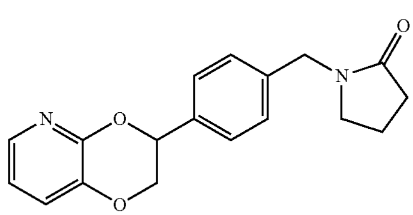 [SMILES: O=C1CCCN1Cc1ccc(C2COc3cccnc3O2)cc1] | 1-[4-[(2,3-dihydro[1,4]dioxino[2,3-b]pyridin-3-yl)benzyl]pyrrolidin-2-one |

TABLE 1-continued

Exemplary compounds of the invention.

| Cpd No. | Structure | Name |
|---|---|---|
| 209 | 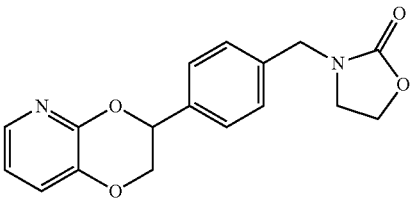 [SMILES: O=C1OCCN1Cc1ccc(C2COc3cccnc3O2)cc1] | 3-[4-(2,3-dihydro[1,4]dioxino[2,3-b]pyridin-3-yl)benzyl]-1,3-oxazolidin-2-one |
| 210 | 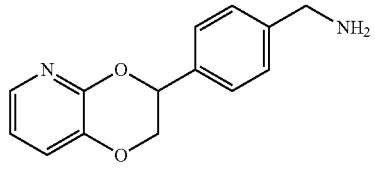 [SMILES: NCc1ccc(C2COc3cccnc3O2)cc1] | 1-[4-(2,3-dihydro[1,4]dioxino[2,3-b]pyridin-3-yl)phenyl]methanamine |
| 211 | 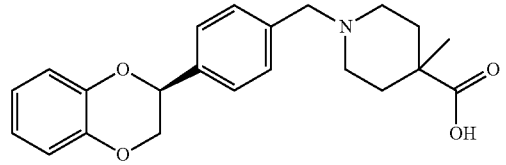 [SMILES: CC1(C(=O)O)CCN(Cc2ccc([C@H]3COc4ccccc4O3)cc2)CC1] | 1-{4-[(2S)-2,3-dihydro-1,4-benzodioxin-2-yl]benzyl}-4-methylpiperidine-4-carboxylic acid |
| 212 | 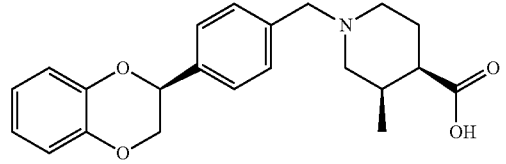 [SMILES: C[C@H]1CN(Cc2ccc([C@H]3COc4ccccc4O3)cc2)CC[C@H]1C(=O)O] | (3R,4R)-1-{4-[(2S)-2,3-dihydro-1,4-benzodioxin-2-yl]benzyl}-3-methylpiperidine-3-carboxylic acid |
| 213 | 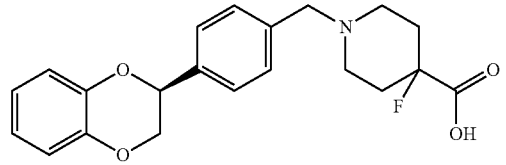 [SMILES: O=C(O)C1(F)CCN(Cc2ccc([C@H]3COc4ccccc4O3)cc2)CC1] | 1-{4-[(2S)-2,3-dihydro-1,4-benzodioxin-2-yl]benzyl}-4-fluoropiperidine-4-carboxylic acid |
| 214 | 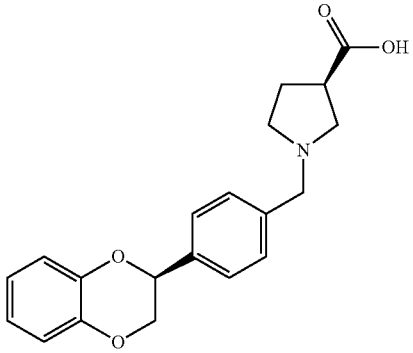 [SMILES: O=C(O)[C@@H]1CCN(Cc2ccc([C@H]3COc4ccccc4O3)cc2)C1] | (3R)-1-{4-[(2S)-2,3-dihydro-1,4-benzodioxin-2-yl]benzyl}pyrrolidine-3-carboxylic acid |

TABLE 1-continued
Exemplary compounds of the invention.
| Cpd No. | Structure | Name |
|---|---|---|
| 215 | 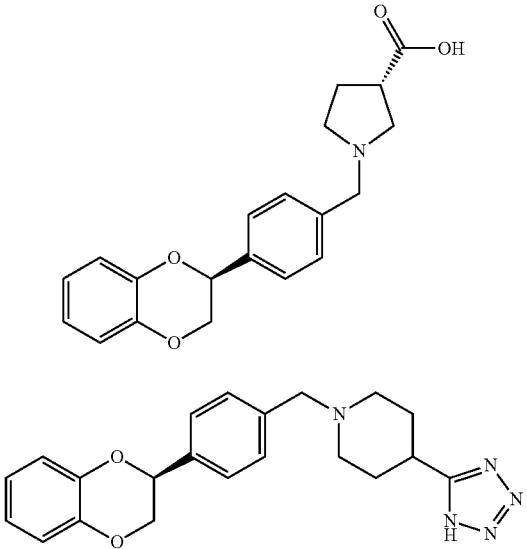 | (3S)-1-{4-[(2S)-2,3-dihydro-1,4-benzodioxin-2-yl]benzyl}pyrrolidine-3-carboxylic acid |
| 216 | 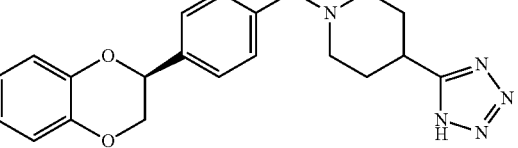 | 1-{4-[(2S)-2,3-dihydro-1,4-benzodioxin-2-yl]benzyl}-4-(1H-tetrazol-5-yl)piperidine |
| 217 | 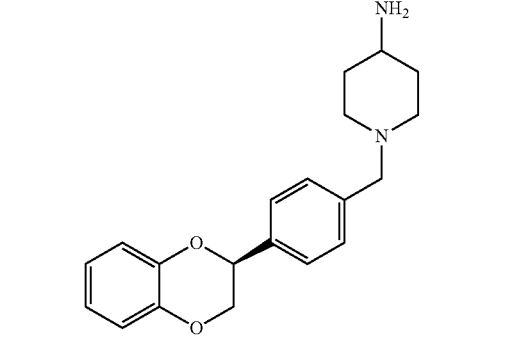 [SMILES: NC1CCN(Cc2ccc([C@H]3COc4ccccc4O3)cc2)CC1] | 1-{4-[(2S)-2,3-dihydro-1,4-benzodioxin-2-yl]benzyl}piperidin-4-amine |
| 218 | 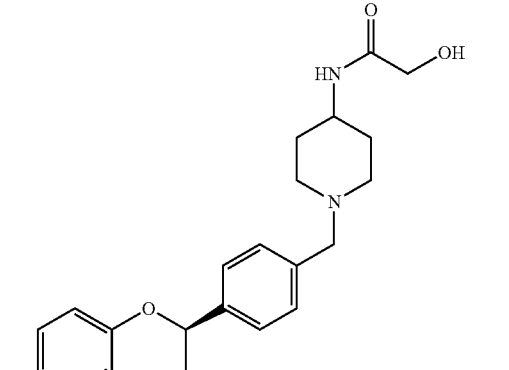 | N-(1-{4-[(1S)-2,3-dihydro-1,4-benzodioxin-2-yl]benzyl}piperidin-4-yl)-2-hydroxyacetamide |

TABLE 1-continued

Exemplary compounds of the invention.

| Cpd No. | Structure | Name |
|---|---|---|
| 219 | 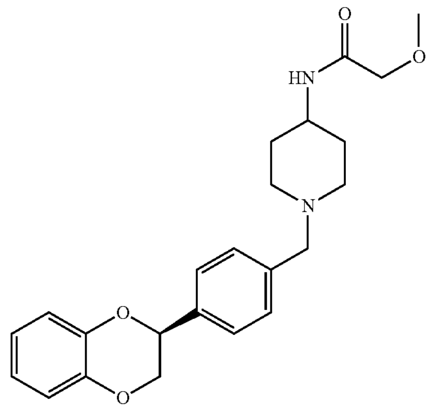 [SMILES: COCC(=O)NC1CCN(Cc2ccc([C@H]3COc4ccccc4O3)cc2)CC1] | N-(1-{4-[(2S)-2,3-dihydro-1,4-benzodioxin-2-yl]benzyl}piperidin-4-yl)-2-methoxyacetamide |
| 220 | 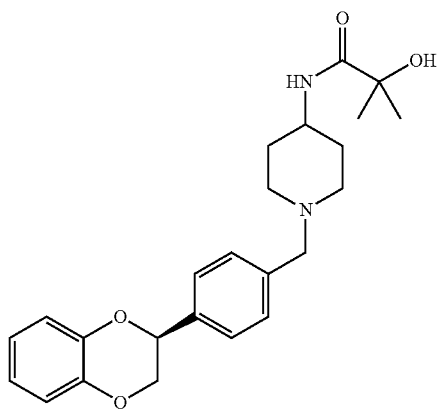 [SMILES: CC(C)(O)C(=O)NC1CCN(Cc2ccc([C@H]3COc4ccccc4O3)cc2)CC1] | N-(1-{4-[(2S)-2,3-dihydro-1,4-benzodioxin-2-yl]benzyl}piperidin-4-yl)-2-hydroxy-2-methylpropanamide |
| 221 | 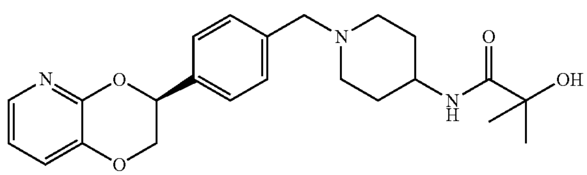 [SMILES: CC(C)(O)C(=O)NC1CCN(Cc2ccc([C@H]3COc4cccnc4O3)cc2)CC1] | N-(1-{4-[(3S)-2,3-dihydro[1,4]dioxino[2,3-b]pyridin-4-yl]benzyl}piperidin-4-yl)-2-hydroxy-2-methylpropanamide |
| 222 | 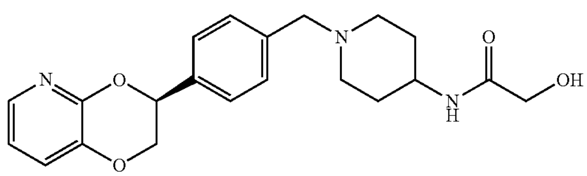 [SMILES: O=C(CO)NC1CCN(Cc2ccc([C@H]3COc4cccnc4O3)cc2)CC1] | N-(1-{4-[(3S)-2,3-dihydro[1,4]dioxino[2,3-b]pyridin-3-yl]benzyl}piperidin-4-yl)-2-hydroxyacetamide |
| 223 | 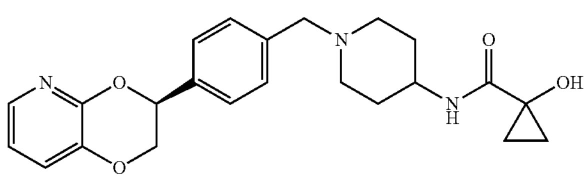 [SMILES: O=C(NC1CCN(Cc2ccc([C@H]3COc4cccnc4O3)cc2)CC1)C1(O)CC1] | N-(1-{4-[(3S)-2,3-dihydro[1,4]dioxino[2,3-b]pyridin-3-yl]benzyl}piperidin-4-yl)-1-hydroxycyclopropanecarboxamide |
| 224 | 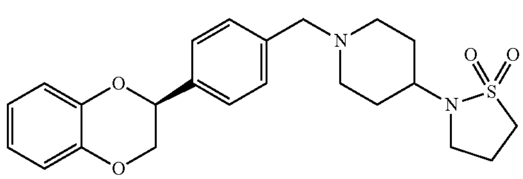 [SMILES: O=S1(=O)CCCN1C1CCN(Cc2ccc([C@H]3COc4ccccc4O3)cc2)CC1] | 1-{4-[(2S)-2,3-dihydro-1,4-benzodioxin-2-yl]benzyl}-4-(1,1-dioxido-1,2-thiazolidin-2-yl)piperidine |

TABLE 1-continued

Exemplary compounds of the invention.

| Cpd No. | Structure | Name |
|---|---|---|
| 225 | 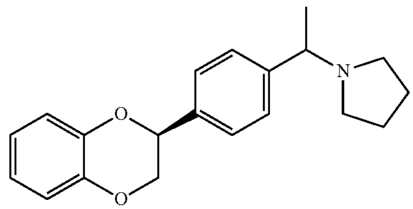 [SMILES: CC(c1ccc([C@H]2COc3ccccc3O2)cc1)N1CCCC1] | 1-(1-{4-[(2S)-2,3-dihydro-1,4-benzodioxin-2-yl]phenyl}ethyl)pyrrolidine |
| 226 | 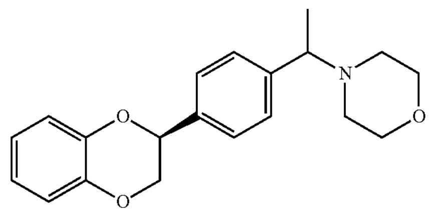 [SMILES: CC(c1ccc([C@H]2COc3ccccc3O2)cc1)N1CCOCC1] | 4-(1-{4-[(2S)-2,3-dihydro-1,4-benzodioxin-2-yl]phenyl}ethyl)morpholine |
| 227 | 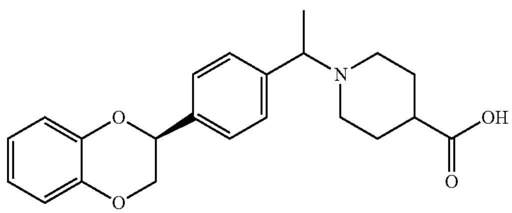 [SMILES: CC(c1ccc([C@H]2COc3ccccc3O2)cc1)N1CCC(C(=O)O)CC1] | 1-(1-{4-[(2S)-2,3-dihydro-1,4-benzodioxin-2-yl]phenyl}ethyl)piperidine-4-carboxylic acid |
| 228 | 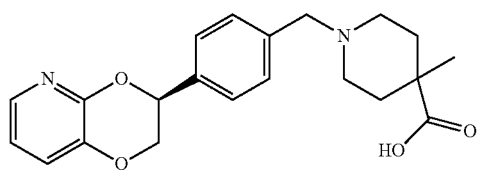 [SMILES: CC1(C(=O)O)CCN(Cc2ccc([C@H]3COc4cccnc4O3)cc2)CC1] | 1-{4-[(3S)-2,3-dihydro[1,4]dioxino[2,3-b]pyridin-3-yl]benzyl}-4-methylpiperidine-4-carboxylic acid |
| 229 | 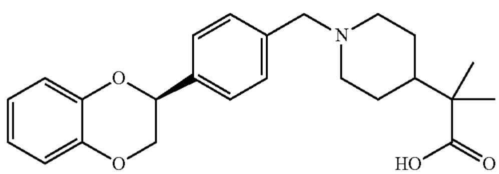 [SMILES: CC(C)(C(=O)O)C1CCN(Cc2ccc([C@H]3COc4ccccc4O3)cc2)CC1] | 2-(1-{4-[(2S)-2,3-dihydro-1,4-benzodioxin-2-yl]benzyl}piperidin-4-yl)-2-methylpropanoic acid |
| 230 | 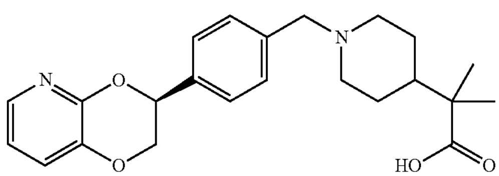 [SMILES: CC(C)(C(=O)O)C1CCN(Cc2ccc([C@H]3COc4cccnc4O3)cc2)CC1] | 2-(1-{4-[(3S)-2,3-dihydro[1,4]dioxin[2,3-b]pyridin-3-yl]benzyl}piperidin-4-yl)-2-methylpropanoic acid |
| 231 | 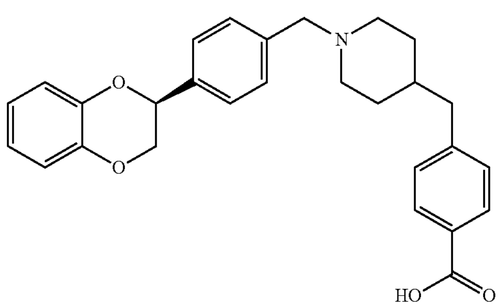 [SMILES: O=C(O)c1ccc(CC2CCN(Cc3ccc([C@H]4COc5ccccc5O4)cc3)CC2)cc1] | 4-[(1-{4-[(2S)-2,3-dihydro-1,4-benzodioxin-2-yl[benzyl}piperidin-4-yl)methyl]benzoic acid |

TABLE 1-continued

Exemplary compounds of the invention.

| Cpd No. | Structure | Name |
| --- | --- | --- |
| 232 | 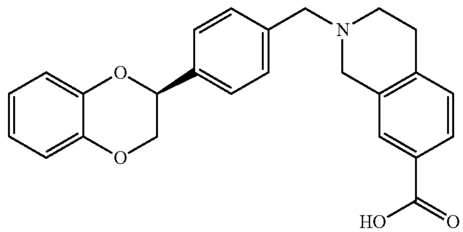 [SMILES: O=C(O)c1ccc2c(c1)CN(Cc1ccc([C@H]3COc4ccccc4O3)cc1)CC2] | 2-{4-[(2S)-2,3-dihydro-1,4-benzodioxin-2-yl]benzyl}-1,2,3,4-tetrahydroisoquinoline-7-carboxylic acid |
| 233 | 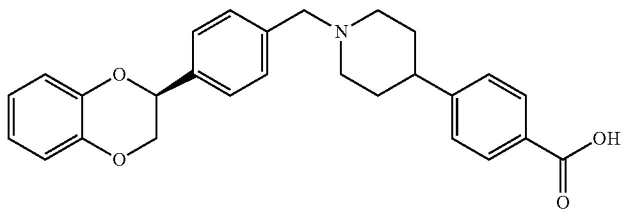 [SMILES: O=C(O)c1ccc(C2CCN(Cc3ccc([C@H]4COc5ccccc5O4)cc3)CC2)cc1] | 4-(1-{4-[(2S)-2,3-dihydro-1,4-benzodioxin-2-yl]benzyl}piperidin-4-yl)benzoic acid |
| 234 | 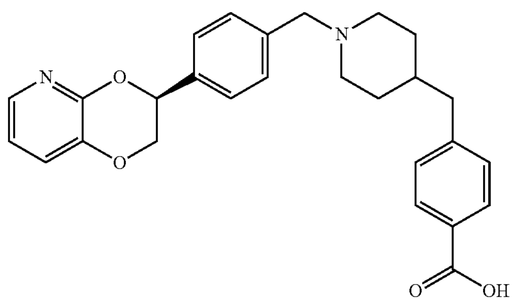 [SMILES: O=C(O)c1ccc(CC2CCN(Cc3ccc([C@H]4COc5cccnc5O4)cc3)CC2)cc1] | 4-[(1-{4-[(3S)-2,3-dihydro[1,4]dioxino[2,3-b]pyridin-3-yl]benzyl}piperidin-4-yl)methyl]benzoic acid |
| 235 | 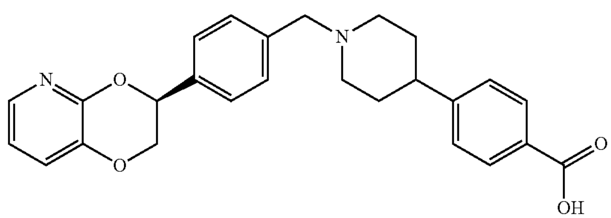 [SMILES: O=C(O)c1ccc(C2CCN(Cc3ccc([C@H]4COc5cccnc5O4)cc3)CC2)cc1] | 4-(1-{4-[(3S)-2,3-dihydro[1,4]dioxino[2,3-b]pyridin-3-yl]benzyl}piperidin-4-yl)benzoic acid |
| 236 | 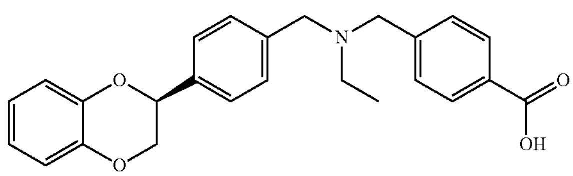 [SMILES: CCN(Cc1ccc(C(=O)O)cc1)Cc1ccc([C@H]2COc3ccccc3O2)cc1] | 4-{[{4-[(2S)-2,3-dihydro-1,4-benzodioxin-2-yl]benzyl}(ethyl)amino]methyl}benzoic acid |
| 237 | 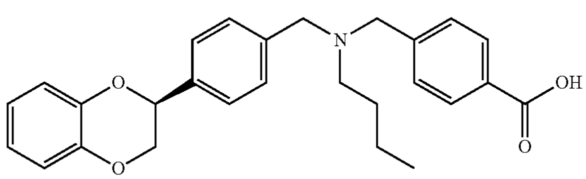 [SMILES: CCCCN(Cc1ccc(C(=O)O)cc1)Cc1ccc([C@H]2COc3ccccc3O2)cc1] | 4-[(butyl{4-[(2S)-2,3-dihydro-1,4-benzodioxin-2-yl]benzyl}amino)methyl]benzoic acid |
| 238 | 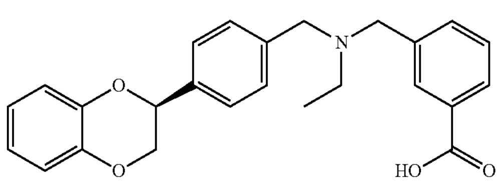 [SMILES: CCN(Cc1ccc([C@H]2COc3ccccc3O2)cc1)Cc1cccc(C(=O)O)c1] | 3-{[{4-[(2S)-2,3-dihydro-1,4-benzodioxin-2-yl]benzyl}(ethyl)amino]methyl}benzoic acid |

TABLE 1-continued

Exemplary compounds of the invention.

| Cpd No. | Structure | Name |
|---|---|---|
| 239 | 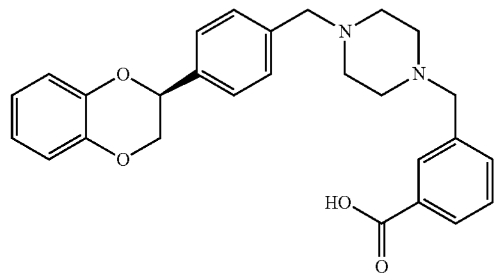 [SMILES: O=C(O)c1cccc(CN2CCN(Cc3ccc([C@H]4COc5ccccc5O4)cc3)CC2)c1] | 3-[(4-{4-[(2S)-2,3-dihydro-1,4-benzodioxin-2-yl]benzyl}piperazin-1-yl)methyl]benzoic acid |
| 240 | 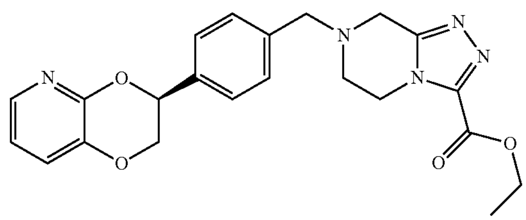 [SMILES: CCOC(=O)c1nnc2n1CCN(Cc1ccc([C@H]3COc4cccnc4O3)cc1)C2] | 7-[(S)-4-(2,3-dihydro-[1,4]dioxino[2,3-b]pyridin-3-yl)-benzyl]-5,6,7,8-tetrahydro-[1,2,4]triazolo[4,3-a]pyrazine-3-carboxylic acid ethyl ester |
| 241 | 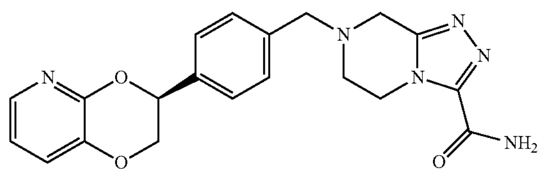 [SMILES: NC(=O)c1nnc2n1CCN(Cc1ccc([C@H]3COc4cccnc4O3)cc1)C2] | 7-[(S)-4-(2,3-Dihydro-[1,4]dioxino[2,3-b]pyridin-3-yl)-benzyl]-5,6,7,8-tetrahydro-[1,2,4]triazolo[4,3-a]pyrazine-3-carboxylic acid amide |
| 242 | 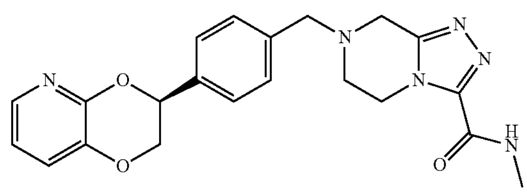 [SMILES: CNC(=O)c1nnc2n1CCN(Cc1ccc([C@H]3COc4cccnc4O3)cc1)C2] | 7-[(S)-4-(2,3-dihydro-[1,4]dioxino[2,3-b]pyridin-3-yl)-benzyl]-5,6,7,8-tetrahydro-[1,2,4]triazolo[4,3-a]pyrazine-3-carboxylic acid methylamide |
| 243 | 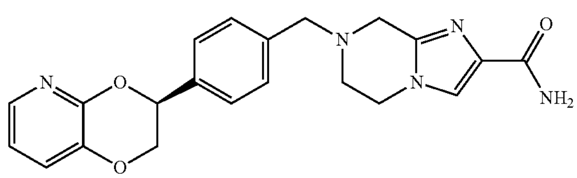 [SMILES: NC(=O)c1cn2c(n1)CN(Cc1ccc([C@H]3COc4cccnc4O3)cc1)CC2] | 7-[(S)-4-(2,3-dihydro-[1,4]dioxino[2,3-b]pyridin-3-yl)-benzyl]-5,6,7,8-tetrahydro-imidazo[1,2-a]pyrazine-2-carboxylic acid amide |
| 244 | 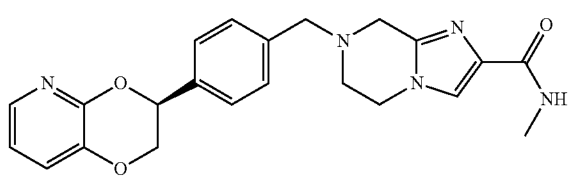 [SMILES: CNC(=O)c1cn2c(n1)CN(Cc1ccc([C@H]3COc4cccnc4O3)cc1)CC2] | 7-[(S)-4-(2,3-dihydro-[1,4]dioxino[2,3-b]pyridin-3-yl)-benzyl]-5,6,7,8-tetrahydro-imidazo[1,2-a]pyrazine-2-carboxylic acid methylamide |
| 245 | 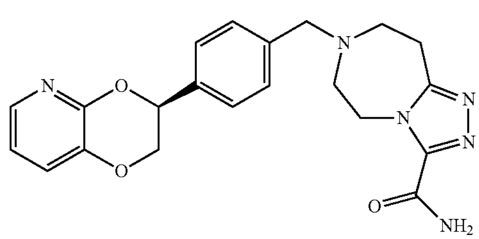 [SMILES: NC(=O)c1nnc2n1CCN(Cc1ccc([C@H]3COc4cccnc4O3)cc1)CC2] | 6-[(S)-4-(2,3-dihydro-[1,4]dioxino[2,3-b]pyridin-3-yl)-benzyl]-5,6,7,8-tetrahydro-4H-1,2,3a,6-tetraaza-azulene-3-carboxylic acid amide |

TABLE 1-continued

Exemplary compounds of the invention.

| Cpd No. | Structure | Name |
|---|---|---|
| 246 | 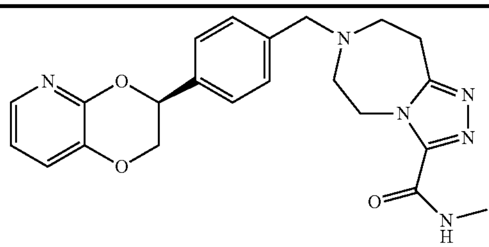 | 6-[(S)-4-(2,3-Dihydro-[1,4]dihydro[2,3-b]pyridin-3-yl)-benzyl]-5,6,7,8-tetrahydro-4H-1,2,3a,6-tetraaza-3-carboxylic acid methylamide |
| 247 | 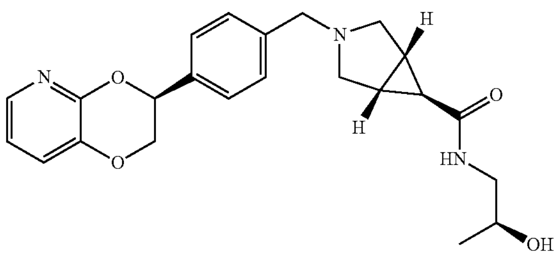 [SMILES: C[C@H](O)CNC(=O)[C@H]1[C@@H]2CN(Cc3ccc([C@H]4COc5cccnc5O4)cc3)C[C@@H]21] | [(1α,5α,6α)-3-[(S)-4-(2,3-dihydro-[1,4]dioxino[2,3-b]pyridin-3-yl)-benzyl]-3-aza-bicyclo[3.1.0]hexane]-6-carboxylic acid ((S)-2-hydroxy-propyl)-amide |
| 248 | 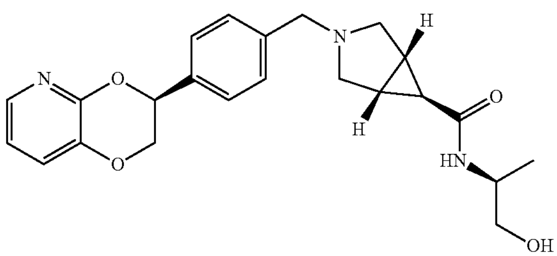 [SMILES: C[C@@H](CO)NC(=O)[C@H]1[C@@H]2CN(Cc3ccc([C@H]4COc5cccnc5O4)cc3)C[C@@H]21] | [(1α,5α,6α)-3-[(S)-4-(2,3-Dihydro-[1,4]dioxino[2,3-b]pyridin-3-yl)-benzyl]-3-aza-bicyclo[3.1.0]hexane-6-carboxylic acid ((S)-2-hydroxy-1-methyl-ethyl)-amide |
| 249 | 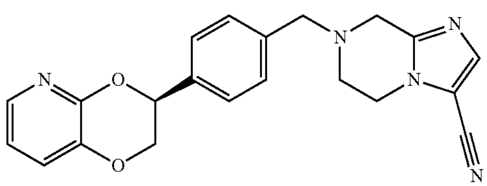 [SMILES: N#Cc1cnc2n1CCN(Cc1ccc([C@H]3COc4cccnc4O3)cc1)C2] | 7-[(S)-4-(2,3-dihydro-[1,4]dioxino[2,3-b]pyridin-3-yl)-benzyl]-5,6,7,8-tetrahydro-imidazo[1,2-a]pyrazine-3-carbonitrile |
| 250 | 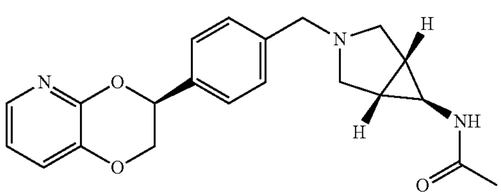 [SMILES: CC(=O)N[C@H]1[C@@H]2CN(Cc3ccc([C@H]4COc5cccnc5O4)cc3)C[C@@H]21] | N-{(1α,5α,6α)-3-[(S)-4-(2,3-Dihydro-[1,4]dioxino[2,3-b]pyridin-3-yl)-benzyl]-3-aza-bicyclo[3.1.0]hex-6-yl}-acetamide |
| 251 | 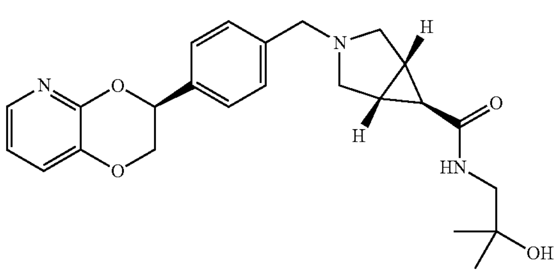 [SMILES: CC(C)(O)CNC(=O)[C@H]1[C@@H]2CN(Cc3ccc([C@H]4COc5cccnc5O4)cc3)C[C@@H]21] | [(1α,5α,6α)-3-[(S)-4-(2,3-Dihydro-[1,4]dioxino[2,3-b]pyridin-3-yl)-benzyl]-3-aza-bicyclo[3.1.0]hexane-6-carboxylic acid (2-hydroxy-2-methyl-propyl)]-amide |
| 252 | 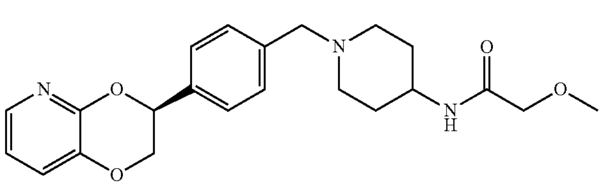 [SMILES: COCC(=O)NC1CCN(Cc2ccc([C@H]3COc4cccnc4O3)cc2)CC1] | N-{1-[(S)-4-(2,3-Dihydro-[1,4]dioxino[2,3-b]pyridin-3-yl)-benzyl]-piperidin-4-yl}-2-methoxy-acetamide |

TABLE 1-continued

Exemplary compounds of the invention.

| Cpd No. | Structure | Name |
|---|---|---|
| 253 | 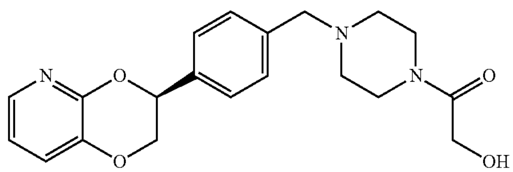 [SMILES: O=C(CO)N1CCN(Cc2ccc([C@H]3COc4cccnc4O3)cc2)CC1] | 1-{4-[(S)-4-(2,3-Dihydro-[1,4]dioxino[2,3-b]pyridin-3-yl)-benzyl]-piperazin-1-yl}-2-hydroxy-ethanone |
| 254 | 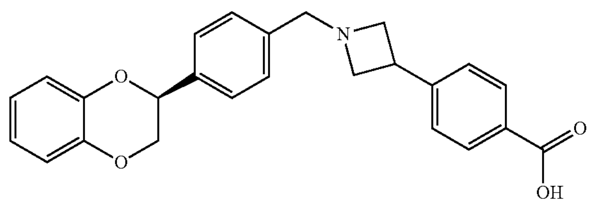 [SMILES: O=C(O)c1ccc(C2CN(Cc3ccc([C@H]4COc5ccccc5O4)cc3)C2)cc1] | 4-{1-[(S)-4-(2,3-Dihydro-benzo[1,4]dioxin-2-yl)-benzyl]-azetidin-3-yl}-benzoic acid |
| 255 | 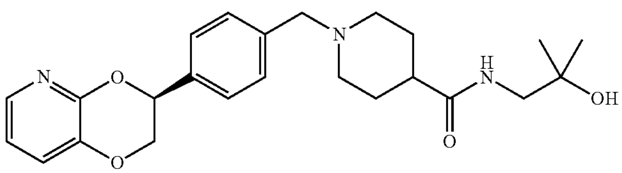 [SMILES: CC(C)(O)CNC(=O)C1CCN(Cc2ccc([C@H]3COc4cccnc4O3)cc2)CC1] | 1-[(S)-4-(2,3-Dihydro[1,4]dioxino[2,3-b]pyridin-3-yl)-benzyl]-piperidine-4-carboxylic acid (2-hydroxy-2-methyl-propyl)-amide |
| 256 | 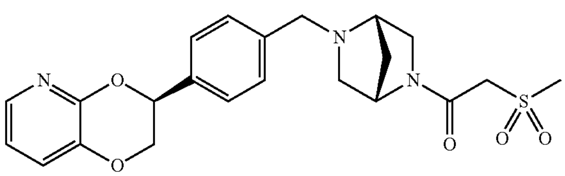 [SMILES: CS(=O)(=O)CC(=O)N1C[C@@H]2C[C@H]1CN2Cc1ccc([C@H]2COc3cccnc3O2)cc1] | 1-{(1S,4S)-5-[(S)-4-(2,3-Dihydro-[1,4]dioxino[2,3-b]pyridin-3-yl)-benzyl]-2,5-diaza-bicyclo[2.2.1]hept-2-yl}-2-methanesulfonyl-ethanone |
| 257 | 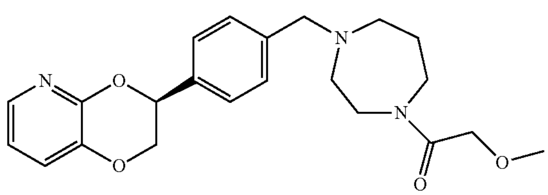 [SMILES: COCC(=O)N1CCCN(Cc2ccc([C@H]3COc4cccnc4O3)cc2)CC1] | 1-{4-[(S)-4-(2,3-Dihydro-[1,4]dioxino[2,3-b]pyridin-3-yl)-benzyl]-[1,4]diazepan-1-yl}-2-methoxy-ethanone |
| 258 | HCl | 5-[(S)-4-(2,3-Dihydro-[1,4]dioxino[2,3-b]pyridin-3-yl)-benzyl]-4,5,6,7-tetrahydro-thiazolo[5,4-c]pyridin-2-ylamine |
| 259 | 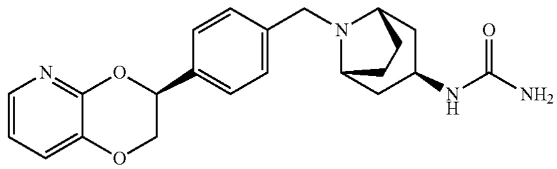 [SMILES: NC(=O)N[C@H]1C[C@H]2CC[C@@H](C1)N2Cc1ccc([C@H]2COc3cccnc3O2)cc1] | {(endo)-8-[(S)-4-(2,3-Dihydro-[1,4]dioxino[2,3-b]pyridin-3-yl)-benzyl]-8-aza-bicyclo[3.2.1]oct-3-yl}-urea |
| 260 | 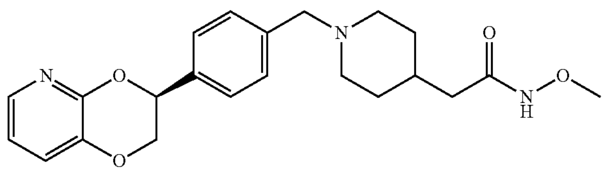 [SMILES: CONC(=O)CC1CCN(Cc2ccc([C@H]3COc4cccnc4O3)cc2)CC1] | 2-{1-[(S)-4-(2,3-Dihydro-[1,4]dioxino[2,3-b]pyridin-3-yl)-benzyl]-piperidin-4-yl}-N-methoxy-acetamide |

TABLE 1-continued

Exemplary compounds of the invention.

| Cpd No. | Structure | Name |
|---|---|---|
| 261 | 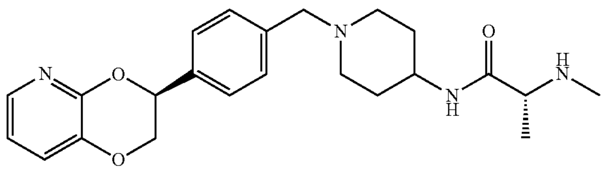 [SMILES: CN[C@H](C)C(=O)NC1CCN(Cc2ccc([C@H]3COc4cccnc4O3)cc2)CC1] | (R)-N-{1-[(S)-4-(2,3-Dihydro-[1,4]dioxino[2,3-b]pyridin-3-yl)-benzyl]-piperidin-4-yl}-2-methylamino-propionamide |
| 262 | 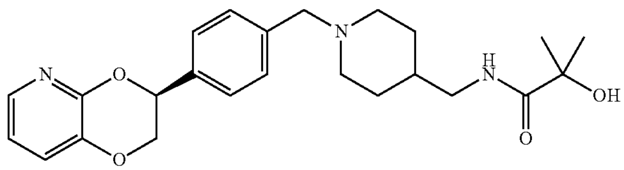 [SMILES: CC(C)(O)C(=O)NCC1CCN(Cc2ccc([C@H]3COc4cccnc4O3)cc2)CC1] | N-{1-[(S)-4-(2,3-Dihydro-[1,4]dioxino[2,3-b]pyridin-3-yl)-benzyl]-piperidin-4-ylmethyl}-2-hydroxy-2-methyl-propionamide |
| 263 | 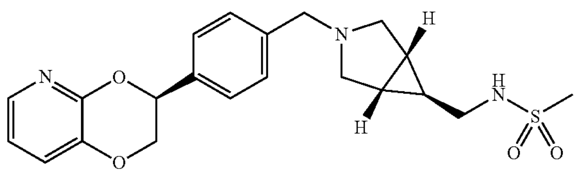 [SMILES: CS(=O)(=O)NC[C@@H]1[C@H]2CN(Cc3ccc([C@H]4COc5cccnc5O4)cc3)C[C@@H]12] | N-{(1α,5α,6α)-3-[(S)-4-(2,3-Dihydro-[1,4]dioxino[2,3-b]pyridin-3-yl)-benzyl]-3-aza-bicyclo[3.1.0]hex-6-ylmethyl}-methanesulfonamide |
| 264 | 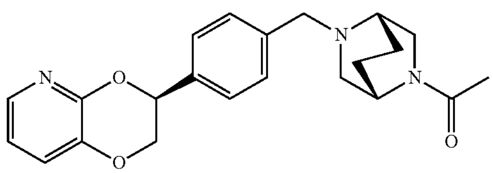 [SMILES: CC(=O)N1C[C@@H]2CC[C@H]1CN2Cc1ccc([C@H]2COc3cccnc3O2)cc1] | 1-{(1S,4S)-5-[(S)-4-(2,3-Dihydro-[1,4]dioxino[2,3-b]pyridin-3-yl)-benzyl]-2,5-diaza-bicyclo[2.2.2]oct-2-yl}-ethanone |
| 265 | 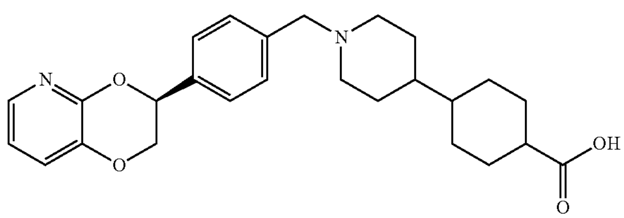 [SMILES: O=C(O)C1CCC(C2CCN(Cc3ccc([C@H]4COc5cccnc5O4)cc3)CC2)CC1] | 4-{1-[(S)-4-(2,3-Dihydro-[1,4]dioxino[2,3-b]pyridin-3-yl)-benzyl]-piperidin-4-yl}-cyclohexanecarboxylic acid |
| 266 | 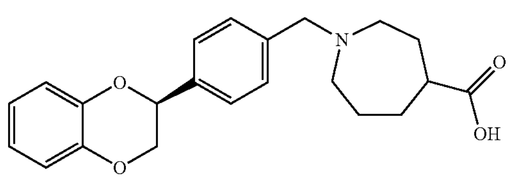 [SMILES: O=C(O)C1CCCN(Cc2ccc([C@H]3COc4ccccc4O3)cc2)CC1] | 1-[(S)-4-(2,3-Dihydro-benzo[1,4]dioxin-2-yl)-benzyl]-azepane-4-carboxylic acid |
| 267 | 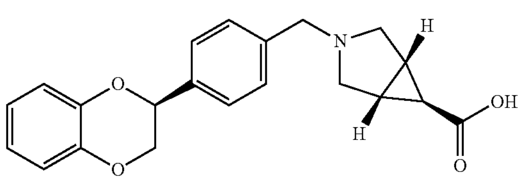 [SMILES: O=C(O)[C@H]1[C@@H]2CN(Cc3ccc([C@H]4COc5ccccc5O4)cc3)C[C@@H]21] | [(1α,5α,6α)-3-[(S)-4-(2,3-Dihydro-benzo[1,4]dioxin-2-yl)-benzyl]-3-aza-bicyclo[3.1.0]hexane-6-carboxylic acid |
| 268 | 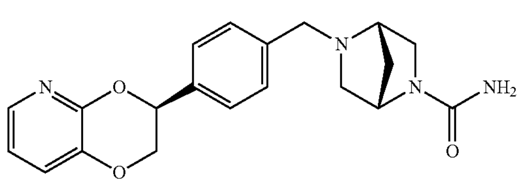 [SMILES: NC(=O)N1C[C@@H]2C[C@H]1CN2Cc1ccc([C@H]2COc3cccnc3O2)cc1] | (1S,4S)-5-[(S)-4-(2,3-Dihydro-[1,4]dioxino[2,3-b]pyridin-3-yl)-benzyl]-3-diaza-bicyclo[2.2.1]heptane-2-carboxylic acid amide |

TABLE 1-continued

Exemplary compounds of the invention.

| Cpd No. | Structure | Name |
|---|---|---|
| 269 | 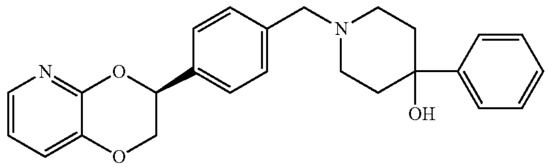 [SMILES: OC1(c2ccccc2)CCN(Cc2ccc([C@H]3COc4cccnc4O3)cc2)CC1] | 1-[(S)-4-(2,3-Dihydro-[1,4]dioxino[2,3-b]pyridin-3-yl)-benzyl]-4-phenyl-piperidin-4-ol |
| 270 | 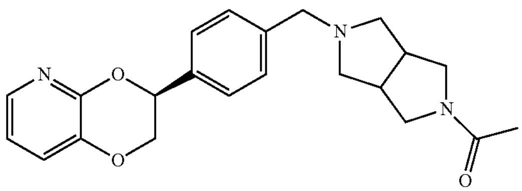 [SMILES: CC(=O)N1CC2CN(Cc3ccc([C@H]4COc5cccnc5O4)cc3)CC2C1] | 1-{5-[(S)-4-(2,3-Dihydro-[1,4]dioxino[2,3-b]pyridin-3-yl)-benzyl]-hexahydro-pyrrolo[3,4-c]pyrrol-2-yl}-ethanone |
| 271 | 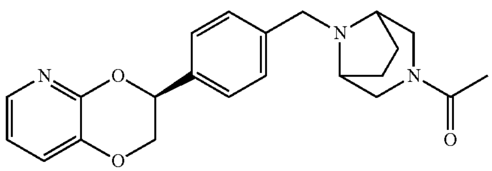 [SMILES: CC(=O)N1CC2CCC(C1)N2Cc1ccc([C@H]2COc3cccnc3O2)cc1] | 1-{8-[(S)-4-(2,3-Dihydro-[1,4]dioxino[2,3-b]pyridin-3-yl)-benzyl]-3,8-diaza-bicyclo[3.2.1]oct-3-yl}-ethanone |
| 272 | 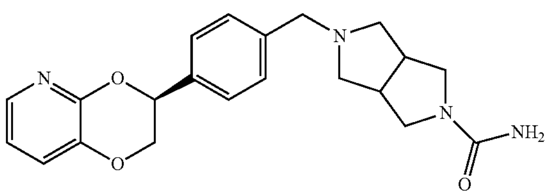 [SMILES: NC(=O)N1CC2CN(Cc3ccc([C@H]4COc5cccnc5O4)cc3)CC2C1] | 5-[(S)-4-(2,3-Dihydro-[1,4]dioxino[2,3-b]pyridin-3-yl)-benzyl]-hexahydro-pyrrolo[3,4-c]pyrrole-2-carboxylic acid amide |
| 273 | 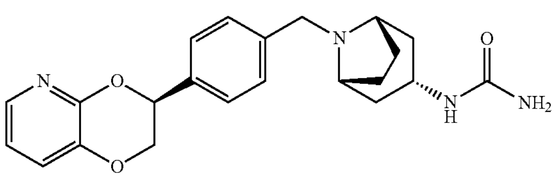 [SMILES: NC(=O)N[C@@H]1C[C@H]2CC[C@@H](C1)N2Cc1ccc([C@H]2COc3cccnc3O2)cc1] | {(exo)-8-[(S)-4-(2,3-Dihydro-[1,4]dioxino[2,3-b]pyridin-3-yl)-benzyl]-8-aza-bicyclo[3.2.1]oct-3-yl}-urea |
| 274 | 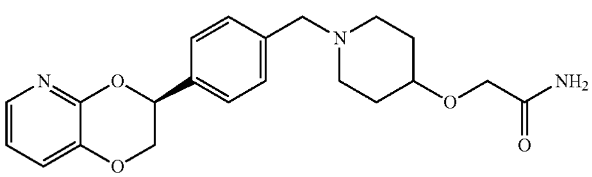 [SMILES: NC(=O)COC1CCN(Cc2ccc([C@H]3COc4cccnc4O3)cc2)CC1] | 2-{1-[(S)-4-(2,3-Dihydro-[1,4]dioxino[2,3-b]pyridin-3-yl)-benzyl]-piperidin-4-yloxy}-acetamide |
| 275 | 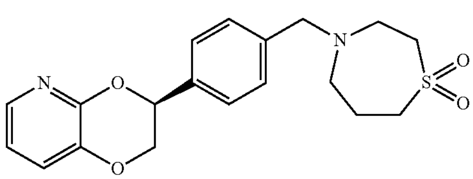 [SMILES: O=S1(=O)CCCN(Cc2ccc([C@H]3COc4cccnc4O3)cc2)CC1] | (S)-3-[4-(1,1-Dioxo-1lambda6-[1,4]thiazepan-4-ylmethyl)-phenyl]-2,3-dihydro-[1,4]dioxino[2,3-b]pyridine |
| 276 | 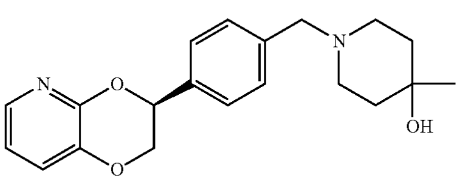 [SMILES: CC1(O)CCN(Cc2ccc([C@H]3COc4cccnc4O3)cc2)CC1] | 1-[(S)-4-(2,3-Dihydro-[1,4]dioxino[2,3-b]pyridin-3-yl)-benzyl]-4-methyl-piperidin-4-ol |

TABLE 1-continued

Exemplary compounds of the invention.

| Cpd No. | Structure | Name |
|---|---|---|
| 277 | 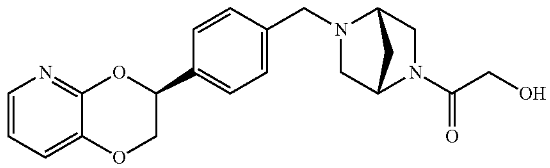 [SMILES: O=C(CO)N1C[C@@H]2C[C@H]1CN2Cc1ccc([C@H]2COc3cccnc3O2)cc1] | 1-{(1S,4S)-5-[(S)-4-(2,3-Dihydro-[1,4]dioxino[2,3-b]pyridin-3-yl)-benzyl]-2,5-diaza-bicyclo[2.2.1]hept-2-yl}-2-hydroxy-ethanone |
| 278 | 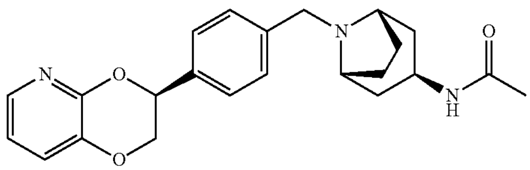 [SMILES: CC(=O)N[C@H]1C[C@H]2CC[C@@H](C1)N2Cc1ccc([C@H]2COc3cccnc3O2)cc1] | N-{(endo)-8-[(S)-4-(2,3-Dihydro-[1,4]dioxino[2,3-b]pyridin-3-yl)-benzyl]-8-aza-bicyclo[3.2.1]oct-3-yl}-acetamide |
| 279 | 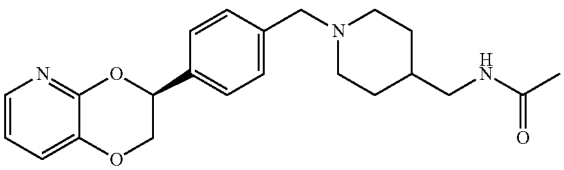 [SMILES: CC(=O)NCC1CCN(Cc2ccc([C@H]3COc4cccnc4O3)cc2)CC1] | N-{1-[(S)-4-(2,3-Dihydro-[1,4]dioxino[2,3-b]pyridin-3-yl)-benzyl]-piperidin-4-ylmethyl}-acetamide |
| 280 | 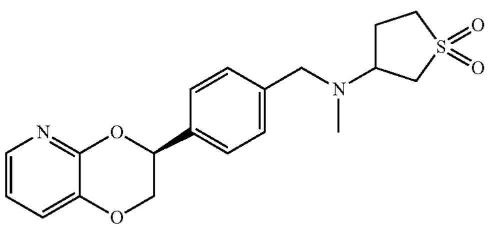 [SMILES: CN(Cc1ccc([C@H]2COc3cccnc3O2)cc1)C1CCS(=O)(=O)C1] | [(S)-4-(2,3-Dihydro-[1,4]dioxino[2,3-b]pyridin-3-yl)-benzyl]-(1,1dioxo-tetrahydro-1lambda-6-thiophen-3-yl)-methyl-amine |
| 281 | 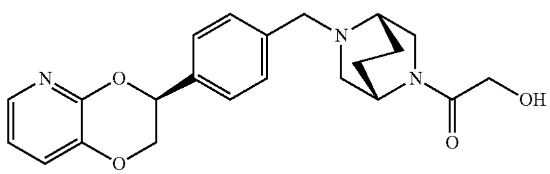 [SMILES: O=C(CO)N1C[C@@H]2CC[C@H]1CN2Cc1ccc([C@H]2COc3cccnc3O2)cc1] | 1-{(1S,4S)-5-[(S)-4-(2,3-Dihydro-[1,4]dioxino[2,3-b]pyridin-3-yl)-benzyl]-2,5-diaza-bicyclo[2.2.2]oct-2-yl}-2-hydroxy-ethanone |
| 282 | 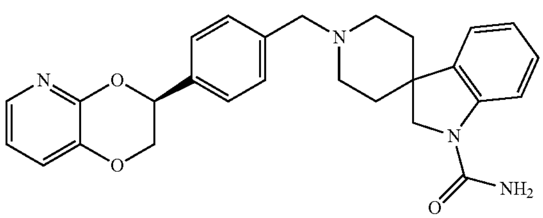 [SMILES: NC(=O)N1CC2(CCN(Cc3ccc([C@H]4COc5cccnc5O4)cc3)CC2)c2ccccc21] | {1-[(S)-4-(2,3-dihydro-[1,4]dioxino[2,3-b]pyridin-3-yl)-benzyl]-spiro-[3H-indole-3,4'-piperidine]-1(2H)-urea |
| 283 | 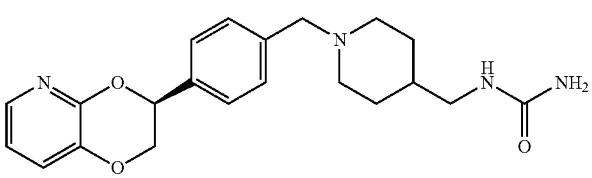 [SMILES: NC(=O)NCC1CCN(Cc2ccc([C@H]3COc4cccnc4O3)cc2)CC1] | {1-[(S)-4-(2,3-Dihydro-[1,4]dioxino[2,3-b]pyridin-3-yl)-benzyl]-piperidin-4-ylmethyl}-urea |
| 284 | 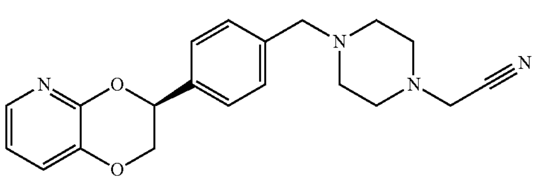 [SMILES: N#CCN1CCN(Cc2ccc([C@H]3COc4cccnc4O3)cc2)CC1] | {4-[(S)-4-(2,3-Dihydro-[1,4]dioxino[2,3-b]pyridin-3-yl)-benzyl]-piperazin-1-yl]-acetonitrile |

TABLE 1-continued

Exemplary compounds of the invention.

| Cpd No. | Structure | Name |
|---|---|---|
| 285 | 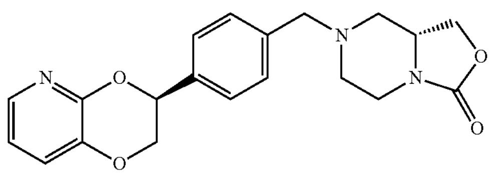 [SMILES: O=C1OC[C@H]2CN(Cc3ccc([C@H]4COc5cccnc5O4)cc3)CCN12] | (R)-7-[(S)-4-(2,3-Dihydro-[1,4]dioxino[2,3-b]pyridin-3-yl)-benzyl]-hexahydro-oxazolo[3,4-a]pyrazin-3-one |
| 286 | 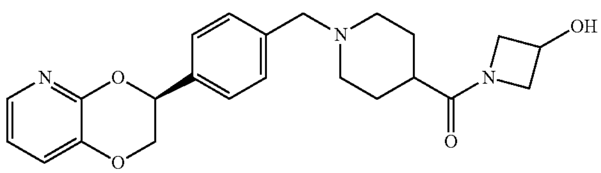 [SMILES: O=C(C1CCN(Cc2ccc([C@H]3COc4cccnc4O3)cc2)CC1)N1CC(O)C1] | {1-[(S)-4-(2,3-Dihydro-[1,4]dioxino[2,3-b]pyridin-3-yl)-benzyl]-piperidin-4-yl}-(3-hydroxy-azetidin-1-yl)-methanone |
| 287 | 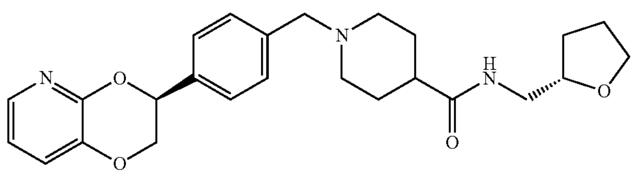 [SMILES: O=C(NC[C@@H]1CCCO1)C1CCN(Cc2ccc([C@H]3COc4cccnc4O3)cc2)CC1] | 1-[(S)-4-(2,3-Dihydro-[1,4]dioxino[2,3-b]pyridin-3-yl)-benzyl]-piperidine-4-carboxylic acid [(S)-1-(tetrahydro-furan-2-yl)methyl]-amide |
| 288 | 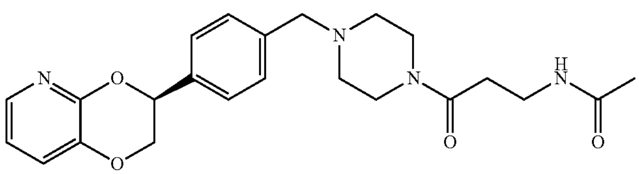 [SMILES: CC(=O)NCCC(=O)N1CCN(Cc2ccc([C@H]3COc4cccnc4O3)cc2)CC1] | N-[3-[3-[[4-[(3S)-2,3-dihydro-[1,4]dioxino[2,3-b]pyridin-3-yl]phenyl]methyl]piperazin-1-yl]-3-oxo-propyl]acetamide |
| 289 | 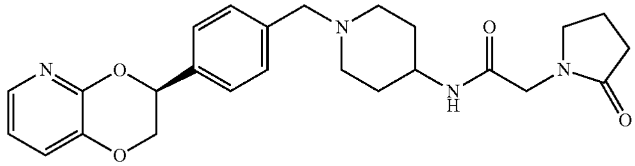 [SMILES: O=C(CN1CCCC1=O)NC1CCN(Cc2ccc([C@H]3COc4cccnc4O3)cc2)CC1] | N-[1-[[4-[(3S)-2,3-dihydro-[1,4]dioxino[2,3-b]pyridin-3-yl]phenyl]methyl]-4-piperidyl]-2-(2-oxopyrrolidin-1-yl)acetamide |
| 290 | 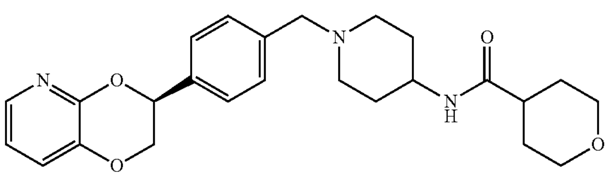 [SMILES: O=C(NC1CCN(Cc2ccc([C@H]3COc4cccnc4O3)cc2)CC1)C1CCOCC1] | N-[1-[[4-[(3S)-2,3-dihydro-[1,4]dioxino[2,3-b]pyridin-3-yl]phenyl]methyl]-4-piperidyl]tetrahydropyran-4-carboxamide |
| 291 | 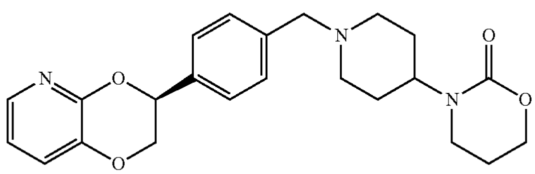 [SMILES: O=C1OCCCN1C1CCN(Cc2ccc([C@H]3COc4cccnc4O3)cc2)CC1] | 3-{1-[(S)-4-(2,3-Dihydro-[1,4]dioxino[2,3-b]pyridin-3-yl)-benzyl]-piperidin-4-yl}-[1,3]oxazin-2-one |
| 292 | 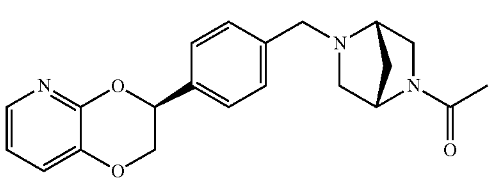 [SMILES: CC(=O)N1C[C@@H]2C[C@H]1CN2Cc1ccc([C@H]2COc3cccnc3O2)cc1] | 1-{(1S,4S)-5-[(S)-4-(2,3-Dihydro-[1,4]dioxino[2,3-b]pyridin-3-yl)-benzyl]-2,5-diaza-bicyclo[2.2.1]hept-2-yl}-ethanone |

TABLE 1-continued

Exemplary compounds of the invention.

| Cpd No. | Structure | Name |
|---|---|---|
| 293 | 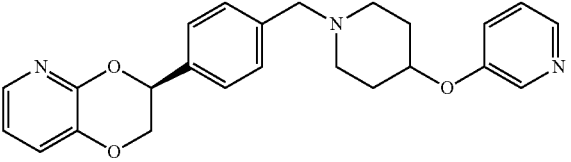 [SMILES: c1cncc(OC2CCN(Cc3ccc([C@H]4COc5cccnc5O4)cc3)CC2)c1] | (S)-3-{4-[4-(Pyridin-3-yloxy)-piperidin-1-ylmethyl]-phenyl]-2,3-dihydro-[1,4]dioxino[2,3-b]pyridine |
| 294 | 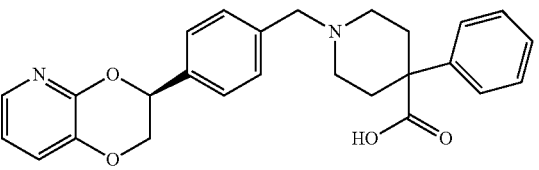 [SMILES: O=C(O)C1(c2ccccc2)CCN(Cc2ccc([C@H]3COc4cccnc4O3)cc2)CC1] | 1-[(S)-4-(2,3-Dihydro-[1,4]dioxino[2,3-b]pyridin-3-yl)-benzyl]-4-phenyl-piperidine-4-carboxylic acid |
| 295 | 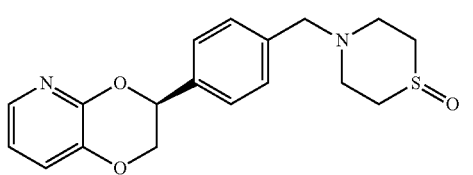 [SMILES: O=S1CCN(Cc2ccc([C@H]3COc4cccnc4O3)cc2)CC1] | (S)-3-[4-(1-Oxo-1lambda4-thiomorpholin-4-ylmethyl)-phenyl]-2,3-dihydro-[1,4]dioxino[2,3-b]pyridine |
| 296 | 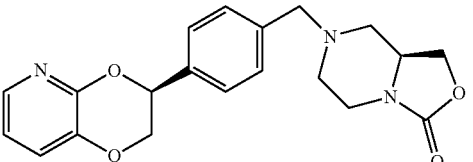 | (S)-7-[(S)-4-(2,3-Dihydro-[1,4]dioxino[2,3-b]pyridin-3-yl)-benzyl]-hexahydro-oxazolo[3,4-a]pyrazin-3-one |

In one embodiment, the invention relates to any of the compounds 240-296 depicted in Table 1, and pharmaceutically acceptable salts thereof.

In another embodiment, the invention relates to a compound selected from the group consisting of:
4-(1-{4-[(2S)-2,3-dihydro-1,4-benzodioxin-2-yl]benzyl}piperidin-4-yl)butanoic acid;
4-(1-{4-[(3S)-2,3-dihydro[1,4]dioxino[2,3-b]pyridin-3-yl]benzyl}piperidin-4-yl)benzoic acid;
(3S)-3-{4[(1s,4s)-7-azabicyclo[2.2.1]hept-7-ylmethyl]phenyl}-2,3-dihydro[1,4]dioxino[2,3-b]pyridine;
N-(1-{4-[(3S)-2,3-dihydro[1,4]dioxino[2,3-b]pyridin-3-yl]benzyl}piperidin-4-yl)methanesulfonamide;
(3S)-3-[4-(azepan-1-ylmethyl)phenyl]-2,3-dihydro[1,4]dioxino[2,3-b]pyridine;
1-{4-[(2S)-2,3-dihydro-1,4-benzodioxin-2-yl]benzyl}-2-methylpiperidine;
7-{4-[(2S)-2,3-dihydro-1,4-benzodioxin-2-yl]benzyl}-1,7-diazaspiro[4.4]nonane-1-carboxamide;
7-{4-[(3S)-2,3-dihydro[1,4]dioxino[2,3-b]pyridin-3-yl]benzyl}-1,7-diazaspiro[4.4]nonan-2-one;
1-{4-[(2S)-2,3-dihydro-1,4-benzodioxin-2-yl]benzyl}piperidine-4-carboxylic acid;
(1-{4-[(2S)-2,3-dihydro-1,4-benzodioxin-2-yl]benzyl}piperidin-4-yl)(morpholin-4-yl)methanone;
8-{4-[(3S)-2,3-dihydro[1,4]dioxino[2,3-b]pyridin-3-yl]benzyl}-1,3,8-triazaspiro[4.5]decane-2,4-dione;
(3S)-3-{4-[(3-methoxypiperidin-1-yl)-methyl]phenyl}-2,3-dihydro[1,4]dioxino[2,3-b]pyridine;
N-(1-{4-[(2S)-2,3-dihydro-1,4-benzodioxin-2-yl]benzyl}pyrrolidin-3-yl)-N-methylacetamide;
1-{4-[(2S)-2,3-dihydro-1,4-benzodioxin-2-yl]benzyl}-4-(1,1-dioxido-1,2-thiazolidin-2-yl)piperidine;
(3R)-1-{4-[(3S)-2,3-dihydro[1,4]dioxino[2,3-b]pyridin-3-yl]benzyl}pyrrolidin-3-ol;
N-(1-{4-[(3S)-2,3-dihydro[1,4]dioxino[2,3-b]pyridin-3-yl]benzyl}piperidin-4-yl)-2-hydroxyacetamide;
4-[(1-{4-[(3S)-2,3-dihydro[1,4]dioxino[2,3-b]pyridin-3-yl]benzyl}piperidin-4-yl)methyl]benzoic acid;
(1-{4-[(3S)-2,3-dihydro[1,4]dioxino[2,3-b]pyridin-3-yl]benzyl}piperidin-4-yl)(morpholin-4-yl)methanone;
(3S)-3-[4-(morpholin-4-ylmethyl)phenyl]-2,3-dihydro[1,4]dioxino[2,3-b]pyridine;
8-{4-[(2S)-2,3-dihydro-1,4-benzodioxin-2-yl]benzyl}-2,8-diazaspiro[4.5]decan-1-one;
1-{4-[(3S)-2,3-dihydro[1,4]dioxino[2,3-b]pyridin-3-yl]benzyl}piperidine-4-carbonitrile;
1-{4-[(2S)-2,3-dihydro-1,4-benzodioxin-2-yl]benzyl}-N-methylpiperidine-4-carboxamide;
8-{4-[(3S)-2,3-dihydro[1,4]dioxino[2,3-b]pyridin-3-yl]benzyl}-2,8-diazaspiro[4.5]decan-1-one;
N-(1-{4-[(3S)-2,3-dihydro[1,4]dioxino[2,3-b]pyridin-3-yl]benzyl}piperidin-4-yl)-2-hydroxy-2-methylpropanamide;
N-(1-{4-[(3S)-2,3-dihydro[1,4]dioxino[2,3-b]pyridin-3-yl]benzyl}piperidin-4-yl)-1-hydroxycyclopropanecarboxamide;
N-{4-[(2S)-2,3-dihydro-1,4-benzodioxin-2-yl]benzyl}-N-ethylcyclopentanamine;
1-{4-[(3S)-2,3-dihydro[1,4]dioxino[2,3-b]pyridin-3-yl]benzyl}-N-methylpiperidine-4-carboxamide;
N-{4-[(3S)-2,3-dihydro[1,4]dioxino[2,3-b]pyridin-3-yl]benzyl}-N-methylcyclopentanamine;
1-[(1-{4-[(3S)-2,3-dihydro[1,4]dioxino[2,3-b]pyridin-3-yl]benzyl}piperidin-3-yl)methyl]pyrrolidin-2-one;
1-{4-[(2S)-2,3-dihydro-1,4-benzodioxin-2-yl]benzyl}-2-methylpyrrolidine;

N-{4-[(3S)-2,3-dihydro[1,4]dioxino[2,3-b]pyridin-3-yl]
benzyl}-2-methyl-1-(pyrrolidin-1-yl)propan-2-amine;
N-cyclohexyl-N-{4-[(2S)-2,3-dihydro-1,4-benzodioxin-2-
yl]benzyl}-N',N'-dimethylethane-1,2-diamine;
N-(1-{4-[(3S)-2,3-dihydro[1,4]dioxino[2,3-b]pyridin-3-yl]
benzyl}piperidin-4-yl)acetamide;
N-{4-[(3S)-2,3-dihydro[1,4]dioxino[2,3-b]pyridin-3-yl]
benzyl}-N-methyl-2-(pyridin-2-yl)ethanamine;
(3S)-3-[4-(pyrrolidin-1-ylmethyl)phenyl]-2,3-dihydro[1,4]
dioxino[2,3-b]pyridine;
1-{4-[(3S)-2,3-dihydro[1,4]dioxino[2,3-b]pyridin-3-yl]
benzyl}piperidine-3-carboxamide;
1-{4-[(3S)-2,3-dihydro[1,4]dioxino[2,3-b]pyridin-3-yl]
benzyl}piperidine-4-carboxamide;
N-(1-{4-[(2S)-2,3-dihydro-1,4-benzodioxin-2-yl]
benzyl}pyrrolidin-3-yl)acetamide;
1-{4-[(3S)-2,3-dihydro[1,4]dioxino[2,3-b]pyridin-3-yl]benzyl}-N-(2-hydroxyethyl)piperidine-4-carboxamide;
(3S)-3-[4-(1,4-oxazepan-4-ylmethyl)phenyl]-2,3-dihydro[1,4]dioxino[2,3-b]pyridine;
1-{4-[(2S)-2,3-dihydro-1,4-benzodioxin-2-yl]benzyl}-N-(2-hydroxyethyl)piperidine-4-carboxamide;
4-(1-{4-[(2S)-2,3-dihydro-1,4-benzodioxin-2-yl]
benzyl}piperidin-4-yl)benzoic acid;
1-(1-{4-[(2S)-2,3-dihydro-1,4-benzodioxin-2-yl]
benzyl}piperidin-4-yl)urea;
7-{4-[(2S)-2,3-dihydro-1,4-benzodioxin-2-yl]benzyl}-1,7-
diazaspiro[4.4]nonan-2-one;
8-{4-[(3S)-2,3-dihydro[1,4]dioxino[2,3-b]pyridin-3-yl]benzyl}-2-methyl-2,8-diazaspiro[4.5]decan-1-one;
1-{4-[(3S)-2,3-dihydro[1,4]dioxino[2,3-b]pyridin-3-yl]
benzyl}piperidin-4-ol;
N-(1-{4-[(2S)-2,3-dihydro-1,4-benzodioxin-2-yl]
benzyl}piperidin-4-yl)methanesulfonamide;
3-(1-{4-[(3S)-2,3-dihydro[1,4]dioxino[2,3-b]pyridin-3-yl]
benzyl}piperidin-4-yl)propan-1-ol;
(3S)-3-{4-[(4-methylpiperidin-1-yl)methyl]phenyl}-2,3-di-
hydro[1,4]dioxino[2,3-b]pyridine;
N-{4-[(3S)-2,3-dihydro[1,4]dioxino[2,3-b]pyridin-3-yl]
benzyl}-N-ethylethanamine;
N-{4-[(3S)-2,3-dihydro[1,4]dioxino[2,3-b]pyridin-3-yl]
benzyl}-1-(methylsulfonyl)piperidin-4-amine;
(3S)-3-{4-[(4-fluoropiperidin-1-yl)methyl]phenyl}-2,3-di-
hydro[1,4]dioxino[2,3-b]pyridine;
1-(4-{4-[(3S)-2,3-dihydro[1,4]dioxino[2,3-b]pyridin-3-yl]
benzyl}-1,4-diazepan-1-yl)ethanone;
[(3R)-1-{4-[(2S)-2,3-dihydro-1,4-benzodioxin-2-yl]
benzyl}piperidin-3-yl]acetic acid;
(1-{4-[(3S)-2,3-dihydro[1,4]dioxino[2,3-b]pyridin-3-yl]
benzyl}piperidin-4-yl)-methanol;
4-[(1-{4-[(2S)-2,3-dihydro-1,4-benzodioxin-2-yl]
benzyl}piperidin-4-yl)methyl]benzoic acid;
(3S)-3-{4-[(4-methyl-1,4-diazepan-1-yl)methyl]phenyl}-2,
3-dihydro[1,4]dioxino[2,3-b]pyridine;
(3S)-3-{4-[(3-methoxypyrrolidin-1-yl)methyl]phenyl}-2,3-
dihydro[1,4]dioxino[2,3-b]pyridine; and
N-{4-[(2S)-2,3-dihydro-1,4-benzodioxin-2-yl]benzyl}-N,2-
dimethylpropan-2-amine; or
a pharmaceutically salt thereof of each of the foregoing.

In another embodiment, the invention relates to a compound selected from the group consisting of:
(3S)-3-[4-(azepan-1-ylmethyl)phenyl]-2,3-dihydro[1,4]di-
oxino[2,3-b]pyridine;
N-{4-[(3S)-2,3-dihydro[1,4]dioxino[2,3-b]pyridin-3-yl]
benzyl}-N-methylcyclopentanamine;
N-(1-{4-[(3S)-2,3-dihydro[1,4]dioxino[2,3-b]pyridin-3-yl]
benzyl}piperidin-4-yl)methanesulfonamide;
(3S)-3-{4-[(3-methoxypiperidin-1-yl)methyl]phenyl}-2,3-
dihydro[1,4]dioxino[2,3-b]pyridine;
(3S)-3-{4-[(4-methylpiperidin-1-yl)methyl]phenyl}-2,3-di-
hydro[1,4]dioxino[2,3-b]pyridine;
N-(1-{4-[(3S)-2,3-dihydro[1,4]dioxino[2,3-b]pyridin-3-yl]
benzyl}piperidin-4-yl)acetamide;
(3S)-3-{4-[(1s,4s)-7-azabicyclo[2.2.1]hept-7-ylmethyl]phe-
nyl}-2,3-dihydro[1,4]dioxino[2,3-b]pyridine;
(3S)-3-[4-(pyrrolidin-1-ylmethyl)phenyl]-2,3-dihydro[1,4]
dioxino[2,3-b]pyridine;
N-{4-[(3S)-2,3-dihydro[1,4]dioxino[2,3-b]pyridin-3-yl]
benzyl}-N-ethylethanamine;
N-(1-{4-[(2S)-2,3-dihydro-1,4-benzodioxin-2-yl]
benzyl}pyrrolidin-3-yl)-N-methylacetamide;
N-{4-[(3S)-2,3-dihydro[1,4]dioxino[2,3-b]pyridin-3-yl]
benzyl}-2-methyl-1-(pyrrolidin-1-yl)propan-2-amine;
1-{4-[(3S)-2,3-dihydro[1,4]dioxino[2,3-b]pyridin-3-yl]
benzyl}piperidin-4-ol;
8-{4-[(3S)-2,3-dihydro[1,4]dioxino[2,3-b]pyridin-3-yl]benzyl}-2,8-diazaspiro[4.5]decan-1-one;
(1-{4-[(3S)-2,3-dihydro[1,4]dioxino[2,3-b]pyridin-3-yl]
benzyl}piperidin-4-yl)(morpholin-4-yl)methanone;
N-(1-{4-[(2S)-2,3-dihydro-1,4-benzodioxin-2-yl]
benzyl}pyrrolidin-3-yl)acetamide;
1-{4-[(3S)-2,3-dihydro[1,4]dioxino[2,3-b]pyridin-3-yl]benzyl}-N-methylpiperidine-4-carboxamide;
7-{4-[(3S)-2,3-dihydro[1,4]dioxino[2,3-b]pyridin-3-yl]benzyl}-1,7-diazaspiro[4.4]nonan-2-one;
(3S)-3-[4-(1,4-oxazepan-4-ylmethyl)phenyl]-2,3-dihydro[1,4]dioxino[2,3-b]pyridine;
3-(1-{4-[(3S)-2,3-dihydro[1,4]dioxino[2,3-b]pyridin-3-yl]
benzyl}piperidin-4-yl)propan-1-ol;
8-{4-[(3S)-2,3-dihydro[1,4]dioxino[2,3-b]pyridin-3-yl]benzyl}-2-methyl-2,8-diazaspiro[4.5]decan-1-one;
(3S)-3-{4-[(4-methyl-1,4-diazepan-1-yl)-methyl]phenyl}-2,
3-dihydro[1,4]dioxino[2,3-b]pyridine;
4-(1-{4-[(2S)-2,3-dihydro-1,4-benzodioxin-2-yl]
benzyl}piperidin-4-yl)benzoic acid;
(3R)-1-{4-[(3S)-2,3-dihydro[1,4]dioxino[2,3-b]pyridin-3-
yl]benzyl}pyrrolidin-3-ol;
1-(4-{4-[(3S)-2,3-dihydro[1,4]dioxino[2,3-b]pyridin-3-yl]
benzyl}-1,4-diazepan-1-yl)ethanone;
1-{4-[(3S)-2,3-dihydro[1,4]dioxino[2,3-b]pyridin-3-yl]
benzyl}piperidine-4-carbonitrile;
N-(1-{4-[(3S)-2,3-dihydro[1,4]dioxino[2,3-b]pyridin-3-yl]
benzyl}piperidin-4-yl)-2-hydroxy-2-methylpropanamide;
1-{4-[(3S)-2,3-dihydro[1,4]dioxino[2,3-b]pyridin-3-yl]
benzyl}piperidine-3-carboxamide;
(1-{4-[(3S)-2,3-dihydro[1,4]dioxino[2,3-b]pyridin-3-yl]
benzyl}piperidin-4-yl)-methanol;
8-{4-[(3S)-2,3-dihydro[1,4]dioxino[2,3-b]pyridin-3-yl]benzyl}-1,3,8-triazaspiro[4.5]decane-2,4-dione;
N-(1-{4-[(3S)-2,3-dihydro[1,4]dioxino[2,3-b]pyridin-3-yl]
benzyl}piperidin-4-yl)-1-hydroxycyclopropanecarboxa-
mide;
1-{4-[(2S)-2,3-dihydro-1,4-benzodioxin-2-yl]benzyl}-N-
(2-hydroxyethyl)piperidine-4-carboxamide;
N-{4-[(3S)-2,3-dihydro[1,4]dioxino[2,3-b]pyridin-3-yl]
benzyl}-1-(methylsulfonyl)piperidin-4-amine;
1-{4-[(3S)-2,3-dihydro[1,4]dioxino[2,3-b]pyridin-3-yl]
benzyl}piperidine-4-carboxamide;
4-(1-{4-[(3S)-2,3-dihydro[1,4]dioxino[2,3-b]pyridin-3-yl]
benzyl}piperidin-4-yl)benzoic acid;
1-{4-[(2S)-2,3-dihydro-1,4-benzodioxin-2-yl]benzyl}-2-
methylpyrrolidine;
1-[(1-{4-[(3S)-2,3-dihydro[1,4]dioxino[2,3-b]pyridin-3-yl]
benzyl}piperidin-3-yl)methyl]pyrrolidin-2-one;

7-{4-[(2S)-2,3-dihydro-1,4-benzodioxin-2-yl]benzyl}-1,7-diazaspiro[4.4]nonan-2-one;
1-(1-{4-[(2S)-2,3-dihydro-1,4-benzodioxin-2-yl]benzyl}piperidin-4-yl)urea;
N-{4-[(2S)-2,3-dihydro-1,4-benzodioxin-2-yl]benzyl}-N-ethylcyclopentanamine;
N-{4-[(3S)-2,3-dihydro[1,4]dioxino[2,3-b]pyridin-3-yl]benzyl}-N-methyl-2-(pyridin-2-yl)ethanamine;
1-{4-[(2S)-2,3-dihydro-1,4-benzodioxin-2-yl]benzyl}-2-methylpiperidine;
1-{4-[(2S)-2,3-dihydro-1,4-benzodioxin-2-yl]benzyl}piperidine-4-carboxylic acid;
4-[(1-{4-[(3S)-2,3-dihydro[1,4]dioxino[2,3-b]pyridin-3-yl]benzyl}piperidin-4-yl)methyl]benzoic acid;
(3S)-3-[4-(morpholin-4-ylmethyl)phenyl]-2,3-dihydro[1,4]dioxino[2,3-b]pyridine;
(3S)-3-{4-[(4-fluoropiperidin-1-yl)-methyl]phenyl}-2,3-dihydro[1,4]dioxino[2,3-b]pyridine;
(1-{4-[(2S)-2,3-dihydro-1,4-benzodioxin-2-yl]benzyl}piperidin-4-yl)(morpholin-4-yl)methanone;
8-{4-[(2S)-2,3-dihydro-1,4-benzodioxin-2-yl]benzyl}-2,8-diazaspiro[4.5]decan-1-one;
N-(1-{4-[(3S)-2,3-dihydro[1,4]dioxino[2,3-b]pyridin-3-yl]benzyl}piperidin-4-yl)-2-hydroxyacetamide;
4-[(1-{4-[(2S)-2,3-dihydro-1,4-benzodioxin-2-yl]benzyl}piperidin-4-yl)-methyl]benzoic acid;
N-(1-{4-[(2S)-2,3-dihydro-1,4-benzodioxin-2-yl]benzyl}piperidin-4-yl)methanesulfonamide;
1-{4-[(2S)-2,3-dihydro-1,4-benzodioxin-2-yl]benzyl}-N-methylpiperidine-4-carboxamide;
4-(1-{4-[(2S)-2,3-dihydro-1,4-benzodioxin-2-yl]benzyl}piperidin-4-yl)butanoic acid;
7-{4-[(2S)-2,3-dihydro-1,4-benzodioxin-2-yl]benzyl}-1,7-diazaspiro[4.4]nonane-1-carboxamide;
N-cyclohexyl-N-{4-[(2S)-2,3-dihydro-1,4-benzodioxin-2-yl]benzyl}-N',N'-dimethylethane-1,2-diamine;
[(3R)-1-{4-[(2S)-2,3-dihydro-1,4-benzodioxin-2-yl]benzyl}piperidin-3-yl]acetic acid;
1-{4-[(2S)-2,3-dihydro-1,4-benzodioxin-2-yl]benzyl}-4-(1,1-dioxido-1,2-thiazolidin-2-yl)piperidine; and
1-{4-[(3S)-2,3-dihydro[1,4]dioxino[2,3-b]pyridin-3-yl]benzyl}-N-(2-hydroxyethyl)piperidine-4-carboxamide; or
a pharmaceutically acceptable salt thereof of each of the foregoing.

In another embodiment, the invention relates to a compound selected from the group consisting of:
4-{4-[(3S)-2,3-Dihydro[1,4]dioxino[2,3-b]pyridin-3-yl]benzyl}piperazine-1-carboxamide;
7-[(S)-4-(2,3-Dihydro-[1,4]dioxino[2,3-b]pyridin-3-yl)-benzyl]-5,6,7,8-tetrahydro-[1,2,4]triazolo[4,3-a]pyrazine-3-carboxylic acid amide;
7-[(S)-4-(2,3-dihydro-[1,4]dioxino[2,3-b]pyridin-3-yl)-benzyl]-5,6,7,8-tetrahydro-[1,2,4]triazolo[4,3-a]pyrazine-3-carboxylic acid methylamide;
7-[(S)-4-(2,3-Dihydro-[1,4]dioxino[2,3-b]pyridin-3-yl)-benzyl]-5,6,7,8-tetrahydro-imidazo[1,2-a]pyrazine-2-carboxylic acid amide;
7-[(S)-4-(2,3-dihydro-[1,4]dioxino[2,3-b]pyridin-3-yl)-benzyl]-5,6,7,8-tetrahydro-imidazo[1,2-a]pyrazine-2-carboxylic acid methylamide;
6-[(S)-4-(2,3-dihydro-[1,4]dioxino[2,3-b]pyridin-3-yl)-benzyl]-5,6,7,8-tetrahydro-4H-1,2,3a,6-tetraaza-azulene-3-carboxylic acid amide;
6-[(S)-4-(2,3-Dihydro-[1,4]dioxino[2,3-b]pyridin-3-yl)-benzyl]-5,6,7,8-tetrahydro-4H-1,2,3a,6-tetraaza-azulene-3-carboxylic acid methylamide;
[(1α,5α,6α)-3-[(S)-4-(2,3-dihydro-[1,4]dioxino[2,3-b]pyridin-3-yl)-benzyl]-3-aza-bicyclo[3.1.0]hexane]-6-carboxylic acid ((S)-2-hydroxy-propyl)-amide;
[(1α,5α,6α)-3-[(S)-4-(2,3-Dihydro-[1,4]dioxino[2,3-b]pyridin-3-yl)-benzyl]-3-aza-bicyclo[3.1.0]hexane]-6-carboxylic acid ((S)-2-hydroxy-1-methyl-ethyl)-amide;
7-[(S)-4-(2,3-Dihydro-[1,4]dioxino[2,3-b]pyridin-3-yl)-benzyl]-5,6,7,8-tetrahydro-imidazo[1,2-a]pyrazine-3-carbonitrile;
N-{(1α,5α,6α)-3-[(S)-4-(2,3-Dihydro-[1,4]dioxino[2,3-b]pyridin-3-yl)-benzyl]-3-aza-bicyclo[3.1.0]hex-6-yl}-acetamide;
[(1α,5α,6α)-3-[(S)-4-(2,3-Dihydro-[1,4]dioxino[2,3-b]pyridin-3-yl)-benzyl]-3-aza-bicyclo[3.1.0]hexane-6-carboxylic acid (2-hydroxy-2-methyl-propyl)]-amide;
N-{1-[(S)-4-(2,3-Dihydro-[1,4]dioxino[2,3-b]pyridin-3-yl)-benzyl]-piperidin-4-yl}-2-methoxy-acetamide;
1-{4-[(S)-4-(2,3-Dihydro-[1,4]dioxino[2,3-b]pyridin-3-yl)-benzyl]-piperazin-1-yl}-2-hydroxy-ethanone;
4-{1-[(S)-4-(2,3-Dihydro-benzo[1,4]dioxin-2-yl)-benzyl]-azetidin-3-yl}-benzoic acid;
1-[(S)-4-(2,3-Dihydro-[1,4]dioxino[2,3-b]pyridin-3-yl)-benzyl]-piperidine-4-carboxylic acid (2-hydroxy-2-methyl-propyl)-amide;
1-{(1S,4S)-5-[(S)-4-(2,3-Dihydro-[1,4]dioxino[2,3-b]pyridin-3-yl)-benzyl]-2,5-diaza-bicyclo[2.2.1]hept-2-yl}-2-methanesulfonyl-ethanone;
1-{4-[(S)-4-(2,3-Dihydro-[1,4]dioxino[2,3-b]pyridin-3-yl)-benzyl]-[1,4]diazepan-1-yl}-2-methoxy-ethanone;
5-[(S)-4-(2,3-Dihydro-[1,4]dioxino[2,3-b]pyridin-3-yl)-benzyl]-4,5,6,7-tetrahydro-thiazolo[5,4-c]pyridin-2-ylamine;
{(endo)-8-[(S)-4-(2,3-Dihydro-[1,4]dioxino[2,3-b]pyridin-3-yl)-benzyl]-8-aza-bicyclo[3.2.1]oct-3-yl}-urea;
2-{1-[(S)-4-(2,3-Dihydro-[1,4]dioxino[2,3-b]pyridin-3-yl)-benzyl]-piperidin-4-yl}-N-methoxy-acetamide;
(R)-N-{1-[(S)-4-(2,3-Dihydro-[1,4]dioxino[2,3-b]pyridin-3-yl)-benzyl]-piperidin-4-yl}-2-methylamino-propionamide;
N-{1-[(S)-4-(2,3-Dihydro-[1,4]dioxino[2,3-b]pyridin-3-yl)-benzyl]-piperidin-4-ylmethyl}-2-hydroxy-2-methyl-propionamide;
N-{(1α,5α,6α)-3-[(S)-4-(2,3-Dihydro-[1,4]dioxino[2,3-b]pyridin-3-yl)-benzyl]-3-aza-bicyclo[3.1.0]hex-6-ylmethyl}-methanesulfonamide;
1-{(1S,4S)-5-[(S)-4-(2,3-Dihydro-[1,4]dioxino[2,3-b]pyridin-3-yl)-benzyl]-2,5-diaza-bicyclo[2.2.2]oct-2-yl}-ethanone;
4-{1-[(S)-4-(2,3-Dihydro-[1,4]dioxino[2,3-b]pyridin-3-yl)-benzyl]-piperidin-4-yl}-cyclohexanecarboxylic acid;
1-[(S)-4-(2,3-Dihydro-benzo[1,4]dioxin-2-yl)-benzyl]-azepane-4-carboxylic acid;
[(1α,5α,6α)-3-[(S)-4-(2,3-Dihydro-benzo[1,4]dioxin-2-yl)-benzyl]-3-aza-bicyclo[3.1.0]hexane]-6-carboxylic acid;
(1S,4S)-5-[(S)-4-(2,3-Dihydro-[1,4]dioxino[2,3-b]pyridin-3-yl)-benzyl]-2,5-diaza-bicyclo[2.2.1]heptane-2-carboxylic acid amide;
1-[(S)-4-(2,3-Dihydro-[1,4]dioxino[2,3-b]pyridin-3-yl)-benzyl]-4-phenyl-piperidin-4-ol;
1-{5-[(S)-4-(2,3-Dihydro-[1,4]dioxino[2,3-b]pyridin-3-yl)-benzyl]-hexahydro-pyrrolo[3,4-c]pyrrol-2-yl}-ethanone;
1-{8-[(S)-4-(2,3-Dihydro-[1,4]dioxino[2,3-b]pyridin-3-yl)-benzyl]-3,8-diaza-bicyclo[3.2.1]oct-3-yl}-ethanone;
5-[(S)-4-(2,3-Dihydro-[1,4]dioxino[2,3-b]pyridin-3-yl)-benzyl]-hexahydro-pyrrolo[3,4-c]pyrrole-2-carboxylic acid amide;

{(exo)-8-[(S)-4-(2,3-Dihydro-[1,4]dioxino[2,3-b]pyridin-3-yl)-benzyl]-8-aza-bicyclo[3.2.1]oct-3-yl}-urea;
2-{1-[(S)-4-(2,3-Dihydro-[1,4]dioxino[2,3-b]pyridin-3-yl)-benzyl]-piperidin-4-yloxy}-acetamide;
(S)-3-[4-(1,1-Dioxo-1lambda6-[1,4]thiazepan-4-ylmethyl)-phenyl]-2,3-dihydro-[1,4]dioxino[2,3-b]pyridine;
1-[(S)-4-(2,3-Dihydro-[1,4]dioxino[2,3-b]pyridin-3-yl)-benzyl]-4-methyl-piperidin-4-ol;
1-{(1S,4S)-5-[(S)-4-(2,3-Dihydro-[1,4]dioxino[2,3-b]pyridin-3-yl)-benzyl]-2,5-diaza-bicyclo[2.2.1]hept-2-yl}-2-hydroxy-ethanone;
N-{(endo)-8-[(S)-4-(2,3-Dihydro-[1,4]dioxino[2,3-b]pyridin-3-yl)-benzyl]-8-aza-bicyclo[3.2.1]oct-3-yl}-acetamide;
N-{1-[(S)-4-(2,3-Dihydro-[1,4]dioxino[2,3-b]pyridin-3-yl)-benzyl]-piperidin-4-ylmethyl}-acetamide;
[(S)-4-(2,3-Dihydro-[1,4]dioxino[2,3-b]pyridin-3-yl)-benzyl]-(1,1-dioxo-tetrahydro-1lambda-6-thiophen-3-yl)-methyl-amine;
1-{(1S,4S)-5-[(S)-4-(2,3-Dihydro-[1,4]dioxino[2,3-b]pyridin-3-yl)-benzyl]-2,5-diaza-bicyclo[2.2.2]oct-2-yl}-2-hydroxy-ethanone;
{1-[(S)-4-(2,3-dihydro-[1,4]dioxino-[2,3-b]pyridin-3-yl)-benzyl]-spiro-[3H-indole-3,4'-piperidine]-1(2H)-urea;
{1-[(S)-4-(2,3-Dihydro-[1,4]dioxino[2,3-b]pyridin-3-yl)-benzyl]-piperidin-4-ylmethyl}-urea;
{4-[(S)-4-(2,3-Dihydro-[1,4]dioxino[2,3-b]pyridin-3-yl)-benzyl]-piperazin-1-yl}-acetonitrile;
(R)-7-[(S)-4-(2,3-Dihydro-[1,4]dioxino[2,3-b]pyridin-3-yl)-benzyl]-hexahydro-oxazolo[3,4-a]pyrazin-3-one;
{1-[(S)-4-(2,3-Dihydro-[1,4]dioxino[2,3-b]pyridin-3-yl)-benzyl]-piperidin-4-yl}-(3-hydroxy-azetidin-1-yl)-methanone;
1-[(S)-4-(2,3-Dihydro-[1,4]dioxino[2,3-b]pyridin-3-yl)-benzyl]-piperidine-4-carboxylic acid [(S)-1-(tetrahydro-furan-2-yl)-methyl]-amide;
N-[3-[4-[[4-[(3S)-2,3-dihydro-[1,4]dioxino[2,3-b]pyridin-3-yl]phenyl]methyl]piperazin-1-yl]-3-oxo-propyl]acetamide;
N-[1-[[4-[(3S)-2,3-dihydro-[1,4]dioxino[2,3-b]pyridin-3-yl]phenyl]methyl]-4-piperidyl]-2-(2-oxopyrrolidin-1-yl)acetamide;
N-[1-[[4-[(3S)-2,3-dihydro-[1,4]dioxino[2,3-b]pyridin-3-yl]phenyl]methyl]-4-piperidyl]tetrahydropyran-4-carboxamide;
3-{1-[(S)-4-(2,3-Dihydro-[1,4]dioxino[2,3-b]pyridin-3-yl)-benzyl]-piperidin-4-yl}-[1,3]oxazinan-2-one;
1-{(1S,4S)-5-[(S)-4-(2,3-Dihydro-[1,4]dioxino[2,3-b]pyridin-3-yl)-benzyl]-2,5-diaza-bicyclo[2.2.1]hept-2-yl}-ethanone;
(S)-3-{4-[4-(Pyridin-3-yloxy)-piperidin-1-ylmethyl]-phenyl}-2,3-dihydro-[1,4]dioxino[2,3-b]pyridine;
1-[(S)-4-(2,3-Dihydro-[1,4]dioxino[2,3-b]pyridin-3-yl)-benzyl]-4-phenyl-piperidine-4-carboxylic acid;
(S)-3-[4-(1-Oxo-1lambda4-thiomorpholin-4-ylmethyl)-phenyl]-2,3-dihydro-[1,4]dioxino[2,3-b]pyridine; and
(S)-7-[(S)-4-(2,3-Dihydro-[1,4]dioxino[2,3-b]pyridin-3-yl)-benzyl]-hexahydro-oxazolo[3,4-a]pyrazin-3-one;
or a pharmaceutically acceptable salt thereof of each of the foregoing.

In another embodiment, the invention relates to a compound selected from the group consisting of:
3-[(4-{4-[(2S)-2,3-dihydro-1,4-benzodioxin-2-yl]benzyl}piperazin-1-yl)-methyl]benzoic acid,
7-[(S)-4-(2,3-dihydro-[1,4]dioxino[2,3-b]pyridin-3-yl)-benzyl]-5,6,7,8-tetrahydro-[1,2,4]triazolo[4,3-a]pyrazine-3-carboxylic acid ethyl ester,
7-[(S)-4-(2,3-Dihydro-[1,4]dioxino[2,3-b]pyridin-3-yl)-benzyl]-5,6,7,8-tetrahydro-[1,2,4]triazolo[4,3-a]pyrazine-3-carboxylic acid amide,
7-[(S)-4-(2,3-dihydro-[1,4]dioxino[2,3-b]pyridin-3-yl)-benzyl]-5,6,7,8-tetrahydro-[1,2,4]triazolo[4,3-a]pyrazine-3-carboxylic acid methylamide,
7-[(S)-4-(2,3-dihydro-[1,4]dioxino[2,3-b]pyridin-3-yl)-benzyl]-5,6,7,8-tetrahydro-imidazo[1,2-a]pyrazine-2-carboxylic acid amide,
7-[(S)-4-(2,3-Dihydro-[1,4]dioxino[2,3-b]pyridin-3-yl)-benzyl]-5,6,7,8-tetrahydro-imidazo[1,2-a]pyrazine-2-carboxylic acid methylamide,
6-[(S)-4-(2,3-dihydro-[1,4]dioxino[2,3-b]pyridin-3-yl)-benzyl]-5,6,7,8-tetrahydro-4H-1,2,3a,6-tetraaza-azulene-3-carboxylic acid amide,
6-[(S)-4-(2,3-Dihydro-[1,4]dioxino[2,3-b]pyridin-3-yl)-benzyl]-5,6,7,8-tetrahydro-4H-1,2,3a,6-tetraaza-azulene-3-carboxylic acid methylamide,
[(1α,5α,6α)-3-[(S)-4-(2,3-dihydro-[1,4]dioxino[2,3-b]pyridin-3-yl)-benzyl]-3-aza-bicyclo[3.1.0]hexane]-6-carboxylic acid ((S)-2-hydroxy-propyl)-amide,
[(1α,5α,6α)-3-[(S)-4-(2,3-Dihydro-[1,4]dioxino[2,3-b]pyridin-3-yl)-benzyl]-3-aza-bicyclo[3.1.0]hexane]-6-carboxylic acid ((S)-2-hydroxy-1-methyl-ethyl)-amide,
7-[(S)-4-(2,3-Dihydro-[1,4]dioxino[2,3-b]pyridin-3-yl)-benzyl]-5,6,7,8-tetrahydro-imidazo[1,2-a]pyrazine-3-carbonitrile,
N-{(1α,5α,6α)-3-[(S)-4-(2,3-Dihydro-[1,4]dioxino[2,3-b]pyridin-3-yl)-benzyl]-3-aza-bicyclo[3.1.0]hex-6-yl}-acetamide,
[(1α,5α,6α)-3-[(S)-4-(2,3-Dihydro-[1,4]dioxino[2,3-b]pyridin-3-yl)-benzyl]-3-aza-bicyclo[3.1.0]hexane-6-carboxylic acid (2-hydroxy-2-methyl-propyl)]-amide,
N-{1-[(S)-4-(2,3-Dihydro-[1,4]dioxino[2,3-b]pyridin-3-yl)-benzyl]-piperidin-4-yl}-2-methoxy-acetamide,
1-{4-[(S)-4-(2,3-Dihydro-[1,4]dioxino[2,3-b]pyridin-3-yl)-benzyl]-piperazin-1-yl}-2-hydroxy-ethanone,
4-{1-[(S)-4-(2,3-Dihydro-benzo[1,4]dioxin-2-yl)-benzyl]-azetidin-3-yl}-benzoic acid,
1-[(S)-4-(2,3-Dihydro-[1,4]dioxino[2,3-b]pyridin-3-yl)-benzyl]-piperidine-4-carboxylic acid (2-hydroxy-2-methyl-propyl)-amide,
1-{(1S,4S)-5-[(S)-4-(2,3-Dihydro-[1,4]dioxino[2,3-b]pyridin-3-yl)-benzyl]-2,5-diaza-bicyclo[2.2.1]hept-2-yl}-2-methanesulfonyl-ethanone,
1-{4-[(S)-4-(2,3-Dihydro-[1,4]dioxino[2,3-b]pyridin-3-yl)-benzyl]-[1,4]diazepan-1-yl}-2-methoxy-ethanone,
5-[(S)-4-(2,3-Dihydro-[1,4]dioxino[2,3-b]pyridin-3-yl)-benzyl]-4,5,6,7-tetrahydro-thiazolo[5,4-c]pyridin-2-ylamine,
{(endo)-8-[(S)-4-(2,3-Dihydro-[1,4]dioxino[2,3-b]pyridin-3-yl)-benzyl]-8-aza-bicyclo[3.2.1]oct-3-yl}-urea,
2-{1-[(S)-4-(2,3-Dihydro-[1,4]dioxino[2,3-b]pyridin-3-yl)-benzyl]-piperidin-4-yl}-N-methoxy-acetamide,
(R)-N-{1-[(S)-4-(2,3-Dihydro-[1,4]dioxino[2,3-b]pyridin-3-yl)-benzyl]-piperidin-4-yl}-2-methylamino-propionamide,
N-{1-[(S)-4-(2,3-Dihydro-[1,4]dioxino[2,3-b]pyridin-3-yl)-benzyl]-piperidin-4-ylmethyl}-2-hydroxy-2-methyl-propionamide,
N-{(1α,5α,6α)-3-[(S)-4-(2,3-Dihydro-[1,4]dioxino[2,3-b]pyridin-3-yl)-benzyl]-3-aza-bicyclo[3.1.0]hex-6-ylmethyl}-methanesulfonamide,
1-{(1S,4S)-5-[(S)-4-(2,3-Dihydro-[1,4]dioxino[2,3-b]pyridin-3-yl)-benzyl]-2,5-diaza-bicyclo[2.2.2]oct-2-yl}-ethanone, 4-{1-[(S)-4-(2,3-Dihydro-[1,4]dioxino[2,3-b]pyridin-3-yl)-benzyl]-piperidin-4-yl}-cyclohexanecarboxylic acid,
1-[(S)-4-(2,3-Dihydro-benzo[1,4]dioxin-2-yl)-benzyl]-azepane-4-carboxylic acid,
[(1α,5α,6α)-3-[(S)-4-(2,3-Dihydro-benzo[1,4]dioxin-2-yl)-benzyl]-3-aza-bicyclo[3.1.0]hexane]-6-carboxylic acid,
(1S,4S)-5-[(S)-4-(2,3-Dihydro-[1,4]dioxino[2,3-b]pyridin-3-yl)-benzyl]-2,5-diaza-bicyclo[2.2.1]heptane-2-carboxylic acid amide,
1-[(S)-4-(2,3-Dihydro-[1,4]dioxino[2,3-b]pyridin-3-yl)-benzyl]-4-phenyl-piperidin-4-ol,
1-{5-[(S)-4-(2,3-Dihydro-[1,4]dioxino[2,3-b]pyridin-3-yl)-benzyl]-hexahydro-pyrrolo[3,4-c]pyrrol-2-yl}-ethanone,
1-{8-[(S)-4-(2,3-Dihydro-[1,4]dioxino[2,3-b]pyridin-3-yl)-benzyl]-3,8-diaza-bicyclo[3.2.1]oct-3-yl}-ethanone,
5-[(S)-4-(2,3-Dihydro-[1,4]dioxino[2,3-b]pyridin-3-yl)-benzyl]-hexahydro-pyrrolo[3,4-c]pyrrole-2-carboxylic acid amide,
{(exo)-8-[(S)-4-(2,3-Dihydro-[1,4]dioxino[2,3-b]pyridin-3-yl)-benzyl]-8-aza-bicyclo[3.2.1]oct-3-yl}-urea,
2-{1-[(S)-4-(2,3-Dihydro-[1,4]dioxino[2,3-b]pyridin-3-yl)-benzyl]-piperidin-4-yloxy}-acetamide,
(S)-3-[4-(1,1-Dioxo-1lambda6-[1,4]thiazepan-4-ylmethyl)-phenyl]-2,3-dihydro-[1,4]dioxino[2,3-b]pyridine,
1-[(S)-4-(2,3-Dihydro-[1,4]dioxino[2,3-b]pyridin-3-yl)-benzyl]-4-methyl-piperidin-4-ol,
1-{(1S,4S)-5-[(S)-4-(2,3-Dihydro-[1,4]dioxino[2,3-b]pyridin-3-yl)-benzyl]-2,5-diaza-bicyclo[2.2.1]hept-2-yl}-2-hydroxy-ethanone,
N-{(endo)-8-[(S)-4-(2,3-Dihydro-[1,4]dioxino[2,3-b]pyridin-3-yl)-benzyl]-8-aza-bicyclo[3.2.1]oct-3-yl}-acetamide,
N-{1-[(S)-4-(2,3-Dihydro-[1,4]dioxino[2,3-b]pyridin-3-yl)-benzyl]-piperidin-4-ylmethyl}-acetamide,
[(S)-4-(2,3-Dihydro-[1,4]dioxino[2,3-b]pyridin-3-yl)-benzyl]-(1,1-dioxo-tetrahydro-1lambda-6-thiophen-3-yl)-methyl-amine,
1-{(1S,4S)-5-[(S)-4-(2,3-Dihydro-[1,4]dioxino[2,3-b]pyridin-3-yl)-benzyl]-2,5-diaza-bicyclo[2.2.2]oct-2-yl}-2-hydroxy-ethanone,
{1-[(S)-4-(2,3-dihydro-[1,4]dioxino-[2,3-b]pyridin-3-yl)-benzyl]-spiro-[3H-indole-3,4'-piperidine]-1(2H)-urea,
{1-[(S)-4-(2,3-Dihydro-[1,4]dioxino[2,3-b]pyridin-3-yl)-benzyl]-piperidin-4-ylmethyl}-urea,
{4-[(S)-4-(2,3-Dihydro-[1,4]dioxino[2,3-b]pyridin-3-yl)-benzyl]-piperazin-1-yl}-acetonitrile,
(R)-7-[(S)-4-(2,3-Dihydro-[1,4]dioxino[2,3-b]pyridin-3-yl)-benzyl]-hexahydro-oxazolo[3,4-a]pyrazin-3-one,
{1-[(S)-4-(2,3-Dihydro-[1,4]dioxino[2,3-b]pyridin-3-yl)-benzyl]-piperidin-4-yl}-(3-hydroxy-azetidin-1-yl)-methanone,
1-[(S)-4-(2,3-Dihydro-[1,4]dioxino[2,3-b]pyridin-3-yl)-benzyl]-piperidine-4-carboxylic acid [(S)-1-(tetrahydro-furan-2-yl)-methyl]-amide,
N-[3-[4-[[4-[(3S)-2,3-dihydro-[1,4]dioxino[2,3-b]pyridin-3-yl]phenyl]methyl]piperazin-1-yl]-3-oxo-propyl]acetamide,
N-[1-[[4-[(3S)-2,3-dihydro-[1,4]dioxino[2,3-b]pyridin-3-yl]phenyl]methyl]-4-piperidyl]-2-(2-oxopyrrolidin-1-yl)acetamide,
N-[1-[[4-[(3S)-2,3-dihydro-[1,4]dioxino[2,3-b]pyridin-3-yl]phenyl]methyl]-4-piperidyl]tetrahydropyran-4-carboxamide,
3-{1-[(S)-4-(2,3-Dihydro-[1,4]dioxino[2,3-b]pyridin-3-yl)-benzyl]-piperidin-4-yl}-[1,3]oxazinan-2-one,
1-{(1S,4S)-5-[(S)-4-(2,3-Dihydro-[1,4]dioxino[2,3-b]pyridin-3-yl)-benzyl]-2,5-diaza-bicyclo[2.2.1]hept-2-yl}-ethanone,
(S)-3-{4-[4-(Pyridin-3-yloxy)-piperidin-1-ylmethyl]-phenyl}-2,3-dihydro-[1,4]dioxino[2,3-b]pyridine,
1-[(S)-4-(2,3-Dihydro-[1,4]dioxino[2,3-b]pyridin-3-yl)-benzyl]-4-phenyl-piperidine-4-carboxylic acid,
(S)-3-[4-(1-Oxo-1lambda4-thiomorpholin-4-ylmethyl)-phenyl]-2,3-dihydro-[1,4]dioxino[2,3-b]pyridine, and
(S)-7-[(S)-4-(2,3-Dihydro-[1,4]dioxino[2,3-b]pyridin-3-yl)-benzyl]-hexahydro-oxazolo[3,4-a]pyrazin-3-one,
or a pharmaceutically acceptable salt thereof of each of the foregoing.

In another embodiment, the invention relates to a compound selected from the group consisting of:
3-[(4-{4-[(2S)-2,3-dihydro-1,4-benzodioxin-2-yl]benzyl}piperazin-1-yl)-methyl]benzoic acid,
7-[(S)-4-(2,3-dihydro-[1,4]dioxino[2,3-b]pyridin-3-yl)-benzyl]-5,6,7,8-tetrahydro-[1,2,4]triazolo[4,3-a]pyrazine-3-carboxylic acid ethyl ester,
7-[(S)-4-(2,3-Dihydro-[1,4]dioxino[2,3-b]pyridin-3-yl)-benzyl]-5,6,7,8-tetrahydro-[1,2,4]triazolo[4,3-a]pyrazine-3-carboxylic acid amide,
7-[(S)-4-(2,3-dihydro-[1,4]dioxino[2,3-b]pyridin-3-yl)-benzyl]-5,6,7,8-tetrahydro-[1,2,4]triazolo[4,3-a]pyrazine-3-carboxylic acid methylamide,
7-[(S)-4-(2,3-dihydro-[1,4]dioxino[2,3-b]pyridin-3-yl)-benzyl]-5,6,7,8-tetrahydro-imidazo[1,2-a]pyrazine-2-carboxylic acid amide,
7-[(S)-4-(2,3-dihydro-[1,4]dioxino[2,3-b]pyridin-3-yl)-benzyl]-5,6,7,8-tetrahydro-imidazo[1,2-a]pyrazine-2-carboxylic acid methylamide,
6-[(S)-4-(2,3-dihydro-[1,4]dioxino[2,3-b]pyridin-3-yl)-benzyl]-5,6,7,8-tetrahydro-4H-1,2,3a,6-tetraaza-azulene-3-carboxylic acid amide,
6-[(S)-4-(2,3-Dihydro-[1,4]dioxino[2,3-b]pyridin-3-yl)-benzyl]-5,6,7,8-tetrahydro-4H-1,2,3a,6-tetraaza-azulene-3-carboxylic acid methylamide,
[(1α,5α,6α)-3-[(S)-4-(2,3-dihydro-[1,4]dioxino[2,3-b]pyridin-3-yl)-benzyl]-3-aza-bicyclo[3.1.0]hexane]-6-carboxylic acid ((S)-2-hydroxy-propyl)-amide,
[(1α,5α,6α)-3-[(S)-4-(2,3-Dihydro-[1,4]dioxino[2,3-b]pyridin-3-yl)-benzyl]-3-aza-bicyclo[3.1.0]hexane]-6-carboxylic acid ((S)-2-hydroxy-1-methyl-ethyl)-amide,
7-[(S)-4-(2,3-Dihydro-[1,4]dioxino[2,3-b]pyridin-3-yl)-benzyl]-5,6,7,8-tetrahydro-imidazo[1,2-a]pyrazine-3-carbonitrile,
N-{(1α,5α,6α)-3-[(S)-4-(2,3-Dihydro-[1,4]dioxino[2,3-b]pyridin-3-yl)-benzyl]-3-aza-bicyclo[3.1.0]hex-6-yl}-acetamide, and
[(1α,5α,6α)-3-[(S)-4-(2,3-Dihydro-[1,4]dioxino[2,3-b]pyridin-3-yl)-benzyl]-3-aza-bicyclo[3.1.0]hexane-6-carboxylic acid (2-hydroxy-2-methyl-propyl)]-amide,
or a pharmaceutically acceptable salt thereof of each of the foregoing.

In another embodiment, the invention relates to a compound selected from the group consisting of:
N-{1-[(S)-4-(2,3-Dihydro-[1,4]dioxino[2,3-b]pyridin-3-yl)-benzyl]-piperidin-4-yl}-2-methoxy-acetamide,
1-{4-[(S)-4-(2,3-Dihydro-[1,4]dioxino[2,3-b]pyridin-3-yl)-benzyl]-piperazin-1-yl}-2-hydroxy-ethanone,
4-{1-[(S)-4-(2,3-Dihydro-benzo[1,4]dioxin-2-yl)-benzyl]-azetidin-3-yl}-benzoic acid,
1-[(S)-4-(2,3-Dihydro-[1,4]dioxino[2,3-b]pyridin-3-yl)-benzyl]-piperidine-4-carboxylic acid (2-hydroxy-2-methyl-propyl)-amide, 1-[(1S,4S)-5-[(S)-4-(2,3-Dihydro-[1,4]dioxino[2,3-b]pyridin-3-yl)-benzyl]-2,5-diaza-bicyclo[2.2.1]hept-2-yl]-2-methanesulfonyl-ethanone,
1-{4-[(S)-4-(2,3-Dihydro-[1,4]dioxino[2,3-b]pyridin-3-yl)-benzyl]-[1,4]diazepan-1-yl}-2-methoxy-ethanone,
5-[(S)-4-(2,3-Dihydro-[1,4]dioxino[2,3-b]pyridin-3-yl)-benzyl]-4,5,6,7-tetrahydro-thiazolo[5,4-c]pyridin-2-ylamine,
{(endo)-8-[(S)-4-(2,3-Dihydro-[1,4]dioxino[2,3-b]pyridin-3-yl)-benzyl]-8-aza-bicyclo[3.2.1]oct-3-yl}-urea,
2-{1-[(S)-4-(2,3-Dihydro-[1,4]dioxino[2,3-b]pyridin-3-yl)-benzyl]-piperidin-4-yl}-N-methoxy-acetamide,
(R)-N-{1-[(S)-4-(2,3-Dihydro-[1,4]dioxino[2,3-b]pyridin-3-yl)-benzyl]-piperidin-4-yl}-2-methylamino-propionamide,
N-{1-[(S)-4-(2,3-Dihydro-[1,4]dioxino[2,3-b]pyridin-3-yl)-benzyl]-piperidin-4-ylmethyl}-2-hydroxy-2-methyl-propionamide,
N-{(1α,5α,6α)-3-[(S)-4-(2,3-Dihydro-[1,4]dioxino[2,3-b]pyridin-3-yl)-benzyl]-3-aza-bicyclo[3.1.0]hex-6-ylmethyl}-methanesulfonamide,
1-[(1S,4S)-5-[(S)-4-(2,3-Dihydro-[1,4]dioxino[2,3-b]pyridin-3-yl)-benzyl]-2,5-diaza-bicyclo[2.2.2]oct-2-yl]-ethanone,
4-{1-[(S)-4-(2,3-Dihydro-[1,4]dioxino[2,3-b]pyridin-3-yl)-benzyl]-piperidin-4-yl}-cyclohexanecarboxylic acid,
1-[(S)-4-(2,3-Dihydro-benzo[1,4]dioxin-2-yl)-benzyl]-azepane-4-carboxylic acid,
[(1α,5α,6α)-3-[(S)-4-(2,3-Dihydro-benzo[1,4]dioxin-2-yl)-benzyl]-3-aza-bicyclo[3.1.0]hexane]-6-carboxylic acid,
(1S,4S)-5-[(S)-4-(2,3-Dihydro-[1,4]dioxino[2,3-b]pyridin-3-yl)-benzyl]-2,5-diaza-bicyclo[2.2.1]heptane-2-carboxylic acid amide,
1-[(S)-4-(2,3-Dihydro-[1,4]dioxino[2,3-b]pyridin-3-yl)-benzyl]-4-phenyl-piperidin-4-ol,
1-{5-[(S)-4-(2,3-Dihydro-[1,4]dioxino[2,3-b]pyridin-3-yl)-benzyl]-hexahydro-pyrrolo[3,4-c]pyrrol-2-yl}-ethanone,
1-{8-[(S)-4-(2,3-Dihydro-[1,4]dioxino[2,3-b]pyridin-3-yl)-benzyl]-3,8-diaza-bicyclo[3.2.1]oct-3-yl}-ethanone,
5-[(S)-4-(2,3-Dihydro-[1,4]dioxino[2,3-b]pyridin-3-yl)-benzyl]-hexahydro-pyrrolo[3,4-c]pyrrole-2-carboxylic acid amide,
{(exo)-8-[(S)-4-(2,3-Dihydro-[1,4]dioxino[2,3-b]pyridin-3-yl)-benzyl]-8-aza-bicyclo[3.2.1]oct-3-yl}-urea, and
2-{1-[(S)-4-(2,3-Dihydro-[1,4]dioxino[2,3-b]pyridin-3-yl)-benzyl]-piperidin-4-yloxy}-acetamide,
or a pharmaceutically acceptable salt thereof of each of the foregoing.

In another embodiment, the invention relates to a compound selected from the group consisting of:
(S)-3-[4-(1,1-Dioxo-1lambda6-[1,4]thiazepan-4-ylmethyl)-phenyl]-2,3-dihydro-[1,4]dioxino[2,3-b]pyridine,
1-[(S)-4-(2,3-Dihydro-[1,4]dioxino[2,3-b]pyridin-3-yl)-benzyl]-4-methyl-piperidin-4-ol,
1-{(1S,4S)-5-[(S)-4-(2,3-Dihydro-[1,4]dioxino[2,3-b]pyridin-3-yl)-benzyl]-2,5-diaza-bicyclo[2.2.1]hept-2-yl}-2-hydroxy-ethanone,
N-{(endo)-8-[(S)-4-(2,3-Dihydro-[1,4]dioxino[2,3-b]pyridin-3-yl)-benzyl]-8-aza-bicyclo[3.2.1]oct-3-yl}-acetamide,
N-{1-[(S)-4-(2,3-Dihydro-[1,4]dioxino[2,3-b]pyridin-3-yl)-benzyl]-piperidin-4-ylmethyl}-acetamide,
[(S)-4-(2,3-Dihydro-[1,4]dioxino[2,3-b]pyridin-3-yl)-benzyl]-(1,1-dioxo-tetrahydro-1lambda-6-thiophen-3-yl)-methyl-amine,
1-{(1S,4S)-5-[(S)-4-(2,3-Dihydro-[1,4]dioxino[2,3-b]pyridin-3-yl)-benzyl]-2,5-diaza-bicyclo[2.2.2]oct-2-yl}-2-hydroxy-ethanone,
1'-[(S)-4-(2,3-dihydro-[1,4]dioxino-[2,3-b]pyridin-3-yl)-benzyl]-spiro-[3H-indole-3,4'-piperidine]-1(2H)-urea, and
{1-[(S)-4-(2,3-Dihydro-[1,4]dioxino[2,3-b]pyridin-3-yl)-benzyl]-piperidin-4-ylmethyl}-urea,
{4-[(S)-4-(2,3-Dihydro-[1,4]dioxino[2,3-b]pyridin-3-yl)-benzyl]-piperazin-1-yl}-acetonitrile,
(R)-7-[(S)-4-(2,3-Dihydro-[1,4]dioxino[2,3-b]pyridin-3-yl)-benzyl]-hexahydro-oxazolo[3,4-a]pyrazin-3-one,
{1-[(S)-4-(2,3-Dihydro-[1,4]dioxino[2,3-b]pyridin-3-yl)-benzyl]-piperidin-4-yl}-(3-hydroxy-azetidin-1-yl)-methanone,
1-[(S)-4-(2,3-Dihydro-[1,4]dioxino[2,3-b]pyridin-3-yl)-benzyl]-piperidine-4-carboxylic acid [(S)-1-(tetrahydro-furan-2-yl)-methyl]-amide,
N-[3-[4-[[4-[(3S)-2,3-dihydro-[1,4]dioxino[2,3-b]pyridin-3-yl]phenyl]methyl]piperazin-1-yl]-3-oxo-propyl]acetamide,
N-[1-[[4-[(3S)-2,3-dihydro-[1,4]dioxino[2,3-b]pyridin-3-yl]phenyl]methyl]-4-piperidyl]-2-(2-oxopyrrolidin-1-yl)acetamide,
N-[1-[[4-[(3S)-2,3-dihydro-[1,4]dioxino[2,3-b]pyridin-3-yl]phenyl]methyl]-4-piperidyl]tetrahydropyran-4-carboxamide,
3-{1-[(S)-4-(2,3-Dihydro-[1,4]dioxino[2,3-b]pyridin-3-yl)-benzyl]-piperidin-4-yl}-[1,3]oxazinan-2-one,
1-{(1S,4S)-5-[(S)-4-(2,3-Dihydro-[1,4]dioxino[2,3-b]pyridin-3-yl)-benzyl]-2,5-diaza-bicyclo[2.2.1]hept-2-yl}-ethanone,
(S)-3-{4-[4-(Pyridin-3-yloxy)-piperidin-1-ylmethyl]-phenyl}-2,3-dihydro-[1,4]dioxino[2,3-b]pyridine,
1-[(S)-4-(2,3-Dihydro-[1,4]dioxino[2,3-b]pyridin-3-yl)-benzyl]-4-phenyl-piperidine-4-carboxylic acid,
(S)-3-[4-(1-Oxo-1lambda4-thiomorpholin-4-ylmethyl)-phenyl]-2,3-dihydro-[1,4]dioxino[2,3-b]pyridine, and
(S)-7-[(S)-4-(2,3-Dihydro-[1,4]dioxino[2,3-b]pyridin-3-yl)-benzyl]-hexahydro-oxazolo[3,4-a]pyrazin-3-one,
or a pharmaceutically acceptable salt thereof of each of the foregoing.

In another embodiment, the invention relates to a pharmaceutical composition comprising one or more compounds of formula (I) as defined in any of the embodiments above, or a pharmaceutically acceptable salt thereof, and a pharmaceutically acceptable carrier or excipient.

In another embodiment, the invention relates to a pharmaceutical composition comprising one or more compounds of formula (I) as defined in any of the embodiments above, or a pharmaceutically acceptable salt thereof, a pharmaceutically acceptable carrier or excipient, and at least one additional pharmacologically active substance.

All terms as used herein in this specification, unless otherwise stated, shall be understood in their ordinary meaning as known in the art. Other more specific definitions are as follows:

The term "$(C_1-C_6)$alkyl" refers to branched and unbranched alkyl groups having from 1 to 6 carbon atoms. Examples of —$(C_1-C_6)$alkyls include methyl, ethyl, n-propyl, isopropyl, n-butyl, sec-butyl, isobutyl, tert-butyl, n-pentane, iso-pentyl, neopentyl, n-hexane, iso-hexanes (e.g., 2-methylpentyl, 3-methylpentyl, 2,3-dimethylbutyl, and 2,2-dimethylbutyl). It will be understood that any chemically feasible carbon atom of the $(C_1-C_6)$alkyl group can be the point of attachment to another group or moiety.

The term "(C$_1$-C$_6$)alkylene" refers to branched and unbranched alkyl groups that function as bridging groups between 2 moieties or groups. Suitable (C$_1$-C$_6$)alkylenes are the same as those described above for "(C$_1$-C$_6$)alkyl." It will be understood that any chemically feasible carbon atom(s) of the (C$_1$-C$_6$)alkylene group can be the points of attachment to the groups or moieties, thereby creating a bridging group.

The term "(C$_3$-C$_6$)cycloalkyl" refers to a nonaromatic 3- to 6-membered monocyclic carbocyclic radical. Examples of "(C$_3$-C$_6$)cycloalkyls" include cyclopropyl, cyclobutyl, cyclohexyl, cyclopentyl and cyclohexyl.

As used herein, the term "(C$_6$-C$_{10}$)aryl" refers to an aromatic hydrocarbon rings containing from six to ten carbon ring and includes monocyclic rings and bicyclic rings where at least one of the rings is aromatic. Non-limiting examples of C$_{6-10}$ aryls include phenyl, indanyl, indenyl, benzocyclobutanyl, dihydronaphthyl, tetrahydronaphthyl, naphthyl, benzocycloheptanyl and benzocycloheptenyl.

As used herein, the term "4 to 14-membered heterocycloalkyl" includes stable nonaromatic fused bicyclic, bridged bicyclic and spirocyclic heterocycloalkyl radicals having 6 to 14 ring atoms; and stable nonaromatic monocyclic heterocycloalkyl radicals having 4 to 8 ring atoms. The 4 to 14-membered heterocycloalkyl ring atoms consist of carbon atoms and one or more, preferably from one to four heteroatoms chosen from nitrogen, oxygen and sulfur. The heterocycloalkyl may be either saturated or partially unsaturated. Non-limiting examples of nonaromatic 4-8 membered monocyclic heterocycloalkyl radicals include tetrahydrofuranyl, azetidinyl, pyrrolidinyl, pyranyl, tetrahydropyranyl, dioxanyl, thiomorpholinyl, 1,1-dioxo-1λ$^6$-thiomorpholinyl, morpholinyl, piperidinyl, piperazinyl, and azepinyl. Non-limiting examples of nonaromatic 6 to 14-membered fused bicyclic heterocycloalkyl radicals include octahydroindolyl, octahydrobenzofuranyl, and octahydrobenzothiophenyl. Non-limiting examples of nonaromatic 6 to 14-membered bridged bicyclic heterocycloalkyl radicals include 2-azabicyclo[2.2.1]heptanyl, 3-azabicyclo[3.1.0]hexanyl, and 3-azabicyclo[3.2.1]octanyl. Non-limiting examples of nonaromatic spirocyclic heterocycloalkyl radicals include 7-aza-spiro[3,3]heptanyl, 7-spiro[3,4]octanyl, and 7-aza-spiro[3,4]octanyl.

As used herein, some of the said bridged bicyclic heterocycloalkyls may contain elements of symmetry such as a plane of symmetry. Although these heterocycloalkyls contain asymmetric centers or carbons, a person of ordinary skill in the art recognizes that these compounds are achiral or "meso". Thus in certain bridged bicyclic heterocycloalkyls, the "endo" and "exo" terminology is utilized to describe the orientation of a substituent on an achiral ring position relative to the bridge moiety. As an example, the term "endo" in [(endo)-N-(8-Aza-bicyclo[3.2.1]oct-3-yl)]-acetamide denotes the configuration in which the acetamide substituent is on the same side as the ethylene-containing bridge (see Intermediate T). In addition, the term "exo" describes an isomer in which the said substituent is on the opposite side as the ethylene-containing bridge.

As used herein, the term "5 to 11-membered heteroaryl" includes aromatic 5 to 6-membered monocyclic heteroaryls and aromatic 7 to 11-membered heteroaryl bicyclic rings where at least one of the rings is aromatic, wherein the heteroaryl ring contains 1-4 heteroatoms such as N, O and S. Non-limiting examples of 5 to 6-membered monocyclic heteroaryl rings include furanyl, oxazolyl, isoxazolyl, oxadiazolyl, pyranyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic rings include benzimidazolyl, 1,3-dihydrobenzoimidazol-2-one, quinolinyl, dihydro-2H-quinolinyl, isoquinolinyl, quinazolinyl, indazolyl, thieno[2,3-d]pyrimidinyl, indolyl, isoindolyl, indazolyl, benzotriazolyl, benzofuranyl, benzopyranyl, benzodioxolyl, benzoxazolyl, benzothiazolyl, pyrrolo[2,3-b]pyridinyl, and imidazo[4,5-b]pyridinyl.

It will be understood that when a heterocycloalkyl or heteroaryl contains a S ring atom, such S ring atom can be present in the ring in its divalent, tetravalent, or hexavalent form, i.e., —S—, —S(O)— or —S(O)$_2$—.

Each aryl or heteroaryl unless otherwise specified includes it's partially or fully hydrogenated derivatives. For example, quinolinyl may include decahydroquinolinyl and tetrahydroquinolinyl, naphthyl may include its hydrogenated derivatives such as tetrahydranaphthyl. Other partially or fully hydrogenated derivatives of the aryl and heteroaryl compounds described herein will be apparent to one of ordinary skill in the art.

The term "heteroatom" as used herein shall be understood to mean atoms other than carbon such as O, N, and S.

The term "halo" or "halogen" refers to fluoro, chloro, bromo or iodo.

The symbol

means point of attachment of a group R to a moiety.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

For all compounds disclosed in this application, in the event the nomenclature is in conflict with the structure, it shall be understood that the compound is defined by the structure.

The invention also relates to pharmaceutical preparations, containing as active substance one or more compounds of the invention, or the pharmaceutically acceptable derivatives thereof, optionally combined with conventional excipients and/or carriers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes the use of any compounds of described above containing one or more asymmetric carbon atoms may occur as racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Some of the compounds of the invention can exist in more than one tautomeric form. The invention includes methods using all such tautomers.

The compounds of the invention are only those which are contemplated to be 'chemically stable' as will be appreciated by those skilled in the art. For example, a compound which would have a 'dangling valency', or a 'carbanion' is not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the invention.

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—($C_1$-$C_4$ alkyl)$^{4+}$ salts.

In addition, within the scope of the invention is use of prodrugs of compounds of the invention. Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

General Synthetic Methods

The compounds of the invention may be prepared by the general methods, examples presented below, and methods known to those of ordinary skill in the art and reported in the chemical literature. In each of the schemes below, the groups $R^1$ to $R^3$ and A are as defined above for the compound of formula (I), unless noted otherwise. Optimum reaction conditions and reaction times may vary depending on the particular reactants used. Unless otherwise specified, solvents, temperatures, pressures and other reaction conditions may be readily selected by one of ordinary skill in the art. Specific procedures are provided in the Synthetic Examples section.

Schemes 1 and 2 below depict the general synthetic procedure for making the compounds of formula (I) wherein X is CH ("the benzodioxane LTAH$_4$ inhibitors").

Scheme 1:
General synthetic scheme for making benzodioxane LTA$_4$H inhibitors

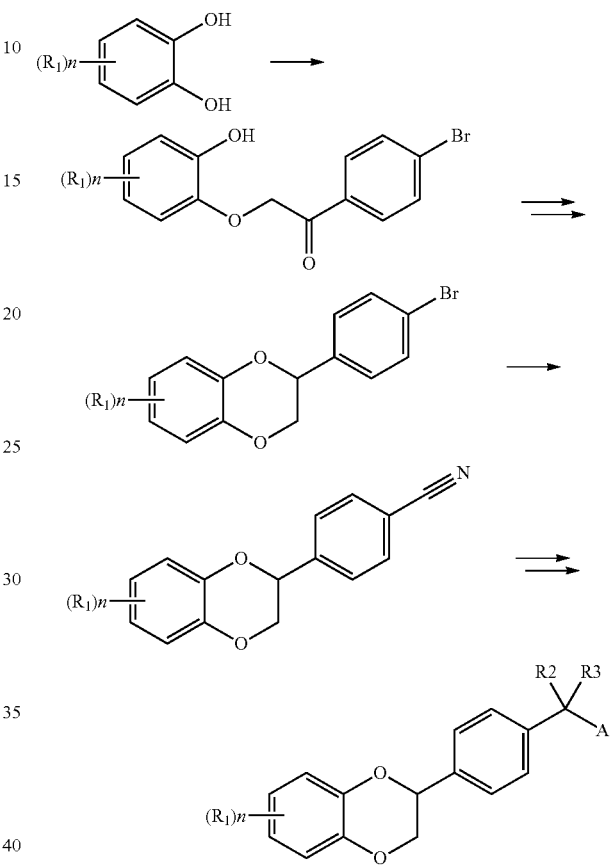

Scheme 2:
Alternative synthetic scheme for making benzodioxane LTA$_4$H inhibitors

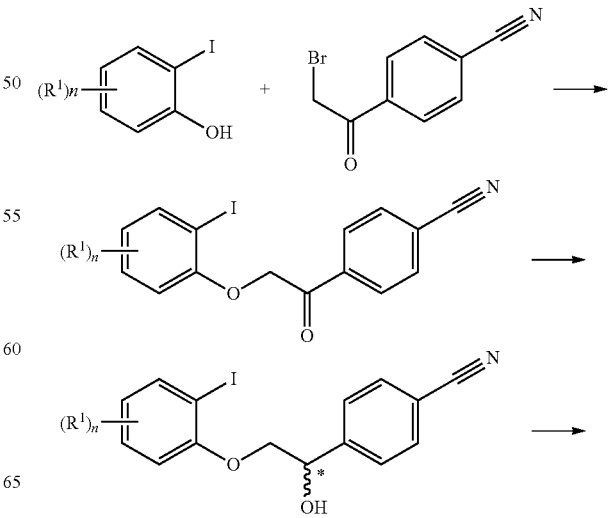

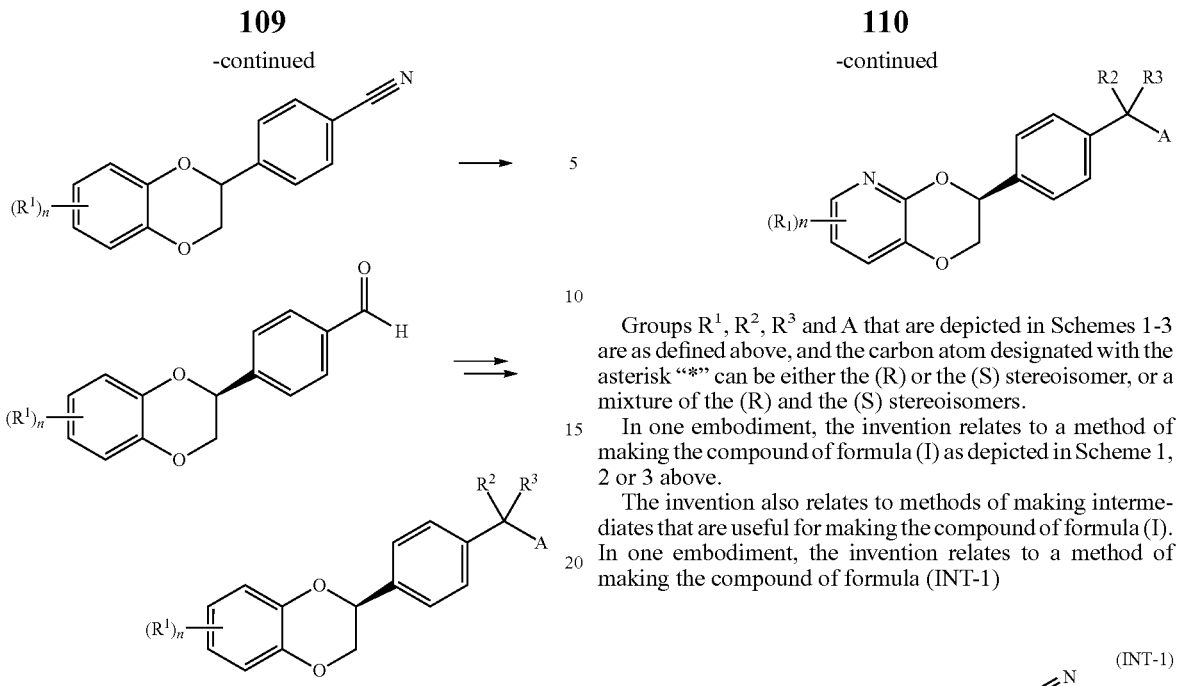

Scheme 3 below depicts the general synthetic procedure for making the compounds of formula (I) wherein X is N ("the 8-azabenzodioxane LTAH₄ inhibitors").

Scheme 3:
General synthetic scheme for 8-azabenzodioxane LTA₄H inhibitors

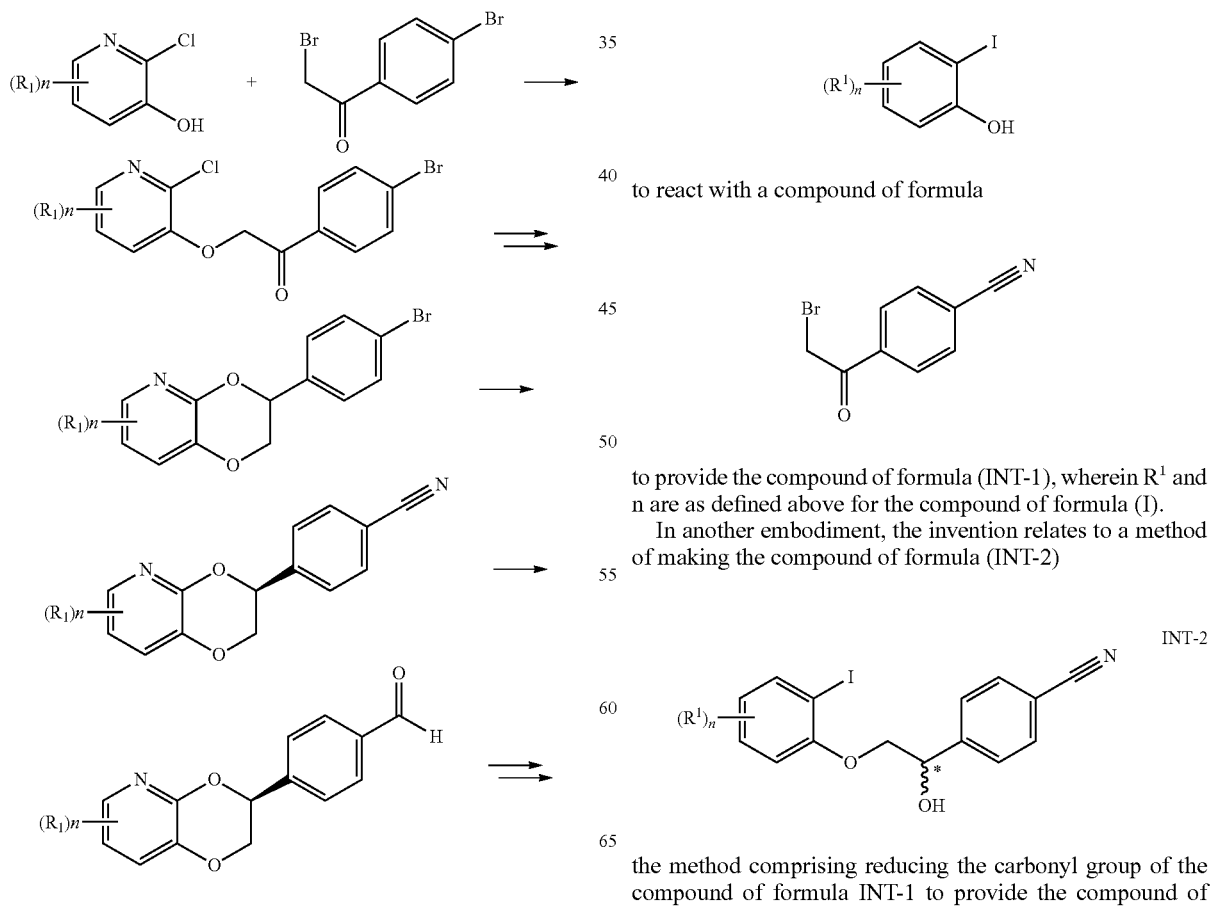

Groups $R^1$, $R^2$, $R^3$ and A that are depicted in Schemes 1-3 are as defined above, and the carbon atom designated with the asterisk "*" can be either the (R) or the (S) stereoisomer, or a mixture of the (R) and the (S) stereoisomers.

In one embodiment, the invention relates to a method of making the compound of formula (I) as depicted in Scheme 1, 2 or 3 above.

The invention also relates to methods of making intermediates that are useful for making the compound of formula (I). In one embodiment, the invention relates to a method of making the compound of formula (INT-1)

the process comprising allowing a compound of formula to react with a compound of formula to provide the compound of formula (INT-1), wherein $R^1$ and n are as defined above for the compound of formula (I).

In another embodiment, the invention relates to a method of making the compound of formula (INT-2)

the method comprising reducing the carbonyl group of the compound of formula INT-1 to provide the compound of formula INT-2, wherein $R^1$ and n are as defined above for the compound of formula (I); and the carbon atom designated with the asterisk "*" can be either the (R) or the (S) stereoisomer, or a mixture of the (R) and the (S) stereoisomers.

In another embodiment, the invention relates to a method of making the compound of formula (INT-3)

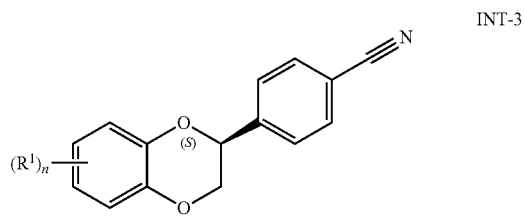

INT-3 the method comprising reducing the carbonyl group of the compound of formula INT-1 in the presence of a chiral transition metal catalyst and formic acid to provide the compound of formula INT-4,

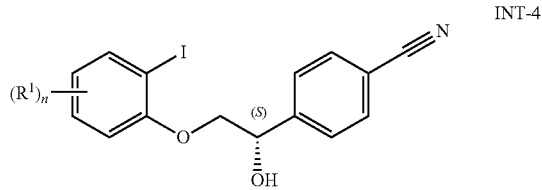

INT-4 and allowing the compound of formula INT-4 to react in the presence of a transition metal salt and 1,10-phenanthroline to provide the compound of formula INT-3.

Starting materials and reagents used in Schemes 1-3 are commercially available or may be prepared from commercially available starting materials by one of ordinary skill in the art using methods described in the chemical literature and in the Synthetic Examples section below.

The examples which follow are illustrative and, as recognized by one skilled in the art, particular reagents or conditions could be modified as needed for individual compounds without undue experimentation.

Synthetic Examples

General Methods

Unless noted otherwise, all reactions are run at room temperature (about 25° C.), under inert atmosphere (e.g., Argon, $N_2$), and under anhydrous conditions. All compounds are characterized by at least one of the following methods: $^1H$ NMR, HPLC, HPLC-MS, and melting point.

Typically, reaction progress is monitored by thin layer chromatography (TLC) or HPLC-MS. Intermediates and products are purified using at least one of the following methods:

Flash chromatography on silica gel,
Recrystallization,
Chiral HPLC using a 20×500 mm Chiralpak AD-H column, or 20×500 mm
Chiralpak OD-H column, and eluting with an isocratic mixture of isopropanol in heptanes with 0.1% diethylamine (DEA) at 7.5 mL/min,
20×250 mm Chiralcel OD-H column, and eluting with an isocratic mixture of isopropanol in heptanes at 7.5 mL/min,
Super Critical Fluid (SCF) Chiral HPLC using a 3.0×25.0 cm RegisPack column, eluting with an isocratic mixture of MeOH, isopropylamine (IPA), and super critical carbon dioxide at 125 bar; 80 mL/min, and/or
Reversed phase HPLC using a C18 semi-preparative column eluting with a gradient of MeCN+0.1% TFA/$H_2O$+0.1% TFA, or MeCN+0.1% formic acid/$H_2O$+0.1% formic acid.

The reported MS data is for observed $[M+H]^+$. For bromine containing compounds, the $[M+H]^+$ is either reported for one or both of the bromine isotopes (i.e., $^{79}Br$ and $^{81}Br$).

LC/MS methods used in to characterize and isolate the compounds of the invention are described in Tables 2a, 2b, and 2c below.

TABLE 2a

LC/MS Methods and retention times (RT).

| LC/MS Method | Time (min) | Mobile Phase | | Flow (mL/min) | Column |
|---|---|---|---|---|---|
| | | $H_2O$ (0.1% FA) | $CH_3CN$ (0.1% FA) | | |
| 1 | 0 | 95 | 5 | 2.5 | Agilent Zorbax |
| | 1.7 | 5 | 95 | 2.5 | C18 SB 3.5 um |
| | 2 | 5 | 95 | 2.5 | 4.6 × 30 mm cartridge |
| | 2.1 | 95 | 5 | 2.5 | |
| | 2.3 | 95 | 5 | 2.5 | |
| 2 | 0 | 70 | 30 | 2.5 | Agilent Zorbax |
| | 1.7 | 5 | 95 | 2.5 | C18 SB 3.5 um |
| | 2 | 5 | 95 | 2.5 | 4.6 × 30 mm cartridge |
| | 2.1 | 70 | 30 | 2.5 | |
| | 2.3 | 70 | 30 | 2.5 | |
| 3 | 0 | 99 | 1 | 2.5 | Agilent Zorbax |
| | 1.7 | 50 | 50 | 2.5 | C18 SB 3.5 um |
| | 2 | 5 | 95 | 2.5 | 4.6 × 30 mm cartridge |
| | 2.1 | 5 | 95 | 2.5 | |
| | 2.3 | 99 | 1 | 2.5 | |
| 4 | 0 | 95 | 5 | 1.5 | Agilent Zorbax |
| | 7 | 5 | 95 | 1.5 | Eclipse XDB-C8 |
| | 9 | 5 | 95 | 1.5 | 5 um 4.6 × 150 mm |
| | 9.3 | 95 | 5 | 1.5 | |
| | 10 | 95 | 5 | 1.5 | |
| 5 | 0 | 99 | 1 | 2.5 | Agilent Zorbax |
| | 1.6 | 80 | 20 | 2.5 | C18 SB 3.5 um |
| | 1.7 | 5 | 95 | 2.5 | 4.6 × 30 mm cartridge |
| | 2 | 5 | 95 | 2.5 | |
| | 2.1 | 99 | 1 | 2.5 | |
| | 2.3 | 99 | 1 | 2.5 | |
| 6 | 0 | 99 | 1 | 1.5 | Agilent Zorbax |
| | 2 | 80 | 20 | 1.5 | Eclipse XDB-C8 |
| | 7 | 5 | 95 | 1.5 | 5 um 4.6 × 150 mm column |
| | 9 | 5 | 95 | 1.5 | |
| | 9.3 | 99 | 1 | 1.5 | |
| | 10 | 99 | 1 | 1.5 | |
| 7 | 0 | 88 | 12 | 1.5 | Agilent SB-C18 1.8 um |
| | 0.25 | 70 | 30 | 1.5 | 3 × 50 mm column |
| | 0.3 | 60 | 40 | 1.5 | |
| | 1.19 | 5 | 95 | 1.5 | |
| | 1.75 | 0 | 100 | 1.5 | |
| 8 | 0 | 60 | 40 | 1.5 | Agilent Eclipse C8 1.8 um |
| | 1.19 | 15 | 85 | 1.5 | 3 × 50 mm column |
| | 1.75 | 0 | 100 | 1.5 | |
| 9 | 0 | 95 | 5 | 1.5 | Agilent SB-AQ 1.8 um |
| | 0.25 | 50 | 50 | 1.5 | 3 × 50 mm column |
| | 0.3 | 70 | 30 | 1.5 | |
| | 1.3 | 10 | 90 | 1.5 | |
| | 1.7 | 0 | 100 | 1.5 | |
| 10 | 0 | 95 | 5 | 1.5 | Agilent SB-C18 1.8 um |
| | 3.8 | 10 | 90 | 1.5 | 3 × 50 mm column |
| | 4.5 | 0 | 100 | 1.5 | |

TABLE 2b

LC/MS Methods and retention times (RT).

| LC/MS Method | Time (min) | Mobile Phase 95% H₂O 2 + 5% CH₃CN (0.05% Formic Acid) | CH₃CN (0.05% Formic Acid) | Flow (mL/min) | Column |
|---|---|---|---|---|---|
| 11 | 0 | 90 | 10 | 0.8 | BEH 2.1 × 50 mm C18, |
|  | 1.19 | 5 | 95 | 0.8 | 1.7 um particle diameter |
|  | 1.7 | 5 | 95 | 0.8 |  |
| 12 | 0 | 90 | 10 | 0.8 | BEH 2.1 × 50 mm C18, |
|  | 1.19 | 0 | 100 | 0.8 | 1.7 um particle diameter |
|  | 1.7 | 0 | 100 | 0.8 |  |
| 13 | 0 | 95 | 5 | 0.6 | Waters HSS T3 2.1 × |
|  | 4.45 | 0 | 100 | 0.6 | 100 mm 18 um column |
|  | 5 | 0 | 100 | 0.6 |  |
| 14 | 0 | 100 | 0 | 0.6 | Waters HSS T3 2.1 × |
|  | 1 | 100 | 0 | 0.6 | 100 mm 18 um column |
|  | 4.45 | 0 | 100 | 0.6 |  |
|  | 5 | 0 | 100 |  |  |
| 15 | 0 | 90 | 10 | 0.6 | BEH 2.1 × 50 mm C18, |
|  | 4.45 | 0 | 100 | 0.6 | 1.7 um particle diameter |
|  | 4.58 | 0 | 100 | 0.6 |  |

TABLE 2c

LC/MS Methods and retention times (RT).

| LC/MS Method | Time (min) | Mobile Phase H₂O (0.1% FA) | CH₃CN (0.1% FA) | Flow (mL/min) | Column |
|---|---|---|---|---|---|
| 16 | 0 | 90 | 10 | 0.5 | Thermo Scientific |
|  | 0.5 | 90 | 10 | 0.5 | Aquasil C18 |
|  | 1.5 | 1 | 99 | 0.5 | 2.1 × 50 mm |
|  | 2.5 | 1 | 99 | 0.5 | 5 um 35° C. |
|  | 3.3 | 90 | 10 | 0.5 |  |
|  | 4.0 | 90 | 10 | 0.5 |  |

Synthesis of Intermediates

Preparation of (S)-4-(2,3-Dihydro-benzo[1,4]dioxin-2-yl)-benzaldehyde (A) according to Method 1 or Method 2 as shown below Method 1

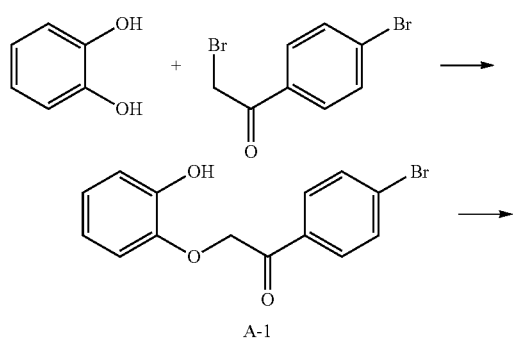

A-1

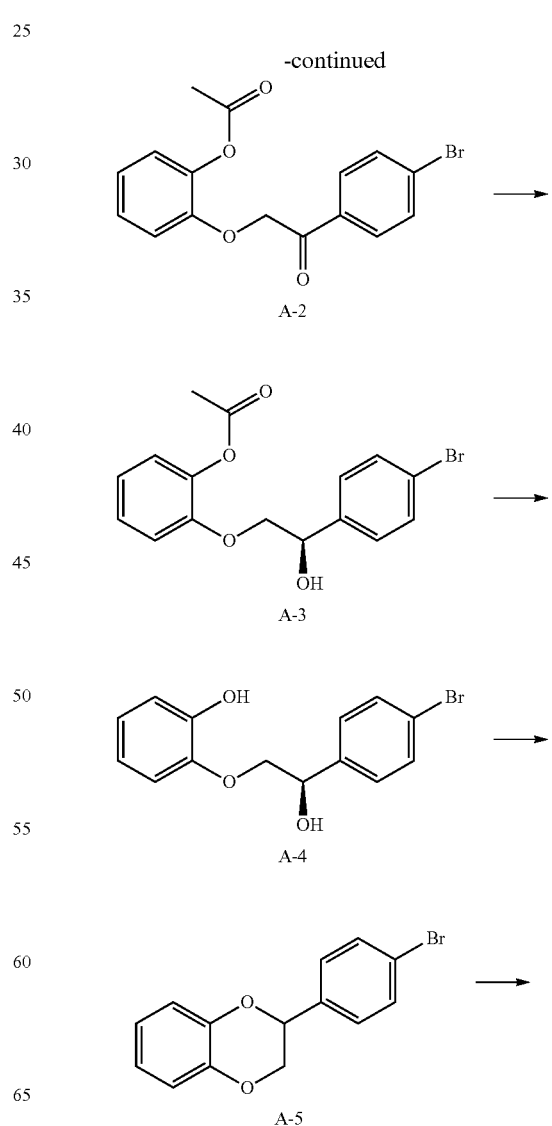

A-2

A-3

A-4

A-5

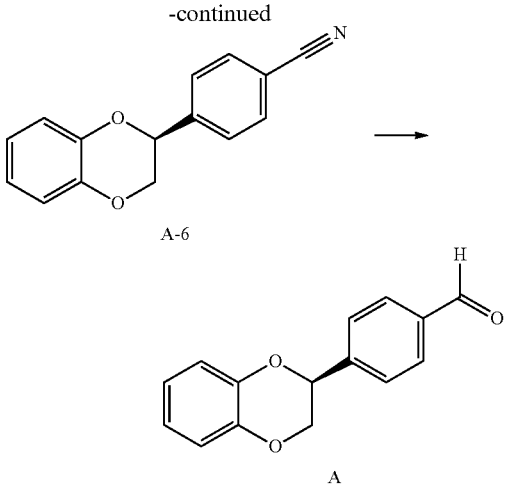

To a stirred solution of pyrocatechol (23.8 g, 216 mmol) in acetone (300 mL) is added cesium carbonate (84.4 g, 259 mmol) and 2-Bromo-1-(4-bromo-phenyl)-ethanone (60 g, 216 mmol). The reaction is stirred at room temperature for 1 hour then water (200 mL) is added. The precipitate is filtered and triturated with EtOAc (150 mL) to give A-1 as a solid.

To a solution of A-1 (50.0 g, 163 mmol) in anhydrous THF (375 mL) is added acetic anhydride (23.0 mL, 244 mmol), TEA (34.0 mL, 244 mmol), and DMAP (199 mg, 1.63 mmol). The reaction mixture is stirred at 40° C. for 45 min, cooled to room temperature and diluted with EtOAc (250 mL). The organic solution is washed with water (2×100 mL), 0.25N HCl (100 mL), saturated sodium bicarbonate solution (100 mL), and brine (100 mL), and dried over $Na_2SO_4$. After removal of volatile solvent, the residue is triturated with 5% EtOAc in heptane (1500 mL). The solid is filtered and air dried to give A-2.

To degassed DMF (500 mL) is added A-2 (41.0 g, 117 mmol), (1S,2S)-(+)-N-(4-Toluenesulfonyl)-1,2-diphenylethylenediamine (756 mg, 2.10 mmol) and Pentamethylcyclopentadienylrhodium(III)dichloride (Cp*RhCl$_2$) dimer (319 mg, 0.520 mmol). The resulting mixture is stirred at 0° C. for 20 minutes under argon sparging and treated dropwise with formic acid/triethylamine complex (5:2, 31 mL, 72 mmol). The reaction mixture is stirred under argon at 0° C. for 2 hours, diluted with EtOAc (600 mL), and washed with half-saturated sodium bicarbonate solution, saturated sodium bicarbonate, and brine. The organic layer is dried over $Na_2SO_4$ and concentrated. The residue is purified through a pad of silica gel (400 mL), eluting with EtOAc/heptane (1:1, 3 L) to give A-3 as a solid.

To a MeOH solution (125 mL) of A-3 (24.6 g, 69.0 mmol) is added a solution of LiOH.H$_2$O (5.8 g, 137 mmol) in water (125 mL). The mixture is stirred at 60° C. for 30 min, cooled to room temperature and concentrated. The residue is diluted with water and neutralized with 1N aqueous HCl to a pH of 6. The resulting mixture is extracted with EtOAc (3×150 mL). The combined organic extracts are washed by saturated sodium bicarbonate solution, brine, dried over $Na_2SO_4$, filtered and concentrated to give A-4 as an oil.

To a 0° C. solution of triphenylphosphine (32.7 g, 125 mmol) and diisopropyl azodicarboxylate (24.7 mL, 125 mmol) in THF (anhydrous, 400 mL) is added a solution of A-4 (35 g, 113 mmol) in THF (anhydrous, 200 mL) over 30 min. The resulting solution is warmed to room temperature, stirred for 1 hour, and concentrated. The residue is vigorously stirred in heptane (1.8 L) for 2 hours. The precipitate is filtered, and rinsed with heptane. The filtrate is concentrated and purified by flash column chromatography on silica gel (0-10% EtOAc in heptane) to give A-5 as a solid.

To an argon-degassed solution of A-5 (30.7 g, 105 mmol) in DMF (anhydrous, 400 mL) is added Zn(CN)$_2$ (12.4 g, 105 mmol), tris(dibenzylideneacetone)dipalladium(0) (Pd$_2$(dba)$_3$) (2.9 g, 3.2 mmol), and 1,1'-bis(diphenylphosphino)ferrocene (dppf) (3.5 g, 6.3 mmol). The resulting mixture is sparged with argon and stirred at 80° C. overnight. The reaction is cooled to room temperature and filtered through a pad of Diatomaceous earth, and rinsed with EtOAc. The filtrate is diluted with water (400 mL) and extracted with EtOAc (2×400 mL). The combined organic extracts are washed with brine and stirred with activated carbon (80 g). After 30 min, the mixture is filtered through a pad of Diatomaceous earth and concentrated. The residue is triturated with 2% EtOAc in heptane (1 L), and filtered to give A-6 as a solid.

A solution of A-6 (11.1 g, 46.7 mmol) in THF (anhydrous, 400 mL) at 0° C. is treated dropwise with DIBAL-H (25 wt % in toluene, 77.8 mL, 117 mmol). The reaction is stirred at 0° C. for 30 min, warmed to room temperature and stirred for 2 hours. The reaction is cooled down to 0° C. and quenched with EtOAc (250 mL) followed by saturated potassium sodium tartrate solution (400 mL). The mixture is diluted with EtOAc (300 mL) and water (300 mL) and stirred for 30 min. The organic layer is separated and washed with water, 1N HCl solution, and brine, and dried over $Na_2SO_4$. After filtering through a pad of Diatomaceous earth, the filtrate is concentrated and purified by flash column chromatography on silica gel (0-30% EtOAc in heptane) to give the title product as a solid.

Method 2

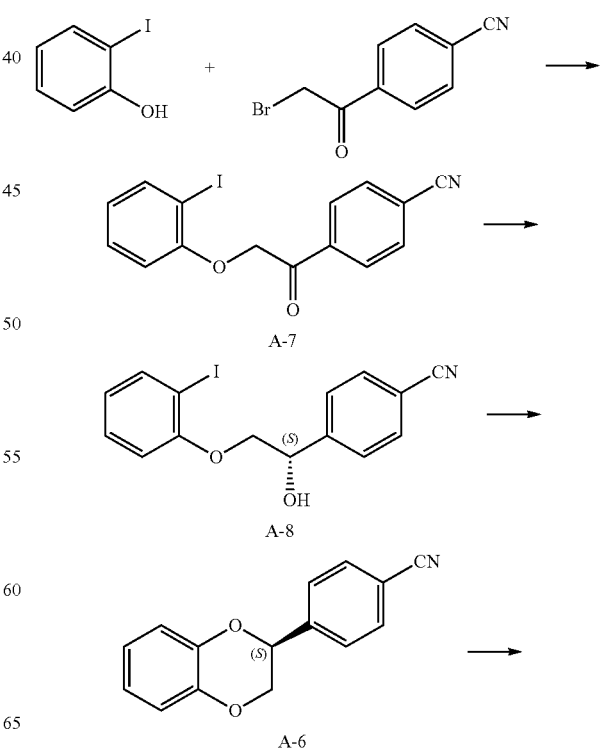

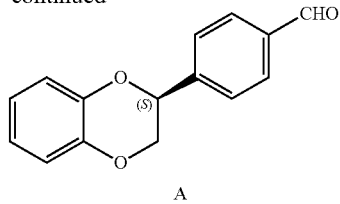

A

2-Iodophenol (110 g, 0.50 mol), potassium carbonate (76.0 g, 0.55 mol) and acetonitrile (165 mL) are charged to a reactor under nitrogen atmosphere and stirred at about 20° C. for about 45 minutes. The reactor contents are treated with a solution of 4-(2-bromoacetyl)benzonitrile (123.2 g, 0.55 mol) in acetonitrile (330 mL). The mixture is stirred at about 20-25° C. for 50 min. The mixture is cooled to about 15° C. and treated with 2N HCl solution (280 mL). The resultant solids are collected by filtration and dried under reduced pressure at about 45° C. to provide A-7: Yield: 172.2 g (98.6 wt %). MS: 386.0 [M+Na]$^+$.

A-7 (20.0 g, 54.3 mmol), (1R,2R)-(−)-N-(4-toluenesulfonyl)-1,2-diphenylethylenediamine (142 mg, 0.380 mmol), pentamethylcyclopentadienylrhodium(III)dichloride dimer (101 mg, 0.163 mmol), acetonitrile (100 mL) and triethylamine (18.2 mL, 130.6 mmol) are charged to a reactor, stirred at about 20° C. for about 1 hour, and cooled to about 0° C. Formic acid (96%, 8.75 mL, 190 mmol) is added at a rate such that the internal temperature does not exceed 15° C. The mixture is stirred at about 5-10° C. for about 30 min followed by treatment with water with vigorous stirring. The solids are collected by filtration and dried under reduced pressure at about 45° C. to provide A-8. Yield: 18.3 g; 90%. Purity: 99.7A %, >99% ee MS: 388.0 [M+Na]$^+$ (see Table 2d below).

TABLE 2d

LC/MS Methods and retention times (RT).

| LC/MS Method | Time (min) | Mobile Phase | | Flow (mL/min) | Column |
| | | H$_2$O (0.1% Formic Acid) | CH$_3$CN (0.1% Formic Acid) | | |
| --- | --- | --- | --- | --- | --- |
| | 0 | 95 | 5 | 0.5 | ZoraxEclipsexDB-C8 |
| | 7 | 5 | 95 | 0.5 | 2.1 × 50 mm; |
| | 9 | 5 | 95 | 0.5 | p/n 971700- |
| | 10 | 95 | 5 | 0.5 | 906; 35° C. |

Post time 2 min

A-8 (20.0 g, 51.7 mmol), CuI (0.985 g, 5.17 mmol), 1,10-phenanthroline (1.86 g, 10.34 mmol) and 1,4-dioxane (200 mL) are charged to a reactor under nitrogen atmosphere, heated at reflux for about 15 to 24 hours, and cooled to about 20° C. The reactor contents are neutralized to about pH5-6 with 6N HCl and filtered. The resultant filtrate is treated with activated charcoal, filtered, concentrated, and crystallized in isopropanol to provide A-6. Yield: 9.9 g, 79.5%. Purity: 99.7 wt %. MS 238.1 [M+h]$^+$ A-6 (8 g, 33.7 mmol) and toluene (40 ml) are charged to a reactor under nitrogen atmosphere, and the resultant solution is cooled about −5 to −10° C. The reactor contents are treated with di-isobutlyaluminum hydride in toluene (1.5M, 24.7 mL). During the addition the temperature of the reactor contents increases to about 5° to 10° C. The reactor contents are then cooled to about 0° C. and stirred for about 2 hours. The contents of the reactor are quenched with 2N HCl (80 mL), stirred for about 2 hours, and filtered through diatomaceous earth. The resulting organic layer is collected and concentrated under reduced pressure to provide A. Yield: 91%. MS: 241.2 (M+H)$^+$.

Preparation of (±)-4-(2,3-Dihydro-benzo[1,4]dioxin-2-yl)-benzaldehyde (B)

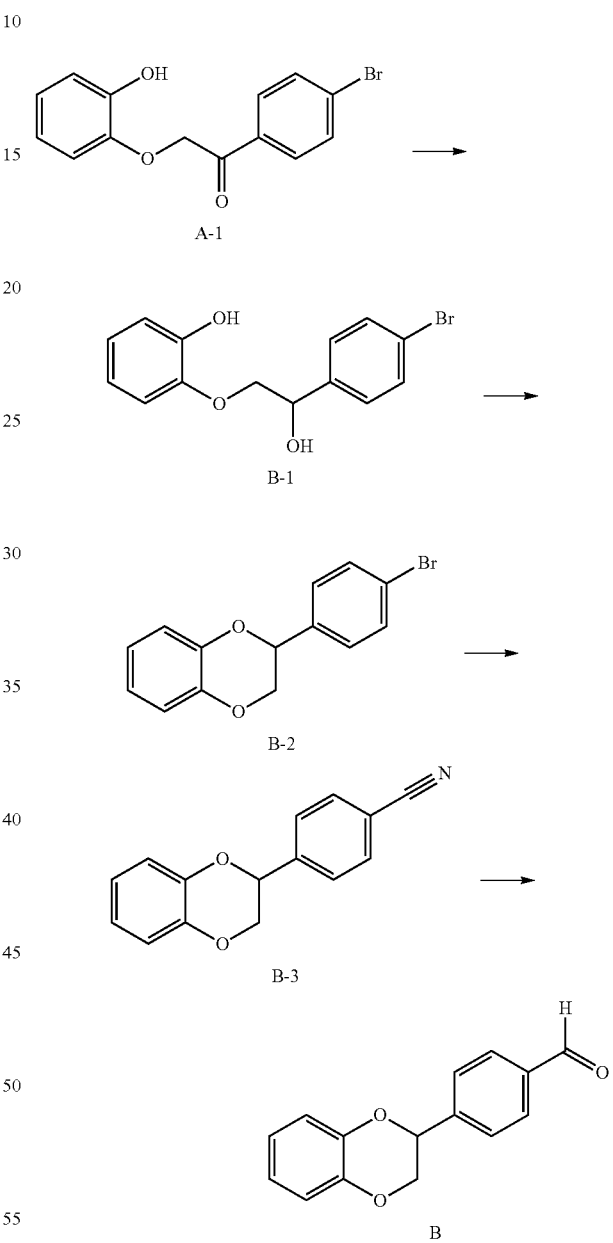

To a stirred solution of A-1 (1.2 g, 3.9 mmol) in EtOH (40 mL) is added sodium borohydride (295 mg, 7.80 mmol). The reaction is stirred for 14 h, quenched with 1N HCl (10 mL) and concentrated to remove the EtOH. The solid residue is filtered, washed with water and dried in vacuo to give B-1 as a solid.

The title product is synthesized from B-1 according to the procedure described for the synthesis of A from A-4. If desired, compound B can be resolved using standard chiral resolution methods that are known to a person of ordinary skill in the art (e.g., chiral chromatography) and are described herein.

Preparation of (S)-4-(2,3-Dihydro-[1,4]dioxino[2,3-b]pyridin-3-yl)-benzaldehyde (C)

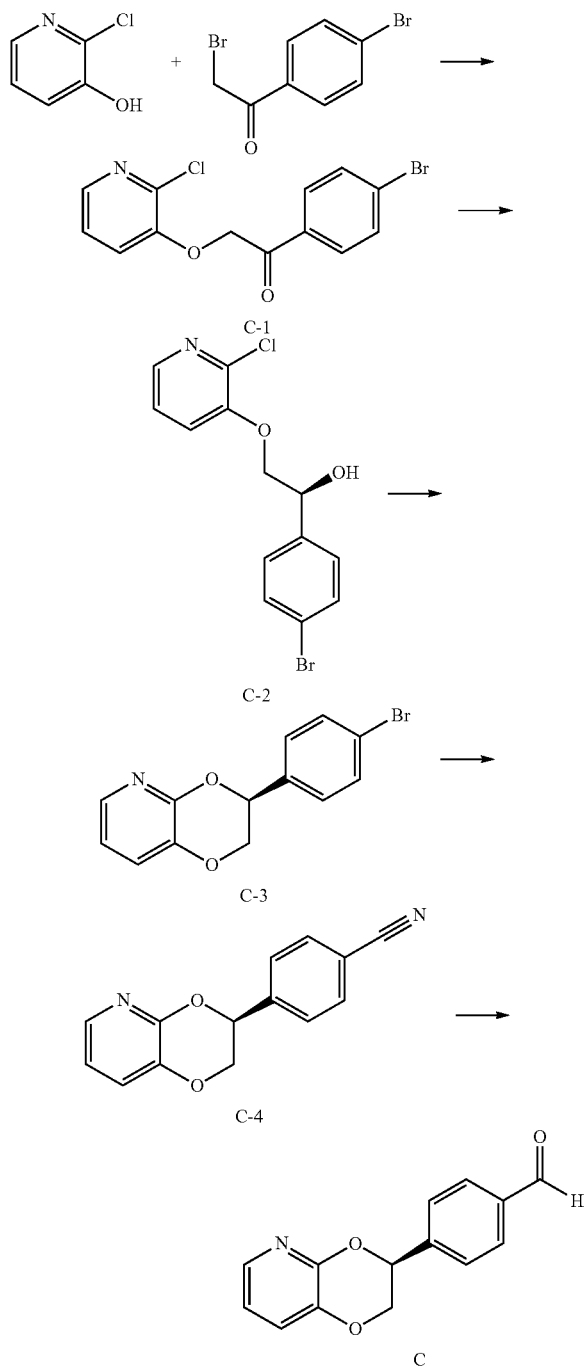

To a solution of 2-chloro-3-hydroxy-pyridine (25.0 g, 193 mmol) and 2,4'-dibromo-acetophenone (53.6 g, 193 mmol) in acetone (400 mL) is added $Cs_2CO_3$ (75.4 g, 232 mmol), and the suspension is stirred at room temperature for 1 h. The reaction is poured into 1 L of water with stirring. Filtration of the mixture gives C-1 as a solid.

A solution of C-1 (30.0 g, 91.9 mmol), Cp*RhCl$_2$ dimer (0.57 g, 0.92 mmol) and N-((1R,2R)-2-Amino-1,2-diphenyl-ethyl)-4-methyl-benzenesulfonamide (1.0 g, 2.8 mmol) in anhydrous DMF (400 mL) is cooled to 0° C. and sparged with argon for 20 minutes before the dropwise addition of formic acid:TEA mixture (5:2 mixture; 28.2 mL). The reaction is stirred at 0° C. with Argon sparging for 1 hr. The reaction mixture is slowly added to 1.5 L of vigorously stirred water. Filtration gives C-2 as a solid.

A solution of C-2 (10.0 g, 30.4 mmol) in DME (350 mL) is heated to 60° C., KHMDS (61.5 mL, 0.5M in toluene) is added slowly and the resulting solution is stirred for 30 minutes. The reaction is cooled to room temperature, quenched with water, concentrated in vacuo and extracted with EtOAc. The combined organics are washed with brine, dried over $Na_2SO_4$, filtered and concentrated. The residue is purified by flash column chromatography (0-40% EtOAc in heptanes) to give C-3 as a solid.

To a degassed solution of C-3 (5.50 g, 18.8 mmol) in anhydrous DMF (100 mL) is added $Zn(CN)_2$ (2.2 g, 18.8 mmol) and dppf (1.0 g, 1.9 mmol) followed by $Pd_2(dba)_3$ (0.86 g, 0.90 mmol), and the reaction is warmed to 80° C. overnight. The reaction is then cooled to room temperature and stirred for 48 h. The mixture is filtered through a bed of Diatomaceous earth, and the filtrate slowly poured into 1 L of vigorously stirred water. The resulting solid is isolated by filtration and purified by flash chromatography on silica gel (0-40% EtOAc in heptanes) to give C-4 as a solid.

A solution of C-4 (3.5 g, 14.7 mmol) in 125 mL of THF is cooled down to 0° C. in a ice bath. 25 mL of 1.5M DIBAL-H (36.7 mmol, 2.5 eq) solution in toluene is added dropwise via addition funnel (over 15 min). The reaction is stirred at 0° C. for 30 min and then allowed to warm to room temperature. The reaction mixture is stirred for 2 h at room temperature. The reaction is cooled to 0° C. and carefully quenched with EtOAc (200 mL total), followed by 100 mL of water and 400 mL of saturated aqueous Rochelle's salt solution, and the mixture is stirred for 5 minutes. The entire mixture is transferred to a separatory funnel and the layers are separated. The aqueous layer is extracted with 100 mL of EtOA twice, and the extracts are combined and washed with 0.5 N HCl (100 mL). Some product is observed in the acid layer. Acid layer is cooled to 0° C., neutralized with saturated $NaHCO_3$, and extracted with EtOAc twice. The organic layers are combined, washed with brine, and dried over anhydrous $Na_2SO_4$, and evaporated. The resulting residue is purified by flash chromatography eluting with 0-80% EtOAc/Heptane to give the title compound as a solid.

Preparation of (±)-4-(2,3-Dihydro-[1,4]dioxino[2,3-b]pyridin-3-yl)-benzaldehyde (D)

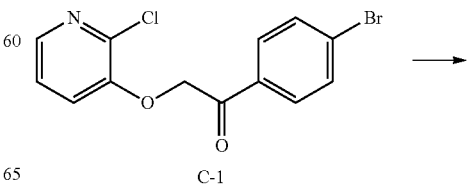

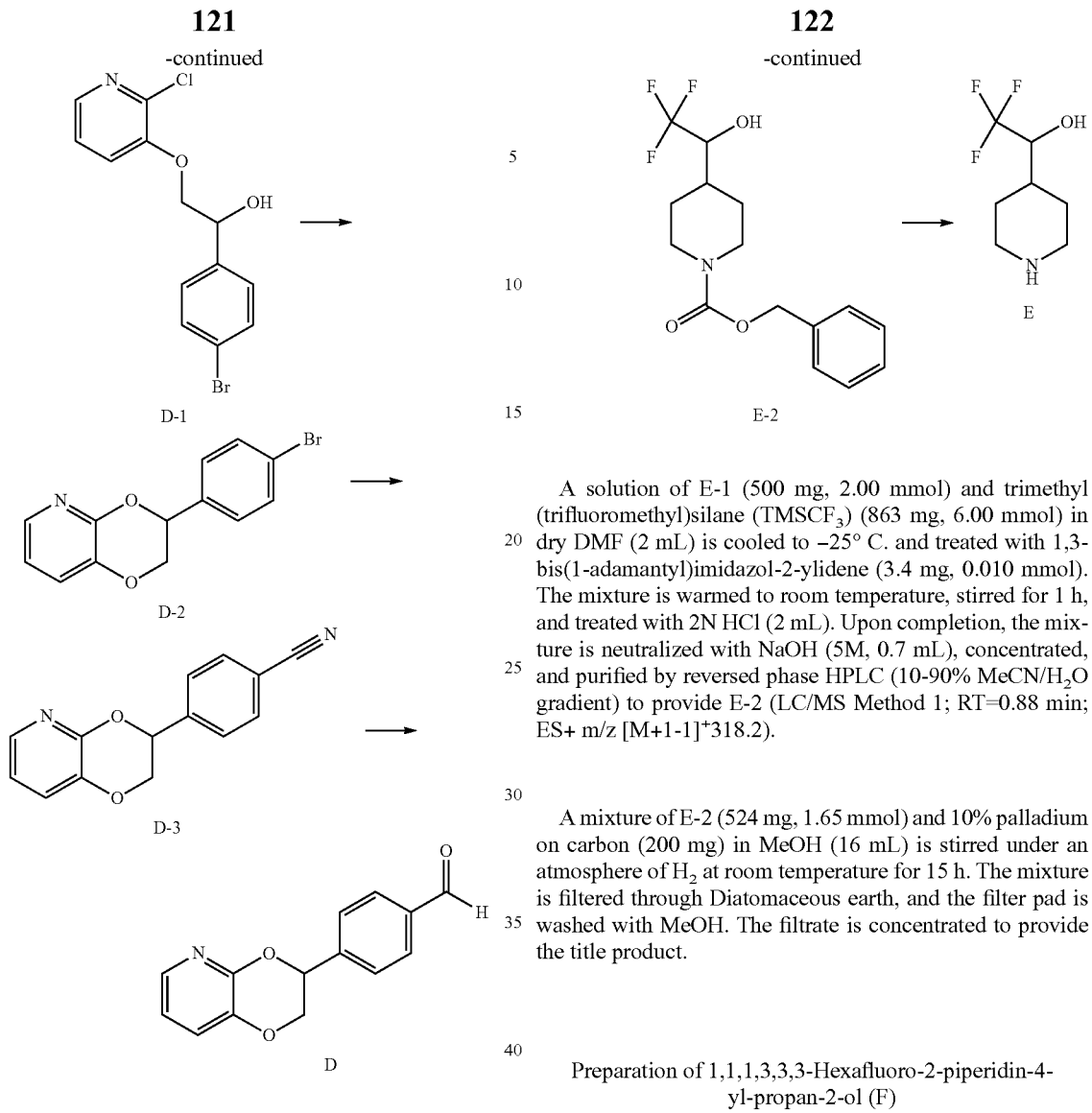

Compound D-1 is synthesized from C-1 according to the procedure described for the synthesis of B-1.

The title compound is synthesized from D-1 according to the procedure described for the synthesis of C from C-2.

Preparation of 2,2,2-trifluoro-1-piperidin-4-yl-ethanol (E)

A solution of E-1 (500 mg, 2.00 mmol) and trimethyl (trifluoromethyl)silane (TMSCF$_3$) (863 mg, 6.00 mmol) in dry DMF (2 mL) is cooled to −25° C. and treated with 1,3-bis(1-adamantyl)imidazol-2-ylidene (3.4 mg, 0.010 mmol). The mixture is warmed to room temperature, stirred for 1 h, and treated with 2N HCl (2 mL). Upon completion, the mixture is neutralized with NaOH (5M, 0.7 mL), concentrated, and purified by reversed phase HPLC (10-90% MeCN/H$_2$O gradient) to provide E-2 (LC/MS Method 1; RT=0.88 min; ES+ m/z [M+1-1]$^+$318.2).

A mixture of E-2 (524 mg, 1.65 mmol) and 10% palladium on carbon (200 mg) in MeOH (16 mL) is stirred under an atmosphere of H$_2$ at room temperature for 15 h. The mixture is filtered through Diatomaceous earth, and the filter pad is washed with MeOH. The filtrate is concentrated to provide the title product.

Preparation of 1,1,1,3,3,3-Hexafluoro-2-piperidin-4-yl-propan-2-ol (F)

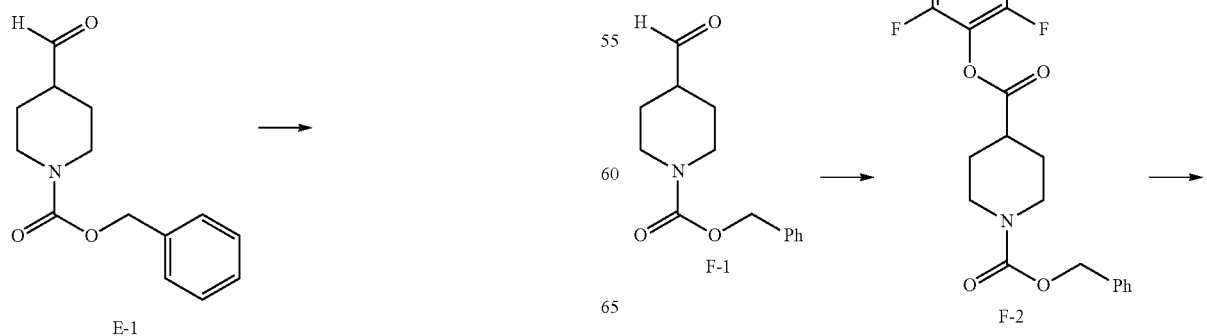

-continued

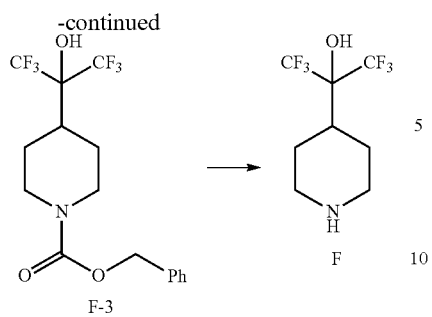

A solution of piperidine-1,4-dicarboxylic acid monobenzyl ester (1.0 g, 3.80 mmol), 2,3,4,5,6-pentafluoro-phenol (0.77 g, 4.18 mmol) and dicyclohexyl-carbodiimide (0.86 g, 4.18 mmol) in dioxane (12 mL) is stirred at room temperature for 16 h. The mixture is filtered and concentrated in vacuo. The residue is purified by flash chromatography (EtOAc/heptane) to give F-2.

To a solution of F-2 (200 mg, 0.47 mmol) in DME (1.0 mL) is added TMSCF$_3$ (139 mg, 0.98 mol) and tetramethylammonium fluoride (43 mg, 0.47 mmol) at −50° C. The resulting mixture is allowed to warm to room temperature and stirred for 16 h. The mixture is concentrated in vacuo and the residue is purified by reverse HPLC (30-95%, MeCN/Water) to give F-3.

A mixture of F-3 (670 mg, 1.74 mmol) and 10% palladium on carbon (210 mg) in MeOH (17 mL) is stirred under an atmosphere of H$_2$ at room temperature for 15 h. The mixture is filtered through Diatomaceous earth and the filter pad is washed with MeOH. The filtrate is concentrated to provide the title product (F).

Preparation of 4-Methyl-piperidine-4-carboxylic acid methyl ester hydrochloride (1-1)

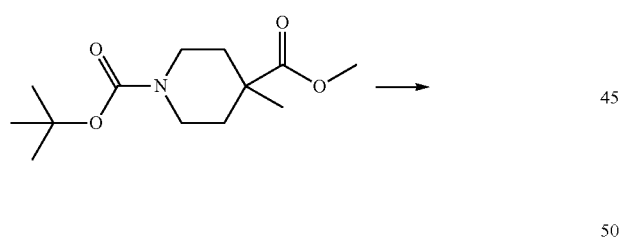

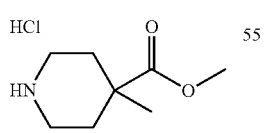

To a stirred solution of 4-methyl-piperidine-1,4-dicarboxylic acid mono-tert-butyl ester (1.00 g, 4.10 mmol) in MeOH (2 mL) is added HCl (5 ml, 4 M in dioxane). After 18 h, the mixture is evaporated to dryness, the residue is dissolved in MeOH (3 mL), and the stirred solution is treated with Et$_2$O (45 ml). The resulting solid is filtered and dried to give the title compound.

The following intermediates are also prepared according to the procedure described for the synthesis of 1-1:

| Intermediate # | Structure |
| --- | --- |
| I-2 | 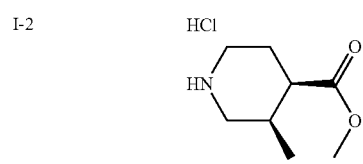 |
| I-3 | 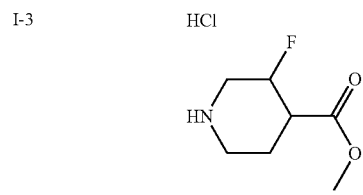 |
| I-4 | 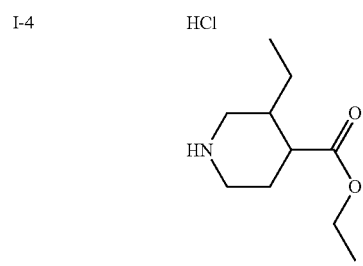 |
| I-5 | 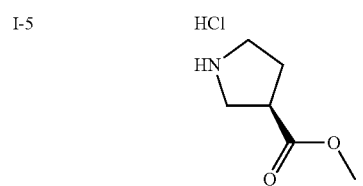 |
| I-6 | 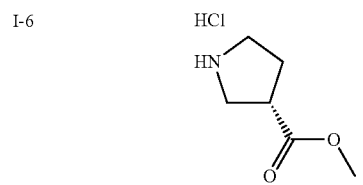 |

Preparation of 1-[(S)-4-(2,3-Dihydro-[1,4]dioxino[2,3-b]pyridin-3-yl)-benzyl]-piperidine-4-carboxylic acid (K)

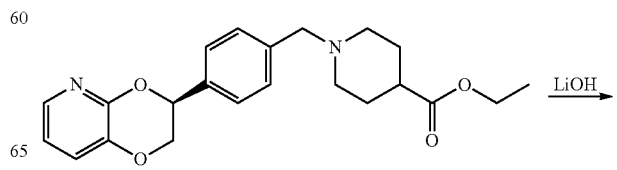

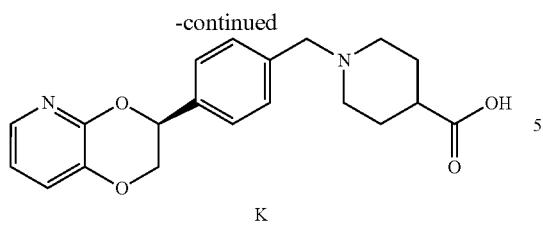

K

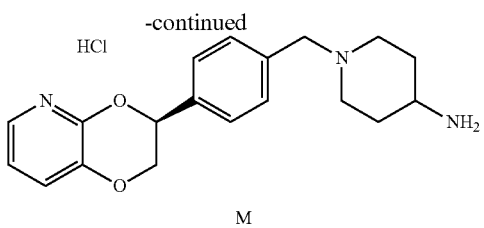

M

To a solution of 1-[(8)-4-(2,3-dihydro-[1,4]dioxino[2,3-b]pyridin-3-yl)-benzyl]-piperidine-4-carboxylic acid ethyl ester (prepared from Intermediate C and piperidine-4-carboxylic acid ethyl ester according to General Method F) (3.00 g, 7.90 mmol) in 4:1 EtOH/water (80 mL) is added LiOH monohydrate (0.994 g, 23.7 mmol) and the reaction stirred overnight at about 25° C. The reaction is concentrated, diluted with water and washed with Et$_2$O (2x). The aqueous layer is lypholized to dryness then purified by silica gel chromatography eluting with 20% (2M NH$_3$ in MeOH)/DCM. The pooled fractions are concentrated and dried to provide the title compound (K) as a foamed solid.

Preparation of Thiomorpholine 1-oxide (L)

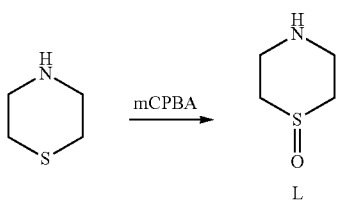 [SMILES: C1CSCCN1 ; O=S1CCNCC1]

L

To a solution of thiomorpholine (500 mg, 4.85 mmol) in DCM (50 mL) is added a solution of mCPBA (1.14, g 5.09 mmol) in DCM (25 mL) dropwise over 10 min at 0° C. The reaction is stirred for 24 h at about 25° C. and concentrated. The residue is dissolved in DCM (10 mL) and MP-carbonate resin added (3.16 g, 9.72 mmol), and the suspension stirred for 1 h. Filtration and concentration affords the title compound (L).

Preparation of 1-[(S)-4-(2,3-Dihydro-[1,4]dioxino[2,3-b]pyridin-3-yl)-benzyl]-piperidin-4-ylamine (M)

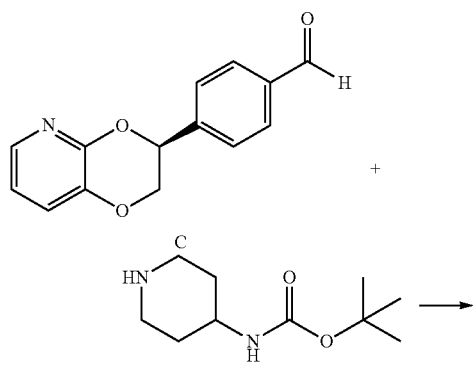

Intermediate M is prepared from Intermediate C and Piperidin-4-yl-carbamic acid tert-butyl ester according to Example 217.

Preparation of (4,5,6,7-Tetrahydro-thiazolo[5,4-c]pyridin-2-yl)-carbamic acid tert-butyl ester (N)

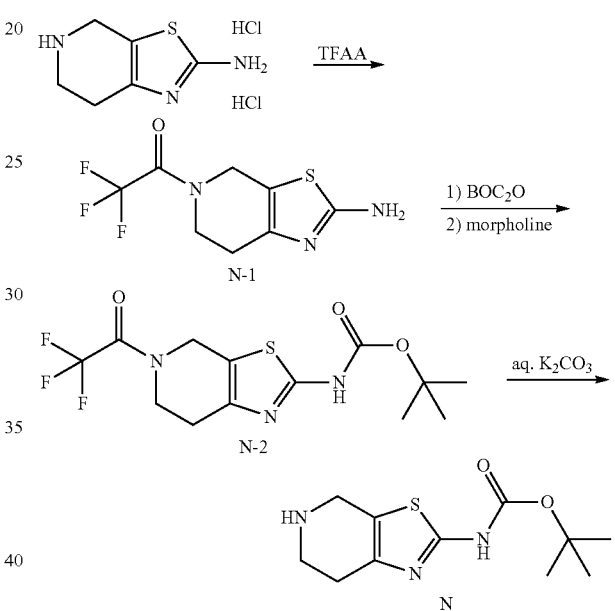

To a solution of 4,5,6,7-tetrahydro-thiazolo[5,4-c]pyridin-2-ylamine dihydrochloride (1.79 g, 7.83 mmol) and DIPEA (4.43 mL, 24.0 mmol) in DCM (20 mL) at 0° C. is added trifluoroacetic anhydride (2.24 mL, 16.0 mmol) in a dropwise fashion. The mixture is stirred for 1 h, diluted with DCM (200 mL) and quenched with sat. NH$_4$Cl (200 mL). The layers are separated and the organic layer washed with water (2×200 mL), brine (200 mL), dried (MgSO4), and concentrated. The residue is purified by silica gel chromatography eluting with 0-10% MeOH/DCM to give 1:1 bistrifluoroacetamide/monotrifluoroacetamide. The mixture is dissolved in EtOH (5 mL) and 4M HCl in 1,4-dioxane (4 mL) is added, and the reaction heated at 60° C. over 2 h. The mixture is concentrated to afford Intermediate (N-1).

To a solution of 1-(2-amino-6,7-dihydro-4H-thiazolo[5,4-c]pyridin-5-yl)-2,2,2-trifluoro-ethanone (3.00 g, 11.9 mmol) and di-tert-butyl dicarbonate (11.8 g, 52.2 mmol) in THF (100 mL) is added catalytic dimethyl-pyridin-4-yl-amine (50 mg, 0.41 mmol) and the reaction stirred at 25° C. for 24 hours. Concentrate the reaction and purify by silica gel chromatography eluting with 0-20% EtOAc/hexane to afford [5-(2,2,2-trifluoro-acetyl)-4,5,6,7-tetrahydro-thiazolo[5,4-c]pyridin-2-yl]-carbamic acid bis(tert-butyl ester) (5.00 g; 11.1 mmol). To a solution of this in THF (20 mL) is added morpholine (3.24 ml; 36.6 mmol) and the reaction stirred at about 25° C. for 24 hours. The reaction is concentrated at 45° C. to give a semi-solid residue. This is suspended in EtOAc (300 mL), washed with water (300 mL) and brine (100 mL), and dried (Na₂SO₄). Concentration and trituration in MeOH (50 mL) affords Intermediate (N-2) as a white solid.

To a suspension of [5-(2,2,2-trifluoro-acetyl)-4,5,6,7-tetrahydro-thiazolo[5,4-c]pyridin-2-yl]-carbamic acid tert-butyl ester (3.50 g, 9.86 mmol) in MeOH (75 mL) is added a solution of potassium carbonate (13.8 g; 98.6 mmol) in water (125 mL) and the reaction stirred at about 25° C. for 24 hours. The suspension is concentrated and the residue suspended in EtOAc (300 mL). This is washed with sat. NH₄Cl (300 mL) then brine (100 mL). Solid product forms in the EtOAc layer. This is filtered off as crop 1. The aqueous layer is extracted with more EtOAc (3×300 mL) and the combined extracts washed with brine and dried (Na₂SO₄). Concentrate to a white solid and combine with the above precipitate. Triturate this in EtOAc (50 mL) and filter to give the title compound (N).

Preparation of (1S,4S)-1-(2,5-Diaza-bicyclo[2.2.1]hept-2-yl)-ethanone hydrochloride (O)

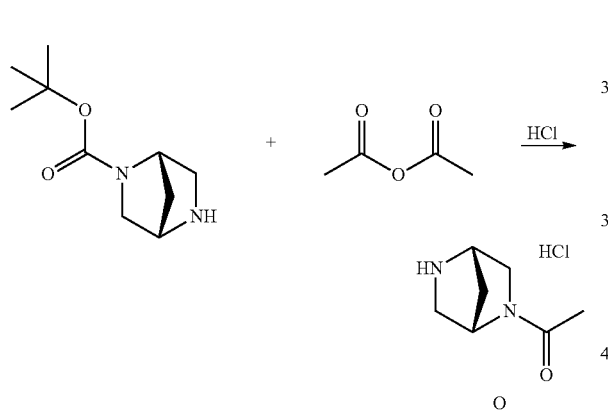

To a solution of (1S,4S)-2,5-diaza-bicyclo[2.2.1]heptane-2-carboxylic acid tert-butyl ester (1.00 g, 5.04 mmol) in DCM (15 mL) is added acetic anhydride (0.52 mL, 5.55 mmol) and the reaction stirred at about 25° C. for 72 hours. The reaction is concentrated, and the residue dissolved in DCM (15 mL) and treated with 4M HCl in 1,4-dioxane (5.04 mL, 20.2 mmol). The reaction is stirred overnight, and the solid filtered to afford the title compound (O).

Preparation of (1S,4S)-2,5-Diaza-bicyclo[2.2.1]heptane-2-carboxylic acid amide hydrochloride (P)

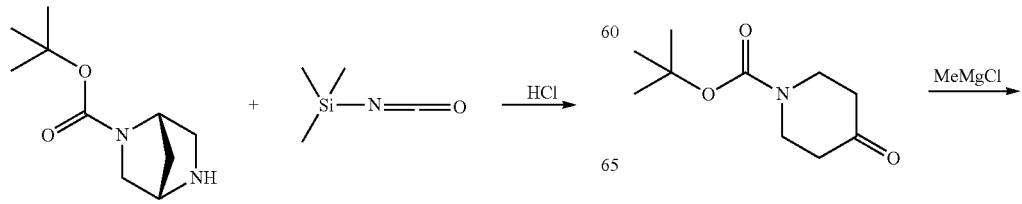

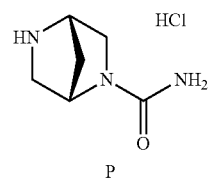

To a solution of (1S,4S)-2,5-diaza-bicyclo[2.2.1]heptane-2-carboxylic acid tert-butyl ester (1.00 g, 5.04 mmol) in DCM (15 mL) is added TMS-isocyanate (2.68 mL, 20.2 mmol) and the reaction stirred at about 25° C. for 72 hours. The reaction is concentrated, and the residue dissolved in DCM (15 mL) and treated with 4M HCl in 1,4-dioxane (5.04 mL, 20.2 mmol). The reaction is stirred overnight, and the solid filtered to afford the title compound (P).

Preparation of (endo)-8-[(S)-4-(2,3-Dihydro-[1,4]dioxino[2,3-b]pyridin-3-yl)-benzyl]-8-aza-bicyclo[3.2.1]oct-3-ylamine dihydrochloride (Q)

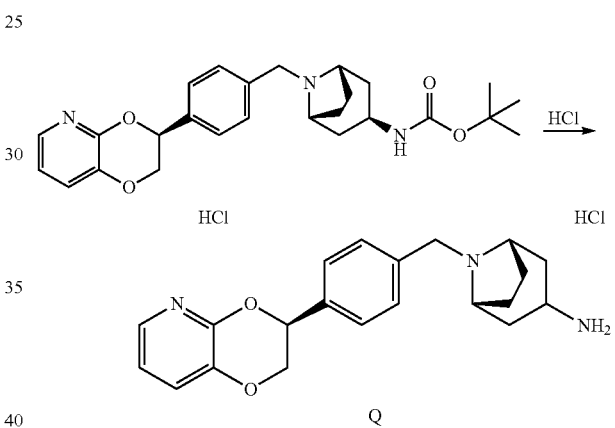

To a solution of {(endo)-8-[(S)-4-(2,3-dihydro-[1,4]dioxino[2,3-b]pyridin-3-yl)-benzyl]-8-aza-bicyclo[3.2.1]oct-3-yl}-carbamic acid tert-butyl ester (prepared from Intermediate C and (endo)-(8-aza-bicyclo[3.2.1]oct-3-yl)-carbamic acid tert-butyl ester according to General Method I) (285 mg, 0.568 mmol) in DCM (15 mL) was added 4M HCl in 1,4-dioxane (6.0 mL; 24.0 mmol) and the reaction stirred at about 25° C. for 24 hours. The reaction was concentrated and the solid suspended in DCM and heptane. Filter the solid to afford the title compound (Q).

Preparation of 4-Methyl-piperidin-4-ol hydrochloride (R)

-continued

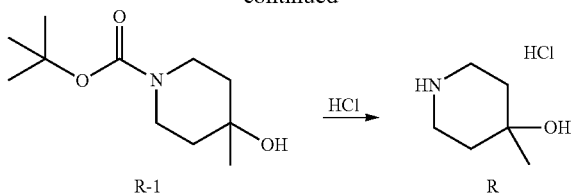

To a solution of 4-oxo-piperidine-1-carboxylic acid tert-butyl ester (1.00 g, 4.92 mmol) in dry THF (50 mL) at −78° C. is added 3.0M methyl magnesium chloride in THF (3.00 mL, 9.00 mmol) dropwise over 1 min. The reaction is warmed to 0° C. over 1 h. The reaction is cooled to −20° C. and quenched by addition of cold sat. NH$_4$Cl (100 mL) with vigorous stirring. To the suspension is added EtOAc (200 mL) and the biphase partitioned. The aqueous layer is re-extracted with EtOAc (200 mL) and the combined organics washed with brine (100 mL) and dried (Na$_2$SO$_4$). The solvent is removed in vacuo to give R-1 as a gum.

To a solution of 4-hydroxy-4-methyl-piperidine-1-carboxylic acid tert-butyl ester (1.08 g, 4.87 mmol) in DCM (25 mL) is added 4M HCl in 1,4-dioxane (20 mL, 80 mmol) and the reaction stirred at about 25° C. for 18 hours. The reaction is concentrated, suspended in Et$_2$O and heptane, and filtered to afford the title compound (R) as a white powder.

Preparation of (S)-3-(4-piperazin-1-ylmethyl-phenyl)-2,3-dihydro-[1,4]dioxino[2,3-b]pyridine (S)

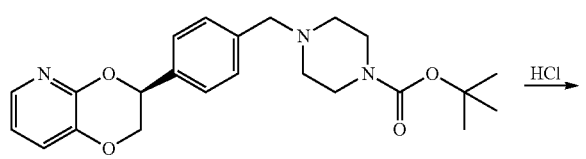

To a solution of 4-[(S)-4-(2,3-dihydro-[1,4]dioxino[2,3-b]pyridin-3-yl)-benzyl]-piperazine-1-carboxylic acid tert-butyl ester (prepared from Intermediate C and piperazine-1-carboxylic acid tert-butyl ester according to General Method N) (7.32 g, 17.8 mmol) in 1,4-dioxane (200 mL) is added 4M HCl in 1,4-dioxane (22.2 mL, 88.9 mmol). The resulting slurry is stirred overnight. The reaction is poured into water (600 mL) and basified with 2M aqueous Na$_2$CO$_3$. The product is extracted with DCM, and the combined extracts washed with brine and dried over Na$_2$SO$_4$ to afford the title compound (S) as an oil that partially crystallizes.

Preparation of (endo)-N-(8-Aza-bicyclo[3.2.1]oct-3-yl)-acetamide (T)

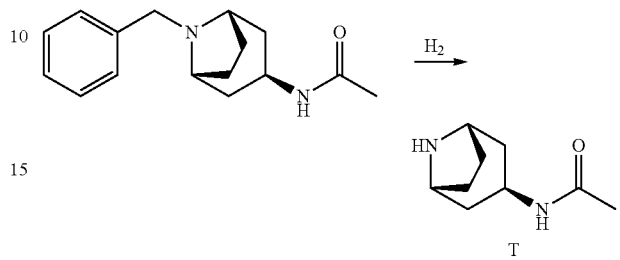

Intermediate T is Prepared according to the procedure described in WO2009/126806A2.

Preparation of 1-(3,8-Diaza-bicyclo[3.2.1]oct-3-yl)-ethanone hydrochloride (U)

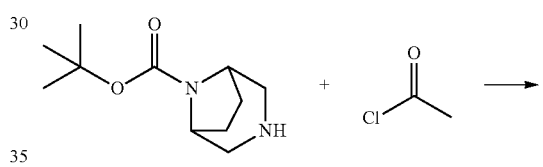

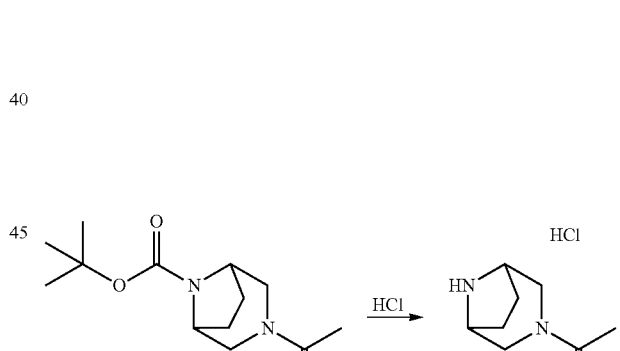

To a solution of 3,8-diaza-bicyclo[3.2.1]octane-8-carboxylic acid tert-butyl ester (1.00 g, 4.71 mmol) and triethylamine (1.41 mL, 10.0 mmol) in DCM (20 mL) cooled to −20° C. is added acetyl chloride (0.36 mL, 5.0 mmol) and the reaction stirred at about 25° C. for 24 hours. The reaction is concentrated, suspended in EtOAc (125 mL) then washed with 0.1M HCl (100 mL), sat. NaHCO$_3$ (100 mL) and brine (50 mL). The organic layer is dried (Na$_2$SO$_4$) and concentrated to give (U-1) as an oil.

To a solution of 3-acetyl-3,8-diaza-bicyclo[3.2.1]octane-8-carboxylic acid tert-butyl ester (1.20 g, 4.49 mmol) in DCM (25 mL) is added 4M HCl in 1,4-dioxane (20.0 mL, 80.0 mmol) and the reaction stirred at about 25° C. for 18 hours.

The reaction is concentrated, suspended in Et$_2$O, and filtered to afford the title compound (U) as a hydroscopic solid.

Preparation of hydrazino-oxo-acetic acid ethyl ester (V)

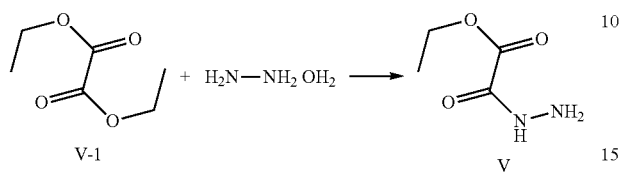

To a solution of V-1 (85.0 g; 0.582 mol) in EtOH is added H$_4$N$_2$·H$_2$O (36.4 g, 0.582 mol) at −15~−25° C. The precipitate is removed by filtration and the filtrate is concentrated to give the title product (V).

Preparation of 5,6,7,8-tetrahydro-[1,2,4]triazolo[4,3-a]pyrazine-3-carboxylic acid ethyl ester. HCl (W)

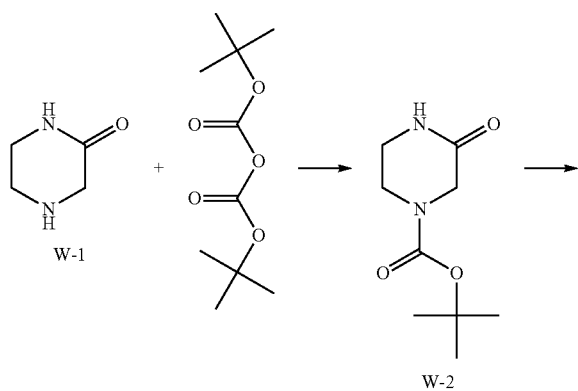

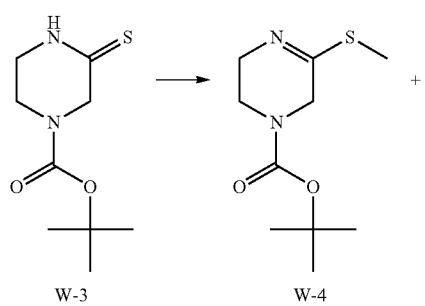

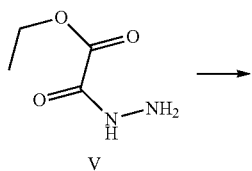

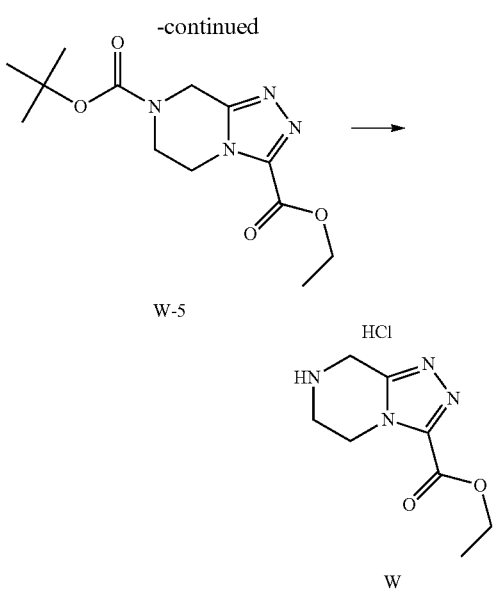

To a stirred solution of W-1 (20.0 g, 0.200 mol) in DCM, is added Boc anhydride (43.6 g, 0.200 mol), and TEA (40.4 g, 0.400 mol). The mixture is stirred at about 25° C. for about 18 hours. The mixture is concentrated and the residue dissolved in EtOAc then extracted with water. The organic layer is concentrated and the residue is purified by silica gel chromatography to give W-2.

To a stirred solution of W-2 (20.0 g, 0.100 mol) in THF, is added P$_2$S$_5$ (6.70 g, 0.03 mol). The reaction is stirred at 60° C. for 12 h. The precipitate is filtered, and the filtrate is evaporated to give crude W-3.

To a stirred solution of crude W-3 (20.0 g, 0.092 mol) in DCM, is added CH$_3$I (150 g, 1.06 mol). The reaction is stirred at about 25° C. for 12 h then concentrated to give crude W-4.

To a stirred solution of crude W-4 (20.0 g, 0.087 mol) in EtOH is added intermediate V (11.5 g, 0.087 mol), and the reaction mixture is stirred at reflux for 12 h. The mixture is concentrated and the residue is purified by silica gel chromatography to give W-5.

To a solution of HCl-MeOH (200 mL) is added W-5 (8.50 g, 28.7 mmol), and the solution is stirred at rt. After 4 h, the solution is concentrated to afford the title compound (W).

Preparation of 5,6,7,8-Tetrahydro-[1,2,4]triazolo[4,3-a]pyrazine-3-carboxylic acid ethyl ester (X)

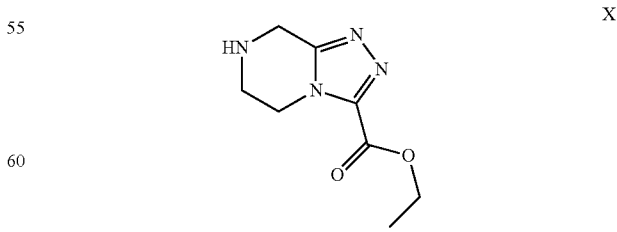

The intermediate X can be synthesized according to the procedure described in Kim, D.; Kowalchick, J. E.; Edmondson, S. D.; Mastracchio, A.; Xu, J.; Eiermann, G. J.; Leiting, B.; Wu, J. K.; Pryor, K. D.; Patel, R. A.; He, H.; Lyons, K. A.; Thornberry, N. A.; Weber, A. E. *Bioorg. Chem. Lett.* 17, 2007, 3373.

Preparation of 5,6,7,8-tetrahydro-4H-1,2,3a,6-tetraaza-azulene-3-carboxylic acid ethyl ester. TFA (Y)

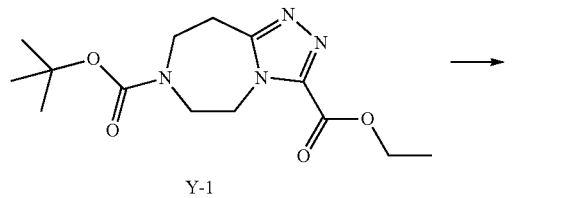

The intermediate Y-1 is synthesized starting from [1,4] diazepan-5-one according to the procedure described for the synthesis of intermediate W-5.

A solution of Y-1 (500 mg, 1.61 mmol) in DCM (5 mL) is treated dropwise with TFA (1.00 mL, 13.0 mmol), and the reaction is stirred over night. The reaction is concentrated to afford the crude title product Y.

Preparation of 5,6,7,8-tetrahydro-imidazo[1,2-a]pyrazine-2-carboxylic acid ethyl ester (Z)

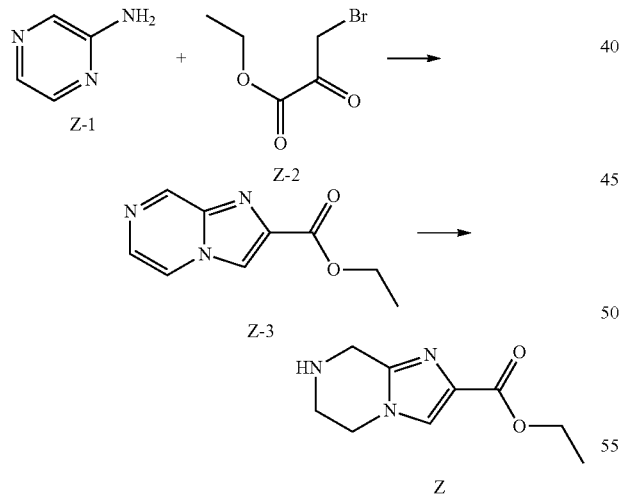

A solution of Z-1 (10.0 g, 105 mmol) in DME (100 mL) is treated dropwise with the Z-2 (16.3 mL, 129 mmol) over 1 h at rt. After 3 h, the mixture is cooled to 0° C. and filtered. The solid is washed with ether (50 mL) and dried under vacuum. The solid is heated in refluxing EtOH (100 mL) for 3 h. The mixture is concentrated, the residue is dissolved in CHCl₃ (100 mL), and basified to pH 9 with sat. NaHCO₃ (100 mL). The suspension is filtered through a pad of Diatomaceous earth, which is washed with water (100 mL) and CHCl₃ (3×100 mL). The phases are separated, and the aqueous layer extracted with CHCl₃ (100 mL). The combined organic extracts are dried over MgSO₄, filtered and concentrated. The residue is crystallized from EtOH (100 mL) to give Z-3.

To a stirred solution of Z-3 (1.00 g, 5.23 mmol) in EtOH (50 mL) is added 5% Pd on carbon (300 mg), and the mixture stirred under a H₂ atmosphere. After 72 h, the mixture is filtered through a pad of Diatomaceous earth, and concentrated to give the title product (Z).

Preparation of [(1α,5α,6α)-3-aza-bicyclo[3.1.0]hexane]-6-carboxylic acid ethyl ester (AA)

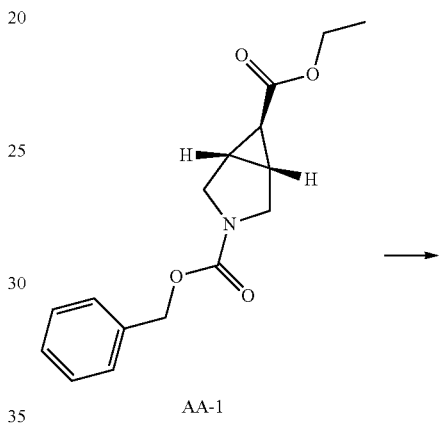

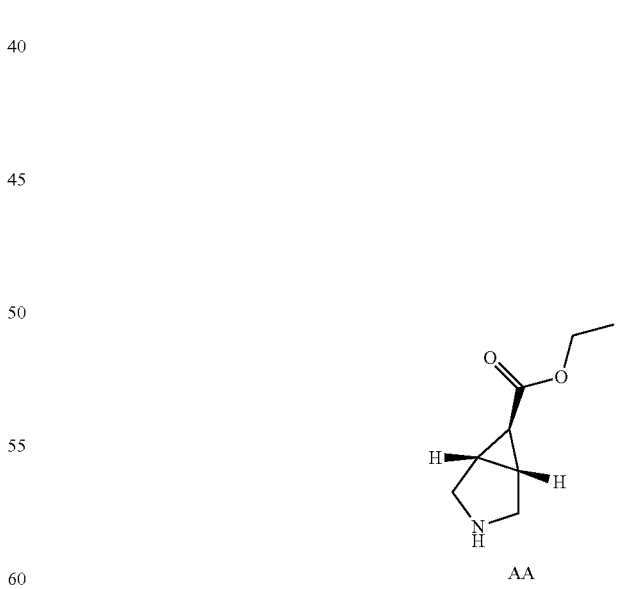

Intermediate AA-1 can be synthesized according to the procedure described in WO2010/116328.

To a solution of AA-1 (700 mg, 2.42 mmol) in MeOH (5 mL) is added 5% Pd/C (52 mg) and the mixture stirred under H₂ at room temperature. After 18 h, the mixture is evacuated and purged with Argon, filtered through a pad of Diatomaceous earth filter aid, and concentrated to give the title product (AA).

Preparation of [(1α,5α,6β)-3-aza-bicyclo[3.1.0]hexane]-6-carboxylic acid ethyl ester (BB)

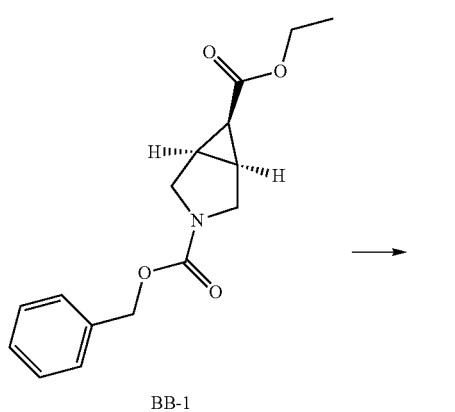

Intermediate BB-1 can be synthesized according to the procedure described in WO2010/116328.

The title product BB is prepared from BB-1 according to the procedure described for intermediate AA.

Preparation of [(1α,5α,6β)-N-(3-Aza-bicyclo[3.1.0]hex-6-yl)]-acetamide (CC)

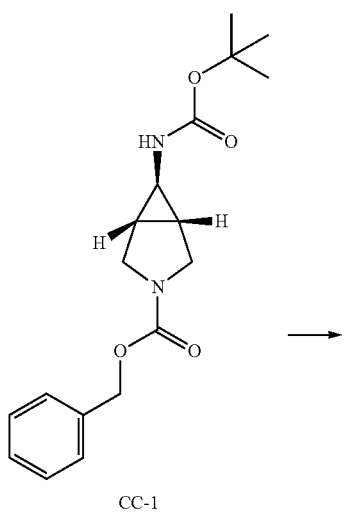

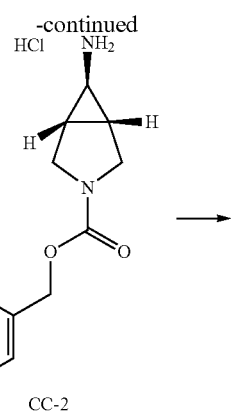

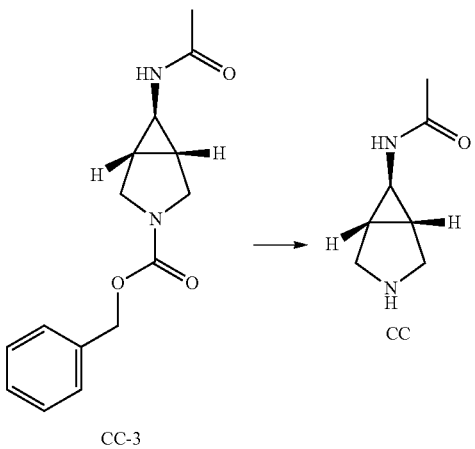

Intermediate CC-1 can be synthesized according to the procedure described in Brighty, K. E., Castaldi, M. J., *Synlett*, 1996, 1097.

To a solution of CC-1 (665 mg, 2.00 mmol) in MeOH (8 mL) is added 4M HCl in 1,4-dioxane (2.5 mL, 10 mmol) and the reaction stirred overnight. The mixture is concentrated and the residue suspended in $Et_2O$. The resulting mixture is isolated to afford CC-2.

To a solution of CC-2 (200 mg, 0.744 mmol) in DCM (3 mL) is added acetic anhydride (0.105 mL, 1.12 mmol) followed by DIPEA (0.26 mL, 1.49 mmol). After stirring overnight, the reaction is diluted with EtOAc (50 mL) and washed with sat. $NH_4Cl$ (25 mL), sat. $NaHCO_3$ (25 mL) and brine (25 mL). The organic layer is dried over $MgSO_4$, filtered, and concentrated to give the crude CC-3.

To a solution of CC-3 (189 mg, 0.689 mmol) in MeOH (5 mL) is added 5% Pd/C (100 mg), and the mixture stirred under $H_2$ at rt. After 18 h, the mixture is filtered through a pad of Diatomaceous earth filter aid, and concentrated to give the title product (CC).

Preparation of 3-bromo-5,6,7,8-tetrahydro-imidazo[1,2-a]pyrazine.TFA (DD)

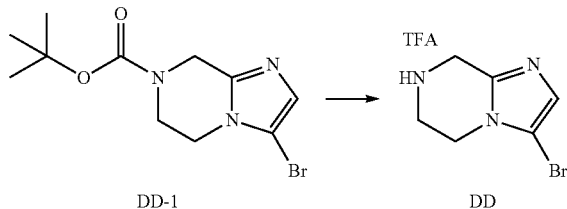 [SMILES: CC(C)(C)OC(=O)N1CCn2c(Br)cnc2C1 ; Brc1cnc2n1CCNC2 ; "DD-1" ; "DD"]

The title product is prepared from DD-1 according to the procedure described for intermediate Y.

Preparation of (S)-3-{4-[(1S,4S)-1-(2,5-Diaza-bicyclo[2.2.1]hept-2-yl)methyl]-phenyl}-2,3-dihydro-[1,4]dioxino[2,3-b]pyridine dihydrochloride (EE)

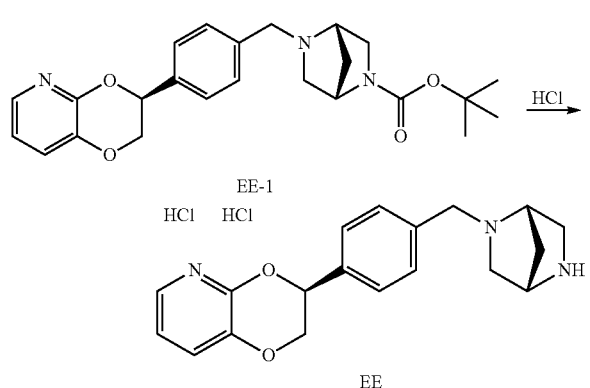

The title product EE is prepared from compound EE-1 (prepared from Intermediate C and (1S,4S)-2,5-diaza-bicyclo[2.2.1]heptane-2-carboxylic acid tert-butyl ester according to General Method N) according to the procedure described for the synthesis of Intermediate Q.

Preparation of (S)-3-(4-[1,4]Diazepan-1-ylmethyl-phenyl)-2,3-dihydro-[1,4]dioxino[2,3-b]pyridine (FF)

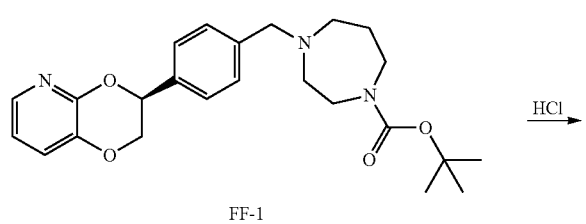

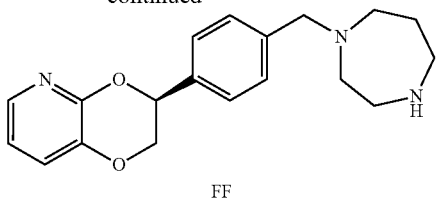

The title product FF is prepared from compound ft-1 (prepared from Intermediate C and [1,4]diazepane-1-carboxylic acid tert-butyl ester according to General Method N) according to the procedure described for the synthesis of Intermediate S.

Preparation of {1-[(S)-4-(2,3-Dihydro-[1,4]dioxino[2,3-b]pyridin-3-yl)-benzyl]-piperidin-4-yl}-acetic acid (GG)

The title product GG is prepared from compound GG-1 (prepared from Intermediate C and piperidin-4-yl-acetic acid methyl ester according to General Method F) according to the procedure used to synthesize Intermediate K.

Preparation of C-{1-[(S)-4-(2,3-Dihydro-[1,4]dioxino[2,3-b]pyridin-3-yl)-benzyl]-piperidin-4-yl}-methylamine dihydrochloride (HH)

The title product HH is prepared from compound HH-1 (prepared from Intermediate C and piperidin-4-ylmethyl-carbamic acid tert-butyl ester according to General Method I) according to the procedure used to synthesize Intermediate Q.

Preparation of {(1α,5α,6α)-3-[(S)-4-(2,3-Dihydro-[1,4]dioxino[2,3-b]pyridin-3-yl)-benzyl]-3-aza-bicyclo[3.1.0]hex-6-yl}-methylamine hydrochloride (II)

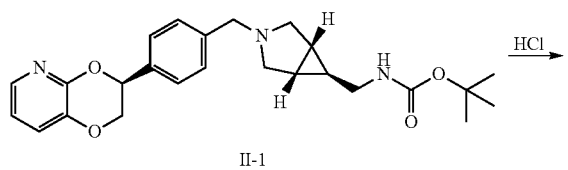

II-1

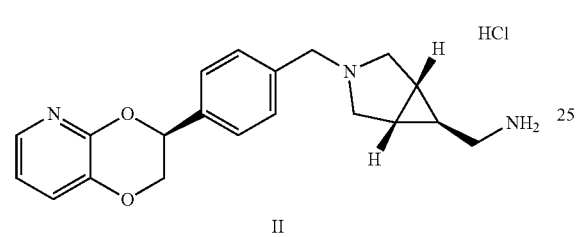

II

The title product II is prepared from compound II-1 (prepared from Intermediate C and [(1α,5α,6α)-1-(3-azabicyclo[3.1.0]hex-6-yl)methyl]-carbamic acid tert-butyl ester according to General Method I) according to the procedure used to synthesize Intermediate Q.

Preparation of (S)-3-{4-[(1S,4S)-1-(2,5-Diaza-bicyclo[2.2.2]oct-2-yl)methyl]-phenyl}-2,3-dihydro-[1,4]dioxino[2,3-b]pyridine (JJ)

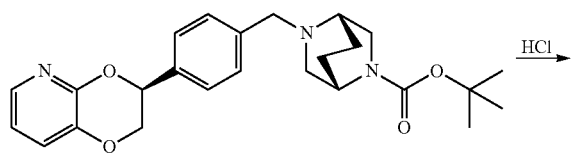

JJ-1

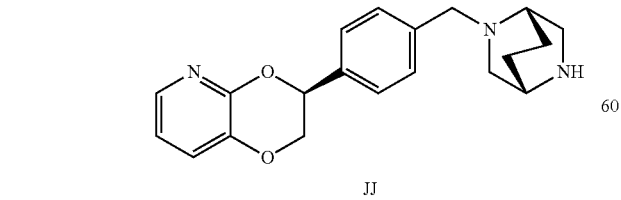

JJ

The title product JJ is prepared from compound JJ-1 (prepared from Intermediate C and (1S,4S)-2,5-diaza-bicyclo

[2.2.2]octane-2-carboxylic acid tert-butyl ester according to General Method J) according to the procedure used to synthesize Intermediate S.

Preparation of 1-(Hexahydro-pyrrolo[3,4-c]pyrrol-2-yl)-ethanone hydrochloride (KK)

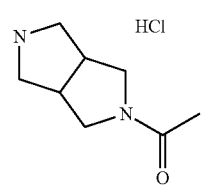

KK

The title product KK is prepared from hexahydro-pyrrolo[3,4-c]pyrrole-2-carboxylic acid tert-butyl ester according to the procedure described for the synthesis of Intermediate O.

Preparation of 1-(Hexahydro-pyrrolo[3,4-c]pyrrol-2-yl)-ethanone hydrochloride (LL)

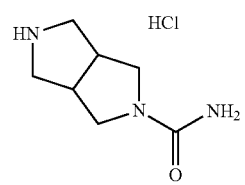

LL

The title product LL is prepared from hexahydro-pyrrolo[3,4-c]pyrrole-2-carboxylic acid tert-butyl ester according to the procedure described for the synthesis of Intermediate P.

Preparation of [(exo)-1-(8-Aza-bicyclo[3.2.1]oct-3-yl)]-urea hydrochloride (MM)

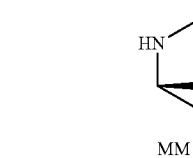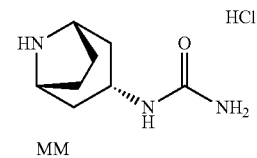

MM

The title product MM is prepared from [(exo)-3-Amino-8-aza-bicyclo[3.2.1]octane]-8-carboxylic acid tert-butyl ester according to the procedure described for the synthesis of Intermediate P.

Preparation of (S)-3-{4-[(1S,4S)-1-(2,5-Diaza-bicyclo[2.2.1]hept-2-yl)methyl]-phenyl}-2,3-dihydro-[1,4]dioxino[2,3-b]pyridine (NN)

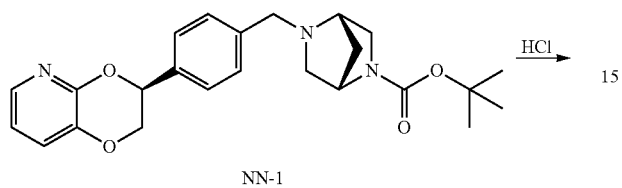

NN-1

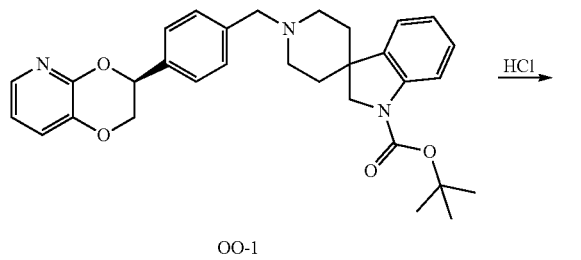

NN

The title product NN is prepared from NN-1 (prepared from Intermediate C and (1S,4S)-2,5-Diaza-bicyclo[2.2.1]-heptane-2-carboxylic acid tert-butyl ester according to General Method N) according to the procedure for synthesis of Intermediate S.

Preparation of {1-[(S)-4-(2,3-dihydro-[1,4]dioxino-[2,3-b]pyridin-3-yl)-benzyl]-spiro-(3,4'-piperidine-3H-indole) (OO)

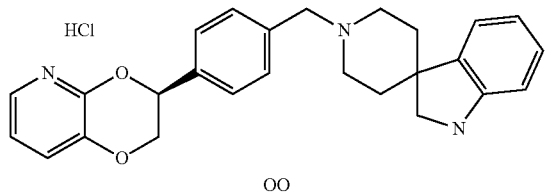

OO-1

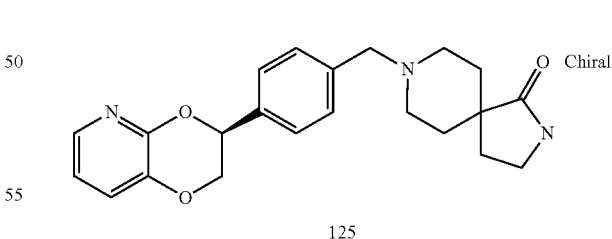

OO

Compound OO is prepared from OO-1 (prepared from Intermediate C and spiro-(3,4'-piperidine-3H-indole) according to General Method D) from the procedure used to prepare Intermediate S.

Synthesis of Compounds of Formula I

General Method A Through N (Protocols for Reductive Amination)

Example of General Method A

Preparation of 8-[(S)-4-(2,3-Dihydro-[1,4]dioxino[2,3-b]pyridin-3-yl)-benzyl]-2,8-diaza-spiro[4.5]decan-1-one (Example 125)

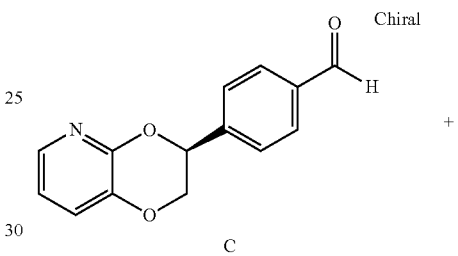

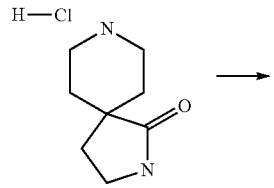

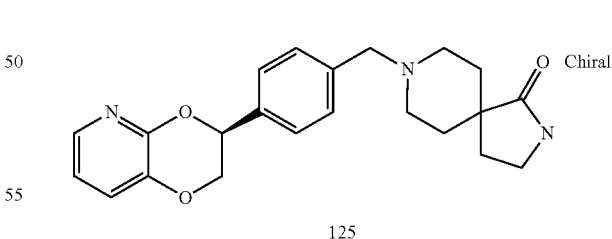

125

TEA (0.12 mL, 0.83 mmol) is added to a mixture of C (100 mg, 0.42 mmol) and 2,8-Diaza-spiro[4.5]decan-1-one; hydrochloride (158 mg, 0.83 mmol) in 2 mL of DCM.

One drop of acetic acid is added, and the mixture is stirred for 10 min, sodiumacetoxyborohydride (132 mg, 0.83 mmol) is added, and the resulting mixture is stirred for 24 h. The solvent is evaporated and the crude mixture is dissolved in 2 ml of MeCN/H$_2$O (1:1). The mixture is purified on a reverse phase C18 semi-preparative HPLC column eluting with a gradient of 0-95% MeCN/H₂O to give the title product.

Example of General Method B

Preparation of (±)-4-[4-(2,3-Dihydro-benzo[1,4]dioxin-2-yl)-benzyl]-piperazine-1-carboxylic acid tert-butyl ester

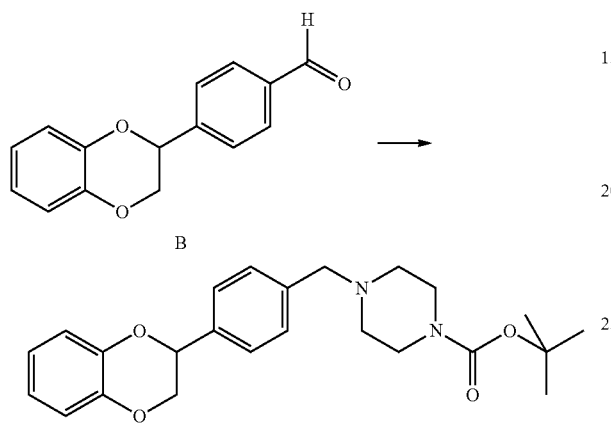

To a solution of B (100 mg, 0.420 mmol), and piperazine-1-carboxylic acid tert-butyl ester (93 mg, 0.50 mmol) in DCE (4 mL) is added acetic acid (50 mg, 0.83 mmol). The mixture is stirred at room temperature for 10 min, treated with sodium triacetoxyborohydride (141 mg, 0.67 mmol), and stirred at room temperature for 16 hours. The reaction is diluted with saturated aqueous sodium bicarbonate (5 mL) and extracted with EtOAc (5 mL×3). The combined organic layers is washed with brine, dried over Na₂SO₄, filtered and concentrated. The residue is purified on a reversed phase C18 semi-preparative HPLC column eluting with a gradient of 5-85% MeCN+0.1% TFA/H₂O+0.1% TFA). The combined fractions are concentrated and basified by saturated aqueous sodium bicarbonate (5 mL) and extracted with EtOAc (5 mL×3). The combined organic phases is washed by brine, dried over Na₂SO₄, filtered, and concentrated to give the title product.

Example of General Method C

Preparation of 4-{1-[(S)-4-(2,3-Dihydro-benzo[1,4]dioxin-2-yl)-benzyl]-piperidin-4-ylmethyl}-benzoic acid methyl ester

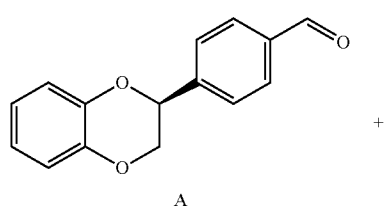

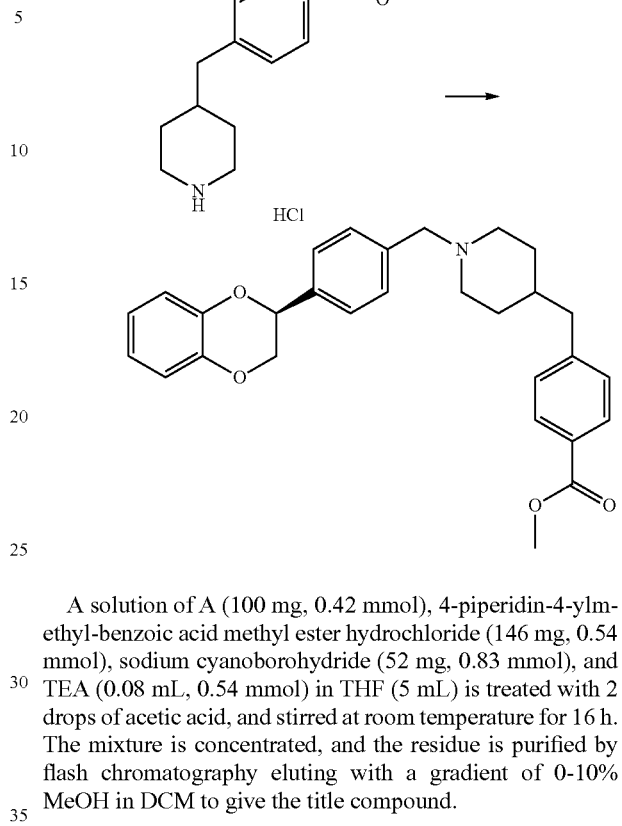

A solution of A (100 mg, 0.42 mmol), 4-piperidin-4-ylmethyl-benzoic acid methyl ester hydrochloride (146 mg, 0.54 mmol), sodium cyanoborohydride (52 mg, 0.83 mmol), and TEA (0.08 mL, 0.54 mmol) in THF (5 mL) is treated with 2 drops of acetic acid, and stirred at room temperature for 16 h. The mixture is concentrated, and the residue is purified by flash chromatography eluting with a gradient of 0-10% MeOH in DCM to give the title compound.

Example of General Method D

Preparation of 1-[4-(2,3-Dihydro-benzo[1,4]dioxin-2-yl)-benzyl]-piperidine-4-carboxylic acid methylamide (Example 25)

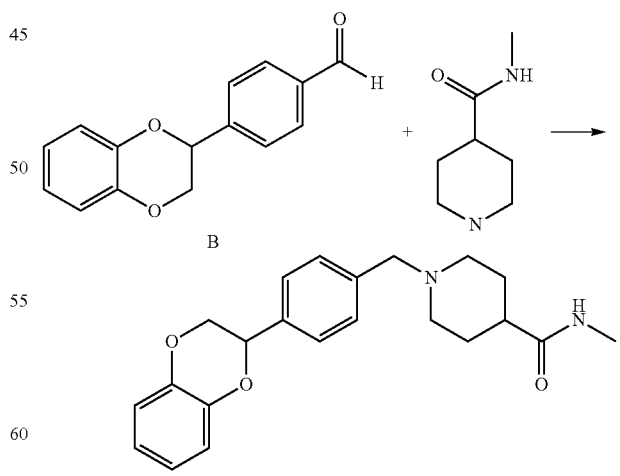

A solution of B (40 mg, 0.17 mmol) and piperidine-4-carboxylic acid methylamide (47.2 mg, 0.332 mmol) is treated with acetic acid (0.01 mL). After shaking for 1 hour, a solution of sodium triacetoxyborohydride (70.6 mg, 0.33 mmol) in DMA (0.5 mL) is added and the resulting mixture is shaken overnight. The mixture is concentrated, diluted with DMSO (0.8 mL), filtered and purified on a C18 semi-preparative HPLC column eluting with a gradient of 5-85% MeCN+ 0.1% TFA/H₂O+0.1% TFA) to provide the title compound.

Example of General Method E

Preparation of 4-{[(S)-4-(2,3-Dihydro-benzo[1,4]dioxin-2-yl)-benzylamino]-methyl}-benzoic acid methyl ester

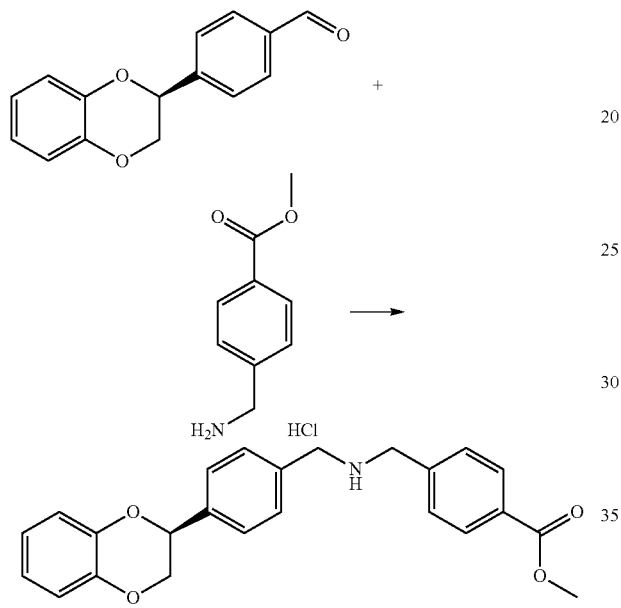

A solution of A (310 mg), methyl 4-(aminomethyl)benzoate hydrochloride (338 mg), sodium cyanoborohydride (162 mg), and DIPEA (0.3 mL) in MeOH (5 mL) is treated with 2 drops of acetic acid, and the resulting mixture is stirred at room temperature for 16 h. The mixture is concentrated, and the residue is purified by flash chromatography eluting with a gradient of 0-10% MeOH in DCM to give the title compound.

Example of General Method F

Preparation of 3-{1-[(S)-4-(2,3-Dihydro-[1,4]dioxino[2,3-b]pyridin-3-yl)-benzyl]-piperidin-4-yl}-[1,3]oxazinan-2-one (Example 291)

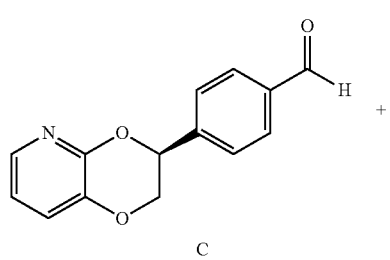

C

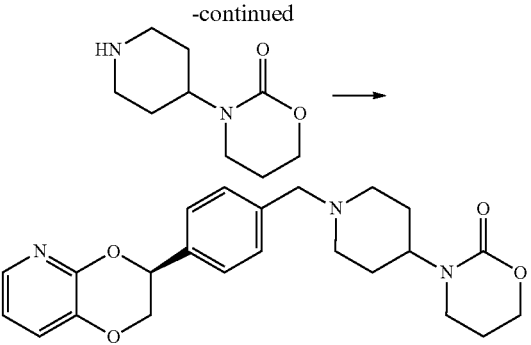

291

A solution of Intermediate C (367 mg, 1.99 mmol) and 3-piperidin-4-yl-[1,3]oxazinan-2-one (400 mg, 1.66 mmol) is stirred in THF (3 mL) for 10 min. To this add sodium triacetoxyborohydride (422 mg, 1.99 mmol) and stir the reaction 24 h. The reaction is quenched with sat. NaHCO₃ and extracted with EtOAc. The combined organics are dried with Na₂SO₄ and concentrated. The residue is purified by reversed phase HPLC eluting with 10-90% MeCN in water (+0.1% TFA), and the concentrated pooled fractions diluted with MeOH and passed through a carbonate resin cartridge to provide the title compound 291 as a free base. (LC/MS method 16: ES+ m/z 410.3 [M+H]+, Rt=2.45 min)

Example of General Method G

Preparation of 4-{1-[(S)-4-(2,3-Dihydro-benzo[1,4]dioxin-2-yl)-benzyl]-azetidin-3-yl}-benzoic acid methyl ester

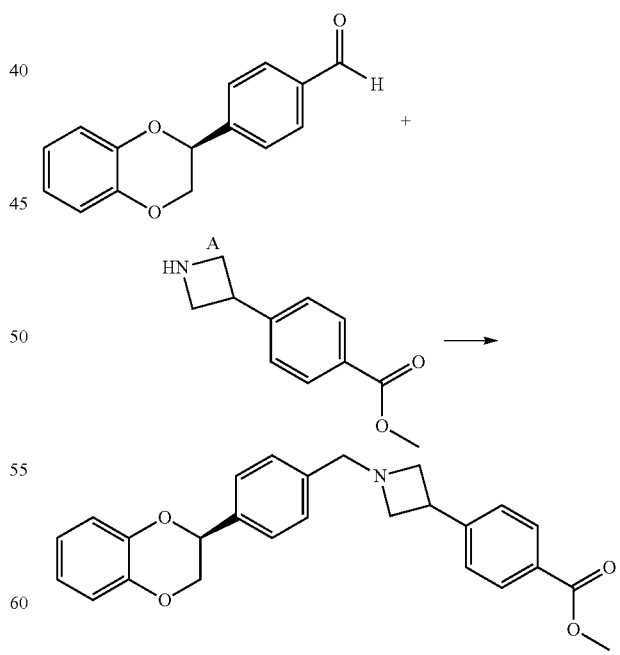

A solution of Intermediate A (300 mg, 1.25 mmoL), 4-azetidin-3-yl-benzoic acid methyl ester hydrochloride (313 mg, 1.37 mmol), and DIPEA (0.261 mL, 1.50 mmol) in DMA (5 mL) is stirred at about 25° C. for 15 minutes. This mixture is treated with sodium triacetoxyborohydride (318 mg, 1.5 mmol) and stirred at about 25° C. for 16 hours. The mixture is quenched with sat. NaHCO₃ solution and the extracted with ethyl acetate. The organic layer is washed with brine, dried over sodium sulfate and concentrated. The residue is purified by silica gel chromatography to give the title compound as a colorless oil.

Example of General Method H

Preparation of (S)-3-[4-(1-Oxo-1lambda4-thiomorpholin-4-ylmethyl)-phenyl]-2,3-dihydro-[1,4]dioxino[2,3-b]pyridine (Example 295)

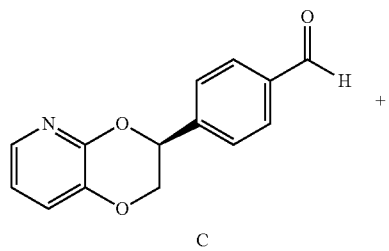

C

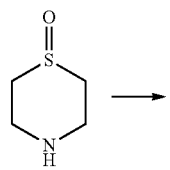

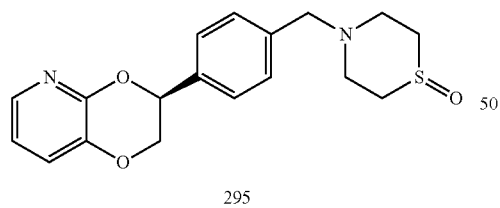

295

To a solution of Intermediate C (60 mg, 0.25 mmol) and thiomorpholine 1-oxide (Intermediate L) (60 mg, 0.50 mmol) in DCM (4 mL) is added TEA (0.10 mL, 0.72 mmol) and the reaction stirred 10 min Sodium triacetoxyborohydride (91 mg, 0.41 mmol) is added and the reaction stirred 24 h. The reaction is quenched with MeOH, concentrated and purified by reversed phase HPLC eluting with 0-50% MeCN in water (0.1% TFA). The concentrated fractions are re-purified by silica gel chromatography eluting with 0-15% MeOH/DCM. The concentrated residue is dissolved in DCM, and washed with sat. NaHCO₃. The organic layer is concentrated and the residue lyophilized from MeCN/water to give the title compound 295 as a solid. (LC/MS method 16: ES+ m/z 345.4 [M+H]+, Rt=0.35 min)

Example of General Method I

Preparation of (1α,5α,6α)-3-[(S)-4-(2,3-Dihydro-[1,4]dioxino[2,3-b]pyridin-3-yl)-benzyl]-3-aza-bicyclo[3.1.0]hexane-6-carboxylic acid ethyl ester

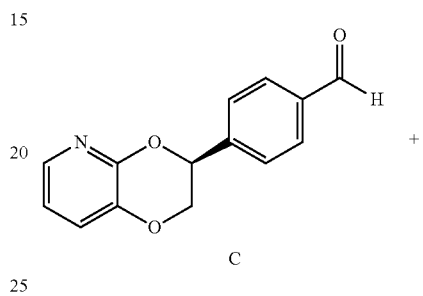

C

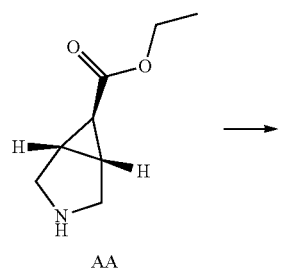

AA

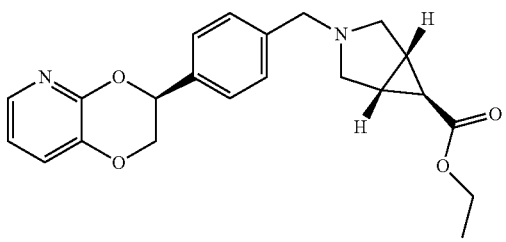

A solution of Intermediate C (4.10 g, 16.5 mmol) and Intermediate AA (4.79 g, 29.9 mmol) in DCM (50 mL) is treated with TEA (3.50 mL, 24.9 mmol) and DMF (10 mL), and the solution is stirred at room temperature for 45 min. To this is added sodium triacetoxyborohydride (6.49 g, 30.0 mmol) and the mixture is stirred for 24 h. The reaction is concentrated and the residue is purified by silica gel chromatography eluting with 0-50% EtOAc in heptane to afford the title compound as an oil which crystallizes.

Example of General Method J

Preparation of 1-{(1S,4S)-5-[(S)-4-(2,3-Dihydro-[1,4]dioxino[2,3-b]pyridin-3-yl)-benzyl]-2,5-diaza-bicyclo[2.2.1]hept-2-yl}-ethanone (Example 292)

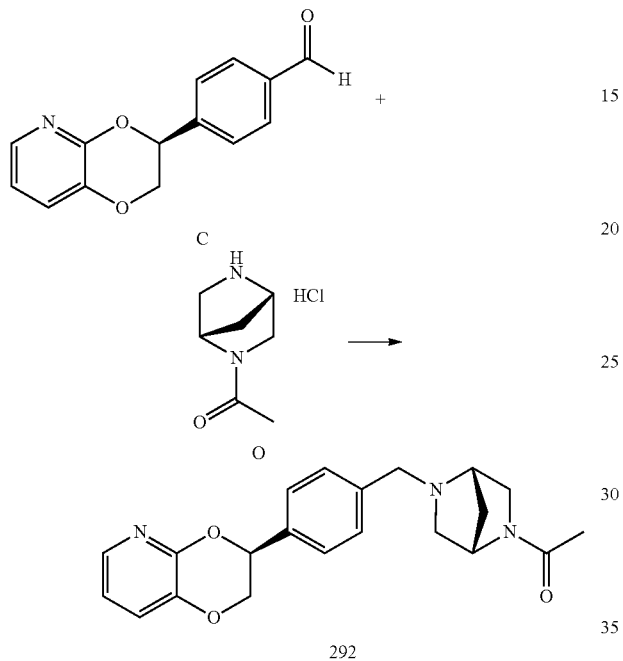

292

To a solution of Intermediate C (100 mg, 0.415 mmol) and Intermediate O (73 mg, 0.42) and TEA (0.086 mL, 0.62 mmol) in 1,4-dioxane (2 mL) is added sodium triacetoxyborohydride (177 mg, 0.833 mmol) and the reaction stirred 72 h. The reaction is quenched with 1M HCl and purified by reverse phase HPLC 0-70% MeCN in water (0.1% formic acid). The pooled and concentrated fractions are dissolved in MeOH and eluted through a carbonate resin plug to give the title compound 292 as a solid after lypholization. (LC/MS method 16: ES+ m/z 366.3 [M+H]+, Rt=0.28 min)

Example of General Method K

Preparation of (S)-3-{4-[4-(Pyridin-3-yloxy)-piperidin-1-ylmethyl]-phenyl}-2,3-dihydro-[1,4]dioxino[2,3-b]pyridine (Example 293)

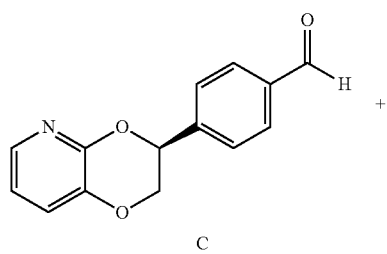

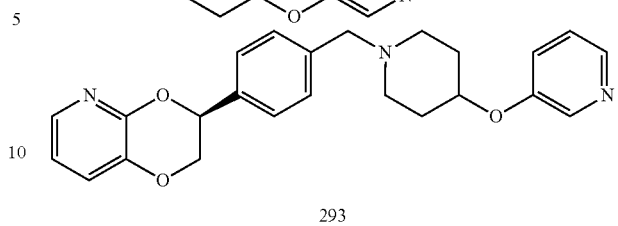

293

A solution of Intermediate C (100 mg; 0.410 mmol) and 3-(piperidin-4-yloxy)-pyridine (122 mg, 0.657 mmol) in DCM (2 mL) and MeOH (0.5 mL) is treated with TEA (0.100 mL, 0.710 mmol) and the suspension is microwaved at 100° C. for 20 min. To this add sodium triacetoxyborohydride (200 mg, 0.925 mmol), acetic acid (0.100 mL, 1.69 mmol), and MeOH (1.5 mL). The reaction is sealed and stirred over 24 h. The reaction is concentrated then purified by reverse-phase HPLC eluting with 10-60% MeCN in water (0.1% TFA). The pooled and concentrated fractions are dried in vacuo to give the title compound 293 as a TFA salt. (LC/MS method 16: ES+ m/z 404.5 [M+H]+, Rt=2.47 min)

Example of General Method L

Preparation of 1-[(S)-4-(2,3-Dihydro-[1,4]dioxino[2,3-b]pyridin-3-yl)-benzyl]-4-phenyl-piperidine-4-carboxylic acid (Example 294)

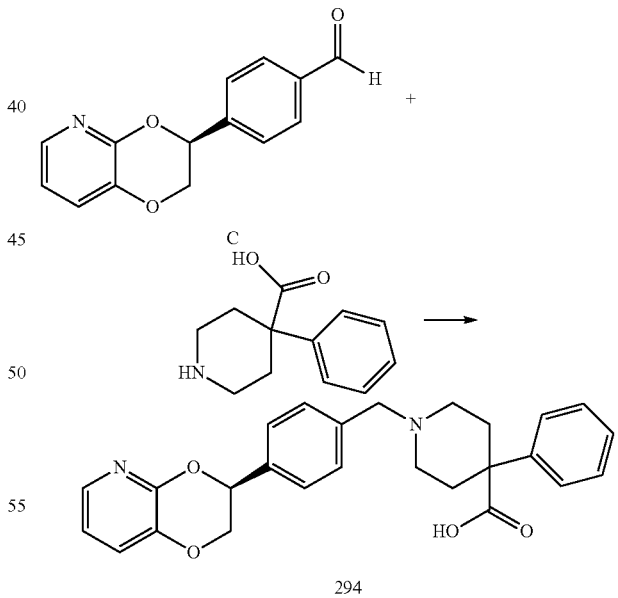

294

A solution of Intermediate C (100 mg, 0.42 mmol) and 4-Phenyl-piperidine-4-carboxylic acid (85 mg, 0.42 mmol) in DMF (5 mL) is stirred for 30 min at rt. To this add sodium triacetoxyborohydride (88 mg, 0.42 mmol) and stir the reaction for 2 h at rt. The reaction is concentrated and purified by reverse-phase HPLC eluting with 10-90% MeCN in water (0.1% TFA). The pooled and concentrated fractions are dried in vacuo to give the title compound 294. (LC/MS method 16: ES+ m/z 431.5 [M+H]+, Rt=2.70 min)

Example of General Method M

Preparation of (S)-7-[(S)-4-(2,3-Dihydro-[1,4]dioxino[2,3-b]pyridin-3-yl)-benzyl]-hexahydro-oxazolo[3,4-a]pyrazin-3-one (Example 296)

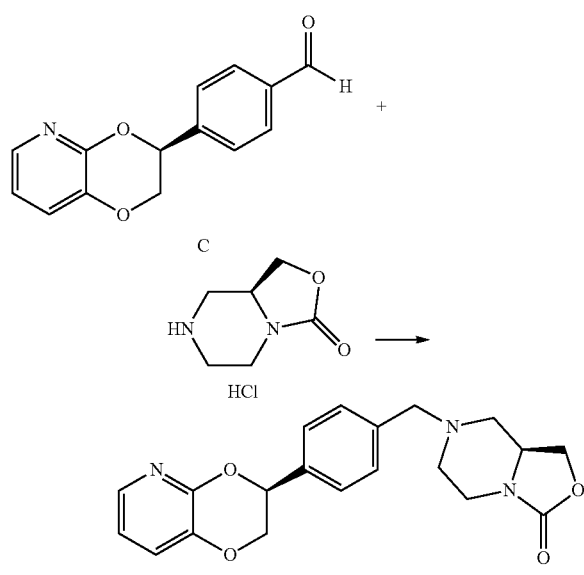

To a solution of Intermediate C (200 mg, 0.829 mmol) and (S)-Hexahydro-oxazolo[3,4-a]pyrazin-3-one hydrochloride (178 mg, 0.995 mmol) in DMF (2 mL) is added sodium cyanoborohydride (156 mg, 2.49 mmol) followed by one drop of acetic acid. The reaction is allowed to stir at about 25° C. for 24 hours. The reaction is concentrated and purified by silica gel chromatography eluting with 75-100% EtOAc/Heptanes. The product fractions are concentrated to provide the title compound 296. (LC/MS method 16: ES+ m/z 368.4 [M+H]+, Rt=2.53 min).

Example of General Method N

Preparation of 4-[(S)-4-(2,3-Dihydro-[1,4]dioxino[2,3-b]pyridin-3-yl)-benzyl]-piperazine-1-carboxylic acid tert-butyl ester

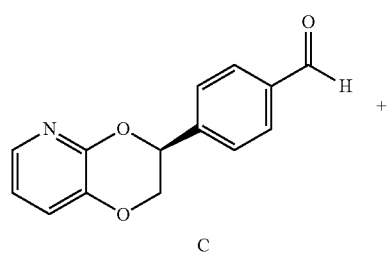

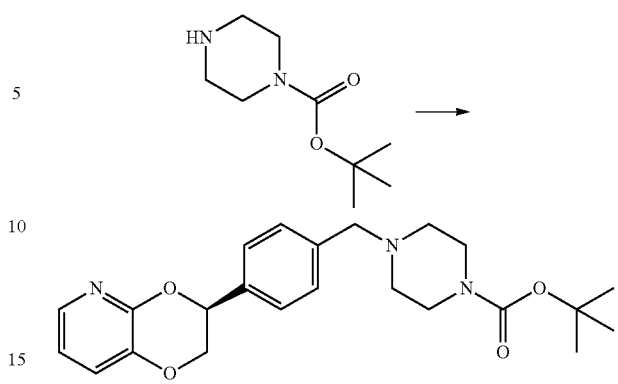

To a solution of Intermediate C (5.00 g, 20.7 mmol) and piperazine-1-carboxylic acid tert-butyl ester (7.72 g, 41.5 mmol) in DCM (250 mL) is added sodium triacetoxyborohydride (8.79 g, 41.5 mmol) and the reaction sealed and stirred overnight. The reaction is quenched with MeOH (25 mL) and poured into vigorously stirring water (500 mL). The solution is basified with 2M aqueous $Na_2CO_3$. The layers are separated and the aqueous layer extracted with DCM. The combined extracts are dried over $Na_2SO_4$ and concentrated. The residue is suspended in heptane and the solid isolated by filtration to give the title compound.

Table 3 provides a summary of the key reagents used to prepare Examples 1-191 according to general methods A, B, C, D, E, or F as depicted in the reaction below.

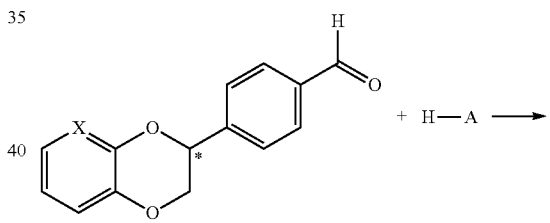

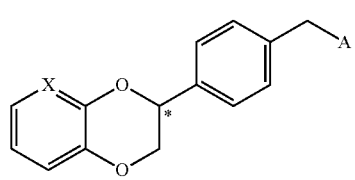

where H-A is

TABLE 3

Examples synthesized by General Method A through N

| Ex # | X | Chirality at * | ---A | Synthesis Method | LC/MS Method | [M + H]+ | Rt (min) |
|---|---|---|---|---|---|---|---|
| 1 | CH | racemic | pyrrolidine | B | 10 | 296.2 | 1.20 |
| 2 | CH | racemic | morpholine | B | 10 | 312.2 | 1.20 |
| 3 | CH | racemic | 4,4-dimethylpiperidine | B | 10 | 338.4 | 1.20 |
| 4 | CH | racemic | 2,8-diazaspiro[4.5]decan-1-one | B | 10 | 379.4 | 1.10 |
| 5 | CH | racemic | 4-fluoropiperidine | B | 10 | 328.4 | 1.11 |
| 6 | CH | racemic | 7-azabicyclo[2.2.1]heptane | B | 10 | 322.4 | 1.13 |
| 7 | CH | racemic | thiomorpholine 1,1-dioxide | B | 10 | 360.4 | 1.40 |
| 8 | CH | S | N,N-dimethylpiperidine-4-carboxamide | B | 10 | 381.3 | 0.67 |
| 9 | CH | racemic | 3-hydroxypyrrolidine | B | 10 | 312.4 | 1.04 |
| 10 | CH | racemic | 3-((2-oxopyrrolidin-1-yl)methyl)piperidine | B | 10 | 407.4 | 1.14 |
| 11 | CH | racemic | 4-acetylpiperazine | B | 10 | 353.40 | 1.47 |

TABLE 3-continued
Examples synthesized by General Method A through N
| Ex # | X | Chirality at * | ---A | Synthesis Method | LC/MS Method | [M + H]+ | Rt (min) |
|---|---|---|---|---|---|---|---|
| 12 | CH | racemic | 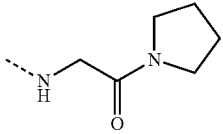 | B | 10 | 353.40 | 1.57 |
| 13 | CH | S | 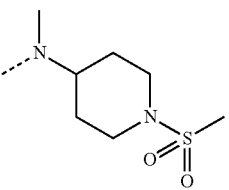 | A | 10 | 417.40 | 1.62 |
| 14 | CH | S | 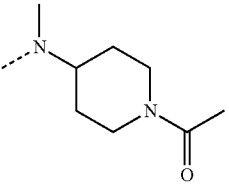 | A | 10 | 381.40 | 1.57 |
| 15 | N | racemic | 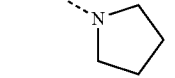 | B | 10 | 297.40 | 0.97 |
| 16 | CH | racemic | 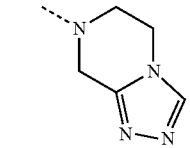 | B | 10 | 349.40 | 2.14 |
| 17 | N | racemic | 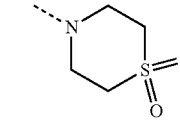 | B | 10 | 361.20 | 1.66 |
| 18 | N | racemic | 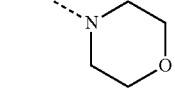 | B | 10 | 313.40 | 0.89 |
| 19 | CH | S | 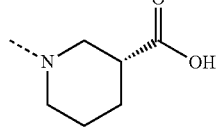 | C | 1 | 354.52 | 0.55 |
| 20 | CH | S | 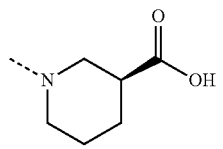 | C | 1 | 354.24 | 0.56 |
| 21 | CH | S | 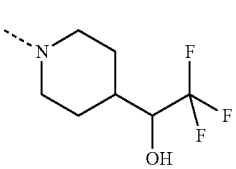 | C | 1 | 408.26 | 0.71 |

TABLE 3-continued

Examples synthesized by General Method A through N

| Ex # | X | Chirality at * | ---A | Synthesis Method | LC/MS Method | [M + H]+ | Rt (min) |
|---|---|---|---|---|---|---|---|
| 22 | CH | S | piperidine-C(OH)(CF3)2 variant | C | 1 | 476.23 | 0.77 |
| 23 | CH | racemic | NH-tBu | D | 11 | 298.2 | 0.7 |
| 24 | CH | racemic | NH-sBu | D | 11 | 298.2 | 0.73 |
| 25 | CH | racemic | 4-(N-methylcarbamoyl)piperidine | D | 11 | 367.3 | 0.66 |
| 26 | CH | racemic | 4-(3-carboxypropyl)piperidine | D | 11 | 396.3 | 0.73 |
| 27 | CH | racemic | 4-(hydroxymethyl)piperidine | D | 11 | 340.2 | 0.66 |
| 28 | CH | racemic | 4-(2-hydroxypropan-2-yl)piperidine | D | 11 | 368.3 | 0.72 |
| 29 | CH | racemic | 4-(3-hydroxypropyl)piperidine | D | 11 | 368.5 | 0.7 |
| 30 | CH | racemic | 4-methyl-1,4-diazepane | D | 11 | 339.2 | 0.56 |
| 31 | CH | racemic | 4-acetyl-1,4-diazepane | D | 11 | 367.2 | 0.65 |

TABLE 3-continued

Examples synthesized by General Method A through N

| Ex # | X | Chirality at * | ---A | Synthesis Method | LC/MS Method | [M + H]+ | Rt (min) |
|---|---|---|---|---|---|---|---|
| 32 | CH | racemic | (1,4-oxazepane) | D | 11 | 326.2 | 0.67 |
| 33 | CH | racemic | N(Me)CH2CH2OMe | D | 11 | 314.2 | 0.71 |
| 34 | CH | racemic | 3-hydroxypyrrolidine | D | 11 | 312.2 | 0.65 |
| 35 | CH | racemic | piperidine-spiro-hydantoin | D | 11 | 394.2 | 0.65 |
| 36 | CH | racemic | 3-methoxyazetidine | D | 11 | 312.4 | 0.68 |
| 37 | CH | racemic | 4-(morpholine-4-carbonyl)piperidine | D | 11 | 423.3 | 0.69 |
| 38 | CH | racemic | 4-(N,N-dimethylacetamido)piperidine | D | 11 | 395.3 | 0.70 |
| 39 | CH | racemic | 4-(methylsulfonyl)piperidine | D | 11 | 388.2 | 0.66 |
| 40 | CH | racemic | azepane | D | 11 | 324.3 | 0.79 |
| 41 | CH | racemic | cyclopentylamine | D | 11 | 310.2 | 0.78 |
| 42 | CH | racemic | N-methyl-N-(2-(pyridin-2-yl)ethyl)amine | D | 11 | 361.2 | 0.79 |

TABLE 3-continued

Examples synthesized by General Method A through N

| Ex # | X | Chirality at * | ---A | Synthesis Method | LC/MS Method | [M + H]+ | Rt (min) |
|---|---|---|---|---|---|---|---|
| 43 | CH | racemic | HN-CH2-cyclopropyl | D | 11 | 296.2 | 0.75 |
| 44 | CH | racemic | 4-hydroxy-4-phenylpiperidin-1-yl | D | 11 | 402.3 | 0.82 |
| 45 | CH | racemic | N,N-diethylamino | D | 11 | 298.2 | 0.75 |
| 46 | CH | racemic | 3-cyanoazetidin-1-yl | D | 11 | 306.8 | 0.73 |
| 47 | CH | racemic | 3-methoxypyrrolidin-1-yl | D | 11 | 326.2 | 0.74 |
| 48 | CH | racemic | 4-(methylsulfonamido)piperidin-1-yl | D | 11 | 403.2 | 0.71 |
| 49 | CH | racemic | N-(2-methyl-1-(pyrrolidin-1-yl)propan-2-yl)amino | D | 11 | 367.2 | 0.68 |
| 50 | CH | racemic | 4-((2-oxopyrrolidin-1-yl)methyl)piperidin-1-yl | D | 11 | 407.3 | 0.73 |
| 51 | CH | racemic | 4-(N,N-dimethylcarbamoyl)piperidin-1-yl | D | 11 | 381.3 | 0.73 |
| 52 | CH | racemic | 4-(N-(2-hydroxyethyl)carbamoyl)piperidin-1-yl | D | 11 | 397.3 | 0.67 |
| 53 | CH | racemic | 4-ureidopiperidin-1-yl | D | 11 | 368.2 | 0.67 |
| 54 | CH | racemic | N-(pyridin-3-ylmethyl)amino | D | 11 | 333.2 | 0.66 |

TABLE 3-continued
Examples synthesized by General Method A through N
| Ex # | X | Chirality at * | ---A | Synthesis Method | LC/MS Method | [M + H]⁺ | Rt (min) |
|---|---|---|---|---|---|---|---|
| 55 | CH | racemic | 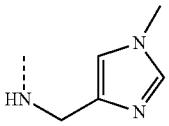 | D | 11 | 336.2 | 0.59 |
| 56 | CH | S | 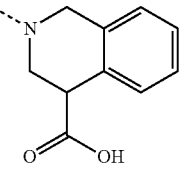 | D | 11 | 402.3 | 0.75 |
| 57 | CH | S | 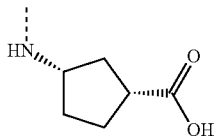 | D | 11 | 354.1 | 0.63 |
| 58 | CH | S | 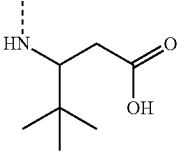 | D | 11 | 370.2 | 0.70 |
| 59 | CH | S | 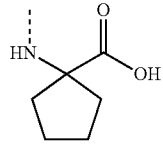 | D | 11 | 354.2 | 0.66 |
| 60 | CH | S | 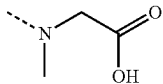 | D | 11 | 314.3 | 0.63 |
| 61 | CH | S | 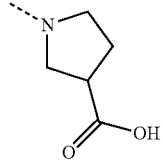 | D | 11 | 340.1 | 0.61 |
| 62 | CH | S | 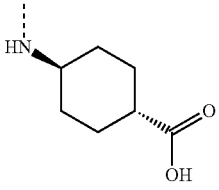 | D | 11 | 367.9 | 0.61 |
| 63 | CH | S | 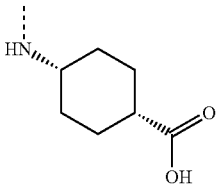 | D | 11 | 368.2 | 0.64 |

TABLE 3-continued

Examples synthesized by General Method A through N

| Ex # | X | Chirality at * | ---A | Synthesis Method | LC/MS Method | [M + H]⁺ | Rt (min) |
|---|---|---|---|---|---|---|---|
| 64 | CH | S | (S)-1-acetyl-3-aminopyrrolidine | D | 11 | 353.8 | 0.63 |
| 65 | CH | S | (R)-1-acetyl-3-aminopyrrolidine | D | 11 | 353.1 | 0.63 |
| 66 | CH | S | trans-4-aminocyclohexanecarboxamide | D | 11 | 367.1 | 0.64 |
| 67 | CH | S | N-methylcyclohexylamine | D | 11 | 337.8 | 0.78 |
| 68 | CH | S | 2-methylpiperidine | D | 11 | 323.9 | 0.73 |
| 69 | CH | S | 3-(hydroxymethyl)piperidine | D | 11 | 339.8 | 0.66 |
| 70 | CH | S | 4-(2-hydroxyethyl)piperidine | D | 11 | 353.9 | 0.67 |
| 71 | CH | S | isopropylamine | D | 11 | 284.3 | 0.68 |
| 72 | CH | S | 1-methoxypropan-2-amine | D | 11 | 313.6 | 0.70 |
| 73 | CH | S | propylamine | D | 11 | 283.8 | 0.7 |
| 74 | CH | S | diethylamine | D | 11 | 283.9 | 0.67 |
| 75 | CH | S | dimethylamine | D | 11 | 269.8 | 0.65 |

TABLE 3-continued

Examples synthesized by General Method A through N

| Ex # | X | Chirality at * | ---A | Synthesis Method | LC/MS Method | [M + H]+ | Rt (min) |
|---|---|---|---|---|---|---|---|
| 76 | CH | S | | D | 11 | 340.2 | 0.65 |
| 77 | CH | S | | D | 11 | 310.2 | 0.70 |
| 78 | CH | S | | D | 11 | 325.9 | 0.65 |
| 79 | CH | S | | D | 11 | 327.1 | 0.61 |
| 80 | CH | S | | D | 11 | 367.9 | 0.76 |
| 81 | CH | S | | D | 11 | 311.7 | 0.71 |
| 82 | CH | S | | D | 11 | 352.9 | 0.64 |
| 83 | CH | S | | D | 11 | 366.9 | 0.67 |
| 84 | CH | S | | D | 11 | 336.2 | 0.73 |
| 85 | CH | S | | D | 11 | 363.8 | 0.76 |

TABLE 3-continued

Examples synthesized by General Method A through N

| Ex # | X | Chirality at * | ---A | Synthesis Method | LC/MS Method | [M + H]+ | Rt (min) |
|---|---|---|---|---|---|---|---|
| 86 | CH | S | (2-carbamoylcyclohexyl)amino | D | 11 | 366.9 | 0.63 |
| 87 | CH | S | (2-(hydroxymethyl)cyclohexyl)amino | D | 11 | 354.4 | 0.68 |
| 88 | CH | S | 3-hydroxypyrrolidin-1-yl | D | 11 | 313.3 | 0.64 |
| 89 | CH | S | (2-(hydroxymethyl)cyclohexyl)amino | D | 11 | 353.9 | 0.70 |
| 90 | CH | S | 4-(hydroxymethyl)piperidin-1-yl | D | 11 | 340.8 | 0.59 |
| 91 | CH | S | 3-hydroxypyrrolidin-1-yl | D | 11 | 311.8 | 0.57 |
| 92 | CH | S | 4-oxoimidazolidin-1-yl | D | 11 | 311.1 | 0.75 |
| 93 | CH | S | 3-(dimethylamino)pyrrolidin-1-yl | D | 11 | 339.1 | 0.49 |
| 94 | CH | S | 2-oxo-[1,4'-bipiperidin]-1'-yl | D | 11 | 407.2 | 0.63 |

TABLE 3-continued

Examples synthesized by General Method A through N

| Ex # | X | Chirality at * | ---A | Synthesis Method | LC/MS Method | [M + H]+ | Rt (min) |
|---|---|---|---|---|---|---|---|
| 95 | CH | S | cyclohexyl-N(CH2-cyclopropyl)- | D | 11 | 377.8 | 0.78 |
| 96 | CH | S | 1-piperidinyl-4-C(O)NH-CH2CH2-OH | D | 11 | 397.3 | 0.56 |
| 97 | CH | S | 2-hydroxycyclohexyl-NH- | D | 11 | 339.8 | 0.65 |
| 98 | CH | S | 4-methoxy-1-piperidinyl | D | 11 | 340.2 | 0.63 |
| 99 | CH | S | 4-((2-oxopyrrolidin-1-yl)methyl)piperidin-1-yl | D | 11 | 407.4 | 0.62 |
| 100 | CH | S | trans-4-methylcyclohexyl-NH- | D | 11 | 338.2 | 0.76 |
| 101 | CH | S | 2-hydroxycyclopentyl-NH- | D | 11 | 325.8 | 0.62 |
| 102 | CH | S | 2-hydroxycyclopentyl-NH- | D | 11 | 325.7 | 0.6 |
| 103 | CH | S | tetrahydropyran-3-yl-NH- | D | 11 | 326.3 | 0.61 |
| 104 | CH | S | cyclohexyl-N(CH2CH2-N(CH3)2)- | D | 11 | 395.2 | 0.8 |
| 105 | CH | S | 2-hydroxycyclohexyl-N(CH3)- | D | 11 | 353.9 | 0.66 |

TABLE 3-continued

Examples synthesized by General Method A through N

| Ex # | X | Chirality at * | ---A | Synthesis Method | LC/MS Method | [M + H]+ | Rt (min) |
|---|---|---|---|---|---|---|---|
| 106 | CH | S | | D | 11 | 353.9 | 0.67 |
| 107 | CH | S | | D | 11 | 325.9 | 0.61 |
| 108 | CH | S | | D | 11 | 352.9 | 0.56 |
| 109 | CH | S | | D | 11 | 338.4 | 0.71 |
| 110 | CH | S | | D | 11 | 353.1 | 0.44 |
| 111 | CH | S | | D | 11 | 348.1 | 0.64 |
| 112 | CH | S | | D | 11 | 374.1 | 0.66 |
| 113 | CH | Racemic | | A | 13 | 354.4 | 1.1 |
| 114 | CH | Racemic | | A | 13 | 353.4 | 1.0 |
| 115 | CH | Racemic | | A | 13 | 314.4 | 1.0 |
| 116 | CH | S | | A | 12 | 393.1 | 1.3 |

TABLE 3-continued
Examples synthesized by General Method A through N
| Ex # | X | Chirality at * | ---A | Synthesis Method | LC/MS Method | [M + H]+ | Rt (min) |
|---|---|---|---|---|---|---|---|
| 117 | CH | S | 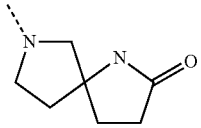 | A | 13 | 365.4 | 1.3 |
| 118 | CH | S | 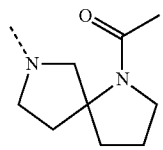 | A | 13 | 393.4 | 1.2 |
| 119 | CH | S | 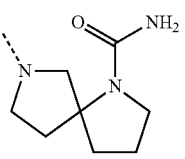 | A | 13 | 393.4 | 1.1 |
| 120 | CH | S | 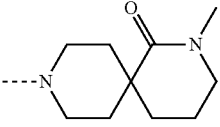 | A | 7 | 407.3 | 0.7 |
| 121 | CH | S | 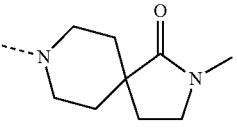 | A | 13 | 393.4 | 1.1 |
| 122 | CH | S | 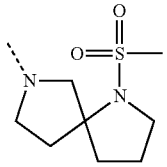 | A | 7 | 429.5 | 0.7 |
| 123 | CH | S | 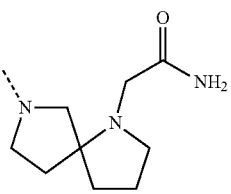 | A | 7 | 408.3 | 0.6 |
| 124 | CH | S | 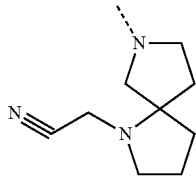 | A | 7 | 390.3 | 0.7 |
| 125 | N | S | 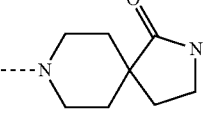 | A | 11 | 380.4 | 0.4 |
| 126 | N | S | 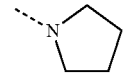 | A | 11 | 297.2 | 0.4 |

TABLE 3-continued
Examples synthesized by General Method A through N
| Ex # | X | Chirality at * | ---A | Synthesis Method | LC/MS Method | [M + H]+ | Rt (min) |
|---|---|---|---|---|---|---|---|
| 127 | N | S | 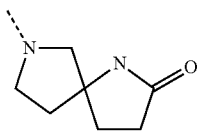 | A | 11 | 366.2 | 0.4 |
| 128 | CH | S | 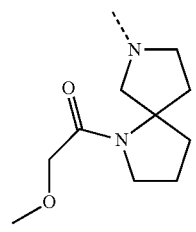 | A | 11 | 423.3 | 0.6 |
| 129 | N | S | 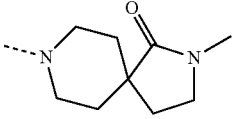 | A | 11 | 394.2 | 0.4 |
| 130 | N | S | 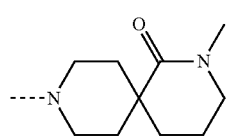 | A | 11 | 408.3 | 0.5 |
| 131 | CH | S | 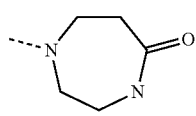 | A | 11 | 339.2 | 0.6 |
| 132 | N | S | 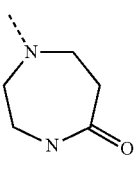 | A | 13 | 340.2 | 0.9 |
| 133 | N | S | 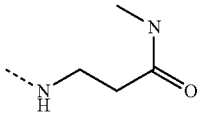 | A | 11 | 328.2 | 0.4 |
| 134 | CH | S | 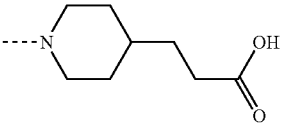 | A | 13 | 382.4 | 0.6 |
| 135 | N | S | 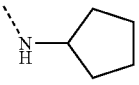 | D | 11 | 311.1 | 0.52 |
| 136 | N | S | 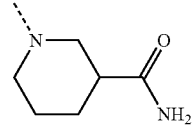 | D | 11 | 354.1 | 0.42 |
| 137 | N | S | 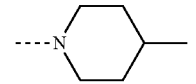 | D | 11 | 325.1 | 0.53 |

TABLE 3-continued

Examples synthesized by General Method A through N

| Ex # | X | Chirality at * | ---A | Synthesis Method | LC/MS Method | [M + H]+ | Rt (min) |
|---|---|---|---|---|---|---|---|
| 138 | N | S | N-CH2CH2-(2-pyridyl), N-methyl | D | 11 | 362.1 | 0.51 |
| 139 | N | S | azepan-1-yl | D | 11 | 325.1 | 0.52 |
| 140 | N | S | N,N-diethylamino (methyl, ethyl) | D | 11 | 285.3 | 0.43 |
| 141 | N | S | N,N-diethylamino | D | 11 | 299.1 | 0.47 |
| 142 | N | S | N-methyl-N-cyclopentylamino | D | 11 | 325.1 | 0.53 |
| 143 | N | S | 4-methyl-1,4-diazepan-1-yl | D | 11 | 340.1 | 0.31 |
| 144 | N | S | (3R)-3-hydroxypyrrolidin-1-yl | D | 11 | 313.1 | 0.41 |
| 145 | N | S | 2-azabicyclo[2.2.1]heptan-2-yl | D | 11 | 323.1 | 0.49 |
| 146 | N | S | 4-(hydroxymethyl)piperidin-1-yl | D | 11 | 341.1 | 0.43 |
| 147 | N | S | (3S)-3-hydroxypyrrolidin-1-yl | D | 11 | 313.1 | 0.41 |
| 148 | N | S | 4-acetyl-1,4-diazepan-1-yl | D | 11 | 368.1 | 0.41 |
| 149 | N | S | 4-(3-hydroxypropyl)piperidin-1-yl | D | 11 | 369.1 | 0.47 |

TABLE 3-continued
Examples synthesized by General Method A through N
| Ex # | X | Chirality at * | ---A | Synthesis Method | LC/MS Method | [M + H]⁺ | Rt (min) |
|---|---|---|---|---|---|---|---|
| 150 | N | S | 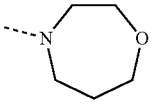 | D | 11 | 327.1 | 0.44 |
| 151 | N | S | 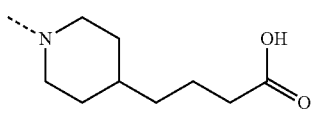 | D | 11 | 397.1 | 0.51 |
| 152 | N | S | 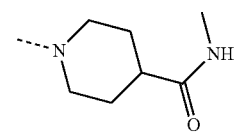 | D | 11 | 368.1 | 0.42 |
| 153 | N | S | 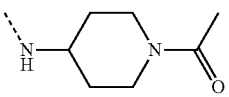 | D | 11 | 368.1 | 0.42 |
| 154 | N | S | 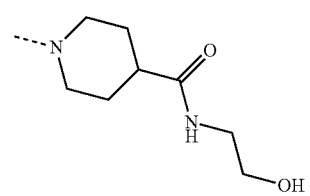 | D | 11 | 398.1 | 0.40 |
| 155 | N | S | 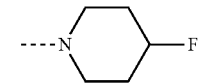 | D | 11 | 329.1 | 0.47 |
| 156 | N | S | 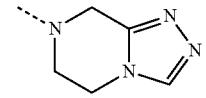 | D | 11 | 350.1 | 0.56 |
| 157 | N | S | 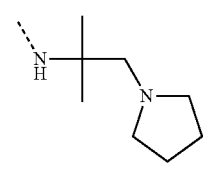 | D | 11 | 368.1 | 0.40 |
| 158 | N | S | 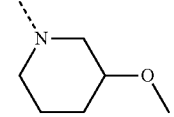 | D | 11 | 341.1 | 0.48 |
| 159 | N | S | 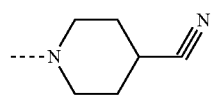 | D | 11 | 336.1 | 0.44 |
| 160 | N | S | 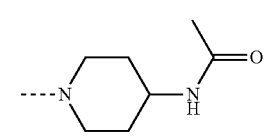 | D | 11 | 368.1 | 0.41 |
| 161 | N | S | 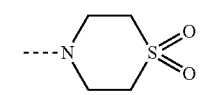 | D | 11 | 361.0 | 0.65 |

TABLE 3-continued

Examples synthesized by General Method A through N

| Ex # | X | Chirality at * | ---A | Synthesis Method | LC/MS Method | [M + H]+ | Rt (min) |
|---|---|---|---|---|---|---|---|
| 162 | N | S | piperidine-C(O)-morpholine | D | 11 | 424.1 | 0.46 |
| 163 | N | S | piperidine-CH2-(2-oxopyrrolidine) | D | 11 | 408.1 | 0.47 |
| 164 | N | S | piperazine-C(O)NH2 | D | 11 | 355.1 | 0.38 |
| 165 | N | S | piperidine-spiro-hydantoin | D | 11 | 395.1 | 0.41 |
| 166 | N | S | 3-methoxyazetidine | D | 11 | 313.1 | 0.45 |
| 167 | N | S | 4-(methylsulfonyl)piperidin-4-ylamine | D | 11 | 404.1 | 0.45 |
| 168 | N | S | 3-methoxypyrrolidine | D | 11 | 327.1 | 0.46 |
| 169 | N | S | N-methyl-4-(methylsulfonyl)piperidin-4-amine | D | 11 | 418.1 | 0.47 |
| 170 | N | S | 4-(2-methoxyethoxy)piperidine | D | 11 | 385.1 | 0.50 |
| 171 | N | S | 2-(piperidin-4-yl)-N,N-dimethylacetamide | D | 11 | 396.1 | 0.47 |
| 172 | N | S | 4-(methylsulfonyl)piperidine | D | 11 | 389.1 | 0.43 |
| 173 | N | S | cyclobutylamine | D | 11 | 297.1 | 0.48 |

TABLE 3-continued

Examples synthesized by General Method A through N

| Ex # | X | Chirality at * | ---A | Synthesis Method | LC/MS Method | [M + H]+ | Rt (min) |
|---|---|---|---|---|---|---|---|
| 174 | CH | S | piperidine-N-SO2Me with 4-NH- | A | 15 | 403.2 | 0.69 |
| 175 | CH | S | piperidine-4-NH-C(O)NH2 | A | 15 | 368.4 | 0.55 |
| 176 | CH | S | piperidine-4-NH-SO2Me | A | 15 | 403.2 | 0.90 |
| 177 | CH | S | piperidine-4-CN | A | 15 | 336.2 | 0.85 |
| 178 | CH | S | piperidine-4-NHC(O)Me | A | 15 | 368.0 | 0.98 |
| 179 | CH | S | piperidine-4-C(O)NHMe | A | 15 | 367.2 | 1.02 |
| 180 | CH | S | piperidine-4-C(O)-morpholine | A | 15 | 423.3 | 1.03 |
| 181 | CH | S | piperidine-4-(CH2)3COOH | A | 15 | 395.9 | 1.13 |
| 182 | CH | S | (3S)-piperidine-3-CH2COOH | A | 15 | 368.2 | 1.04 |
| 183 | CH | S | (3R)-piperidine-3-CH2COOH | A | 15 | 368.2 | 1.05 |
| 184 | CH | S | pyrrolidine-3-CH2COOH | A | 15 | 354.2 | 0.99 |
| 185 | N | S | piperazine-N-C(O)Me | A | 14 | 354.4 | 2.09 |

TABLE 3-continued

Examples synthesized by General Method A through N

| Ex # | X | Chirality at * | ---A | Synthesis Method | LC/MS Method | [M + H]+ | Rt (min) |
|---|---|---|---|---|---|---|---|
| 186 | N | S | piperidine-N-OH | A | 14 | 327.1 | 2.13 |
| 187 | N | S | piperidine-NH-C(O)NH2 | A | 14 | 369.2 | 2.09 |
| 188 | N | S | piperazine-N-S(O)2-CH3 | A | 14 | 390.4 | 2.22 |
| 189 | N | S | piperidine-C(O)OH | A | 14 | 355.1 | 2.16 |
| 190 | N | S | piperidine-NH-S(O)2-CH3 | A | 14 | 404.2 | 2.16 |
| 191 | CH | S | cyclopentane-NH, COOH | A | 14 | 353.8 | 0.63 |

Examples 192 and 193

Preparation of (S)-1-[4-(2,3-Dihydro-benzo[1,4]dioxin-2-yl)-benzyl]-piperidin-4-ol (192), and (R)-1-[4-(2,3-Dihydro-benzo[1,4]dioxin-2-yl)-benzyl]-piperidin-4-ol (193)

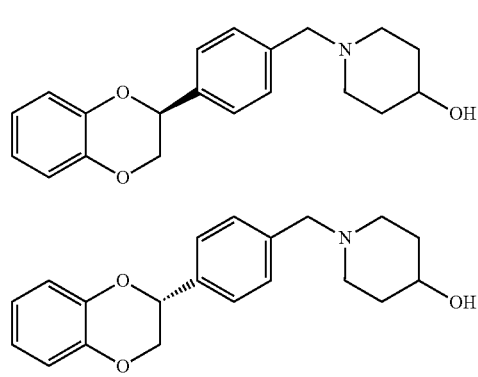

A racemic mixture of 192 and 193 is prepared from intermediate B and 4-hydroxypiperidine according to the General Method B, and resolved by SCF Chiral HPLC using 20% MeOH, 1% IPA, and super critical carbon dioxide to give 192 as the first-eluting peak, and 193 as the second-eluting peak.

192: LC/MS Method 10; Rt=0.98 min; [M+H]+=326.4. 193: LC/MS Method 10; Rt=0.98 min.; [M+H]+=326.4.

Examples 194 and 195

Preparation of 8-[(S)-4-(2,3-Dihydro-benzo[1,4]dioxin-2-yl)-benzyl]-2,8-diaza-spiro[4.5]decan-1-one (194) and (8-[(R)-4-(2,3-Dihydro-benzo[1,4]dioxin-2-yl)-benzyl]-2,8-diaza-spiro[4.5]decan-1-one (195)

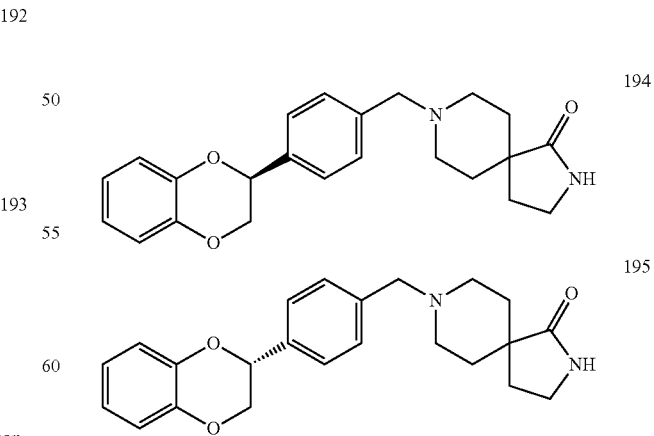

Compound 4 (racemate) is resolved by SCF Chiral HPLC using 55% methanol, 1% isopropylamine, and super critical carbon dioxide to give 194 as the first-eluting peak, and 195 as the second-eluting peak. 194: LC/MS Method 10; Rt=1.10 min.; [M+H]+=379.4. 195: LC/MS Method 10; Rt=1.09 min; [M+H]+=379.4.

Examples 196 and 197

Preparation of 1-[(S)-4-(2,3-dihydro-benzo[1,4]dioxin-2-yl)-benzyl]-pyrrolidine (196) and 1-[(R)-4-(2,3-dihydro-benzo[1,4]dioxin-2-yl)-benzyl]-pyrrolidine (197)

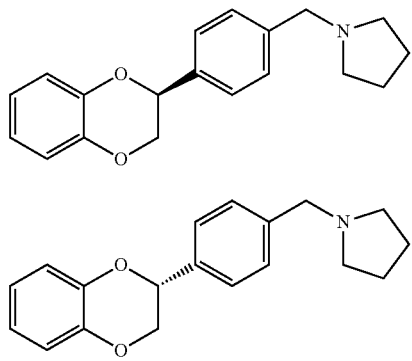

Compound 1 (racemate) is resolved by HPLC using a Chiralpak AD-H column, and eluting with 7% IPA in heptanes with 0.1% DEA to give 196 as the first-eluting peak, and 197 as the second-eluting peak. 196: LC/MS Method 10; Rt=1.21 min; [M+H]+=296.2. 197: LC/MS Method 10; Rt=1.21 min; [M+H]+=296.2.

Examples 198 and 199

Preparation of 4-[(S)-4-(2,3-dihydro-benzo[1,4]dioxin-2-yl)-benzyl]-morpholine (198) and 4-[(R)-4-(2,3-dihydro-benzo[1,4]dioxin-2-yl)-benzyl]-morpholine (199)

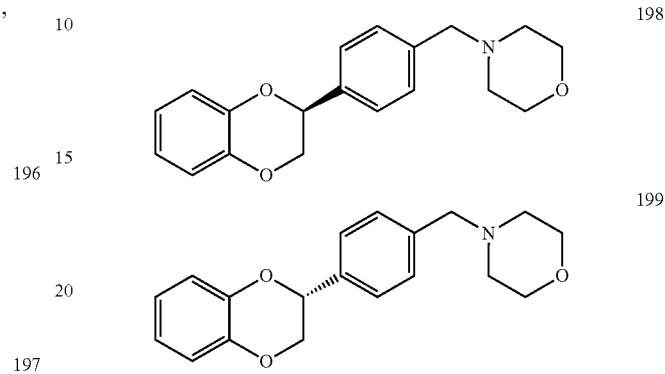

Compound 2 (racemate) is resolved by HPLC using a Chiralpak OD-H column and eluting with 7% IPA in heptanes with 0.1% DEA to give 198 as the first-eluting peak and 199 as the second-eluting peak. 198: LC/MS Method 10; Rt=1.20 min; [M+H]+=312.4. 199: LC/MS Method 10; Rt=1.21 min; [M+H]+=312.4.

Examples 200 and 201

Preparation of (S)-1-[4-(2,3-dihydro-benzo[1,4]dioxin-2-yl)-benzyl]-piperidine-4-carboxylic acid (200) and (R)-1-[4-(2,3-Dihydro-benzo[1,4]dioxin-2-yl)-benzyl]-piperidine-4-carboxylic acid (201)

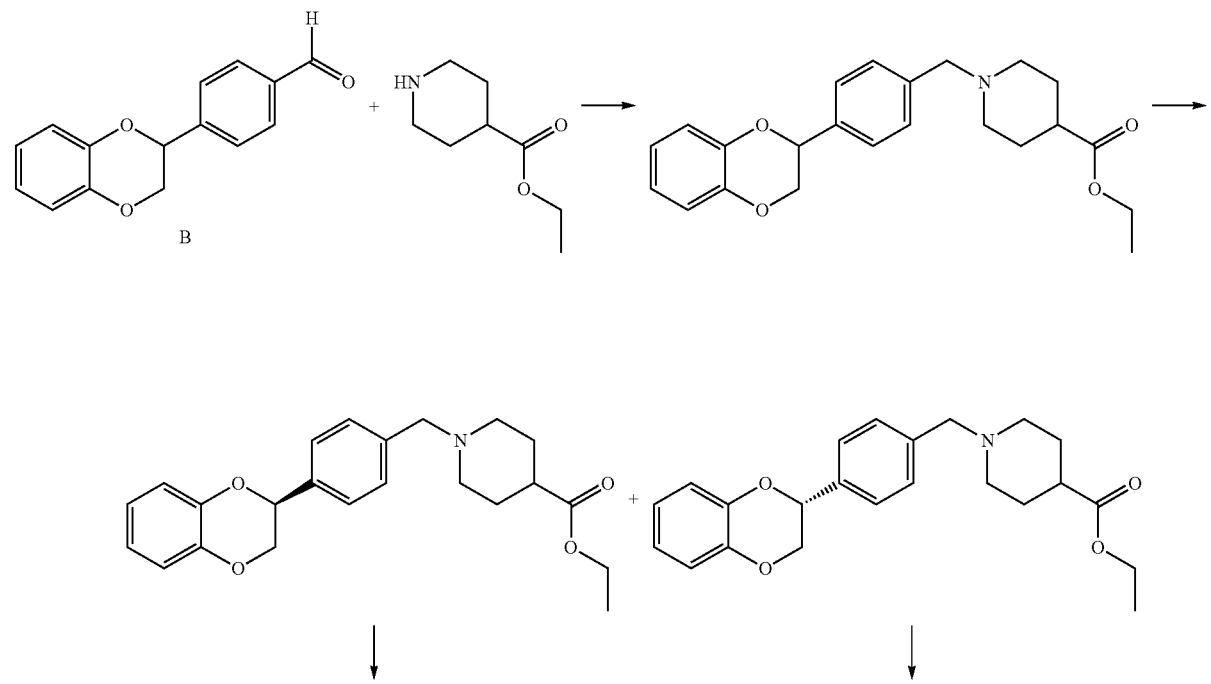

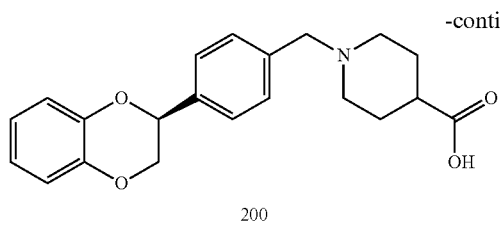

200

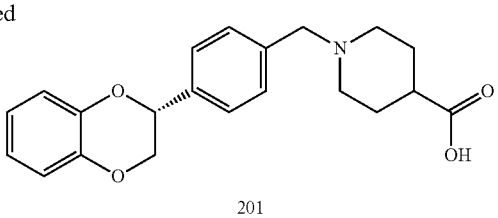

201

1-[4-(2,3-Dihydro-benzo[1,4]dioxin-2-yl)-benzyl]-piperidine-4-carboxylic acid ethyl ester is prepared from intermediate B and ethyl isonipecotate according to the procedure described in General Method B, and resolved by HPLC using a Chiralpak OD-H column, and eluting with 12% IPA in heptanes with 0.1% DEA to give (S)-1-[4-(2,3-dihydro-benzo[1,4]dioxin-2-yl)-benzyl]-piperidine-4-carboxylic acid ethyl ester as the first-eluting peak, and (R)-1-[4-(2,3-dihydro-benzo[1,4]dioxin-2-yl)-benzyl]-piperidine-4-carboxylic acid ethyl ester as the second-eluting peak.

Compound 200:

Method 1: (S)-1-[4-(2,3-Dihydro-benzo[1,4]dioxin-2-yl)-benzyl]-piperidine-4-carboxylic acid ethyl ester (145 mg, 0.380 mmol) and lithium hydroxide monohydrate (48 mg, 1.1 mmol) are heated in a 1:1 mixture of MeOH/water (2 mL) at 75° C. for 2 hours. The reaction mixture is acidified with TFA (300 µL). The resulting white precipitate is filtered off, washed with water, and dried to give compound 200. LC/MS Method 10; Rt=1.14 min; [M+H]$^+$=382.4.

Method 2: A mixture of intermediate A (7.5 g, 29.66 mmol) and piperidine-4-carboxylic acid ethyl ester (5.27 mL, 34.1 mmol) in 2-methyl-THF (40 mL) is stirred at about 20° C. for about 45 min in a reactor. A second reactor is charged with sodium triacetoxyborohydride (8.8 g, 41.5 mmol) and 2-methyl-THF (50 ml) and the contents stirred at about 20° C. for about 30 min. The solution from the first reactor is transferred to the second reactor, stirred at about 22° C. for about 16 hours, and treated with water. The resultant organic phase is collected, washed with a saturated solution of sodium bicarbonate and 5% brine solution, and concentrated to provide (S)-1-[4-(2,3-Dihydro-benzol-[1,4]dioxin-2-yl)-benzyl]-piperidine-4-carboxylic acid ethyl ester. Yield: 76%. MS: 382.2 (M+H)$^+$.

(S)-1-[4-(2,3-Dihydro-benzo[1,4]dioxin-2-yl)-benzyl]-piperidine-4-carboxylic acid ethyl ester (229 g, 381.46 mmol), tetrahydrofuran (366 mL) and N-methylpyrrolidinone (275 mL) are charged to a reactor and cooled to about 0° C. The reactor contents are treated with 4N NaOH (525 mL) while maintaining the reaction temperature below 5° C. The mixture is warmed to about 20° C., stirred for about 16 hours, and cooled to about 5° C. The reactor contents are treated with 2N HCl (110 mL) while maintaining the internal temperature below 15° C. Additional 2N HCl is added until a pH of about 4.5-5.0 is achieved. Water (750 mL) is added over 30 minutes, the mixture is stirred for about 2 hours, and filtered. The resultant solids are dried under reduced pressure to provide compound 200. Yield: 87%. MS: 354.2 (M+H)$^+$.

Compound 201:

Compound 201 is prepared according to the procedure described in Method 1 above for the synthesis of compound 200 except that (R)-1-[4-(2,3-Dihydro-benzo[1,4]dioxin-2-yl)-benzyl]-piperidine-4-carboxylic acid ethyl ester is used instead of (S)-1-[4-(2,3-Dihydro-benzo[1,4]dioxin-2-yl)-benzyl]-piperidine-4-carboxylic acid ethyl ester LC/MS Method 10; Rt=1.13 min.; MS: 382.4 [M+H]$^+$.

Alternatively, compound 201 can also be prepared according to the procedure described in Method 2 above for the synthesis of compound 200 except that (R)-4-(2,3-dihydro-benzo[1,4]dioxin-2-yl)-benzaldehyde (the R enantiomer of intermediate A) is used instead of (S)-4-(2,3-dihydro-benzo[1,4]dioxin-2-yl)-benzaldehyde (A). (R)-4-(2,3-dihydro-benzo[1,4]dioxin-2-yl)-benzaldehyde can be prepared by resolution of intermediate B using the methods described above.

Example 202

Preparation of 4-[4-(7-Fluoro-2,3-dihydro-benzo[1,4]dioxin-2-yl)-benzyl]-morpholine (202)

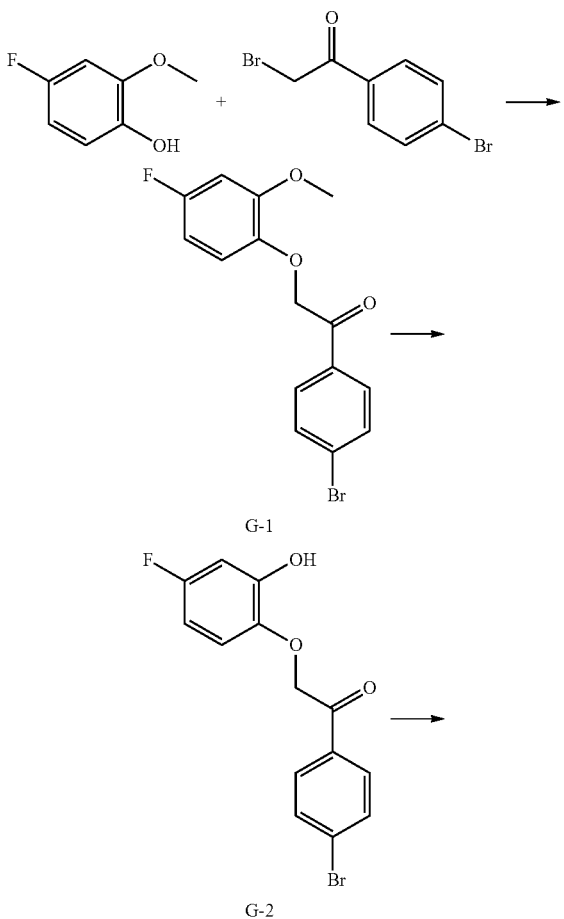

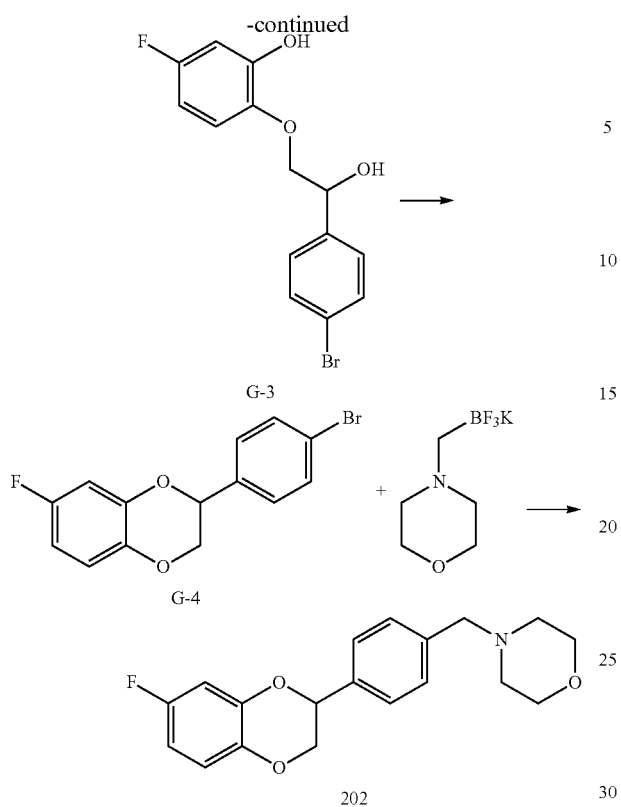

A solution of 4-fluoro-2-methoxy-phenol (3.0 g, 21.1 mmol) in acetone (250 mL) is treated with cesium carbonate (8.3 g, 25.3 mmol) followed by 2-bromo-1-(4-bromo-phenyl)-ethanone (5.9 g, 21.1 mmol). The resulting mixture is stirred at room temperature for 2 h. Water (600 mL) is added slowly to the vigorously stirring solution. After stirring for 30 minutes, the precipitate is filtered off and washed with copious water to give 1-(4-bromo-phenyl)-2-(4-fluoro-2-methoxy-phenoxy)-ethanone (G-1).

G-1 (3.0 g, 8.85 mmol) is dissolved in DCM (30 mL) and cooled to 0° C. Aluminum chloride (2.9 g, 22.1 mmol) is added in one portion and the reaction is stirred at 0° C. for 10 minutes. Ethanethiol (1.6 mL, 22.1 mmoL) is added and the reaction is stirred at 0° C. for 30 minutes. The reaction mixture is poured onto ice and the resulting slurry is stirred for 30 minutes. The product is the extracted with EtOAc (3×50 mL). The combined organic extracts are dried over sodium sulfate, concentrated, and purified by flash column chromatography on silica gel (0 to 50% EtOAc in heptane) to provide 1-(4-bromo-phenyl)-2-(4-fluoro-2-hydroxy-phenoxy)-ethanone (G-2).

To a solution of G-2 (1.25 g, 3.85 mmol) in EtOH (25 mL) is added sodium borohydride (291 mg, 7.69 mmol), and the mixture is stirred at room temperature for 2 h. Water (5 mL) is added, and the resulting mixture is stirred at room temperature for 1 h. The reaction mixture is concentrated, and the residue is dissolved in 1N HCl and extracted with EtOAc. The organic layer is washed with brine, dried over sodium sulfate, and concentrated. The residue is purified by flash column chromatography on silica gel (0 to 40% EtOAc in heptane) to provide 2-[2-(4-bromo-phenyl)-2-hydroxy-ethoxy]-5-fluoro-phenol (G-3).

Triphenylphosphine (918 mg, 3.5 mmol) is dissolved in THF (25 mL) and cooled to 0° C. Diisopropyl azodicarboxylate (0.7 mL, 3.5 mmoL) is added to the mixture and stirred at 0° C. for 20 minutes. The mixture is then treated dropwise over 5 minutes with a solution of G-3 (1.1 g, 3.33 mmol) in THF (10 mL), and the resulting mixture is stirred at 0° C. for 30 minutes and at room temperature for 30 minutes. The reaction mixture is concentrated, and the residue is purified by flash column chromatography on silica gel (0 to 40% EtOAc in heptane) to give 2-(4-bromo-phenyl)-7-fluoro-2,3-dihydro-benzo[1,4]dioxine (G-4).

A solution of G-4 (200 mg, 0.65 mmol), potassium (morpholin-4-yl)methyltrifluoroborate (134 mg, 0.65 mmol), palladium(II) acetate (4.3 mg, 0.019 mmol), 2-dicyclohexylphosphino-2',4',6'-tri-isopropyl-1,1'-biphenyl (19 mg, 0.039 mmol), and cesium carbonate (632 mg, 1.9 mmol) in 10:1 THF/water (2 mL) is stirred at 95° C. for 18 h under an atmosphere of nitrogen. The mixture is taken up in EtOAc, and the organic layer is washed with water, brine, dried over $Na_2SO_4$, and concentrated. The residue is purified by preparative C18 reversed phase HPLC (MeCN/water; 0.1% TFA) to give the title compound. LC/MS Method 10; Rt=1.09 min; $[M+H]^+$=354.4.

Example 203

Preparation of 1-[4-(7-Fluoro-2,3-dihydro-benzo[1,4]dioxin-2-yl)-benzyl]-pyrrolidine (203)

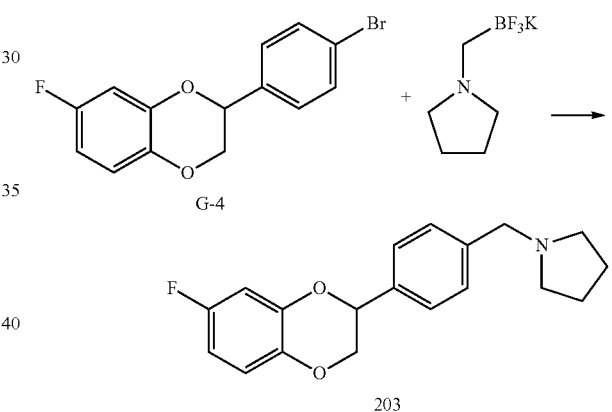

The title compound is prepared from G-4 and Potassium 1-trifluoroboratomethylpyrrolidine according to the procedure described for the synthesis of compound 202. 203: LC/MS Method 10; Rt=1.07 min; $[M+H]^+$=354.4.

Examples 204 and 205

Preparation of (S)-3-(4-Morpholin-4-ylmethyl-phenyl)-2,3-dihydro-[1,4]dioxino[2,3-b]pyridine (204) and (R)-3-(4-Morpholin-4-ylmethyl-phenyl)-2,3-dihydro-[1,4]dioxino[2,3-b]pyridine (205)

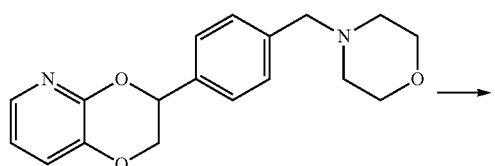

18

-continued

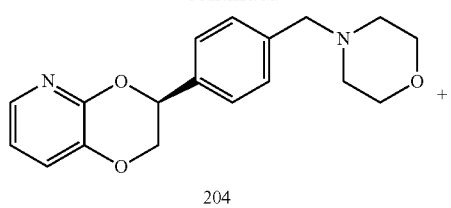
204

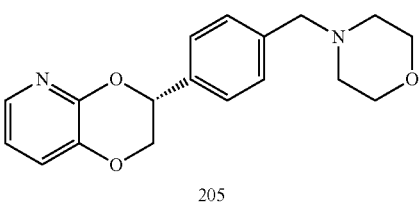
205

Compound 18 (racemate) is resolved by HPLC using a Chiralcel OD-H column eluting with 28% isopropanol in heptane to give compound 204 (LCMS method 15: ES+ m/z 313.2 [M+H]+, rt=0.47 min) and compound 205 (LCMS method 15: ES+ m/z 313.2 [M+H]+, rt=0.50 min)

Examples 206 and 207

Preparation of 1-{4-[(3S)-2,3-dihydro[1,4]dioxino[2,3-b]pyridin-3-yl]benzyl}piperidine-4-carboxamide (206) and 1-{4-[(3R)-2,3-dihydro[1,4]dioxino[2,3-b]pyridin-3-yl]benzyl}piperidine-4-carboxamide (207).

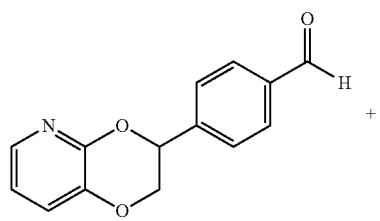

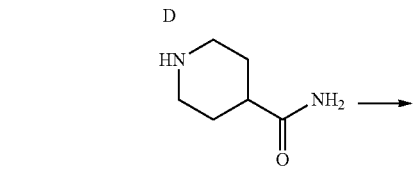

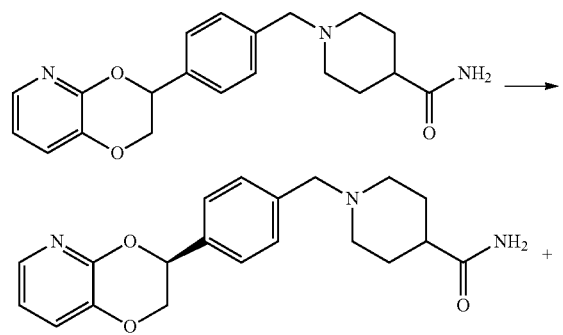
206

-continued

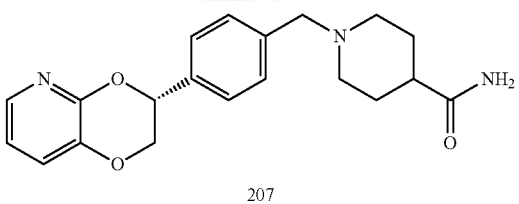
207

The racemic form of 1-[4-(2,3-dihydro-[1,4]dioxino[2,3-b]pyridin-3-yl)-benzyl]-piperidine-4-carboxylic acid amide is prepared from compound 4-(2,3-dihydro-[1,4]dioxino[2,3-b]pyridin-3-yl)-benzaldehyde and piperidine-4-carboxylic acid amide according to the general method B. Compounds 206 and 207 are resolved from the corresponding racemic compound by chiral HPLC according to the procedure described for Examples 204 and 205:

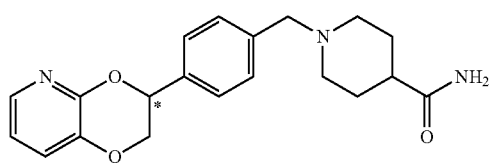 [SMILES: NC(=O)C1CCN(Cc2ccc(C3COc4cccnc4O3)cc2)CC1]

TABLE 4

Preparation of compounds 206 and 207.

| Ex # | Chirality at * | MS Method | [M + H]+ | rt (min) |
| --- | --- | --- | --- | --- |
| 206 | S | 15 | 354.2 | 0.47 |
| 207 | R | 15 | 354.2 | 0.45 |

Example 208

Preparation of 11-[4-(2,3-dihydro-[1,4]dioxino[2,3-b]pyridin-3-yl)-benzyl]-pyrrolidin-2-one (208)

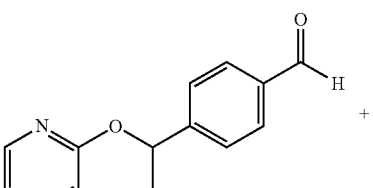
D

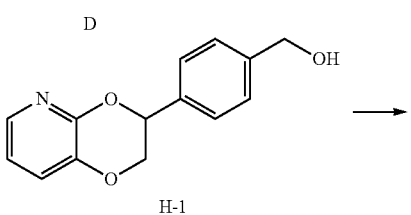
H-1

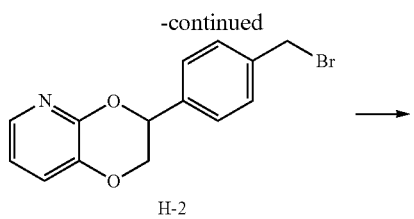

H-2

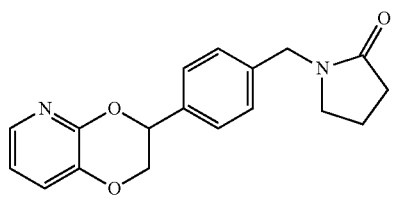

208

A solution of D (1.0 g, 4.15 mmol) in THF (50 mL) is treated with sodium borohydride (188 mg, 5.00 mmol) at 0° C. The resulting mixture is allowed to warm to room temperature and stirred at room temperature for 1 h. The reaction mixture is concentrated and the residue dissolved in EtOAc. The organic solution is washed with water and brine, dried over sodium sulfate, and concentrated. The residue is purified by flash column chromatography (silica gel) with MeOH in DCM (from 2% to 8%) to give [4-(2,3-dihydro-[1,4]dioxino[2,3-b]pyridin-3-yl)-phenyl]-methanol H-1.

A solution of H-1 (400 mg, 1.64 mmol) in THF (10 mL) is treated with triphenylphosphine dibromide (1.39 g, 3.29 mmol) and imidazole (224 mg, 3.29 mmol) at room temperature, and the resulting mixture is stirred at room temperature for 72 h. The mixture is diluted with water and extracted with EtOAc (25 mL, 3×). The combined organic layers are washed with brine, dried over sodium sulfate, and concentrated. The residue is purified by flash column chromatography (silica gel) with EtOAc in heptane (from 15% to 50%) to give 3-(4-Bromomethyl-phenyl)-2,3-dihydro-[1,4]dioxino[2,3-b]pyridine H-2.

A solution of pyrrolidinone (18 mg, 0.21 mmol) in anhydrous DMF (2 mL) is treated with sodium hydride (60% dispersion in mineral oil, 7.8 mg, 0.2 mmol), and the mixture is stirred at room temperature for 15 minutes. Intermediate H-2 (50 mg, 0.16 mmol) is added, and the mixture is stirred at 50° C. After 15 minutes, the mixture is quenched with water and extracted with EtOAc. The organic layer is concentrated, and the residue is purified by reversed phase HPLC eluting with a gradient of 5-85% of MeCN in H₂O (+0.1% TFA). The desired fractions are concentrated. The residue is dissolved in EtOAc, washed with saturated aqueous NaHCO₃, brine, and dried over Na₂SO₄. The solution is then filtered and concentrated to give the title compound as a solid (LCMS method 10: ES⁺ m/z 311.4 [M+H]⁺, Rt=1.84 min)

Example 209

3-[4-(2,3-dihydro[1,4]dioxino[2,3-b]pyridin-3-yl)benzyl]-1,3-oxazolidin-2-one (209)

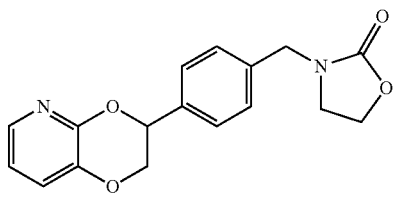 [SMILES: O=C1OCCN1Cc1ccc(C2COc3cccnc3O2)cc1]

Compound 209 is prepared from intermediate H-2 according to the procedure described for the synthesis of 208. (LCMS method 10: ES⁺ m/z 313.4 [M+H]⁺, Rt=1.72 min)

Example 210

Preparation of 4-(2,3-Dihydro-[1,4]dioxino[2,3-b]pyridin-3-yl)-benzylamine (210)

A solution of H-1 (340 mg, 1.4 mmol), triphenylphosphine (550 mg, 2.1 mmol) and diphenylphosphophyl azide (0.45 mL, 2.1 mmol) in anhydrous THF (30 mL) is treated with diisopropyl azodicarboxylate (0.41 mL, 2.1 mmol). The reaction is stirred at room temperature for 24 hours, diluted with water (50 mL), and extracted with EtOAc (3×50 mL). The combined organic solution is washed with brine, dried over Na₂SO₄, filtered and concentrated. The residue is purified by flash chromatography eluting with a gradient of 10-50% EtOAc in Heptane to give H-3 as an oil.

A solution of H-3 (390 mg, 78% pure, 1.1 mmol) and triphenylphosphine (446 mg, 1.7 mmol) in THF (20 mL) is treated with water (0.2 mL, 11.3 mmol). The mixture is stirred at 40° C. for 24 hours, cooled to room temperature, diluted with water (25 mL), and extracted with EtOAc (3×25 mL).

The combined organic solution is washed with brine, dried over Na$_2$SO$_4$, filtered, and concentrated. The residue is purified by reversed phase HPLC eluting with a gradient of 5-85% MeCN in H$_2$O (+0.1% TFA). The combined fractions is concentrated, basified with saturated aqueous NaHCO$_3$ (10 mL), and extracted with EtOAc (10 mL×3). The combined organic phase is washed with brine, dried over Na$_2$SO$_4$, and concentrated to give the title compound as a solid (LCMS method 10: ES$^+$ m/z 243.4 [M+H]$^+$, Rt=0.57 min).

Example 211

Preparation of 1-[(S)-4-(2,3-Dihydro-benzo[1,4]dioxin-2-yl)-benzyl]-4-methyl-piperidine-4-carboxylic acid (211)

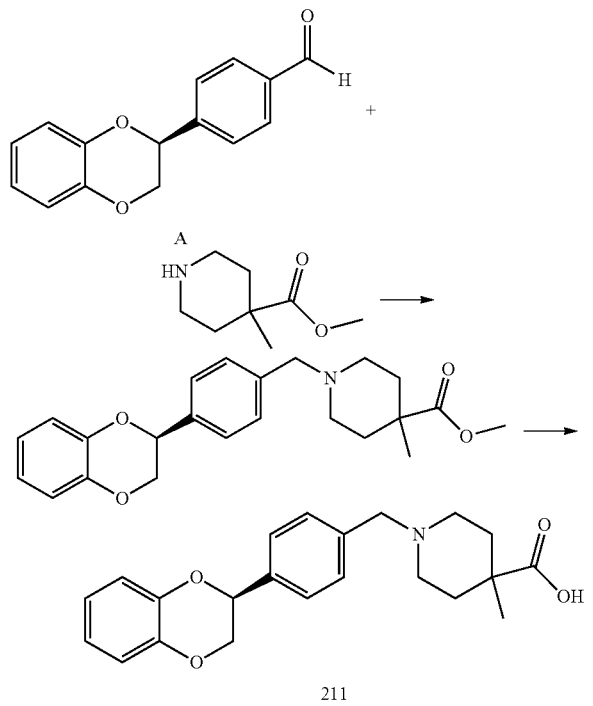

211

Intermediate A (100 mg, 0.42 mmol), methyl-piperidine-4-carboxylic acid methyl ester hydrochloride (105 mg, 0.54 mmol), and TEA (75 uL, 0.54 mmol) are stirred in dry THF (3 mL) for 10 minutes. Sodium triacetoxyborohydride (176 mg) is added and stirred for 4 h. The mixture is diluted with saturated NaHCO$_3$ and extracted with EtOAc. The organic layer is washed with brine, dried over Na$_2$SO$_4$, filtered, and concentrated. The residue is purified by flash chromatography eluting with a gradient of 0-3% MeOH in DCM to give 1-[(S)-4-(2,3-dihydro-benzo[1,4]dioxin-2-yl)-benzyl]-4-methyl-piperidine-4-carboxylic acid methyl ester.

A solution of 1-[(S)-4-(2,3-dihydro-benzo[1,4]dioxin-2-yl)-benzyl]-4-methyl-piperidine-4-carboxylic acid methyl ester in MeOH (2 mL) is treated with a solution of LiOH.H$_2$O (52 mg, 1.23 mmol) in water (2 mL). The mixture is heated to 70° C. for 2 h, concentrated, and treated with TFA (96 uL, 1.23 mmol). The mixture is diluted with water and extracted with EtOAc/THF. The organic layer is dried over Na$_2$SO$_4$, filtered through Diatomaceous earth, and concentrated. The residue is purified by reversed phase HPLC eluting with a gradient of 5-80% MeCN in water (+0.1% TFA) to provide the title compound as the TFA salt (LC/MS method 1: ES$^+$ m/z 368.23 [M+H]$^+$; Rt=0.62 min)

Examples 212-215

Preparation of Compounds 212-215

Compounds 212-215 are prepared from intermediates I-2, I-3, I-5 and I-6 according to the procedure described for the synthesis of compound 211 and shown in Table 5.

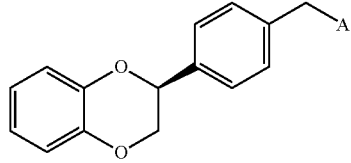

TABLE 5

Preparation of compounds 212-215.

| Ex # | ---A | MS Method | [M + H]$^+$ | Rt (min) |
|---|---|---|---|---|
| 212 | cis (structure) | 1 | 368.24 | 0.62 |
| 213 | (structure with F) | 1 | 372.20 | 0.61 |
| 214 | (structure) | 1 | 341.20 | 0.61 |
| 215 | (structure) | 1 | 341.23 | 0.58 |

Example 216

Preparation of, 1-[(S)-4-(2,3-Dihydro-benzo[1,4]dioxin-2-yl)-benzyl]-4-(1H-tetrazol-5-yl)-piperidine (216)

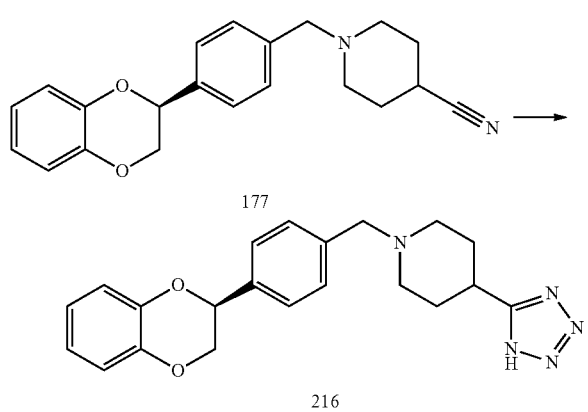

To a solution of 177 (115 mg, 0.34 mmol) in DMF (2 mL) is added NaN₃ (89.0 mg, 1.38 mmol) and NH₄Cl (147 mg, 2.75 mmol). The mixture is heated at 120° C. for 18 h. Additional NaN₃ (89.0 mg, 1.38 mmol) is added, and the reaction is stirred at 120° C. for an additional 72 h. The reaction is filtered, and the filtrate is purified by reversed phase HPLC eluting with a gradient of 5-80% MeCN in water (+0.1% TFA to provide the title compound (LC/MS method 1: ES⁺ m/z 378.2 [M+H]⁺; Rt=0.54 min)

Example 217

Preparation of 1-[(S)-4-(2,3-Dihydro-benzo[1,4]dioxin-2-yl)-benzyl]-piperidin-4-ylamine (217)

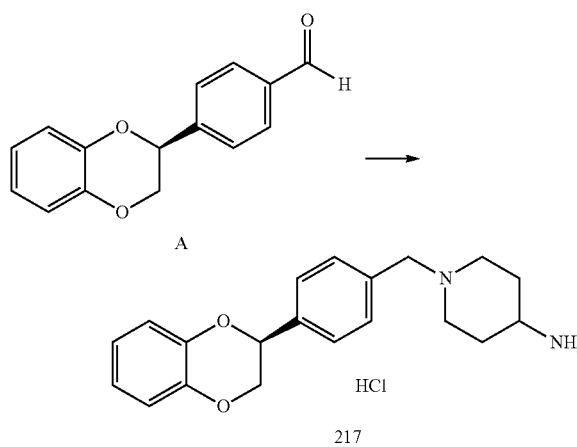

A solution of intermediate A (300 mg, 1.25 mmol) and piperidin-4-yl-carbamic acid tert-butyl ester (300 mg, 1.5 mmol, 1.2 equiv.) is stirred in dry THF (3 mL) for 10 minutes. Sodium triacetoxyborohydride (316 mg, 1.49 mmol) is added, and the reaction is stirred for 18 h. The reaction is concentrated and partitioned between EtOAc and saturated aqueous NaHCO₃. The organic layer is dried over Na₂SO₄, filtered, and concentrated. The residue is purified by flash chromatography eluting with a gradient of 0-5% MeOH in DCM. The residue is dissolved in MeOH (1 mL), treated with HCl (10 mL, 4M in dioxane), and stirred for 18 h. The reaction is diluted with Et₂O (40 mL) and filtered to provide the title compound as the HCl salt (LC/MS method 1: ES+ m/z 325.2 [M+H]⁺, Rt=0.35 min).

Example 218

Preparation of N-{1-[(S)-4-(2,3-Dihydro-benzo[1,4]dioxin-2-yl)-benzyl]-piperidin-4-yl}-2-hydroxy-acetamide (218)

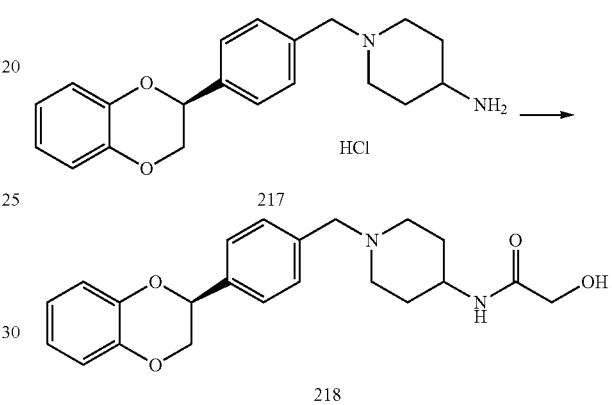

A solution of compound 217 (80 mg, 0.22 mmol), TEA (0.09 mL, 0.67 mmol), hydroxyacetic acid (22 mg, 0.29 mmol) and TBTU (93 mg, 0.29 mmol) in DMF (2 mL) is stirred for 2 h. The reaction is filtered and purified by reversed phase HPLC eluting with a gradient of 0-80% MeCN in water (+0.1% TFA) to provide the title compound as a TFA salt (LC/MS method 1: ES+ m/z 383.2 [M+H]⁺, Rt=0.59 min)

Examples 219-220

Preparation of N-(1-{4-[(2S)-2,3-dihydro-1,4-benzodioxin-2-yl]benzyl}piperidin-4-yl)-2-methoxyacetamide (219) and N-(1-{4-[(2S)-2,3-dihydro-1,4-benzodioxin-2-yl]benzyl}piperidin-4-yl)-2-hydroxy-2-methylpropanamide (220)

Compounds 219 through 223 are prepared and according to the procedure described for compound 218 and shown in Table 6. The products are purified by reversed phase HPLC or flash chromatography eluting with a gradient of 0-10% MeOH in DCM.

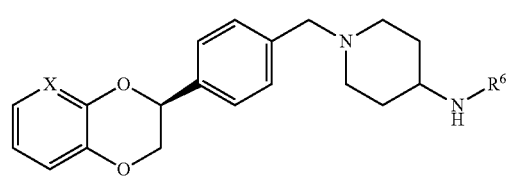

TABLE 6

Preparation of compounds 219-223.

| Ex # | X | ---R⁶ | MS Method | [M + H]⁺ | Rt (min) |
|---|---|---|---|---|---|
| 219 | CH | (ketone with OMe) | 1 | 397.08 | 0.61 |
| 220 | CH | (ketone with C(CH₃)₂OH) | 1 | 411.30 | 0.55 |
| 221 | N | (ketone with C(CH₃)₂OH) | 1 | 412.27 | 0.48 |
| 222 | N | (ketone with CH₂OH) | 1 | 384.22 | 0.43 |
| 223 | N | (ketone with cyclopropyl-OH) | 1 | 410.26 | 0.47 |

Example 224

Preparation of 1-[(S)-4-(2,3-Dihydro-benzo[1,4]dioxin-2-yl)-benzyl]-4-(1,1-dioxo-1λ⁶-isothiazolidin-2-yl)-piperidine (224)

To a stirred solution of compound 217 (535 mg, 1.65 mmol) in THF (10 mL) is added 3-chloro-propane-1-sulfonyl chloride (0.40 mL, 3.3 mmol) and pyridine (0.27 mL). After 18 h, the mixture is diluted with saturated NaHCO₃ and extracted with EtOAc. The organic layer is dried over Na₂SO₄, filtered, and concentrated. The residue is purified by flash chromatography eluting with a gradient of 0-10% MeOH in DCM to provide 3-chloro-propane-1-sulfonic acid {1-[(S)-4-(2,3-dihydro-benzo[1,4]dioxin-2-yl)-benzyl]-piperidin-4-yl}-amide. LC/MS method 1: ES+ m/z 465.2 [M]⁺, Rt=0.68 min).

To a solution of 3-chloro-propane-1-sulfonic acid {1-[(S)-4-(2,3-dihydro-benzo[1,4]dioxin-2-yl)-benzyl]-piperidin-4-yl}-amide (410 mg, 0.88 mmol) in DMF (5 mL) is added NaH (60% dispersion in mineral oil, 71 mg, 1.8 mmol). The reaction is heated to 80° C. for 1 h, diluted with EtOAc, washed with water and brine, dried over Na₂SO₄, filtered, and concentrated. The residue is purified by reversed phase HPLC eluting with a gradient of 0-80% MeCN in water (+0.1% TFA). The desired fractions are lyophilized, partitioned between saturated aqueous NaHCO₃ and EtOAc. The organic layer is dried over Na₂SO₄, filtered and concentrated to provide the title compound (LC/MS method 1: ES+ m/z 429.4 [M+H]⁺, Rt=0.63 min)

Example 225

Preparation of 1-{1-[(S)-4-(2,3-dihydro-benzo[1,4]dioxin-2-yl)-phenyl]-ethyl}-pyrrolidine (225)

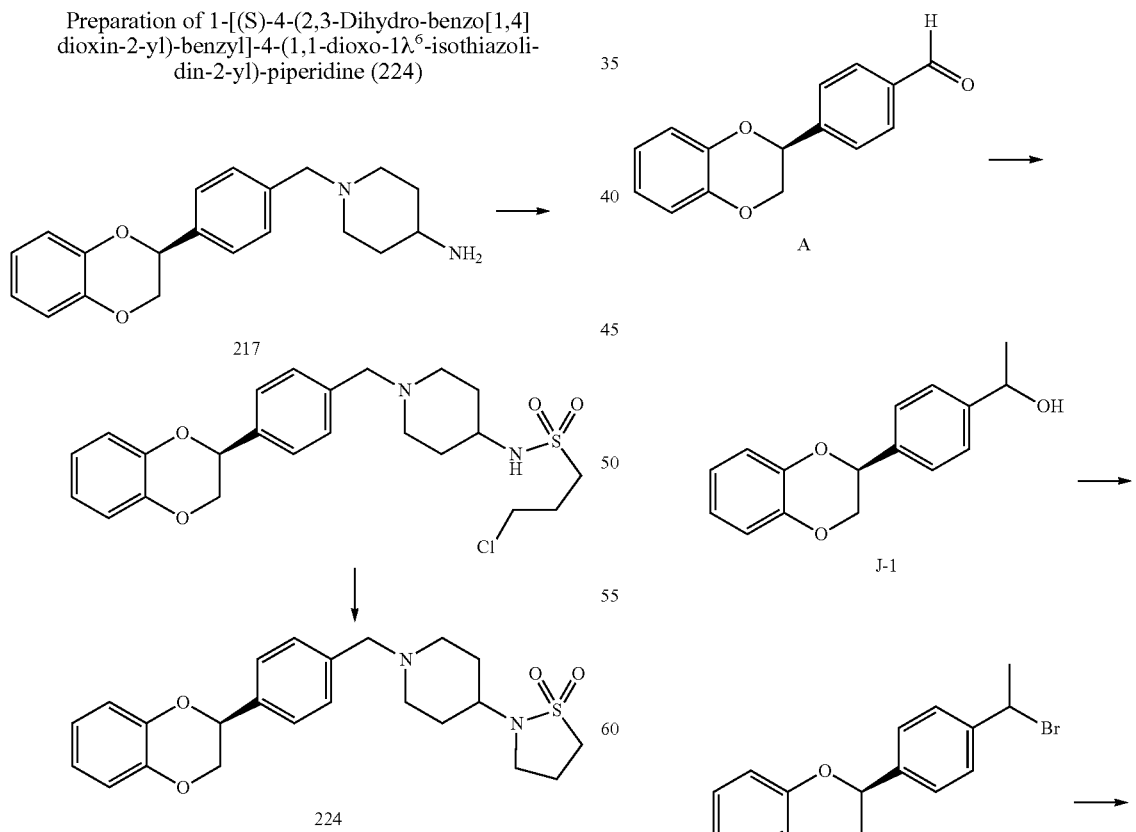

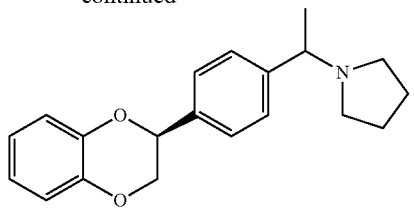

225

A solution of A (1.0 g, 4.16 mmol) in THF (10 mL) is treated with 1.4M methylmagnesium bromide solution in toluene at 0° C. The resulting mixture is stirred at 0° C. for 1 h. The mixture is then quenched with saturated ammonium chloride solution and extracted with EtOAc. The organic solution is dried over Na$_2$SO$_4$, filtered, and concentrated. The residue is purified by flash chromatography eluting with a gradient of 0-30% EtOAc in heptane to give 1-[(S)-4-(2,3-dihydro-benzo[1,4]dioxin-2-yl)-phenyl]-ethanol (J-1).

A solution of J-1 (500 mg, 1.95 mmol) in THF (10 mL) is treated with triphenylphosphine dibromide (1.65 g, 3.90 mmol) and imidazole (265 mg, 3.90 mmol) at room temperature, and the resulting mixture is stirred at room temperature for 72 h. The mixture is diluted with water and extracted with EtOAc (25 mL, 3×). The combined organic layers are washed with brine, dried over sodium sulfate, and concentrated. The residue is purified by flash column chromatography (silica gel) with EtOAc in Heptane (from 0% to 30%) to give (S)-2-[4-(1-bromo-ethyl)-phenyl]-2,3-dihydro-benzo-[1,4]dioxine J.

A mixture of intermediate J (560 mg, 90% pure, 1.58 mmol) in pyrrolidine (0.5 mL) is heated at 60° C. for 18 h. The reaction is diluted with MeOH and purified by reversed phase HPLC eluting with a gradient of 5-80% MeCN in water (+0.1% TFA). The desired fractions are combined, diluted with EtOAc, and washed with saturated aqueous NaHCO$_3$. The organic layer is dried over Na$_2$SO$_4$, filtered, and concentrated. The residue is dissolved in Et$_2$O (2 mL), treated with HCl (2 mL, 2M in Et$_2$O), and concentrated to provide the title product as the HCl salt (LC/MS method 1: ES+ m/z 311.2 [M+H]$^+$, Rt=0.63 min)

Example 226

4-(1-{4-[(2S)-2,3-dihydro-1,4-benzodioxin-2-yl]phenyl}ethyl)morpholine (226)

Compound 226 is prepared from intermediate J and morpholine according to the procedure described for the synthesis of compound 225.

| Ex # | MS Method | [M + H]$^+$ | Rt (min) |
|---|---|---|---|
| 226 | 1 | 327.20 | 0.89 |

Example 227

Preparation of 1-{1-[(S)-4-(2,3-dihydro-benzo[1,4]dioxin-2-yl)-phenyl]-ethyl}-piperidine-4-carboxylic acid (227)

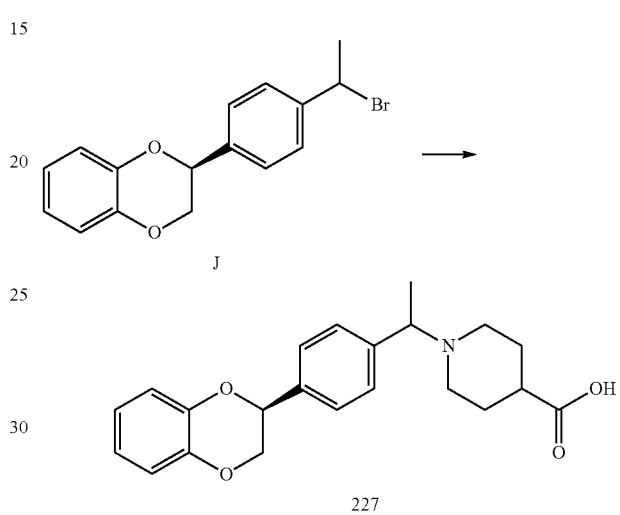

A mixture of intermediate J (188 mg, 0.59 mmol) and piperidine-4-carboxylic acid ethyl ester (0.5 mL, 3.24 mmol) is heated at 60° C. for 18 h. The reaction is diluted with MeOH and purified by reversed phase HPLC eluting with a gradient of 5-80% CH$_3$CN in water (+0.1% TFA). The desired fractions are combined, diluted with EtOAc, and washed with saturated aqueous NaHCO$_3$. The organic layer is dried over Na$_2$SO$_4$, filtered, and concentrated. The residue is dissolved in a mixture of MeOH (4 mL) and water (4 mL) containing KOH (110 mg, 2 mmol) and heated at 50° C. for 18 h. The mixture is concentrated, treated with TFA (0.15 mL, 2 mmol), and extracted with EtOAc. The organic layer is dried over Na$_2$SO$_4$, filtered, and concentrated to provide the title compound as the TFA salt (LCMS method 7: ES+ m/z 369.2 [M+H]$^+$, Rt=0.56 min)

Example 228

Preparation of 1-[(S)-4-(2,3-Dihydro-[1,4]dioxino[2,3-b]pyridin-3-yl)-benzyl]-4-methyl-piperidine-4-carboxylic acid formate salt (228)

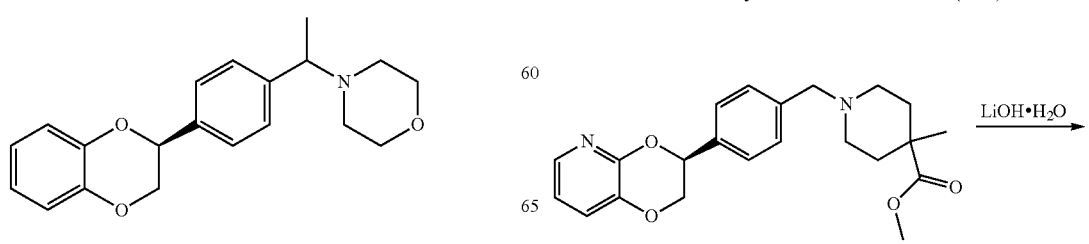

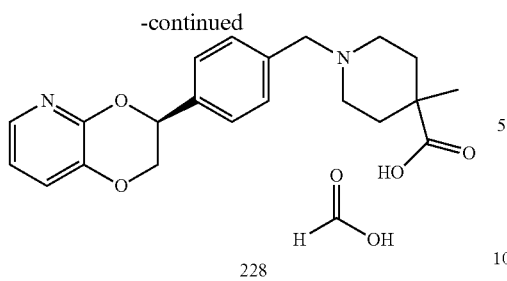
228

A mixture of 1-[(S)-4-(2,3-Dihydro-[1,4]dioxino[2,3-b]pyridin-3-yl)-benzyl]-4-methyl-piperidine-4-carboxylic acid methyl ester (prepared according to the General Method A) (43 mg, 0.10 mmol), LiOH.H₂O (21 mg, 0.5 mmol), MeOH (3 mL), and water (1 mL) is warmed to 50° C. overnight. The reaction is concentrated, neutralized with 1 N aqueous HCl, and purified by reversed phase HPLC eluting with a gradient of 0-70% MeCN in water (+0.1% formic acid) to afford the title compound as the formate salt (LCMS method 15: ES+ m/z 382.8 [M+H]⁺, Rt=0.54 min)

Example 229

Preparation of 2-{1-[(S)-4-(2,3-Dihydro-benzo[1,4]dioxin-2-yl)-benzyl]-piperidin-4-yl}-2-methyl-propionic acid formate salt (229)

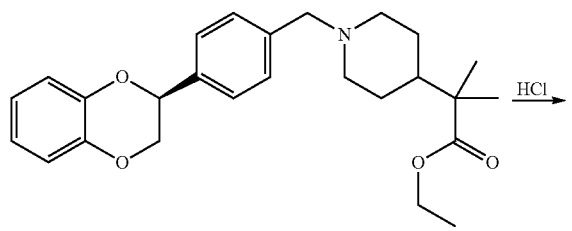

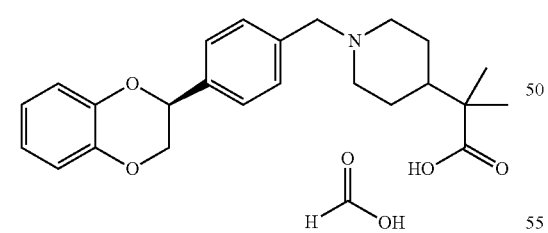
229

2-{1-[(S)-4-(2,3-Dihydro-benzo[1,4]dioxin-2-yl)-benzyl]-piperidin-4-yl}-2-methyl-propionic acid ethyl ester (prepared according to General Method A) (226 mg, 0.430 mmol) is treated with HCl (1.5 mL, 4M in dioxane, 6 mmol) and 1 mL of water. The mixture is warmed to 140° C. for 1 hour, concentrated, diluted with water, and neutralized with 2N aqueous Na₂CO₃. The aqueous layer is decanted and the remaining residue is purified by reversed phase HPLC eluting with a gradient of 0-70% MeCN in water (+0.1% formic acid) to afford the title compound as the formate salt (LCMS method 15: ES+ m/z 395.8 [M+H]⁺, Rt=1.25 min)

Example 230

Preparation of 2-{1-[(S)-4-(2,3-Dihydro-[1,4]dioxino[2,3-b]pyridin-3-yl)-benzyl]-piperidin-4-yl}-2-methyl-propionic acid formate salt (230)

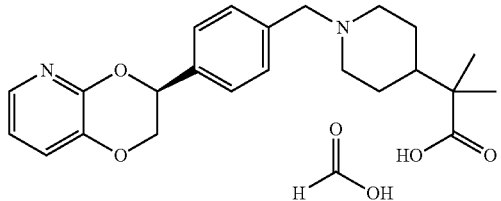

Compound 230 is prepared according to the procedure described for the synthesis of compound 229.

Example 231

Preparation of 4-{1-[(S)-4-(2,3-Dihydro-benzo[1,4]dioxin-2-yl)-benzyl]-piperidin-4-ylmethyl}-benzoic acid (231)

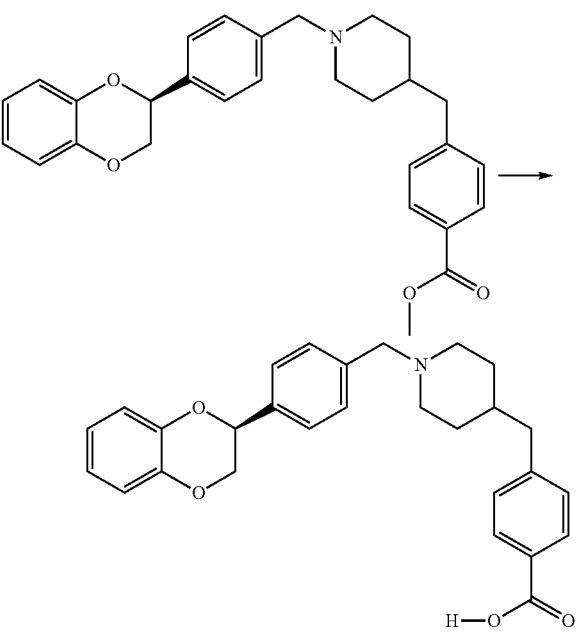
231

A mixture of 4-{1-[(S)-4-(2,3-dihydro-benzo[1,4]dioxin-2-yl)-benzyl]-piperidin-4-ylmethyl}-benzoic acid methyl ester (prepared according to General Method C) (80 mg, 0.17 mmol), LiOH.H₂O (15 mg, 0.36 mmol), MeOH (3 mL) and water (0.5 mL) is stirred at room temperature for 16 h. The reaction mixture is neutralized with acetic acid and concentrated. The residue is triturated with water to give the title compound.

Examples 231-235
Preparation of Compounds 231-235
Compounds 231-235 are prepared according to the procedure described for the synthesis of compound 231 as shown in Table 7 below.
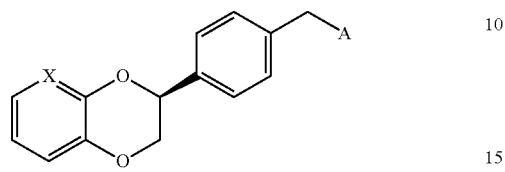
TABLE 7
| Ex # | X | ---A | MS Method | [M + H]+ | Rt (min) |
|---|---|---|---|---|---|
| 231 | CH | piperidine-CH2-C6H4-COOH | 4 | 444.30 | 1.42 |
| 232 | CH | tetrahydroisoquinoline-COOH | 4 | 402.25 | 1.28 |
| 233 | CH | piperidine-C6H4-COOH | 4 | 430.26 | 1.21 |
| 234 | N | piperidine-CH2-C6H4-COOH | 4 | 445.29 | 0.81 |
| 235 | N | piperidine-C6H4-COOH | 3 | 431.25 | 1.59 |

Example 236

Preparation of 4-({[(S)-4-(2,3-Dihydro-benzo[1,4] dioxin-2-yl)-benzyl]-ethyl-amino}-methyl)-benzoic acid (236)

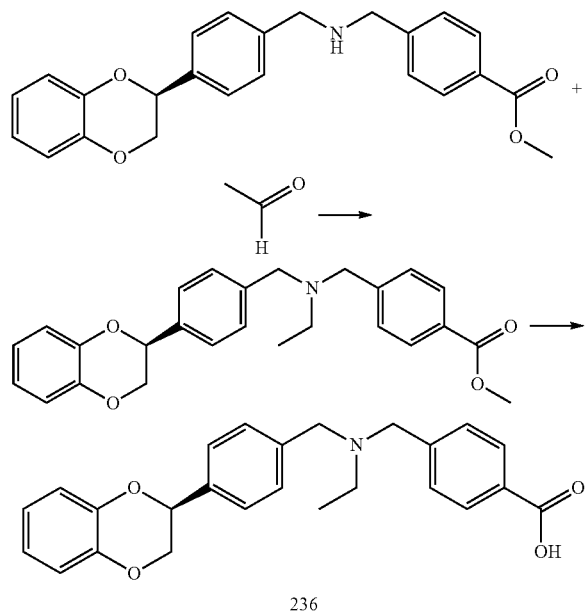

236

A mixture of 4-{[(S)-4-(2,3-dihydro-benzo[1,4]dioxin-2-yl)-benzylamino]-methyl}-benzoic acid methyl ester (prepared according to General Method E) (130 mg, 0.33 mmol), acetaldehyde (0.03 mL, 0.50 mmol), and sodium cyanoborohydride (42 mg, 0.67 mmol) in MeOH (15 mL) is treated with 2 drops of acetic acid. The mixture is stirred at room temperature for 16 h, and concentrated. The residue is purified by flash chromatography eluting with a gradient of 0-10% MeOH in DCM to give 4-({[(S)-4-(2,3-dihydro-benzo[1,4] dioxin-2-yl)-benzyl]-ethyl-amino}-methyl)-benzoic acid methyl ester.

A mixture of 4-({[(S)-4-(2,3-dihydro-benzo[1,4]dioxin-2-yl)-benzyl]-ethyl-amino}-methyl)-benzoic acid methyl ester (65 mg, 0.16 mmol), LiOH.H$_2$O (23 mg, 0.55 mmol), MeOH (5 mL) and water (0.5 mL) is stirred at room temperature for 16 h. The reaction mixture is neutralized with acetic acid and concentrated. The residue is diluted with water and DCM, phases are separated, the organic layer is dried over Na$_2$SO$_4$, filtered and concentrated. The residue is purified by flash chromatography eluting with a gradient of 0-10% MeOH in DCM to give the title compound.

Examples 236-238

Preparation of Compounds 236-238

Compounds 236-238 are prepared according to the procedure described for the synthesis of compound 236 and as shown in Table 8 below.

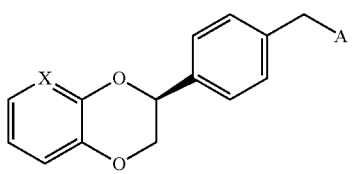

TABLE 8

Preparation of compounds 236-238.

| Ex # | X | ---A | MS Method | [M + H]$^+$ | Rt (min) |
|---|---|---|---|---|---|
| 236 | CH | ethyl-N-CH$_2$-C$_6$H$_4$-COOH | 3 | 404.40 | 1.86 |
| 237 | CH | butyl-N-CH$_2$-C$_6$H$_4$-COOH | 3 | 432.29 | 2.29 |
| 238 | CH | ethyl-N-CH$_2$-(3-COOH-C$_6$H$_4$) | 3 | 404.26 | 1.98 |

Example 239

Preparation of 3-{4-[(S)-4-(2,3-Dihydro-benzo[1,4] dioxin-2-yl)-benzyl]-piperazin-1-ylmethyl}-benzoic acid (239)

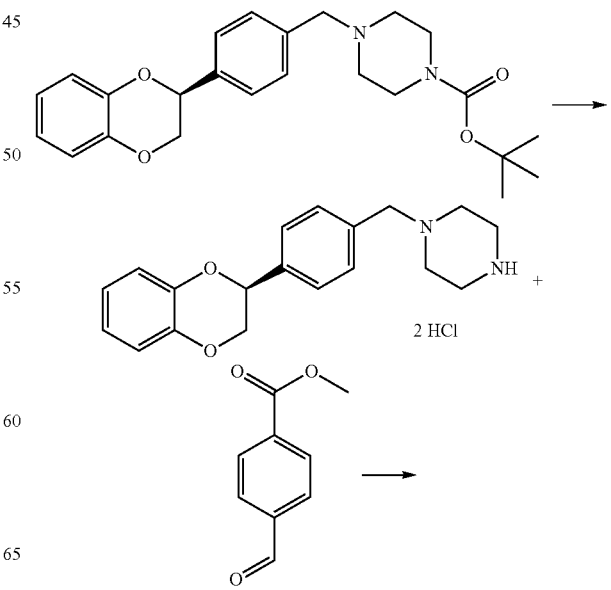

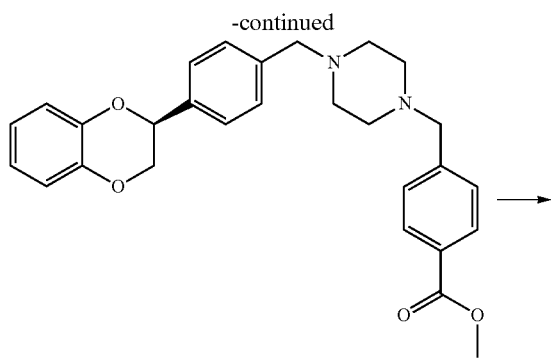

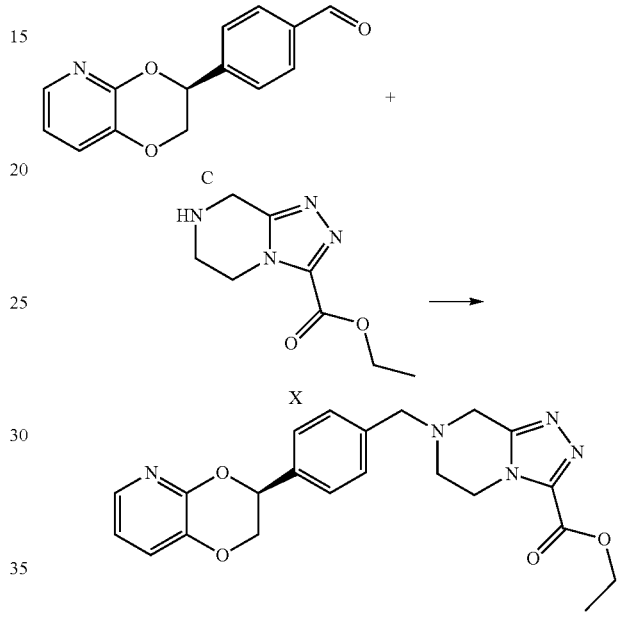

Methanol (30 mL) is added dropwise to acetyl chloride (1.4 mL) at 0° C. The solution is added to 4-[(S)-4-(2,3-dihydro-benzo[1,4]dioxin-2-yl)-benzyl]-piperazine-1-carboxylic acid tert-butyl ester (408 mg, 0.99 mmol) (prepared according to the General Method E). The resulting mixture is stirred at room temperature for 16 h and concentrated. The residue is suspended in a mixture of heptane and EtOAc, and the precipitate is collected and dried under vacuum to give 1-[(S)-4-(2,3-dihydro-benzo[1,4]dioxin-2-yl)-benzyl]-piperazine dihydrochloride.

A solution of 1-[(S)-4-(2,3-dihydro-benzo[1,4]dioxin-2-yl)-benzyl]-piperazine dihydrochloride (80 mg, 0.21 mmol), 4-formyl-benzoic acid methyl ester (41 mg, 0.25 mmol), sodium cyanoborohydride (26 mg, 0.42 mmol), and DIPEA (0.07 mL, 0.42 mmol) in MeOH (5 mL) is treated with 2 drops of acetic acid. The resulting mixture is stirred at room temperature for 16 h, concentrated, diluted with water, and extracted with ethyl acetate. The organic layer is washed with brine, dried over $Na_2SO_4$, filtered, and concentrated. The residue is purified by flash chromatography eluting with a gradient of 0-10% MeOH in DCM to give 4-{4-[(S)-4-(2,3-dihydro-benzo[1,4]dioxin-2-yl)-benzyl]-piperazin-1-ylmethyl}-benzoic acid methyl ester.

A mixture of 4-{4-[(S)-4-(2,3-dihydro-benzo[1,4]dioxin-2-yl)-benzyl]-piperazin-1-ylmethyl}-benzoic acid methyl ester (48 mg, 0.11 mmol), LiOH.$H_2O$ (15 mg, 0.37 mmol), dioxane (5 mL), and water (0.5 mL) is stirred at room temperature for 16 h. The reaction mixture is neutralized with acetic acid and concentrated. The residue is triturated with water to give the title compound (LCMS method 4: ES+ m/z 445.2 [M+H]$^+$, Rt=1.31 min).

Example 240

Preparation of 7-[(S)-4-(2,3-dihydro-[1,4]dioxino[2,3-b]pyridin-3-yl)-benzyl]-5,6,7,8-tetrahydro-[1,2,4]triazolo[4,3-a]pyrazine-3-carboxylic acid ethyl ester (240)

A solution of Intermediates C (4.88 g, 20.0 mmol) and X (4.76 g, 24.3 mmol) in dry DCE (145 mL) is stirred for 20 min Sodium triacetoxyborohydride (8.58 g, 40.5 mmol) is added, and the reaction is stirred at rt overnight. The mixture is diluted with DCM and washed with sat. $NaHCO_3$ and brine, dried over $Na_2SO_4$, filtered and concentrated. The residue is purified by silica gel chromatography eluting with 0-10% MeOH in DCM to afford the title product 240. (LC/MS method 16: ES+ m/z 422.3 [M+H]+, Rt=2.81 min)

Example 241

Preparation of 7-[(S)-4-(2,3-Dihydro-[1,4]dioxino[2,3-b]pyridin-3-yl)-benzyl]-5,6,7,8-tetrahydro-[1,2,4]triazolo[4,3-a]pyrazine-3-carboxylic acid amide (241)

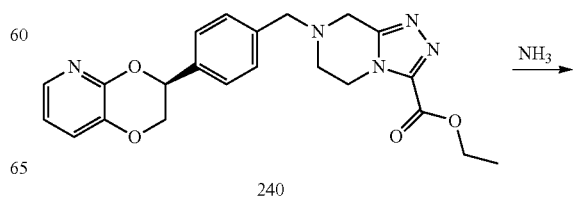

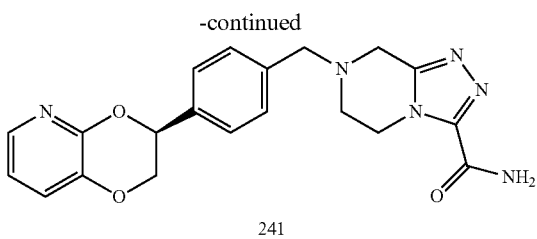

241

A solution of compound 240 (6.98 g, 16.6 mmol) in a solution of ammonia in methanol (102 mL, 7 mmol) is stirred at 90° C. in a pressure tube for 22 h. The mixture is gradually cooled to rt. The mixture is filtered, and the solids are washed with chilled methanol then air dried to give the title product 241. (LC/MS method 16: ES+ m/z 393.3 [M+H]+, Rt=2.60 min)

Example 242

Preparation of 7-[(S)-4-(2,3-dihydro-[1,4]dioxino[2,3-b]pyridin-3-yl)-benzyl]-5,6,7,8-tetrahydro-[1,2,4]triazolo[4,3-a]pyrazine-3-carboxylic acid methylamide (242)

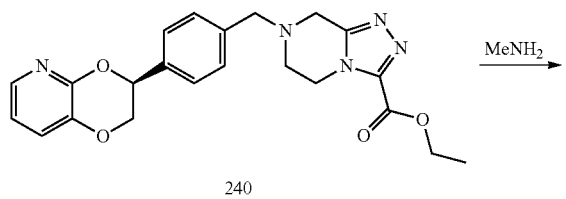

240

MeNH₂ →

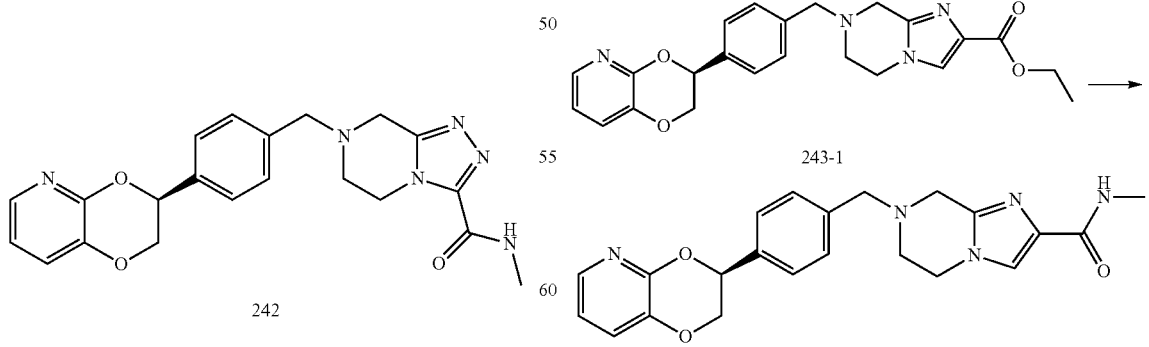

242

The solution of compound 240 (75 mg, 0.18 mmol) in a solution of 33% methylamine in ethanol (1.0 mL) is stirred at 90° C. in a pressure tube. After 18 hours, the mixture is gradually cooled to rt. The mixture is filtered, and the solids are washed with chilled ethanol and chilled methanol then air dried to give the title product. (LC/MS method 16: ES+ m/z 407.3 [M+H]+, Rt=2.73 min)

Example 243

Preparation of 7-[(S)-4-(2,3-dihydro-[1,4]dioxino[2,3-b]pyridin-3-yl)-benzyl]-5,6,7,8-tetrahydro-imidazo[1,2-a]pyrazine-2-carboxylic acid amide (243)

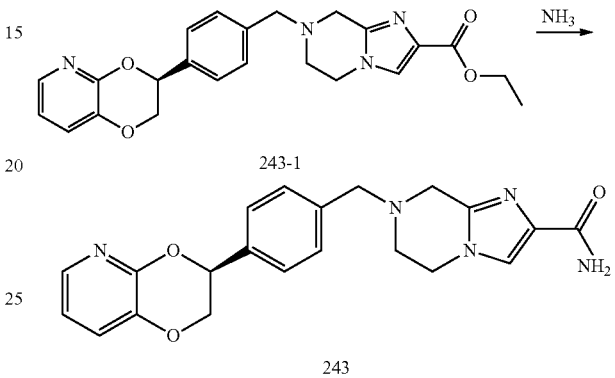

243-1

243

Compound 243-1 is synthesized from Intermediates C (200 mg, 0.829 mmol) and Z (324 mg, 1.66 mmol) according to the procedure described for the synthesis of compound 240.

The title compound 243 is synthesized from compound 243-1 (70 mg, 0.17 mmol) according to the procedure described for the synthesis of compound 241. (LC/MS method 16: ES+ m/z 392.4 [M+H]+, Rt=2.58 min)

Example 244

Preparation of 7-[(S)-4-(2,3-dihydro-[1,4]dioxino[2,3-b]pyridin-3-yl)-benzyl]-5,6,7,8-tetrahydro-imidazo[1,2-a]pyrazine-2-carboxylic acid methylamide (244)

243-1

244

The title compound 244 is synthesized from compound 243-1 (75 mg, 0.18 mmol) according to the procedure described for the synthesis of compound 242. (LC/MS method 16: ES+ m/z 406.3 [M+H]+, Rt=2.52 min)

Example 245

Preparation of 6-[(S)-4-(2,3-dihydro-[1,4]dioxino[2,3-b]pyridin-3-yl)-benzyl]-5,6,7,8-tetrahydro-4H-1,2,3a,6-tetraaza-azulene-3-carboxylic acid amide (245)

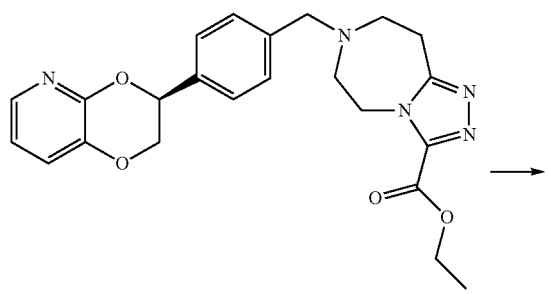

245-1

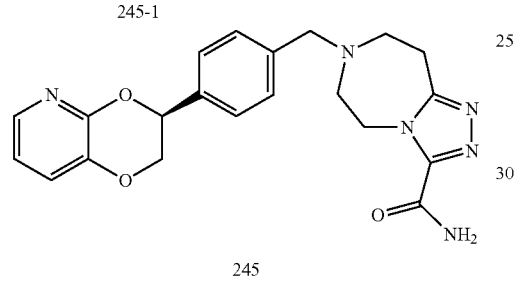

245

Compound 245-1 is synthesized from Intermediates C (360 mg, 1.49 mmol) and Y (519 mg, 1.60 mmol) according to General Method A.

The title compound 245 is synthesized from compound 245-1 (275 mg, 0.631 mmol) according to the procedure described for the synthesis of compound 241. (LC/MS method 16: ES+ m/z 407.5 [M+H]+, Rt=0.35 min)

Example 246

Preparation of 6-[(S)-4-(2,3-Dihydro-[1,4]dioxino[2,3-b]pyridin-3-yl)-benzyl]-5,6,7,8-tetrahydro-4H-1,2,3a,6-tetraaza-azulene-3-carboxylic acid methylamide (246)

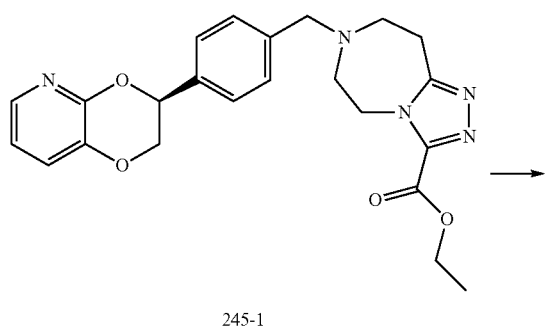

245-1

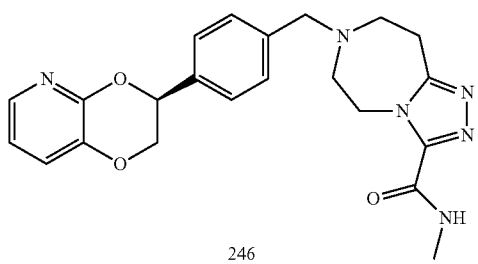

246

The title compound 246 is synthesized from compound 245-1 (80 mg, 0.18 mmol) according to the procedure described for the synthesis of compound 242. (LC/MS method 16: ES+ m/z 421.4 [M+H]+, Rt=2.61 min)

Example 247

Preparation of [(1α,5α,6α)-3-[(S)-4-(2,3-dihydro-[1,4]dioxino[2,3-b]pyridin-3-yl)-benzyl]-3-aza-bicyclo[3.1.0]hexane]-6-carboxylic acid ((S)-2-hydroxy-propyl)-amide (247)

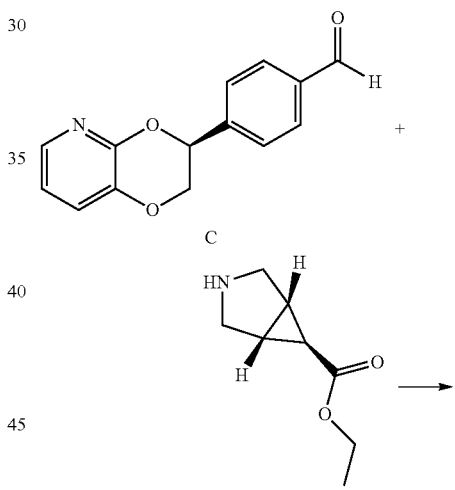

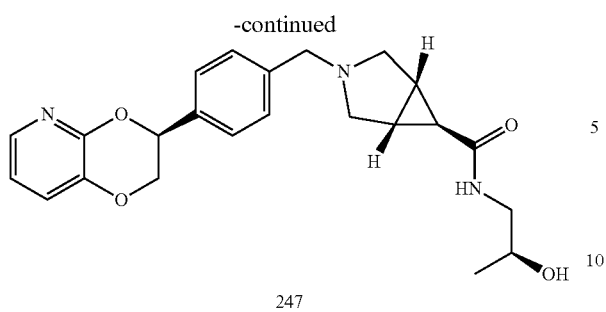

247

Compound 247-1 is synthesized from Intermediates C (400 mg, 1.66 mmol) and AA (796 mg, 5.13 mmol) according to the procedure described for the synthesis of compound 240.

A solution of compound 247-1 (631 mg, 1.66 mmol) in a mixture of THF, MeOH, and H₂O (3:1:1) is treated with LiOH.H₂O (278 mg, 6.63 mmol). The resulting mixture is stirred at rt. Upon completion, the reaction mixture is acidified with TFA and concentrated. The mixture is dissolved in DCM and concentrated (3 times) to give crude compound 247-2.

To a solution of 247-2 (200 mg), and DIPEA (0.129 mL, 2.54 mmol) in DMF (2.0 mL) is added TBTU (407 mg, 1.26 mmol). The mixture is stirred at rt for 15 min and treated with the (S)-1-amino-propan-2-ol (0.200 mL, 2.54 mmol). After 18 hours, the mixture is quenched with MeOH and the crude is purified by reverse phase HPLC eluting with 5-95% MeCN in water (+0.1% TFA). Product fractions are pooled and lyophilized. The solid is dissolved in MeOH, passed through a carbonate resin cartridge, and concentrated. The residue is purified by silica gel chromatography (0-100% EtOAC in heptanes, followed by 0-10% MeOH in DCM) to give the title product 247. (LC/MS method 16: ES+ m/z 410.4 [M+H]+, Rt=1.46 min).

Example 248

Preparation of [(1α,5α,6α)-3-[(S)-4-(2,3-Dihydro-[1,4]dioxino[2,3-b]pyridin-3-yl)-benzyl]-3-aza-bicyclo[3.1.0]hexane]-6-carboxylic acid ((S)-2-hydroxy-1-methyl-ethyl)-amide (248)

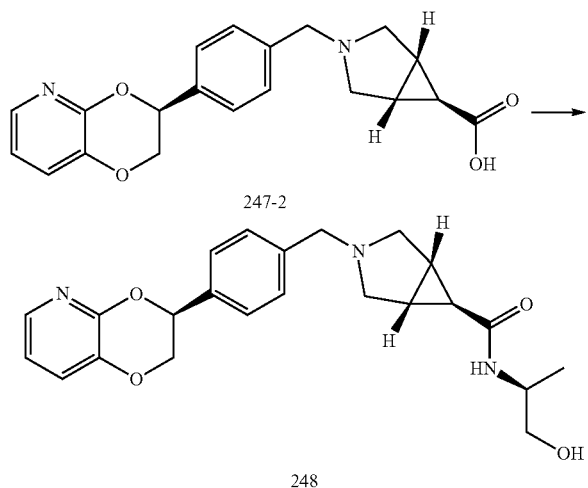

248

The title compound 248 is synthesized from compound 247-2 (200 mg) according to the procedure described for the synthesis of compound 247. (LC/MS method 16: ES+ m/z 410.4 [M+H]+, Rt=1.45 min)

Example 249

Preparation of 7-[(S)-4-(2,3-Dihydro-[1,4]dioxino[2,3-b]pyridin-3-yl)-benzyl]-5,6,7,8-tetrahydro-imidazo[1,2-a]pyrazine-3-carbonitrile (249)

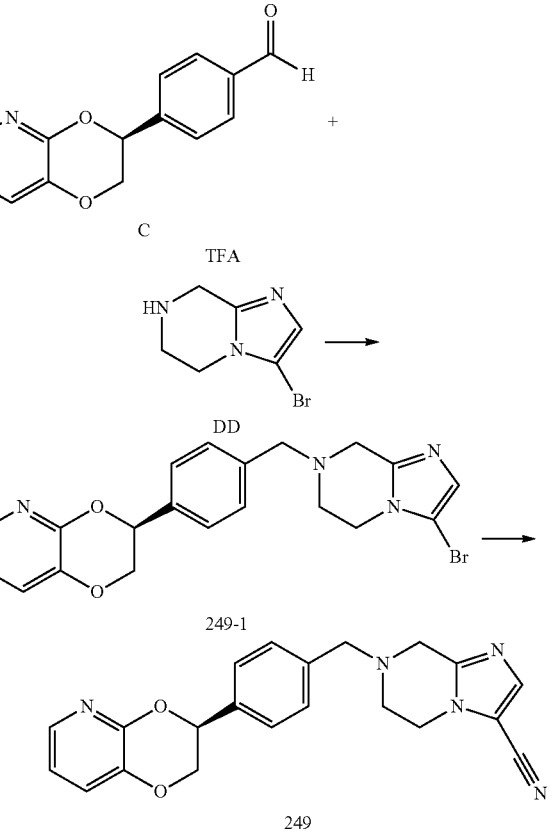

249

Compound 249-1 is synthesized from Intermediates C (200 mg, 0.829 mmol) and DD (518 mg, 1.64 mmol) according to General Method A.

A stirred mixture of 249-1 (80 mg, 0.19 mmol), dppf (10 mg, 0.019 mmol), Zn(CN)₂ (22 mg, 0.19 mmol), and Pd₂(dba)₃ (9 mg, 0.009 in degassed DMF (1 mL) is evacuated and purged with Ar, and stirred at 90° C. under an Ar atmosphere. After 18 hours, the mixture is filtered through a pad of Diatomaceous earth filter aid and rinsed with EtOAc (2×10 mL). The filtrate is diluted with EtOAc (10 mL) and extracted with sat. NaHCO₃ (20 mL). The phases are separated and the aqueous layer is extracted with EtOAc (3×10 mL). The combined organic layers are extracted with brine (20 mL), dried over MgSO₄, filtered and concentrated. The residue is purified by silica gel chromatography eluting with 0-100% EtOAc in heptane. The residue is further purified reverse phase HPLC eluting with 5-95% MeCN in water (+0.1% TFA). All fractions containing the desired product are pooled and lyophilized. The solid is dissolved in MeOH, passed through a carbonate resin cartridge, and concentrated to give the title product 249. (LC/MS method 16: ES+ m/z 374.4 [M+H]+, Rt=2.75 min).

Example 250

Preparation of N-{(1α,5α,6α)-3-[(S)-4-(2,3-Dihydro-[1,4]dioxino[2,3-b]pyridin-3-yl)-benzyl]-3-azabicyclo[3.1.0]hex-6-yl}-acetamide (250)

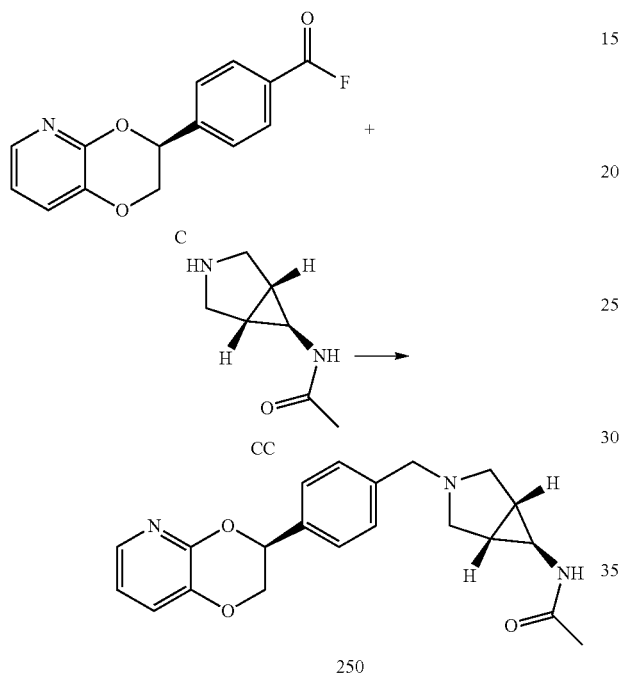

The title compound 250 is synthesized from Intermediates C (100 mg, 0.415 mmol) and CC (88 mg, 0.63 mmol) according to the method described for the synthesis of compound 240. (LC/MS method 16: ES+ m/z 366.5 [M+H]+, Rt=0.33 min)

Example 251

Preparation of [(1α,5α,6α)-3-[(S)-4-(2,3-Dihydro-[1,4]dioxino[2,3-b]pyridin-3-yl)-benzyl]-3-aza-bicyclo[3.1.0]hexane-6-carboxylic acid (2-hydroxy-2-methyl-propyl)]-amide (251)

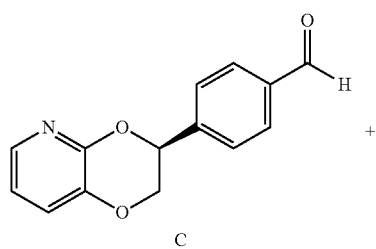

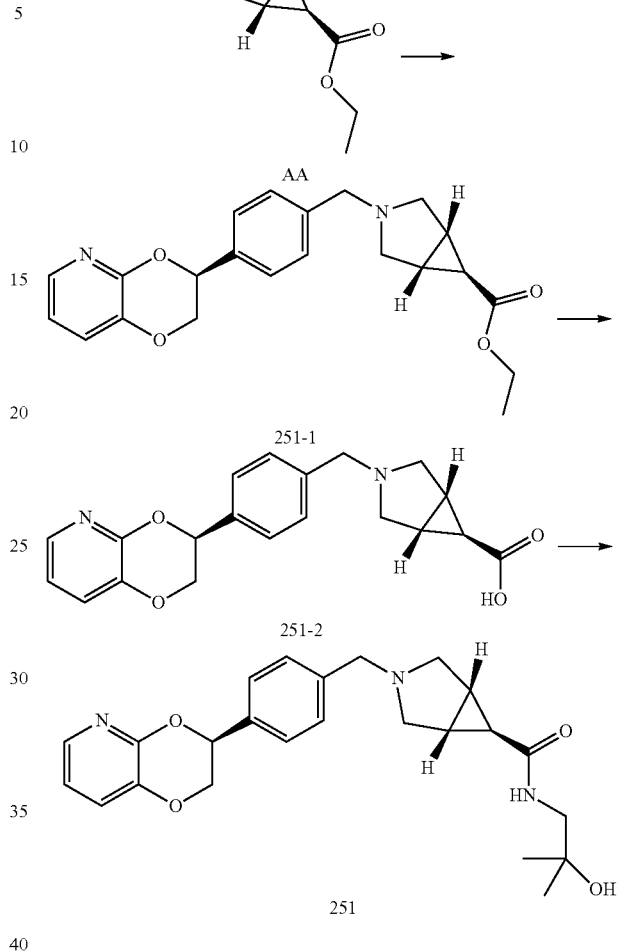

A mixture of Intermediate C (34.0 g, 136 mmol) and the HCl salt of Intermediate AA (40.0 g, 202 mmol) in DCM (800 mL) is treated with TEA (50.0 ml, 355 mmol) and DMF (200 mL). After stirring at room temperature for 90 min, sodium triacetoxyborohydride (59.0 g, 272 mmol) is added and the reaction is stirred for 72 hours. The mixture is concentrated, quenched with a mixture of water and sat. NaHCO$_3$ (1000 mL, 1:1), and extracted with EtOAc (2×1000 mL). The combined organic layers are washed with brine (200 mL), dried over Na$_2$SO$_4$, filtered and concentrated. The residue is purified by silica gel chromatography eluting with 3:1→1:1 heptane/EtOAc. Fractions containing the product are pooled and concentrated to approx 300 mL. The solid product is filtered, and washed with hexanes to give a crop of 251-1. The impure filtrate is re-purified by silica gel chromatography (3:1→1:1 heptane/EtOAc). Fractions are concentrated, filtered and washed with hexanes to yield another crop of 251-1.

To a suspension of 251-1 (49.5 g, 128 mmol) in EtOH (800 mL) is added water (400 mL) and sodium hydroxide (16.0 g, 388 mmol). After stirring for 18 hours at rt, the reaction mixture is concentrated. The resultant residue is dissolved in water (500 mL), cooled to −10° C., and slowly neutralized with HCl (460 mL, 1M) over 15 min to achieve a final pH of 4. The mixture is concentrated to dryness, and the residue is stirred in a hot mixture of MeOH and DCM (1000 mL, 1:1). The mixture is filtered, and the solid is washed with a 1:1 mixture of MeOH and DCM. The filtrate is concentrated and the resulting solid is dried under vacuum in a desiccator over P₂O₅. The solid is re-suspended in a hot mixture of MeOH and DCM (500 mL, 1:1). Acetone (500 mL) is added, the mixture is filtered, and the solid is washed with MeOH and acetone. The filtrate is concentrated and the resulting solid is dried under vacuum in a desiccator over P₂O₅ to provide 251-2.

To a solution of 251-2 (51.7 g, 128 mmol) in DMF (1000 mL) is added HATU (70.0 g, 183 mmol) and DIPEA (100 mL, 560 mmol), and the reaction mixture is stirred at rt. After 60 min, 1-amino-2-methyl-propan-2-ol (24.0 g, 261 mmol) is added and the reaction is stirred at rt for 96 hours. The reaction mixture is concentrated and the residue is dissolved in EtOAc (1000 mL). The aqueous layer is extracted with EtOAc (2×1000 mL). The organic layers are washed with a mixture of water and sat. NaHCO₃ (1000 mL, 1:1), brine (200 mL), dried over Na₂SO₄ and filtered. The filtrate is stored for 1 hour, and the resultant solids are filtered, washed with EtOAc (3×100 mL) and dried. The solid is stirred in EtOAc at 45° C. for 30 min, filtered, washed with EtOAc (2×50 mL), and dried under vacuum in a desiccator over P₂O₅ to give the title product 251. (LC/MS method 16: ES+ m/z 424.4 [M+H]+, Rt=1.47 min)

Example 252

Preparation of N-{1-[(S)-4-(2,3-Dihydro-[1,4]dioxino[2,3-b]pyridin-3-yl)-benzyl]-piperidin-4-yl}-2-methoxy-acetamide (252)

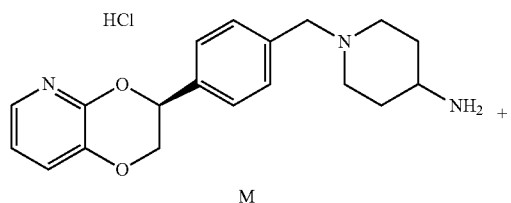

To Intermediate M (75 mg, 0.23 mmol) in THF (1 mL) & TEA (0.128 mL, 0.92 mmol) was added Methoxy-acetyl chloride (0.042 mL, 0.46 mmol). The reaction was stirred for 10 min then quenched with MeOH and purified by reversed phase HPLC eluting with 0-60% MeCN in water (+0.1% TFA) to provide the title compound 252. (LC/MS method 16: ES+ m/z 398.4 [M+H]+, Rt=0.31 min)

Example 253

Preparation of 1-{4-[(S)-4-(2,3-Dihydro-[1,4]dioxino[2,3-b]pyridin-3-yl)-benzyl]-piperazin-1-yl}-2-hydroxy-ethanone (253)

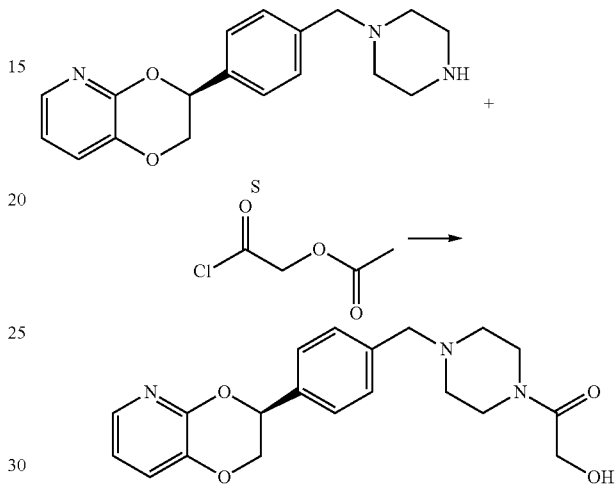

To a solution of Intermediate S (5.80 g, 17.7 mmol) in DCM (200 mL) at 0° C. is added acetic acid chlorocarbonyl-methyl ester (2.16 mL, 19.5 mmol) followed by DIPEA (7.50 mL, 35.4 mmol) and the mixture stirred at rt for 1 h. The reaction was concentrated and the residue dissolved in 4:1 MeOH/water (100 mL) then treated with LiOH monohydrate (2.23 g, 53.1 mmol). After 72 h, the reaction is poured into ice water and the resulting solid isolated by filtration. The solid is suspended in refluxing tert-butylmethyl ether (400 mL) for 20 min and the remaining undissolved material separated out by filtration. The cooled filtrate produces a solid that is then isolated by filtration in several crops. The undissolved material from the first filtration is dissolved in refluxing 1,4-dioxane and cooled to give an additional crop of solid. The crops are combined to give the title product 253. (LC/MS method 16: ES+ m/z 370.3 [M+H]+, Rt=0.35 min)

Example 254

Preparation of 4-{1-[(S)-4-(2,3-Dihydro-benzo[1,4]dioxin-2-yl)-benzyl]-azetidin-3-yl}-benzoic acid (254)

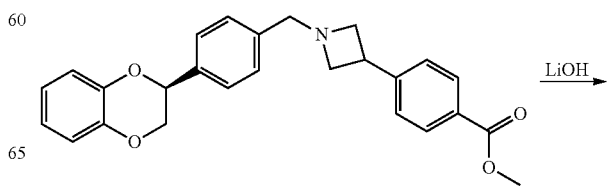

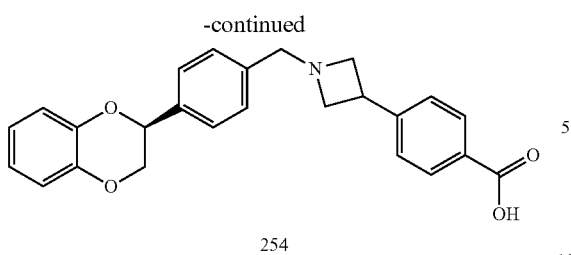

254

A solution of 4-{1-[(S)-4-(2,3-Dihydro-benzo[1,4]dioxin-2-yl)-benzyl]-azetidin-3-yl}-benzoic acid methyl ester (prepared from Intermediate A and 4-Azetidin-3-yl-benzoic acid methyl ester according to General Method G) (504 mg, 1.21 mmol) and lithium hydroxide monohydrate (210 mg, 5.0 mmol) in 1,4-dioxane (10 mL) and water (1.0 mL) is stirred at 50° C. for 16 h. The mixture is neutralized with 1M HCl and concentrated. The residue is triturated with water to give the title compound 254 as a solid. (LC/MS method 16: ES+ m/z 402.5 [M+H]+, Rt=2.70 min)

Example 255

Preparation of 1-[(S)-4-(2,3-Dihydro-[1,4]dioxino[2,3-b]pyridin-3-yl)-benzyl]-piperidine-4-carboxylic acid (2-hydroxy-2-methyl-propyl)-amide (255)

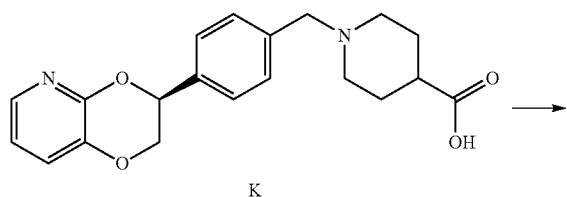

K

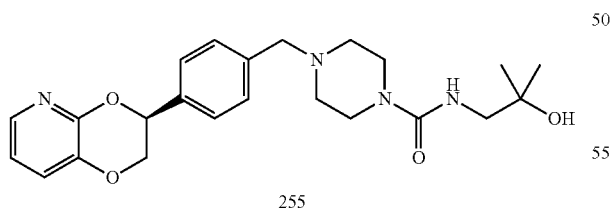

255

To a solution of Intermediate K (50 mg, 0.14 mmol) in DMA (1 mL) is added HATU (59 mg, 0.16 mmol) followed by 1-amino-2-methyl-propan-2-ol (14 mg, 0.16 mmol) as a solution in DMA (1 mL) and DIEA (0.10 mL, 0.56 mmol) and the mixture stirred at rt overnight. Add water (0.1 mL) and purify by reversed phase HPLC eluting with 10-90% MeCN in water (+0.1% TFA). The concentrated pooled fractions are dissolved in 1:1 methanol/DCE and passed through a carbonate resin cartridge to provide the title compound 255 as a free base. (LC/MS method 16: ES+ m/z 426.5 [M+H]+, Rt=1.48 min)

Example 256

Preparation of 1-{(1S,4S)-5-[(S)-4-(2,3-Dihydro-[1,4]dioxino[2,3-b]pyridin-3-yl)-benzyl]-2,5-diaza-bicyclo[2.2.1]hept-2-yl}-2-methanesulfonyl-ethanone (256)

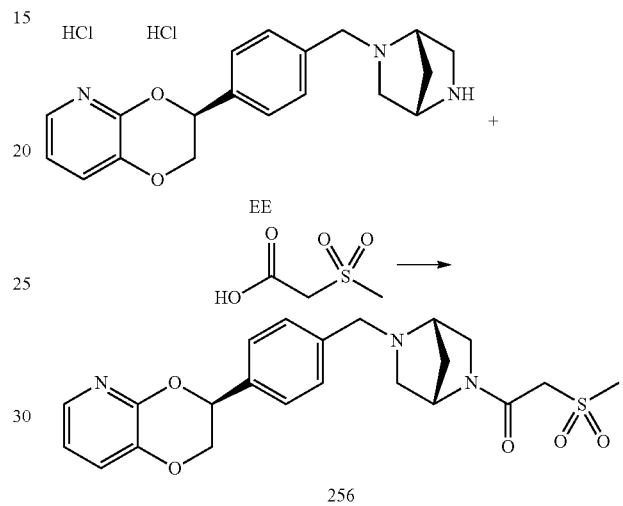

256

To a solution of methanesulfonyl-acetic acid (42 mg, 0.30 mmol) in THF (2 mL) is added TBTU (97 mg, 0.30 mmol) and the solution stirred 30 min. To this add Intermediate EE (100 mg, 0.202 mmol) followed by DIPEA (0.129 mL, 0.737 mmol) and stir at rt overnight. The reaction was purified twice by reverse phase HPLC eluting with 0-70% MeCN in water (0.1% formic acid). The pooled and concentrated fractions are dissolved in MeOH and treated with a carbonate resin to give the title compound 256 as the solid free base. (LC/MS method 16: ES+ m/z 444.4 [M+H]+, Rt=0.34 min)

Example 257

Preparation of 1-{4-[(S)-4-(2,3-Dihydro-[1,4]dioxino[2,3-b]pyridin-3-yl)-benzyl]-[1,4]diazepan-1-yl}-2-methoxy-ethanone (257)

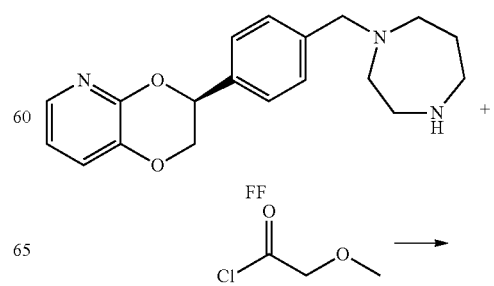

-continued

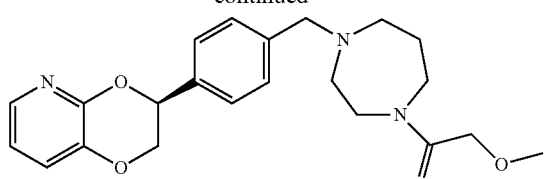

257

To a solution of FF (40 mg, 0.12 mmol) and TEA (0.034 mL, 0.25 mmol) in THF (1.0 mL) is added Methoxy-acetyl chloride (13 mg, 0.12 mmol). The reaction is stirred for 1 h then quenched with MeOH and purified by reverse phase HPLC eluting with 0-60% MeCN in water (0.1% TFA) to afford the title compound 257. (LC/MS method 16: ES+ m/z 398.4 [M+H]+, Rt=2.50 min).

Example 258

Preparation of 5-[(S)-4-(2,3-Dihydro-[1,4]dioxino[2,3-b]pyridin-3-yl)-benzyl]-4,5,6,7-tetrahydro-thiazolo[5,4-c]pyridin-2-ylamine (258)

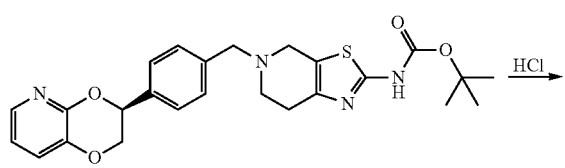

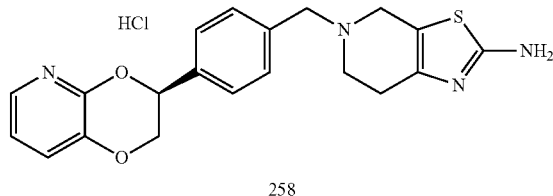

258

To a solution of {5-[(S)-4-(2,3-Dihydro-[1,4]dioxino[2,3-b]pyridin-3-yl)-benzyl]-4,5,6,7-tetrahydro-thiazolo[5,4-c]pyridin-2-yl}-carbamic acid tert-butyl ester (prepared from Intermediate N according to General Method K) (50 mg, 0.10 mmol) in DCM (2 mL) with several drops MeOH is added 4M HCl in 1,4-dioxane (1.0 mL, 4.0 mmol) and the reaction stirred at rt for 16 h. The reaction is concentrated, suspended in Et₂O and filtered to give the title compound 258. (LC/MS method 16: ES+ m/z 381.4 [M+H]+, Rt=0.36 m)

Example 259

Preparation of {(endo)-8-[(S)-4-(2,3-Dihydro-[1,4]dioxino[2,3-b]pyridin-3-yl)-benzyl]-8-aza-bicyclo[3.2.1]oct-3-yl}-urea (259)

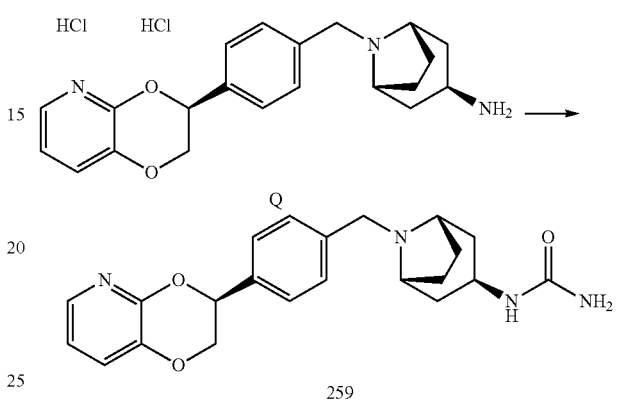

259

To a solution of Intermediate Q (100 mg, 0.212 mmol) in DCM (2 mL) and TEA (0.100 mL, 0.710 mmol) is added TMS-isocyanate (0.075 mL, 0.47 mmol) and the reaction stirred at rt for 24 h. The reaction is concentrated and the residue purified by reverse phase HPLC eluting with 10-55% MeCN in water (0.1% TFA). The pooled and concentrated fractions are dissolved in MeOH and eluted through a carbonate resin plug and concentrated to afford the title product 259. (LC/MS method 16: ES+ m/z 395.5 [M+H]+, Rt=2.47 min)

Example 260

Preparation of 2-{1-[(S)-4-(2,3-Dihydro-[1,4]dioxino[2,3-b]pyridin-3-yl)-benzyl]-piperidin-4-yl}-N-methoxy-acetamide (260)

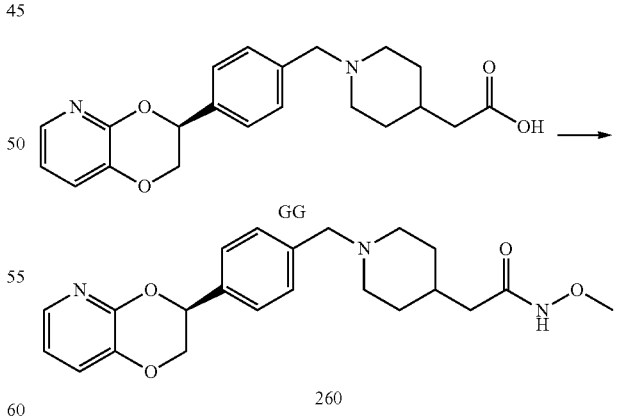

260

A solution of Intermediate GG (96 mg, 0.26 mmol), O-methyl-hydroxylamine hydrochloride (26 mg, 0.31 mmol), TEA (0.11 mL, 0.78 mmol), and TBTU (101 mg, 0.313 mmol) in DMF (2 mL) is heated at 60° C. overnight. The reaction is concentrated and the residue purified by reverse phase HPLC eluting with 10-26% MeCN in water (0.1% formic acid). The

Example 261

Preparation of (R)-N-{1-[(S)-4-(2,3-Dihydro-[1,4]dioxino[2,3-b]pyridin-3-yl)-benzyl]-piperidin-4-yl}-2-methylamino-propionamide (261)

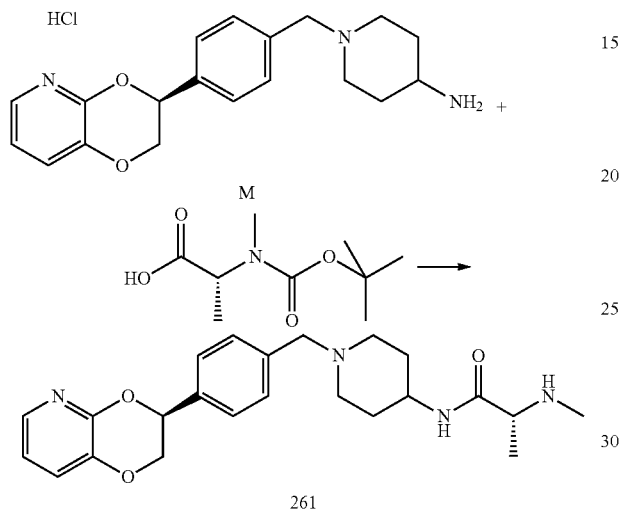

A solution of Intermediate M (100 mg, 0.276 mmol), (R)-2-(tert-butoxycarbonyl-methyl-amino)-propionic acid (67 mg, 0.33 mmol), TEA (0.115 mL, 0.828 mmol), and TBTU (106 mg, 0.331 mmol) in DMF (2 mL) is heated at 60° C. overnight. The reaction is diluted with EtOAc, rinsed with sat. NaHCO₃, and the organics dried and concentrated. The residue is purified by silica gel chromatography eluting with 0-10% MeOH/DCM. The pooled and concentrated product fractions are treated with 4M HCl in 1,4-dioxane (5 mL) and stirred overnight. The reaction is concentrated and purified by reverse phase HPLC eluting with 10-90% MeCN in water (0.1% TFA). The concentrated product fractions are dissolved in MeOH and eluted through a carbonate resin cartridge to afford the title compound 261. (LC/MS method 16: ES+ m/z 411.4 [M+H]+, Rt=0.33 min)

Example 262

Preparation of N-{1-[(S)-4-(2,3-Dihydro-[1,4]dioxino[2,3-b]pyridin-3-yl)-benzyl]-piperidin-4-ylmethyl}-2-hydroxy-2-methyl-propionamide (262)

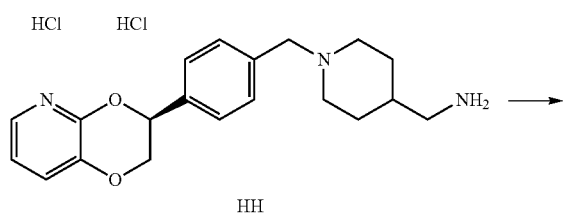

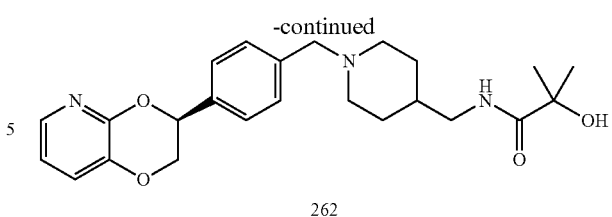

To a solution of 2-Hydroxy-2-methyl-propionic acid (67 mg, 0.64 mmol) in DMF (2 mL) is added HATU (249 mg, 0.636 mmol) followed by DIPEA (0.200 mL, 1.13 mmol) and the reaction stirred at rt 10 min. This is added to Intermediate HH (125 mg, 0.212 mmol) and the reaction stirred at rt for 72 h. The reaction is concentrated and purified by reverse-phase HPLC eluting with 10-65% MeCN in water (0.1% TFA). Concentrated product fractions are further purified by silica gel chromatography eluting with 10% (2M NH₃ in MeOH)/DCM to afford the title compound 262. (LC/MS method 16: ES+ m/z 426.4 [M+H]+, Rt=2.69 min).

Example 263

Preparation of N-{(1α,5α,6α)-3-[(S)-4-(2,3-Dihydro-[1,4]dioxino[2,3-b]pyridin-3-yl)-benzyl]-3-azabicyclo[3.1.0]hex-6-ylmethyl}-methanesulfonamide (263)

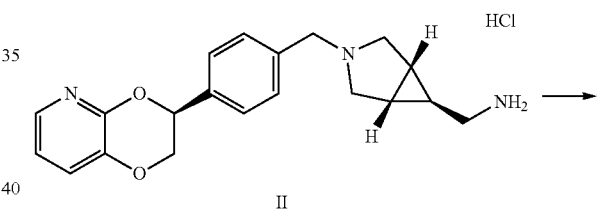

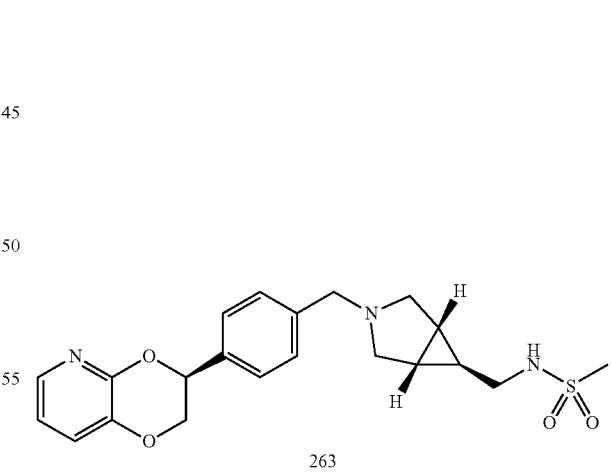

To a solution of II (120 mg; 0.244 mmol) in pyridine (2 mL) at 0° C. is added Methanesulfonyl chloride (0.096 mL, 1.22 mmol) and the reaction stirred at rt 18 h. The reaction is concentrated and purified by reverse phase prep-HPLC eluting with 10-60% MeCN in water (0.1% TFA). Concentrated product fractions are further purified by silica gel chromatography eluting with 10% (2M NH₃ in MeOH)/DCM to afford

Example 264

Preparation of 1-{(1S,4S)-5-[(S)-4-(2,3-Dihydro-[1,4]dioxino[2,3-b]pyridin-3-yl)-benzyl]-2,5-diaza-bicyclo[2.2.2]oct-2-yl}-ethanone (264)

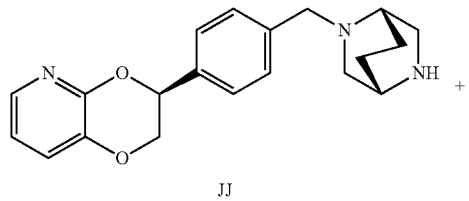

JJ

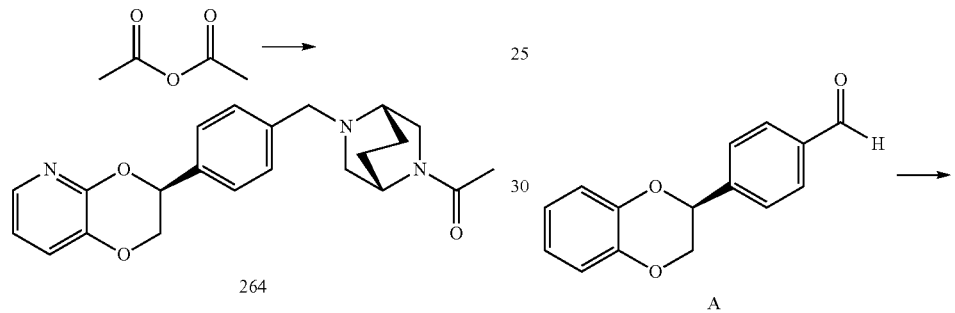

264

To a solution of Intermediate JJ (42 mg, 0.12 mmol) in 1,4-dioxane (2 mL) is added acetic anhydride (0.018 mL, 0.19 mmol) followed by TEA (0.026 mL, 0.19 mmol) and the reaction stirred at rt for 72 h. The suspension is dissolved by the addition of 1M aqueous HCl and purified by reverse phase HPLC eluting with 0-70% MeCN in water (0.1% formic acid) to afford a solid. The material is dissolved in MeOH and eluted through a carbonate resin cartridge, concentrated and lyophilized to afford the title compound 264. (LC/MS method 16: ES+ m/z 380.4 [M+H]+, Rt=2.51 min)

Example 265

Preparation of 4-{1-[(S)-4-(2,3-Dihydro-[1,4]dioxino[2,3-b]pyridin-3-yl)-benzyl]-piperidin-4-yl}-cyclohexanecarboxylic acid (265)

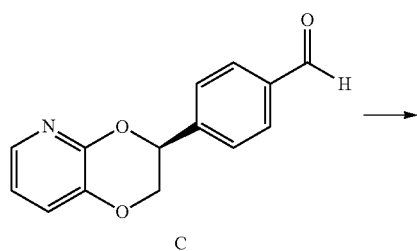

C

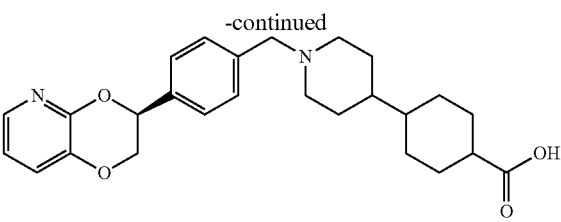

265

Compound 265 is prepared from Intermediate C and 4-piperidin-4-yl-cyclohexanecarboxylic acid according to General Method H. (LC/MS method 16: ES+ m/z 437.4 [M+H]+, Rt=2.58 min).

Example 266

Preparation of 1-[(S)-4-(2,3-Dihydro-benzo[1,4]dioxin-2-yl)-benzyl]-azepane-4-carboxylic acid (266)

A

266

Compound 266 is synthesized from Intermediate A and azepane-4-carboxylic acid according to General Method B. (LC/MS method 16: ES+ m/z 368.3 [M+H]+, Rt=2.76 min)

Example 267

Preparation of [(1α,5α,6α)-3-[(S)-4-(2,3-Dihydro-benzo[1,4]dioxin-2-yl)-benzyl]-3-aza-bicyclo[3.1.0]hexane]-6-carboxylic acid (267)

A

-continued

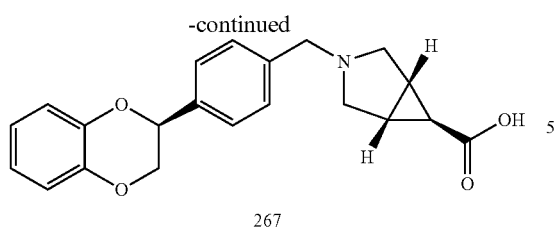

267

Compound 267 is synthesized from Intermediate A and Intermediate AA according to General Method D, and the procedure described for the synthesis of Example 231. (LC/MS method 16: ES+ m/z 352.3 [M+H]+, Rt=2.61 min)

Example 268

Preparation of (1S,4S)-5-[(S)-4-(2,3-Dihydro-[1,4]dioxino[2,3-b]pyridin-3-yl)-benzyl]-2,5-diaza-bicyclo[2.2.1]heptane-2-carboxylic acid amide (268)

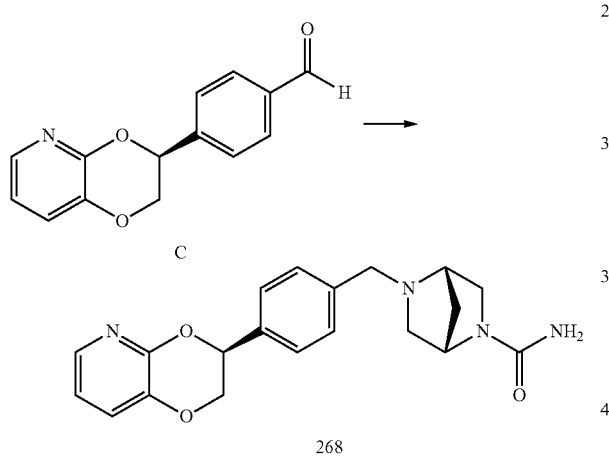

268

Compound 268 is synthesized from Intermediate C and Intermediate P according to General Method J. (LC/MS method 16: ES+ m/z 367.3 [M+H]+, Rt=0.27 min)

Example 269

Preparation of 1-[(S)-4-(2,3-Dihydro-[1,4]dioxino[2,3-b]pyridin-3-yl)-benzyl]-4-phenyl-piperidin-4-ol (269)

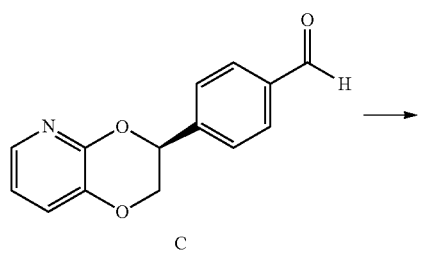

-continued

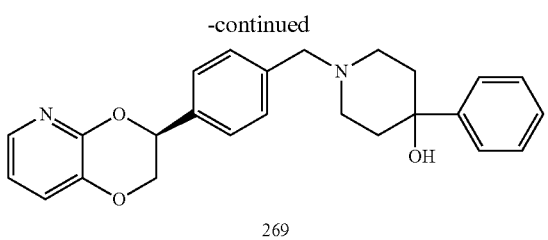

269

Compound 269 is synthesized from Intermediate C and 4-phenyl-piperidin-4-ol according to General Method K. (LC/MS method 16: ES+ m/z 403.4 [M+H]+, Rt=2.68 min)

Example 270

Preparation of 1-{5-[(S)-4-(2,3-Dihydro-[1,4]dioxino[2,3-b]pyridin-3-yl)-benzyl]-hexahydro-pyrrolo[3,4-c]pyrrol-2-yl}-ethanone (270)

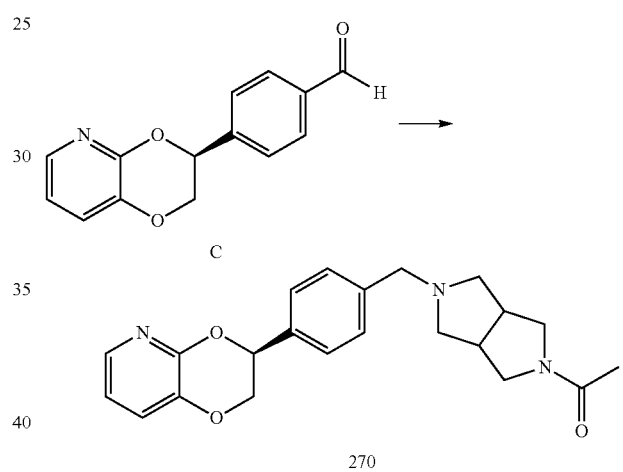

270

Compound 270 is synthesized from Intermediate C and Intermediate KK according to General Method J. (LC/MS method 16: ES+ m/z 380.4 [M+H]+, Rt=2.49 min)

Example 271

Preparation of 1-{8-[(S)-4-(2,3-Dihydro-[1,4]dioxino[2,3-b]pyridin-3-yl)-benzyl]-3,8-diaza-bicyclo[3.2.1]oct-3-yl}-ethanone (271)

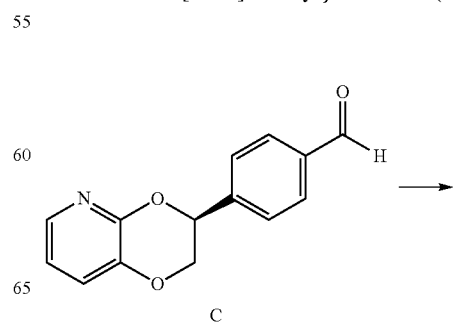

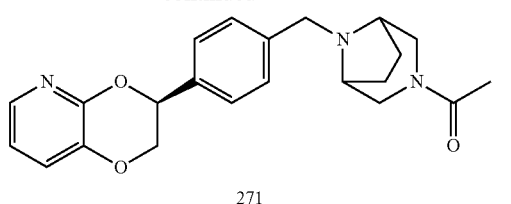

271

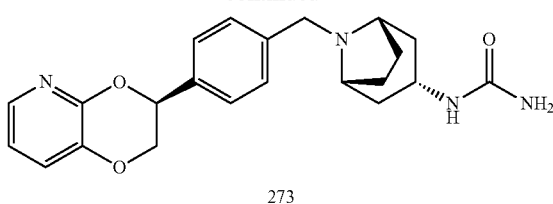

273

Compound 271 is synthesized from Intermediate C and Intermediate U according to General Method H. (LC/MS method 16: ES+ m/z 380.5 [M+H]+, Rt=2.52 min)

Compound 273 is prepared from Intermediate C and Intermediate MM according to General Method I. (LC/MS method 16: ES+ m/z 395.2 [M+H]+, Rt=0.30 min)

Example 272

Preparation of 5-[(S)-4-(2,3-Dihydro-[1,4]dioxino[2,3-b]pyridin-3-yl)-benzyl]-hexahydro-pyrrolo[3,4-c]pyrrole-2-carboxylic acid amide (272)

Example 274

Preparation of 2-{1-[(S)-4-(2,3-Dihydro-[1,4]dioxino[2,3-b]pyridin-3-yl)-benzyl]-piperidin-4-yloxy}-acetamide (274)

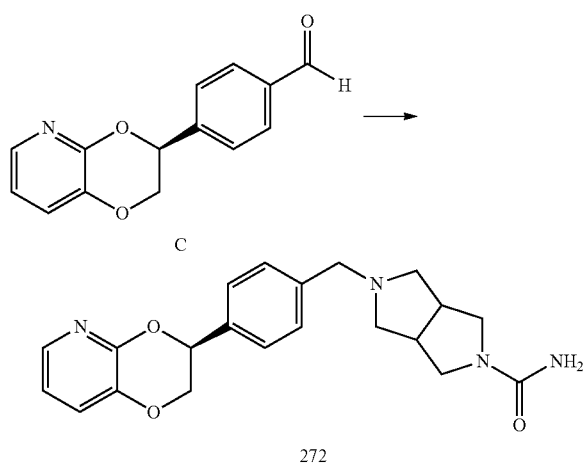

272

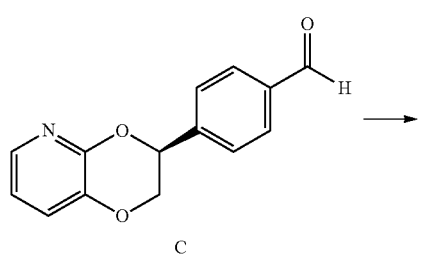

274

Compound 272 is synthesized from Intermediate C and Intermediate LL according to General Method J. (LC/MS method 16: ES+ m/z 381.3 [M+H]+, Rt=0.28 min)

Compound 274 is synthesized from Intermediate C and 2-(piperidin-4-yloxy)acetamide according to General Method K. (LC/MS method 16: ES+ m/z 384.3 [M+H]+, Rt=0.32 min)

Example 273

Preparation of {(exo)-8-[(S)-4-(2,3-Dihydro-[1,4]dioxino[2,3-b]pyridin-3-yl)-benzyl]-8-aza-bicyclo[3.2.1]oct-3-yl}-urea (273)

Example 275

Preparation of (S)-3-[4-(1,1-Dioxo-1lambda6-[1,4]thiazepan-4-ylmethyl)-phenyl]-2,3-dihydro-[1,4]dioxino[2,3-b]pyridine (275)

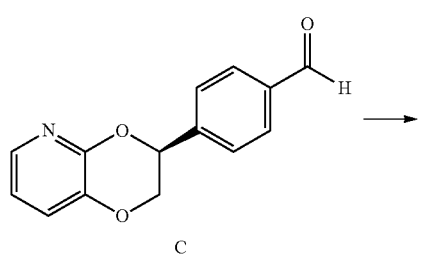

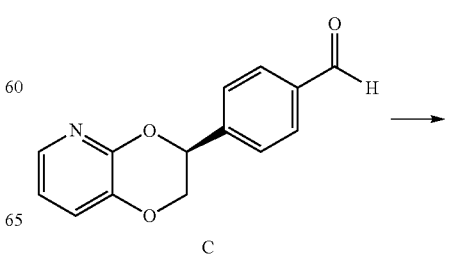

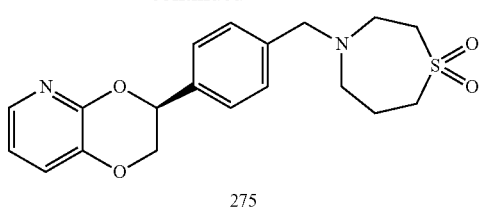

275

Compound 275 is synthesized from Intermediate C and [1,4]thiazepane 1,1-dioxide according to General Method H. (LC/MS method 16: ES+ m/z 375.4 [M+H]+, Rt=2.51 min)

Example 276

Preparation of 1-[(S)-4-(2,3-Dihydro-[1,4]dioxino[2,3-b]pyridin-3-yl)-benzyl]-4-methyl-piperidin-4-ol (276)

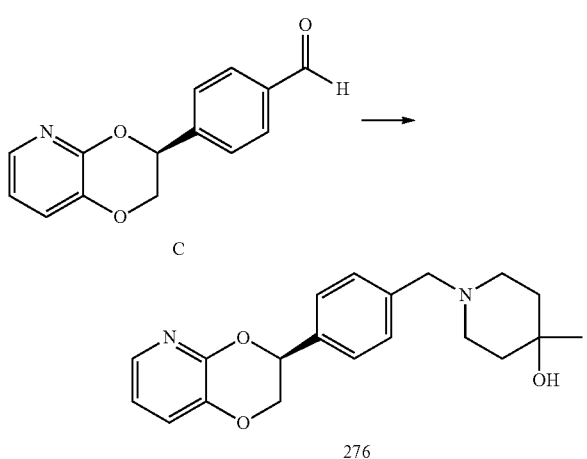

276

Compound 276 is synthesized from Intermediate C and Intermediate R according to General Method K. (LC/MS method 16: ES+ m/z 341.2 [M+H]+, Rt=2.50 min)

Example 277

Preparation of 1-{(1S,4S)-5-[(S)-4-(2,3-Dihydro-[1,4]dioxino[2,3-b]pyridin-3-yl)-benzyl]-2,5-diaza-bicyclo[2.2.1]hept-2-yl}-2-hydroxy-ethanone (277)

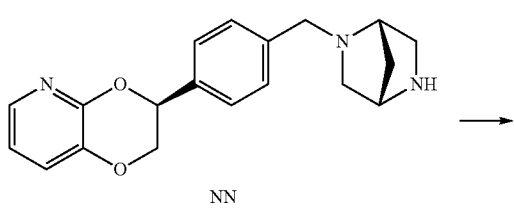

NN

Compound 277 is synthesized from Intermediate NN and acetic acid chlorocarbonylmethyl ester according to the procedure used to synthesize Example 253. (LC/MS method 16: ES+m/z 382.4 [M+H]+, Rt=0.34 min)

Example 278

Preparation of N-{(endo)-8-[(S)-4-(2,3-Dihydro-[1,4]dioxino[2,3-b]pyridin-3-yl)-benzyl]-8-aza-bicyclo[3.2.1]oct-3-yl}-acetamide (278)

278

Compound 278 is synthesized from Intermediate C and Intermediate T according to General Method I. (LC/MS method 16: ES+ m/z 394.4 [M+H]+, Rt=0.34 min)

Example 279

Preparation of N-{1-[(S)-4-(2,3-Dihydro-[1,4]dioxino[2,3-b]pyridin-3-yl)-benzyl]-piperidin-4-ylmethyl}-acetamide (279)

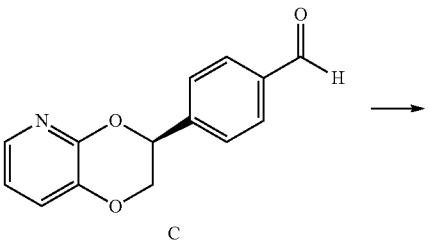

C

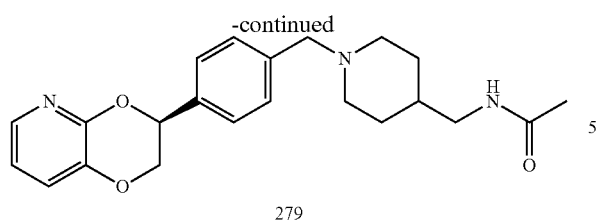

279

Compound 279 is synthesized from Intermediate C and N-piperidin-4-ylmethyl-acetamide according to General Method H. (LC/MS method 16: ES+ m/z 382.4 [M+H]+, Rt=2.50 min)

Example 280

Preparation of [(S)-4-(2,3-Dihydro-[1,4]dioxino[2,3-b]pyridin-3-yl)-benzyl]-(1,1-dioxo-tetrahydro-1lambda-6-thiophen-3-yl)-methyl-amine (280)

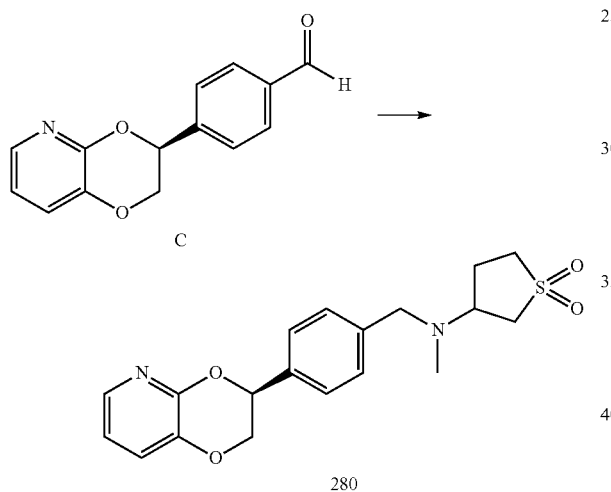

280

Compound 280 is synthesized from Intermediate C and (1,1-dioxo-tetrahydro-1lambda-6-thiophen-3-yl)-methyl-amine according to General Method N. (LC/MS method 16: ES+ m/z 375.4 [M+H]+, Rt=2.66 min)

Example 281

Preparation of 1-{(1S,4S)-5-[(S)-4-(2,3-Dihydro-[1,4]dioxino[2,3-b]pyridin-3-yl)-benzyl]-2,5-diaza-bicyclo[2.2.2]oct-2-yl}-2-hydroxy-ethanone (281)

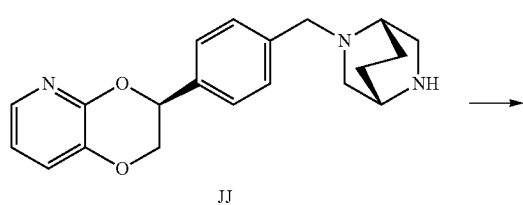

JJ

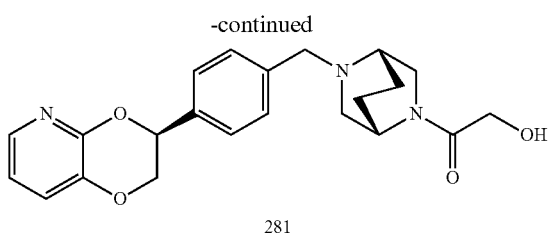

281

Compound 281 is synthesized from Intermediate JJ and acetic acid chlorocarbonylmethyl ester according to the procedure used to synthesize Example 253. (LC/MS method 16: ES+ m/z 396.5 [M+H]+, Rt=2.41 min)

Example 282

Preparation of {1-[(S)-4-(2,3-dihydro-[1,4]dioxino-[2,3-b]pyridin-3-yl)-benzyl]-spiro-[3H-indole-3,4'-piperidine]-1(2H)-urea (282)

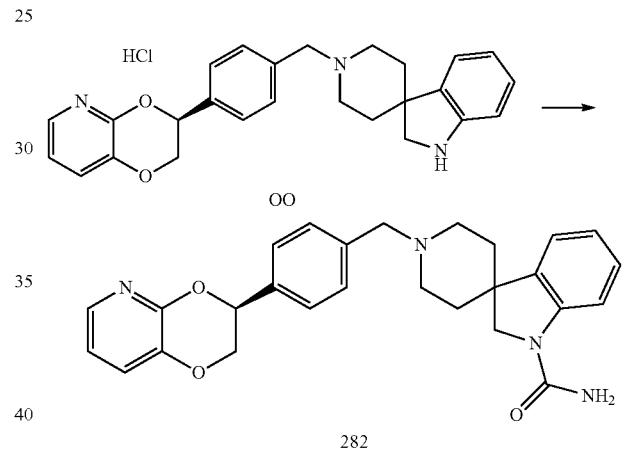

282

Compound 282 is synthesized from Intermediate OO and TMS-isocyanate according to the procedure used to synthesize Example 259. (LC/MS method 16: ES+ m/z 457.3 [M+H]+, Rt=2.58 min)

Example 283

Preparation of {1-[(S)-4-(2,3-Dihydro-[1,4]dioxino[2,3-b]pyridin-3-yl)-benzyl]-piperidin-4-ylmethyl}-urea (283)

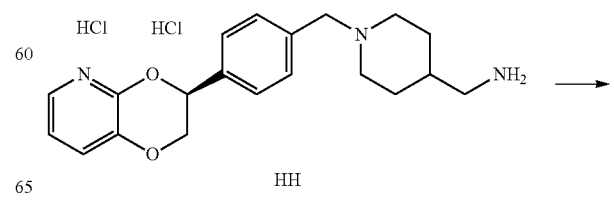

HH

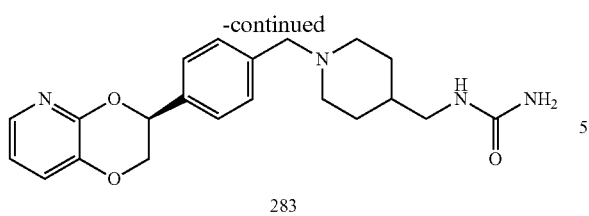

283

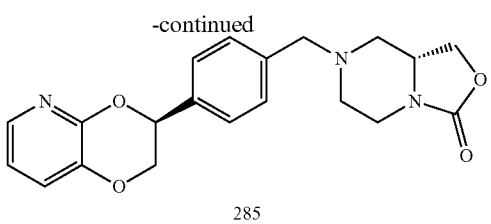

285

Compound 283 is synthesized from Intermediate C and Intermediate HH according to the procedure used to synthesize Example 253. (LC/MS method 16: ES+ m/z 383.4 [M+H]+, Rt=2.45 min)

Compound 285 is synthesized from Intermediate C and (R)-hexahydro-oxazolo[3,4-a]pyrazin-3-one according to General Method M. (LC/MS method 16: ES+ m/z 368.4 [M+H]+, Rt=2.52 min).

Example 284

Preparation of {4-[(S)-4-(2,3-Dihydro-[1,4]dioxino[2,3-b]pyridin-3-yl)-benzyl]-piperazin-1-yl}-acetonitrile (284)

Example 286

Preparation of {1-[(S)-4-(2,3-Dihydro-[1,4]dioxino[2,3-b]pyridin-3-yl)-benzyl]-piperidin-4-yl}-(3-hydroxy-azetidin-1-yl)-methanone (286)

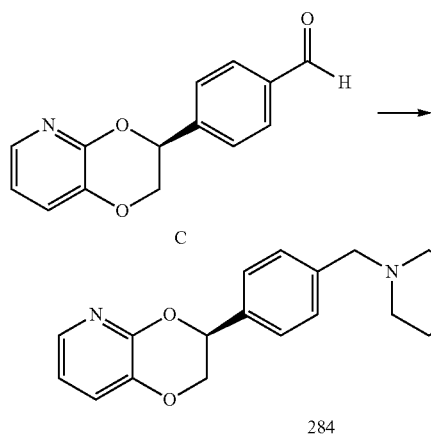

284

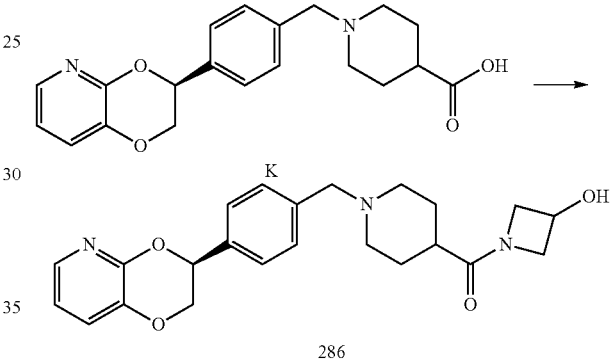

286

Compound 284 is synthesized from Intermediate C and piperazin-1-yl-acetonitrile (prepared from 4-Cyanomethyl-piperazine-1-carboxylic acid tert-butyl ester according to the procedure used to synthesize Intermediate U from U-1) according to General Method F. (LC/MS method 16: ES+ m/z 351.3 [M+H]+, Rt=2.68 min)

Compound 286 is synthesized from Intermediate K and azetidin-3-ol according to the procedure used to synthesize Example 255. (LC/MS method 16: ES+ m/z 410.4 [M+H]+, Rt=0.35 min)

Example 285

Preparation of (R)-7-[(S)-4-(2,3-Dihydro-[1,4]dioxino[2,3-b]pyridin-3-yl)-benzyl]-hexahydro-oxazolo[3,4-a]pyrazin-3-one (285)

Example 287

Preparation of 1-[(S)-4-(2,3-Dihydro-[1,4]dioxino[2,3-b]pyridin-3-yl)-benzyl]-piperidine-4-carboxylic acid [(S)-1-(tetrahydro-furan-2-yl)methyl]-amide (287)

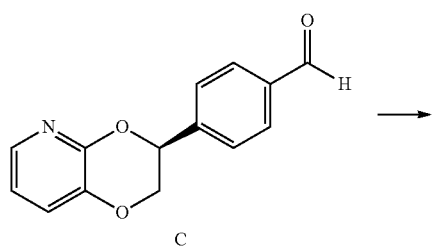

C

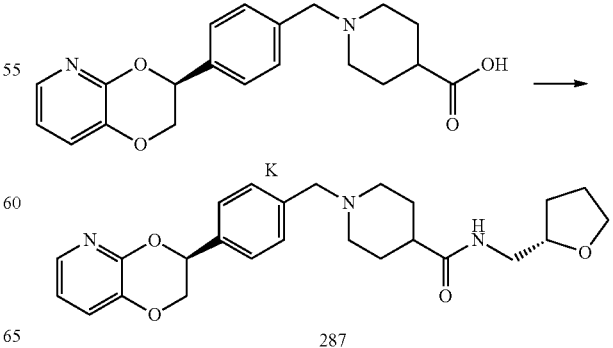

287

Compound 287 is synthesized from Intermediate K and C—[(S)-1-(tetrahydro-furan-2-yl)]-methylamine according to the procedure used to synthesize Example 255. (LC/MS method 16: ES+ m/z 438.4 [M+H]+, Rt=2.56 min)

Example 288

Preparation of N-[3-[4-[[4-[(3S)-2,3-dihydro-[1,4]dioxino[2,3-b]pyridin-3-yl]phenyl]methyl]piperazin-1-yl]-3-oxo-propyl]acetamide (288)

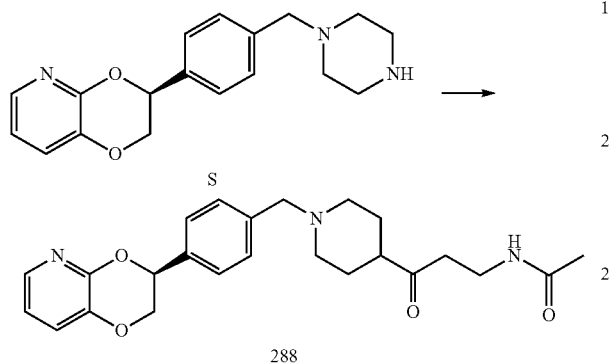

Compound 288 is synthesized from Intermediate A and 3-acetylamino-propionic acid according to the procedure used to synthesize Example 262. (LC/MS method 16: ES+ m/z 425.4 [M+H]+, Rt=1.47 min)

Example 289

Preparation of N-[1-[[4-[(3S)-2,3-dihydro-[1,4]dioxino[2,3-b]pyridin-3-yl]phenyl]methyl]-4-piperidyl]-2-(2-oxopyrrolidin-1-yl)acetamide (289)

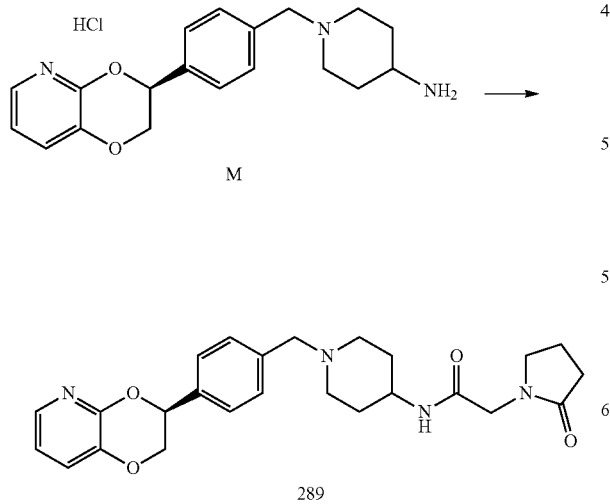

Compound 289 is synthesized from Intermediate M and (2-Oxo-pyrrolidin-1-yl)-acetic acid according to the procedure used to synthesize Example 261. (LC/MS method 16: ES+ m/z 451.4 [M+H]+, Rt=2.51 min)

Example 290

Preparation of N-[1-[[4-[(3S)-2,3-dihydro-[1,4]dioxino[2,3-b]pyridin-3-yl]phenyl]methyl]-4-piperidyl]tetrahydropyran-4-carboxamide (290)

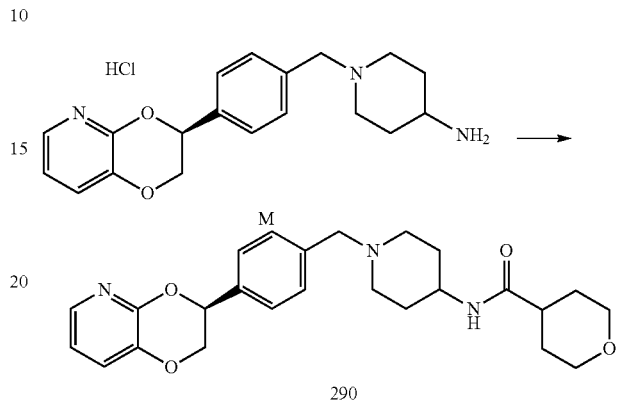

Compound 290 is synthesized from Intermediate M and Tetrahydro-pyran-4-carboxylic acid according to the procedure used to synthesize Example 261. (LC/MS method 16: ES+m/z 438.4 [M+H]+, Rt=1.44 mM)

Example 164

Preparation of 4-{4-[(3S)-2,3-dihydro[1,4]dioxino[2,3-b]pyridin-3-yl]benzyl}piperazine-1-carboxamide (164)

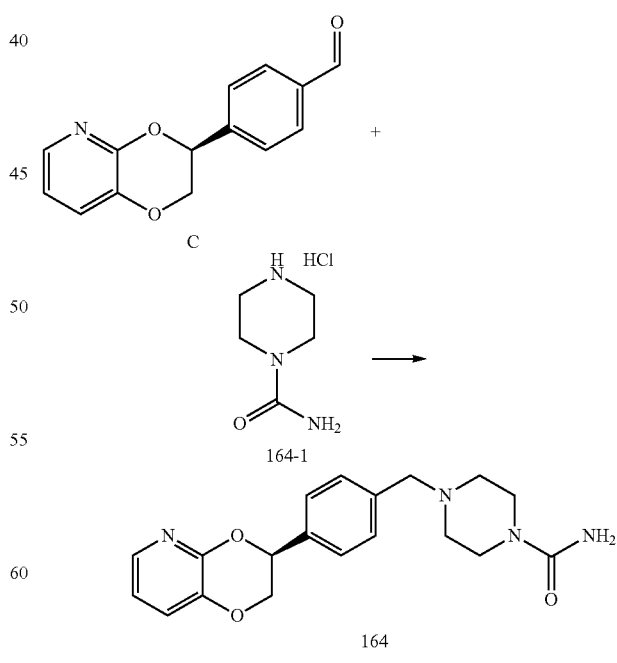

To a solution of Intermediate C (30.0 g, 124 mmol) in DCM (500 mL) is added 164-1 (26.7 g, 161 mmol) followed by TEA (20.9 mL, 149 mmol). After stirring for 10 mM at rt, sodium triacetoxyborohydride (36.0 g, 161 mmol) is added and the mixture stirred at rt for 24 hours. The reaction mixture is washed with sat.NaHCO₃ (2×300 mL), and brine (400 mL). The organic layer is dried over Na₂SO₄, filtered and concentrated. The solid is triturated twice in ethyl ether at 65° C. After the second filtration, the resultant solid is recrystallized from ethanol to afford the title compound 164. (LC/MS method 11: ES+ m/z 355.1 [M+H]+, Rt=0.38 mM)

Assessment of Biological Properties

The compounds of the invention are assessed for the ability to interact with human LTA₄ hydrolase in an enzymatic assay that measures the ability of the enzyme to cleave the peptide bond of arginyl-aminomethylcoumarin (Arg-AMC). LTA₄H Enzyme (1 nM final), Arg-AMC substrate (50 μM final), and compound are combined in a reaction buffer (50 mM Tris-HCl (pH 7.5), 100 mM KCl, 0.5% bovine serum albumin) at room temperature for 1 h. The formation of product is assessed by measuring the fluorescence of aminomethylcoumarin product (excitation wavelength 380 nm/emission wavelength 460 nm). In general, the preferred potency range ($IC_{50}$) of compounds in the LTA₄H Enzyme assay is between 0.1 nM to 10 μM, the more preferred potency range is 0.1 nM to 0.1 μM, and the most preferred potency range is 0.1 nM to 10 nM.

TABLE 9

$IC_{50}$ values of LTA₄H Enzyme assay.

| Example | IC₅₀ (nM) | Example | IC₅₀ (nM) | Example | IC₅₀ (nM) | Example | IC₅₀ (nM) |
|---|---|---|---|---|---|---|---|
| 1 | 0.38 | 61 | 0.60 | 121 | 0.37 | 181 | 0.042 |
| 2 | 2.45 | 62 | 1.79 | 122 | 0.91 | 182 | 0.29 |
| 3 | 2.57 | 63 | 7.90 | 123 | 0.73 | 183 | 0.48 |
| 4 | 0.74 | 64 | 0.83 | 124 | 2.45 | 184 | 0.11 |
| 5 | 2.96 | 65 | 1.15 | 125 | 0.16 | 185 | 0.59 |
| 6 | 0.46 | 66 | 1.79 | 126 | 0.18 | 186 | 0.24 |
| 7 | 2.79 | 67 | 0.61 | 127 | 0.12 | 187 | 0.07 |
| 8 | 0.32 | 68 | 0.10 | 128 | 0.65 | 188 | 0.87 |
| 9 | 1.49 | 69 | 0.60 | 129 | 0.23 | 189 | 0.16 |
| 10 | 0.75 | 70 | 0.57 | 130 | 0.51 | 190 | 0.09 |
| 11 | 2.95 | 71 | 1.88 | 131 | 1.73 | 191 | 1.62 |
| 12 | 10.19 | 72 | 1.80 | 132 | 0.91 | 192 | 0.43 |
| 13 | 0.36 | 73 | 3.65 | 133 | 1.75 | 193 | 5.35 |
| 14 | 0.27 | 74 | 1.00 | 134 | 0.47 | 194 | 0.15 |
| 15 | 0.36 | 75 | 4.51 | 135 | 0.47 | 195 | 1.59 |
| 16 | 2.32 | 76 | 1.90 | 136 | 0.19 | 196 | 0.39 |
| 17 | 0.77 | 77 | 0.18 | 137 | 0.26 | 197 | 2.69 |
| 18 | 1.14 | 78 | 1.40 | 138 | 0.18 | 198 | 2.28 |
| 19 | 0.73 | 79 | 0.51 | 139 | 0.10 | 199 | 40.12 |
| 20 | 1.30 | 80 | 0.71 | 140 | 0.38 | 200 | 0.12 |
| 21 | 4.43 | 81 | 0.31 | 141 | 0.26 | 201 | 1.59 |
| 22 | 200.00 | 82 | 0.20 | 142 | 0.17 | 202 | 23.37 |
| 23 | 5.20 | 83 | 0.13 | 143 | 0.30 | 203 | 2.94 |
| 24 | 5.90 | 84 | 2.69 | 144 | 0.14 | 204 | 0.15 |
| 25 | 0.76 | 85 | 0.45 | 145 | 0.09 | 205 | 27.50 |
| 26 | 0.43 | 86 | 0.92 | 146 | 0.29 | 206 | 0.19 |
| 27 | 1.20 | 87 | 0.69 | 147 | 0.35 | 207 | 0.86 |
| 28 | 3.40 | 88 | 0.54 | 148 | 0.28 | 208 | 21.45 |
| 29 | 2.04 | 89 | 1.40 | 149 | 0.24 | 209 | 12.41 |
| 30 | 1.77 | 90 | 0.77 | 150 | 0.21 | 210 | 19.00 |
| 31 | 1.54 | 91 | 0.54 | 151 | 0.10 | 211 | 0.69 |
| 32 | 1.80 | 92 | 35.99 | 152 | 0.17 | 212 | 0.49 |
| 33 | 3.19 | 93 | 1.98 | 153 | 0.82 | 213 | 0.81 |
| 34 | 1.89 | 94 | 0.45 | 154 | 0.20 | 214 | 0.47 |
| 35 | 0.26 | 95 | 0.49 | 155 | 0.28 | 215 | 0.70 |
| 36 | 4.45 | 96 | 0.22 | 156 | 0.91 | 216 | 0.13 |
| 37 | 1.05 | 97 | 2.87 | 157 | 0.18 | 217 | 2.28 |
| 38 | 1.14 | 98 | 0.61 | 158 | 0.13 | 218 | 0.37 |
| 39 | 2.14 | 99 | 0.37 | 159 | 0.16 | 219 | 0.49 |
| 40 | 0.82 | 100 | 2.36 | 160 | 0.18 | 220 | 0.47 |
| 41 | 3.71 | 101 | 1.90 | 161 | 0.41 | 221 | 0.16 |
| 42 | 0.69 | 102 | 2.68 | 162 | 0.14 | 222 | 0.14 |
| 43 | 4.42 | 103 | 2.40 | 163 | 0.17 | 223 | 0.16 |
| 44 | 0.69 | 104 | 0.18 | 164 | 0.84 | 224 | 0.13 |

TABLE 9-continued $IC_{50}$ values of LTA₄H Enzyme assay.

| Example | IC₅₀ (nM) | Example | IC₅₀ (nM) | Example | IC₅₀ (nM) | Example | IC₅₀ (nM) |
|---|---|---|---|---|---|---|---|
| 45 | 0.90 | 105 | 0.51 | 165 | 0.13 | 225 | 5.30 |
| 46 | 24.82 | 106 | 0.46 | 166 | 0.68 | 226 | 42.95 |
| 47 | 1.73 | 107 | 1.35 | 167 | 0.27 | 227 | 1.40 |
| 48 | 0.16 | 108 | 0.87 | 168 | 0.31 | 228 | 0.61 |
| 49 | 0.32 | 109 | 0.17 | 169 | 0.33 | 229 | 3.85 |
| 50 | 0.60 | 110 | 2.15 | 170 | 0.47 | 230 | 1.24 |
| 51 | 0.82 | 111 | 2.25 | 171 | 0.45 | 231 | 0.29 |
| 52 | 0.75 | 112 | 1.07 | 172 | 0.53 | 232 | 2.75 |
| 53 | 0.42 | 113 | 2.49 | 173 | 0.73 | 233 | 0.22 |
| 54 | 5.93 | 114 | 0.77 | 174 | 0.60 | 234 | 0.14 |
| 55 | 3.63 | 115 | 3.03 | 175 | 0.22 | 235 | 0.08 |
| 56 | 6.08 | 116 | 0.82 | 176 | 0.24 | 236 | 6.04 |
| 57 | 13.66 | 117 | 0.23 | 177 | 1.45 | 237 | 0.81 |
| 58 | 1.36 | 118 | 0.45 | 178 | 0.35 | 238 | 0.55 |
| 59 | 89.24 | 119 | 0.10 | 179 | 0.16 | 239 | 0.15 |
| 60 | 31.02 | 120 | 0.51 | 180 | 0.12 | 240 | 0.56 |
| 241 | 0.50 | 242 | 0.60 | 243 | 0.42 | 244 | 0.26 |
| 245 | 0.32 | 246 | 0.29 | 247 | 0.17 | 248 | 0.17 |
| 249 | 0.25 | 250 | 0.56 | 251 | 0.16 | 252 | 0.15 |
| 253 | 0.70 | 254 | 0.24 | 255 | 0.17 | 256 | 0.49 |
| 257 | 0.48 | 258 | 0.37 | 259 | 0.30 | 260 | 0.57 |
| 261 | 2.50 | 262 | 0.51 | 263 | 0.49 | 264 | 0.09 |
| 265 | 0.16 | 266 | 0.22 | 267 | 0.30 | 268 | 0.11 |
| 269 | 0.20 | 270 | 0.14 | 271 | 0.65 | 272 | 0.09 |
| 273 | 0.16 | 274 | 0.15 | 275 | 0.70 | 276 | 1.20 |
| 277 | 0.30 | 278 | 0.26 | 279 | 0.34 | 280 | 2.40 |
| 281 | 0.17 | 282 | 0.17 | 283 | 0.36 | 284 | 3.90 |
| 285 | 1.00 | 286 | 0.35 | 287 | 0.19 | 288 | 0.88 |
| 289 | 0.40 | 290 | 0.20 | 291 | 0.19 | 292 | 0.16 |
| 293 | 0.24 | 294 | 5.80 | 295 | 0.79 | 296 | 0.32 |

The compounds of the invention are additionally tested in a human whole blood (HWB) assay to determine their ability to inhibit the synthesis of LTB₄ in a cellular system. Compounds are combined with heparinized human whole blood and incubated for 15 minutes at 37° C. Calcimycin (20 μM final, prepared in phosphate-buffered saline, pH 7.4) is then added and the mixture is incubated for another 30 minutes at 37° C. The samples are centrifuged for 5 min at low speed (1500×g) and the plasma layer is removed. Plasma LTB₄ concentrations are then measured using an antibody-based homogenous time-resolved fluorescence method (CisBio, Bedford, Mass.). In general, the preferred potency range ($IC_{50}$) of compounds in the HWB assay is between 10 nM to 10 μM, the more preferred potency range is 10 nM to 1 μM, and the most preferred potency range is 10 nM to 100 nM. The potencies of representative compounds of the invention in the HWB assays are shown in Table 10.

TABLE 10

$IC_{50}$ values of LTB₄ production inhibition assay in human whole blood.

| Example | IC₅₀, (nM) | Example | IC₅₀, (nM) | Example | IC₅₀, (nM) | Example | IC₅₀, (nM) |
|---|---|---|---|---|---|---|---|
| 139 | 13 | 175 | 73 | 52 | 145 | 61 | 250 |
| 142 | 24 | 173 | 73 | 219 | 149 | 118 | 256 |
| 190 | 26 | 109 | 76 | 183 | 151 | 174 | 268 |
| 158 | 28 | 138 | 76 | 14 | 155 | 87 | 268 |
| 137 | 28 | 68 | 81 | 53 | 155 | 9 | 285 |
| 160 | 28 | 81 | 81 | 64 | 158 | 229 | 290 |
| 145 | 28 | 200 | 83 | 156 | 159 | 25 | 294 |
| 126 | 32 | 220 | 91 | 121 | 159 | 85 | 305 |
| 141 | 33 | 185 | 92 | 178 | 160 | 227 | 307 |
| 140 | 33 | 237 | 95 | 69 | 165 | 26 | 308 |
| 83 | 33 | 134 | 95 | 214 | 169 | 116 | 310 |
| 157 | 35 | 234 | 95 | 18 | 176 | 123 | 312 |

TABLE 10-continued

IC$_{50}$ values of LTB$_4$ production inhibition assay in human whole blood.

| Example | IC$_{50}$ (nM) | Example | IC$_{50}$ (nM) | Example | IC$_{50}$ (nM) | Example | IC$_{50}$ (nM) |
|---|---|---|---|---|---|---|---|
| 186 | 36  | 204 | 95   | 187 | 177 | 37  | 324 |
| 168 | 39  | 155 | 95   | 1   | 179 | 67  | 346 |
| 125 | 39  | 99  | 95   | 98  | 180 | 10  | 352 |
| 241 | 110 | 242 | 170  | 243 | 99  | 244 | 120 |
| 245 | 130 | 246 | 91   | 247 | 68  | 248 | 58  |
| 249 | 58  | 250 | 84   | 251 | 63  | 252 | 42  |
| 253 | 110 | 254 | 84   | 255 | 76  | 256 | 110 |
| 257 | 270 | 258 | 210  | 259 | 790 | 260 | 100 |
| 261 | 260 | 262 | 170  | 263 | 130 | 264 | 17  |
| 265 | 150 | 266 | 98   | 267 | 73  | 268 | 66  |
| 269 | 36  | 270 | 35   | 271 | 110 | 272 | 71  |
| 273 | 110 | 274 | 100  | 275 | 170 | 276 | 240 |
| 277 | 65  | 278 | 73   | 279 | 93  | 280 | 230 |
| 281 | 37  | 282 | 61   | 283 | 540 | 284 | 290 |
| 285 | 200 | 286 | 190  | 287 | 55  | 288 | 150 |
| 289 | 170 | 290 | 48   | 291 | 56  | 292 | 24  |
| 293 | 52  | 294 | 1300 | 295 | 120 | 296 | 90  |
| 240 | 140 |     |      |     |     | 164 | 100 |

Methods of Use

The compounds of the invention are effective inhibitors of leukotriene A$_4$ hydrolase (LTA$_4$H) and thus inhibit leukotriene production. Therefore, in one embodiment of the invention, there is provided methods of treating leukotriene-mediated disorders using compounds of the invention. In another embodiment, there is provided methods of treating cardiovascular, inflammatory, allergic, pulmonary and fibrotic diseases, renal diseases and cancer using compounds of the invention.

In one embodiment, the invention relates to the use of a compound of the invention for the preparation of a medicament for the treatment leukotriene-mediated disorders. In another embodiment, the invention relates to the use of a compound of the invention, for the preparation of a medicament for treating cardiovascular, inflammatory, allergic, pulmonary and fibrotic diseases, renal diseases and cancer.

In one embodiment, the invention relates to a compound of the invention for use as a medicament for the treatment leukotriene-mediated disorders. In another embodiment, the invention relates to a compound of the invention for use in a method of treating cardiovascular, inflammatory, allergic, pulmonary and fibrotic diseases, renal diseases and cancer.

Without wishing to be bound by theory, by inhibiting the activity of LTA$_4$H, the compounds of the invention block the production of LTB$_4$ resulting from the oxidation of arachidonic acid by 5-LO and subsequent metabolism. Thus, the inhibition of LTA$_4$H activity is an attractive means for preventing and treating a variety of diseases mediated by LTB$_4$. These include:

Cardiovascular diseases including atherosclerosis, myocardial infarction, stroke, aortic aneurysm, sickle cell crisis, ischemia-reperfusion injury, pulmonary arterial hypertension and sepsis;

Allergic diseases including asthma, allergic rhinitis, rhinosinusitis, atopic dermatitis and urticaria;

Fibrotic diseases including airway remodeling in asthma, idiopathic pulmonary fibrosis, scleroderma, asbestosis;

Pulmonary syndromes including adult respiratory distress syndrome, viral bronchiolitis, obstructive sleep apnea, chronic obstructive pulmonary disease, cystic fibrosis, and bronchopulmonary dysplasia;

Inflammatory diseases including rheumatoid arthritis, osteoarthritis, gout, glomerulonephritis, interstitial cystitis, psoriasis, inflammatory bowel disease systemic lupus erythematosus, transplant rejection, inflammatory and allergic ocular diseases;

Cancer including solid tumors, leukemias and lymphomas; and Renal diseases such as glomerulonephritis.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased antagonist activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Non-limiting examples of other pharmacologically active substances include those described below for Combination Therapy.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by *Remington: The Science and Practice of Pharmacy*, 20th Edition, A. Gennaro (ed.), Lippincott Williams & Wilkins, 2000; *Handbook of Pharmaceutical Additives*, Michael & Irene Ash (eds.), Gower, 1995; *Handbook of Pharmaceutical Excipients*, A. H. Kibbe (ed.), American Pharmaceutical Ass'n, 2000; H. C. Ansel and N. G. Popovish, *Pharmaceutical Dosage Forms and Drug Delivery*

*Systems,* 5th ed., Lea and Febiger, 1990; each of which is incorporated herein by reference in their entireties to better describe the state of the art.

Combination Therapy

The compounds of the invention may be administered alone or in combination with at least one additional active agent. Thus, in one embodiment, the invention relates to a pharmaceutical composition comprising one or more compounds of the invention in combination with at least one additional agent. In another embodiment, the invention relates a method of treating diseases mediated by $LTB_4$, the method comprising administering a therapeutically effective amount of one or more compounds of the invention in combination with a pharmaceutically effective amount of at least one additional agent.

Nonlimiting examples of additional active agents include statins (or HMG-CoA reductase inhibitors); cholesterol ester transfer protein (CETP) inhibitors (or antagonists); fibrates, niacin derivatives, Lp-PLA2-inhibitors (e.g., darapladib, varespladib), antiplatelets and anticoagulants.

In one embodiment, the additional active agent is a statin. In another embodiment, the additional active agent is a statin selected from the group consisting of atorvastatin, fluvastatin, lovastatin, pitavastatin, pravastatin, rosuvastatin, and simvastatin.

In one embodiment, the additional active agent is a CETP inhibitor. In another embodiment, the additional active agent is a CETP inhibitor selected from the group consisting of anacetrapib, dalcetrapib, evacetrapib, TA-8995 (Mitsubishi Tanabe Pharma), ATH-03 (Affris), DRL-17822 (Dr. Reddy's). In yet another embodiment, the additional active is selected from dalcetrapib and anacetrapib.

As one of skill in the art would expect, the forms of the compounds of the invention utilized in a particular pharmaceutical formulation will be selected (e.g., salts) that possess suitable physical characteristics (e.g., water solubility) that are required for the formulation to be efficacious.

What is claimed is:

1. A compound selected from the group consisting of:
3-[(4-{4-[(2S)-2,3-dihydro-1,4-benzodioxin-2-yl] benzyl}piperazin-1-yl)methyl]benzoic acid,
7-[(S)-4-(2,3-dihydro-[1,4]dioxino[2,3-b]pyridin-3-yl)-benzyl]-5,6,7,8-tetrahydro-[1,2,4]triazolo[4,3-a]pyrazine-3-carboxylic acid ethyl ester,
7-[(S)-4-(2,3-Dihydro-[1,4]dioxino[2,3-b]pyridin-3-yl)-benzyl]-5,6,7,8-tetrahydro-[1,2,4]triazolo[4,3-a]pyrazine-3-carboxylic acid amide,
7-[(S)-4-(2,3-dihydro-[1,4]dioxino[2,3-b]pyridin-3-yl)-benzyl]-5,6,7,8-tetrahydro-[1,2,4]triazolo[4,3-a]pyrazine-3-carboxylic acid methylamide,
7-[(S)-4-(2,3-dihydro-[1,4]dioxino[2,3-b]pyridin-3-yl)-benzyl]-5,6,7,8-tetrahydro-imidazo[1,2-a]pyrazine-2-carboxylic acid amide,
7-[(S)-4-(2,3-dihydro-[1,4]dioxino[2,3-b]pyridin-3-yl)-benzyl]-5,6,7,8-tetrahydro-imidazo[1,2-a]pyrazine-2-carboxylic acid methylamide,
6-[(S)-4-(2,3-dihydro-[1,4]dioxino[2,3-b]pyridin-3-yl)-benzyl]-5,6,7,8-tetrahydro-4H-1,2,3a,6-tetraaza-azulene-3-carboxylic acid amide,
6-[(S)-4-(2,3-Dihydro-[1,4]dioxino[2,3-b]pyridin-3-yl)-benzyl]-5,6,7,8-tetrahydro-4H-1,2,3a,6-tetraaza-azulene-3-carboxylic acid methylamide,
[(1α,5α,6α)-3-[(S)-4-(2,3-dihydro-[1,4]dioxino[2,3-b]pyridin-3-yl)-benzyl]-3-aza-bicyclo[3.1.0]hexane]-6-carboxylic acid ((S)-2-hydroxy-propyl)-amide,
[(1α,5α,6α)-3-[(S)-4-(2,3-Dihydro-[1,4]dioxino[2,3-b]pyridin-3-yl)-benzyl]-3-aza-bicyclo[3.1.0]hexane]-6-carboxylic acid ((S)-2-hydroxy-1-methyl-ethyl)-amide,
7-[(S)-4-(2,3-Dihydro-[1,4]dioxino[2,3-b]pyridin-3-yl)-benzyl]-5,6,7,8-tetrahydro-imidazo[1,2-a]pyrazine-3-carbonitrile,
N-{(1α,5α,6α)-3-[(S)-4-(2,3-Dihydro-[1,4]dioxino[2,3-b]pyridin-3-yl)-benzyl]-3-aza-bicyclo[3.1.0]hex-6-yl}-acetamide,
[(1α,5α,6α)-3-[(S)-4-(2,3-Dihydro-[1,4]dioxino[2,3-b]pyridin-3-yl)-benzyl]-3-aza-bicyclo[3.1.0]hexane-6-carboxylic acid (2-hydroxy-2-methyl-propyl)]-amide,
N-{1-[(S)-4-(2,3-Dihydro-[1,4]dioxino[2,3-b]pyridin-3-yl)-benzyl]-piperidin-4-yl}-2-methoxy-acetamide,
1-{4-[(S)-4-(2,3-Dihydro-[1,4]dioxino[2,3-b]pyridin-3-yl)-benzyl]-piperazin-1-yl}-2-hydroxy-ethanone,
4-{1-[(S)-4-(2,3-Dihydro-benzo[1,4]dioxin-2-yl)-benzyl]-azetidin-3-yl}-benzoic acid,
1-[(S)-4-(2,3-Dihydro-[1,4]dioxino[2,3-b]pyridin-3-yl)-benzyl]-piperidine-4-carboxylic acid (2-hydroxy-2-methyl-propyl)-amide,
1-{(1S,4S)-5-[(S)-4-(2,3-Dihydro-[1,4]dioxino[2,3-b]pyridin-3-yl)-benzyl]-2,5-diaza-bicyclo[2.2.1]hept-2-yl}-2-methanesulfonyl-ethanone,
1-{4-[(S)-4-(2,3-Dihydro-[1,4]dioxino[2,3-b]pyridin-3-yl)-benzyl]-[1,4]diazepan-1-yl}-2-methoxy-ethanone,
5-[(S)-4-(2,3-Dihydro-[1,4]dioxino[2,3-b]pyridin-3-yl)-benzyl]-4,5,6,7-tetrahydro-thiazolo[5,4-c]pyridin-2-ylamine,
{(endo)-8-[(S)-4-(2,3-Dihydro-[1,4]dioxino[2,3-b]pyridin-3-yl)-benzyl]-8-aza-bicyclo[3.2.1]oct-3-yl}-urea,
2-{1-[(S)-4-(2,3-Dihydro-[1,4]dioxino[2,3-b]pyridin-3-yl)-benzyl]-piperidin-4-yl}-N-methoxy-acetamide,
(R)-N-{1-[(S)-4-(2,3-Dihydro-[1,4]dioxino[2,3-b]pyridin-3-yl)-benzyl]-piperidin-4-yl}-2-methylamino-propionamide,
N-{1-[(S)-4-(2,3-Dihydro-[1,4]dioxino[2,3-b]pyridin-3-yl)-benzyl]-piperidin-4-ylmethyl}-2-hydroxy-2-methyl-propionamide,
N-{(1α,5α,6α)-3-[(S)-4-(2,3-Dihydro-[1,4]dioxino[2,3-b]pyridin-3-yl)-benzyl]-3-aza-bicyclo[3.1.0]hex-6-ylmethyl}-methanesulfonamide,
1-{(1S,4S)-5-[(S)-4-(2,3-Dihydro-[1,4]dioxino[2,3-b]pyridin-3-yl)-benzyl]-2,5-diaza-bicyclo[2.2.2]oct-2-yl}-ethanone,
4-{1-[(S)-4-(2,3-Dihydro-[1,4]dioxino[2,3-b]pyridin-3-yl)-benzyl]-piperidin-4-yl}-cyclohexanecarboxylic acid,
1-[(S)-4-(2,3-Dihydro-benzo[1,4]dioxin-2-yl)-benzyl]-azepane-4-carboxylic acid,
[(1α,5α,6α)-3-[(S)-4-(2,3-Dihydro-benzo[1,4]dioxin-2-yl)-benzyl]-3-aza-bicyclo[3.1.0]hexane]-6-carboxylic acid,
(1S,4S)-5-[(S)-4-(2,3-Dihydro-[1,4]dioxino[2,3-b]pyridin-3-yl)-benzyl]-2,5-diaza-bicyclo[2.2.1]heptane-2-carboxylic acid amide,
1-[(S)-4-(2,3-Dihydro-[1,4]dioxino[2,3-b]pyridin-3-yl)-benzyl]-4-phenyl-piperidin-4-ol,
1-{5-[(S)-4-(2,3-Dihydro-[1,4]dioxino[2,3-b]pyridin-3-yl)-benzyl]-hexahydro-pyrrolo[3,4-c]pyrrol-2-yl}-ethanone,
1-{8-[(S)-4-(2,3-Dihydro-[1,4]dioxino[2,3-b]pyridin-3-yl)-benzyl]-3,8-diaza-bicyclo[3.2.1]oct-3-yl}-ethanone,
5-[(S)-4-(2,3-Dihydro-[1,4]dioxino[2,3-b]pyridin-3-yl)-benzyl]-hexahydro-pyrrolo[3,4-c]pyrrole-2-carboxylic acid amide, {(exo)-8-[(S)-4-(2,3-Dihydro-[1,4]dioxino[2,3-b]pyridin-3-yl)-benzyl]-8-aza-bicyclo[3.2.1]oct-3-yl}-urea,
2-{1-[(S)-4-(2,3-Dihydro-[1,4]dioxino[2,3-b]pyridin-3-yl)-benzyl]-piperidin-4-yloxy}-acetamide,
(S)-3-[4-(1,1-Dioxo-1lambda6-[1,4]thiazepan-4-ylmethyl)-phenyl]-2,3-dihydro-[1,4]dioxino[2,3-b]pyridine,
1-[(S)-4-(2,3-Dihydro-[1,4]dioxino[2,3-b]pyridin-3-yl)-benzyl]-4-methyl-piperidin-4-ol,
1-{(1S,4S)-5-[(S)-4-(2,3-Dihydro-[1,4]dioxino[2,3-b]pyridin-3-yl)-benzyl]-2,5-diaza-bicyclo[2.2.1]hept-2-yl}-2-hydroxy-ethanone,
N-{(endo)-8-[(S)-4-(2,3-Dihydro-[1,4]dioxino[2,3-b]pyridin-3-yl)-benzyl]-8-aza-bicyclo[3.2.1]oct-3-yl}-acetamide,
N-{1-[(S)-4-(2,3-Dihydro-[1,4]dioxino[2,3-b]pyridin-3-yl)-benzyl]-piperidin-4-ylmethyl}-acetamide,
[(S)-4-(2,3-Dihydro-[1,4]dioxino[2,3-b]pyridin-3-yl)-benzyl]-(1,1-dioxo-tetrahydro-1lambda-6-thiophen-3-yl)-methyl-amine,
1-{(1S,4S)-5-[(S)-4-(2,3-Dihydro-[1,4]dioxino[2,3-b]pyridin-3-yl)-benzyl]-2,5-diaza-bicyclo[2.2.2]oct-2-yl}-2-hydroxy-ethanone,
{1-[(S)-4-(2,3-dihydro-[1,4]dioxino-[2,3-b]pyridin-3-yl)-benzyl-spiro-[3H-indole-3,4'-piperidine]-1 (2H)-urea,
{1-[(S)-4-(2,3-Dihydro-[1,4]dioxino[2,3-b]pyridin-3-yl)-benzyl]-piperidin-4-ylmethyl}-urea,
{4-[(S)-4-(2,3-Dihydro-[1,4]dioxino[2,3-b]pyridin-3-yl)-benzyl]-piperazin-1-yl}-acetonitrile,
(R)-7-[(S)-4-(2,3-Dihydro-[1,4]dioxino[2,3-b]pyridin-3-yl)-benzyl]-hexahydro-oxazolo[3,4-a]pyrazin-3-one,
{1-[(S)-4-(2,3-Dihydro-[1,4]dioxino[2,3-b]pyridin-3-yl)-benzyl]-piperidin-4-yl}-(3-hydroxy-azetidin-1-yl)-methanone,
1-[(S)-4-(2,3-Dihydro-[1,4]dioxino[2,3-b]pyridin-3-yl)-benzyl]-piperidine-4-carboxylic acid [(S)-1-(tetrahydro-furan-2-yl)methyl]-amide,
N-[3-[4-[[4-[(3S)-2,3-dihydro-[1,4]dioxino[2,3-b]pyridin-3-yl]phenyl]methyl]piperazin-1-yl]-3-oxo-propyl]acetamide,
N-[1-[[4-[(3S)-2,3-dihydro-[1,4]dioxino[2,3-b]pyridin-3-yl]phenyl]methyl]-4-piperidyl]-2-(2-oxopyrrolidin-1-yl)acetamide,
N-[1-[[4-[(3S)-2,3-dihydro-[1,4]dioxino[2,3-b]pyridin-3-yl]phenyl]methyl]-4-piperidyl]tetrahydropyran-4-carboxamide,
3-{1-[(S)-4-(2,3-Dihydro-[1,4]dioxino[2,3-b]pyridin-3-yl)-benzyl]-piperidin-4-yl}-[1,3]oxazinan-2-one,
1-{(1S,4S)-5-[(S)-4-(2,3-Dihydro-[1,4]dioxino[2,3-b]pyridin-3-yl)-benzyl]-2,5-diaza-bicyclo[2.2.1]hept-2-yl}-ethanone,
(S)-3-{4-[4-(Pyridin-3-yloxy)-piperidin-1-ylmethyl]-phenyl}-2,3-dihydro-[1,4]dioxino[2,3-b]pyridine,
1-[(S)-4-(2,3-Dihydro-[1,4]dioxino[2,3-b]pyridin-3-yl)-benzyl]-4-phenyl-piperidine-4-carboxylic acid,
(S)-3-[4-(1-Oxo-1 lambda4-thiomorpholin-4-ylmethyl)-phenyl]-2,3-dihydro-[1,4]dioxino[2,3-b]pyridine, and
(S)-7-[(S)-4-(2,3-Dihydro-[1,4]dioxino[2,3-b]pyridin-3-yl)-benzyl]-hexahydro-oxazolo[3,4-a]pyrazin-3-one,
or a pharmaceutically acceptable salt thereof of each of the foregoing.

2. The compound of claim 1 selected from the group consisting of:
3-[(4-{4-[(2S)-2,3-dihydro-1,4-benzodioxin-2-yl]benzyl}piperazin-1-yl)methyl]benzoic acid,
7-[(S)-4-(2,3-dihydro-[1,4]dioxino[2,3-b]pyridin-3-yl)-benzyl]-5,6,7,8-tetrahydro-[1,2,4]triazolo[4,3-a]pyrazine-3-carboxylic acid ethyl ester,
7-[(S)-4-(2,3-Dihydro-[1,4]dioxino[2,3-b]pyridin-3-yl)-benzyl]-5,6,7,8-tetrahydro-[1,2,4]triazolo[4,3-a]pyrazine-3-carboxylic acid amide,
7-[(S)-4-(2,3-Dihydro-[1,4]dioxino[2,3-b]pyridin-3-yl)-benzyl]-5,6,7,8-tetrahydro-[1,2,4]triazolo[4,3-a]pyrazine-3-carboxylic acid methylamide,
7-[(S)-4-(2,3-Dihydro-[1,4]dioxino[2,3-b]pyridin-3-yl)-benzyl]-5,6,7,8-tetrahydro-imidazo[1,2-a]pyrazine-2-carboxylic acid amide,
7-[(S)-4-(2,3-Dihydro-[1,4]dioxino[2,3-b]pyridin-3-yl)-benzyl]-5,6,7,8-tetrahydro-imidazo[1,2-a]pyrazine-2-carboxylic acid methylamide,
6-[(S)-4-(2,3-dihydro-[1,4]dioxino[2,3-b]pyridin-3-yl)-benzyl]-5,6,7,8-tetrahydro-4H-1,2,3a,6-tetraaza-azulene-3-carboxylic acid amide,
6-[(S)-4-(2,3-Dihydro-[1,4]dioxino[2,3-b]pyridin-3-yl)-benzyl]-5,6,7,8-tetrahydro-4H-1,2,3a,6-tetraaza-azulene-3-carboxylic acid methylamide,
[(1α,5α,6α)-3-[(S)-4-(2,3-dihydro-[1,4]dioxino[2,3-b]pyridin-3-yl)-benzyl]-3-aza-bicyclo[3.1.0]hexane]-6-carboxylic acid ((S)-2-hydroxy-propyl)-amide,
[(1α,5α,6α)-3-[(S)-4-(2,3-Dihydro-[1,4]dioxino[2,3-b]pyridin-3-yl)-benzyl]-3-aza-bicyclo[3.1.0]hexane]-6-carboxylic acid ((S)-2-hydroxy-1-methyl-ethyl)-amide,
7-[(S)-4-(2,3-Dihydro-[1,4]dioxino[2,3-b]pyridin-3-yl)-benzyl]-5,6,7,8-tetrahydro-imidazo[1,2-a]pyrazine-3-carbonitrile,
N-{(1α,5α,6α)-3-[(S)-4-(2,3-Dihydro-[1,4]dioxino[2,3-b]pyridin-3-yl)-benzyl]-3-aza-bicyclo[3.1.0]hex-6-yl}-acetamide, and
[(1α,5α,6α)-3-[(S)-4-(2,3-Dihydro-[1,4]dioxino[2,3-b]pyridin-3-yl)-benzyl]-3-aza-bicyclo[3.1.0]hexane-6-carboxylic acid (2-hydroxy-2-methyl-propyl)]-amide,
or a pharmaceutically acceptable salt thereof of each of the foregoing.

3. The compound of claim 1 selected from the group consisting of:
N-{1-[(S)-4-(2,3-Dihydro-[1,4]dioxino[2,3-b]pyridin-3-yl)-benzyl]-piperidin-4-yl}-2-methoxy-acetamide,
1-{4-[(S)-4-(2,3-Dihydro-[1,4]dioxino[2,3-b]pyridin-3-yl)-benzyl]-piperazin-1-yl}-2-hydroxy-ethanone,
4-{1-[(S)-4-(2,3-Dihydro-benzo[1,4]dioxin-2-yl)-benzyl]-azetidin-3-yl}-benzoic acid,
1-[(S)-4-(2,3-Dihydro-[1,4]dioxino[2,3-b]pyridin-3-yl)-benzyl]-piperidine-4-carboxylic acid (2-hydroxy-2-methyl-propyl)-amide,
1-{(1S,4S)-5-[(S)-4-(2,3-Dihydro-[1,4]dioxino[2,3-b]pyridin-3-yl)-benzyl]-2,5-diaza-bicyclo[2.2.1]hept-2-yl}-2-methanesulfonyl-ethanone,
1-{4-[(S)-4-(2,3-Dihydro-[1,4]dioxino[2,3-b]pyridin-3-yl)-benzyl]-[1,4]diazepan-1-yl}-2-methoxy-ethanone,
5-[(S)-4-(2,3-Dihydro-[1,4]dioxino[2,3-b]pyridin-3-yl)-benzyl]-4,5,6,7-tetrahydro-thiazolo[5,4-c]pyridin-2-ylamine,
{(endo)-8-[(S)-4-(2,3-Dihydro-[1,4]dioxino[2,3-b]pyridin-3-yl)-benzyl]-8-aza-bicyclo[3.2.1]oct-3-yl}-urea,
2-{1-[(S)-4-(2,3-Dihydro-[1,4]dioxino[2,3-b]pyridin-3-yl)-benzyl]-piperidin-4-yl}-N-methoxy-acetamide,
(R)-N-{1-[(S)-4-(2,3-Dihydro-[1,4]dioxino[2,3-b]pyridin-3-yl)-benzyl]-piperidin-4-yl}-2-methylamino-propionamide,
N-{1-[(S)-4-(2,3-Dihydro-[1,4]dioxino[2,3-b]pyridin-3-yl)-benzyl]-piperidin-4-ylmethyl}-2-hydroxy-2-methyl-propionamide, N-{(1α,5α,6α)-3-[(S)-4-(2,3-Dihydro-[1,4]dioxino[2,3-b]pyridin-3-yl)-benzyl]-3-aza-bicyclo[3.1.0]hex-6-ylmethyl}-methanesulfonamide,
1-{(1S,4S)-5-[(S)-4-(2,3-Dihydro-[1,4]dioxino[2,3-b]pyridin-3-yl)-benzyl]-2,5-diaza-bicyclo[2.2.2]oct-2-yl}-ethanone,
4-{1-[(S)-4-(2,3-Dihydro-[1,4]dioxino[2,3-b]pyridin-3-yl)-benzyl]-piperidin-4-yl}-cyclohexanecarboxylic acid,
1-[(S)-4-(2,3-Dihydro-benzo[1,4]dioxin-2-yl)-benzyl]-azepane-4-carboxylic acid,
[(1α,5α,6α)-3-[(S)-4-(2,3-Dihydro-benzo[1,4]dioxin-2-yl)-benzyl]-3-aza-bicyclo[3.1.0]hexane]-6-carboxylic acid,
(1S,4S)-5-[(S)-4-(2,3-Dihydro-[1,4]dioxino[2,3-b]pyridin-3-yl)-benzyl]-2,5-diaza-bicyclo[2.2.1]heptane-2-carboxylic acid amide,
1-[(S)-4-(2,3-Dihydro-[1,4]dioxino[2,3-b]pyridin-3-yl)-benzyl]-4-phenyl-piperidin-4-ol,
1-{5-[(S)-4-(2,3-Dihydro-[1,4]dioxino[2,3-b]pyridin-3-yl)-benzyl]-hexahydro-pyrrolo[3,4-c]pyrrol-2-yl}-ethanone,
1-{8-[(S)-4-(2,3-Dihydro-[1,4]dioxino[2,3-b]pyridin-3-yl)-benzyl]-3,8-diaza-bicyclo[3.2.1]oct-3-yl}-ethanone,
5-[(S)-4-(2,3-Dihydro-[1,4]dioxino[2,3-b]pyridin-3-yl)-benzyl]-hexahydro-pyrrolo[3,4-c]pyrrole-2-carboxylic acid amide,
{(exo)-8-[(S)-4-(2,3-Dihydro-[1,4]dioxino[2,3-b]pyridin-3-yl)-benzyl]-8-aza-bicyclo[3.2.1]oct-3-yl}-urea, and
2-{1-[(S)-4-(2,3-Dihydro-[1,4]dioxino[2,3-b]pyridin-3-yl)-benzyl]-piperidin-4-yloxy}-acetamide,
or a pharmaceutically acceptable salt thereof of each of the foregoing.

4. The compound of claim 1 selected from the group consisting of:
(S)-3-[4-(1,1-Dioxo-1lambda6-[1,4]thiazepan-4-ylmethyl)-phenyl]-2,3-dihydro-[1,4]dioxino[2,3-b]pyridine,
1-[(S)-4-(2,3-Dihydro-[1,4]dioxino[2,3-b]pyridin-3-yl)-benzyl]-4-methyl-piperidin-4-ol,
1-{(1S,4S)-5-[(S)-4-(2,3-Dihydro-[1,4]dioxino[2,3-b]pyridin-3-yl)-benzyl]-2,5-diaza-bicyclo[2.2.1]hept-2-yl}-2-hydroxy-ethanone,
N-{(endo)-8-[(S)-4-(2,3-Dihydro-[1,4]dioxino[2,3-b]pyridin-3-yl)-benzyl]-8-aza-bicyclo[3.2.1]oct-3-yl}-acetamide,
N-{1-[(S)-4-(2,3-Dihydro-[1,4]dioxino[2,3-b]pyridin-3-yl)-benzyl]-piperidin-4-ylmethyl}-acetamide,
[(S)-4-(2,3-Dihydro-[1,4]dioxino[2,3-b]pyridin-3-yl)-benzyl]-(1,1-dioxo-tetrahydro-1lambda-6-thiophen-3-yl)-methyl-amine,
1-{(1S,4S)-5-[(S)-4-(2,3-Dihydro-[1,4]dioxino[2,3-b]pyridin-3-yl)-benzyl]-2,5-diaza-bicyclo[2.2.2]oct-2-yl}-2-hydroxy-ethanone,
{1-[(S)-4-(2,3-dihydro-[1,4]dioxino-[2,3-b]pyridin-3-yl)-benzyl]-spiro-[3H-indole-3,4'-piperidine]-1 (2H)-urea, and
{1-[(S)-4-(2,3-Dihydro-[1,4]dioxino[2,3-b]pyridin-3-yl)-benzyl]-piperidin-4-ylmethyl}-urea,
{4-[(S)-4-(2,3-Dihydro-[1,4]dioxino[2,3-b]pyridin-3-yl)-benzyl]-piperazin-1-yl}-acetonitrile,
(R)-7-[(S)-4-(2,3-Dihydro-[1,4]dioxino[2,3-b]pyridin-3-yl)-benzyl]-hexahydro-oxazolo[3,4-a]pyrazin-3-one,
{1-[(S)-4-(2,3-Dihydro-[1,4]dioxino[2,3-b]pyridin-3-yl)-benzyl]-piperidin-4-yl}-(3-hydroxy-azetidin-1-yl)-methanone,
1-[(S)-4-(2,3-Dihydro-[1,4]dioxino[2,3-b]pyridin-3-yl)-benzyl]-piperidine-4-carboxylic acid [(S)-1-(tetrahydro-furan-2-yl)methyl]-amide,
N-[3-[4-[[4-[(3S)-2,3-dihydro-[1,4]dioxino[2,3-b]pyridin-3-yl]phenyl]methyl]piperazin-1-yl]-3-oxo-propyl] acetamide,
N-[1-[[4-[(3S)-2,3-dihydro-[1,4]dioxino[2,3-b]pyridin-3-yl]phenyl]methyl]-4-piperidyl]-2-(2-oxopyrrolidin-1-yl)acetamide,
N-[1-[[4-[(3S)-2,3-dihydro-[1,4]dioxino[2,3-b]pyridin-3-yl]phenyl]methyl]-4-piperidyl]tetrahydropyran-4-carboxamide,
3-{1-[(S)-4-(2,3-Dihydro-[1,4]dioxino[2,3-b]pyridin-3-yl)-benzyl]-piperidin-4-yl}-[1,3]oxazinan-2-one,
1-{(1S,4S)-5-[(S)-4-(2,3-Dihydro-[1,4]dioxino[2,3-b]pyridin-3-yl)-benzyl]-2,5-diaza-bicyclo[2.2.1]hept-2-yl}-ethanone,
(S)-3-{4-[4-(Pyridin-3-yloxy)-piperidin-1-ylmethyl]-phenyl}-2,3-dihydro-[1,4]dioxino[2,3-b]pyridine,
1-[(S)-4-(2,3-Dihydro-[1,4]dioxino[2,3-b]pyridin-3-yl)-benzyl]-4-phenyl-piperidine-4-carboxylic acid,
(S)-3-[4-(1-Oxo-1 lambda4-thiomorpholin-4-ylmethyl)-phenyl]-2,3-dihydro-[1,4]dioxino[2,3-b]pyridine, and
(S)-7-[(S)-4-(2,3-Dihydro-[1,4]dioxino[2,3-b]pyridin-3-yl)-benzyl]-hexahydro-oxazolo[3,4-a]pyrazin-3-one,
or a pharmaceutically acceptable salt thereof of each of the foregoing.

5. A pharmaceutical composition comprising one or more compounds of claim 1, or a pharmaceutically acceptable salt thereof, and a pharmaceutically acceptable carrier or excipient.

6. A pharmaceutical composition comprising one or more compounds of claim 2, or a pharmaceutically acceptable salt thereof, and a pharmaceutically acceptable carrier or excipient.

7. A pharmaceutical composition comprising one or more compounds of claim 3, or a pharmaceutically acceptable salt thereof, and a pharmaceutically acceptable carrier or excipient.

8. A pharmaceutical composition comprising one or more compounds of claim 4, or a pharmaceutically acceptable salt thereof, and a pharmaceutically acceptable carrier or excipient.

9. The pharmaceutical composition of claim 1, further comprising at least one additional pharmacologically active substance.

10. A method of treating a cardiovascular disease comprising administering a pharmaceutically effective amount of a compound of claim 1, or a pharmaceutically acceptable salt thereof, to a patient in need thereof.

11. A method of treating a cardiovascular disease comprising administering a pharmaceutically composition of claim 5, to a patient in need thereof.

12. The method of claim 10 wherein said cardiovascular disease is selected from the group consisting of atherosclerosis, myocardial infarction, stroke, aortic aneurysm, sickle cell crisis, ischemia-reperfusion injury, pulmonary arterial hypertension and sepsis.

13. The method of claim 10, wherein the cardiovascular disease is atherosclerosis.

14. The method of claim 11 wherein said cardiovascular disease is selected from the group consisting of atherosclerosis, myocardial infarction, stroke, aortic aneurysm, sickle cell crisis, ischemia-reperfusion injury, pulmonary arterial hypertension and sepsis.

15. The method of claim 11, wherein the cardiovascular disease is atherosclerosis.

16. A method of treating atherosclerosis, comprising administering a pharmaceutically effective amount of a compound of claim 1, or a pharmaceutically acceptable salt thereof, to a patient in need thereof.

* * * * *